US009115137B2

(12) United States Patent
Hung et al.

(10) Patent No.: US 9,115,137 B2
(45) Date of Patent: Aug. 25, 2015

(54) 2,3,4,5-TETRAHYDRO-1H-PYRIDO[4,3-B]INDOLE COMPOUNDS AND METHODS OF USE THEREOF

(75) Inventors: David T. Hung, Redwood City, CA (US); Andrew Asher Protter, Palo Alto, CA (US); Sarvajit Chakravarty, Mountain View, CA (US); Rajendra Parasmal Jain, Pune (IN)

(73) Assignee: Medivation Technologies, Inc., San Francisco, CA (US)

( * ) Notice: Subject to any disclaimer, the term of this patent is extended or adjusted under 35 U.S.C. 154(b) by 705 days.

(21) Appl. No.: 12/360,061

(22) Filed: Jan. 26, 2009

(65) Prior Publication Data

US 2010/0022580 A1    Jan. 28, 2010

Related U.S. Application Data

(60) Provisional application No. 61/062,430, filed on Jan. 25, 2008, provisional application No. 61/062,394, filed on Jan. 25, 2008.

(51) Int. Cl.
| | | |
|---|---|---|
| *A61K 31/44* | (2006.01) | |
| *C07D 487/14* | (2006.01) | |
| *C07D 471/04* | (2006.01) | |
| *C07D 471/14* | (2006.01) | |
| *C07D 487/04* | (2006.01) | |

(52) U.S. Cl.
CPC ............ *C07D 487/14* (2013.01); *C07D 471/04* (2013.01); *C07D 471/14* (2013.01); *C07D 487/04* (2013.01)

(58) Field of Classification Search
USPC .......................................... 514/292; 546/117
See application file for complete search history.

(56) References Cited

U.S. PATENT DOCUMENTS

| | | | |
|---|---|---|---|
| 5,360,800 A * | 11/1994 | Coates et al. ................. 514/215 |
| 5,817,756 A | 10/1998 | Kyle et al. | |
| 6,187,785 B1 | 2/2001 | Zefirov et al. | |
| 7,071,206 B2 | 7/2006 | Zefirov et al. | |
| 8,338,408 B2 | 12/2012 | Hung et al. | |
| 8,338,447 B2 | 12/2012 | Hung et al. | |
| 8,362,277 B2 | 1/2013 | McKnight et al. | |
| 8,541,437 B2 | 9/2013 | Ivashchenko et al. | |
| 8,546,381 B2 | 10/2013 | Hung et al. | |
| 8,569,287 B2 | 10/2013 | Hung et al. | |
| 8,604,074 B2 | 12/2013 | McKnight et al. | |
| 8,735,440 B2 | 5/2014 | McKnight et al. | |
| 8,741,919 B2 * | 6/2014 | Jain et al. ...................... 514/292 |
| 8,791,132 B2 | 7/2014 | Protter et al. | |
| 8,815,843 B2 | 8/2014 | Protter et al. | |
| 8,859,561 B2 | 10/2014 | Jain et al. | |
| 8,877,797 B2 | 11/2014 | McKnight et al. | |
| 8,906,925 B2 | 12/2014 | Hung et al. | |
| 8,907,097 B2 | 12/2014 | Hung et al. | |
| 8,927,571 B2 | 1/2015 | Jain et al. | |
| 2001/0020028 A1 | 9/2001 | Zefirov et al. | |
| 2002/0115682 A1 | 8/2002 | Zefirov et al. | |
| 2004/0044022 A1 | 3/2004 | Zefirov, Jr. et al. | |
| 2005/0277117 A1 | 12/2005 | Ofer | |
| 2006/0140866 A1 | 6/2006 | Zefirov et al. | |
| 2007/0117834 A1 | 5/2007 | Hung | |
| 2007/0117835 A1 | 5/2007 | Hung | |
| 2007/0179174 A1 | 8/2007 | Bachurin et al. | |
| 2007/0225316 A1 | 9/2007 | Bachurin et al. | |
| 2008/0234310 A1 | 9/2008 | Bachurin et al. | |
| 2009/0239854 A1 | 9/2009 | Hung et al. | |
| 2009/0270412 A1 | 10/2009 | Hung et al. | |
| 2010/0029706 A1 | 2/2010 | Miller et al. | |
| 2010/0087471 A1 | 4/2010 | Schrimpf et al. | |
| 2010/0099667 A1 | 4/2010 | Hung et al. | |
| 2010/0099700 A1 | 4/2010 | Hung | |
| 2010/0152108 A1 | 6/2010 | Hung et al. | |
| 2010/0152163 A1 | 6/2010 | Hung et al. | |
| 2010/0152225 A1 | 6/2010 | Hung | |
| 2010/0178277 A1 | 7/2010 | Hung et al. | |
| 2010/0216814 A1 | 8/2010 | Hung et al. | |
| 2010/0249105 A1 | 9/2010 | Schrimpf et al. | |
| 2010/0286188 A1 | 11/2010 | Bachurin et al. | |
| 2011/0046368 A1 | 2/2011 | Ivashchenko et al. | |
| 2011/0112132 A1 | 5/2011 | Bachurin et al. | |
| 2011/0237582 A1 | 9/2011 | Jain et al. | |

(Continued)

FOREIGN PATENT DOCUMENTS

| | | |
|---|---|---|
| EP | 2 236 511 A2 | 10/2010 |
| GB | 2209335 A | 5/1989 |

(Continued)

OTHER PUBLICATIONS

Zefirov et al. (JP 09216882 A; 1997); CaPlus Accession No. 1997:558054.*
Patani et al.; "Bioisosterism: A Rational Approach in Drug Design"; Chem. Rev.; 1996: 3147-3176.*
Bartolini, L. et al. (1996). "Aniracetam Restores Object Recognition Impaired by Age, Scopolamine, and Nucleus Basalis Lesions," *Pharmacology Biochemistry Behavior* 53(2):277-283.
Berge, S.M. et al. (Jan. 1977). "Pharmaceutical Salts," *Journal of Pharmaceutical Sciences* 66(1):1-19.

(Continued)

*Primary Examiner* — Rei-Tsang Shiao
(74) *Attorney, Agent, or Firm* — Morrison & Foerster LLP

(57) ABSTRACT

Provided are new tricyclic compounds that may be used to modulate a histamine receptor in an individual. Compounds are described, including new 2,3,4,5-tetrahydro-1H-pyrido[4,3-b]indole compounds. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder.

23 Claims, No Drawings

(56) References Cited

U.S. PATENT DOCUMENTS

| | | |
|---|---|---|
| 2011/0245272 A1 | 10/2011 | Jain et al. |
| 2011/0269777 A1 | 11/2011 | Bachurin et al. |
| 2012/0022096 A1 | 1/2012 | McKnight et al. |
| 2012/0101121 A1 | 4/2012 | Bachurin et al. |
| 2012/0136008 A1 | 5/2012 | Jain et al. |
| 2013/0040977 A1 | 2/2013 | McKnight et al. |
| 2013/0053366 A1 | 2/2013 | Protter et al. |
| 2013/0053367 A1 | 2/2013 | Protter et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0172366 A1 | 7/2013 | Jain et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190322 A1 | 7/2013 | Hung et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0024643 A1 | 1/2014 | Hung et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |

FOREIGN PATENT DOCUMENTS

| | | |
|---|---|---|
| JP | 1-151578 A | 6/1989 |
| JP | 9-216882 A | 8/1997 |
| JP | 2005-523892 A | 8/2005 |
| JP | 2007-526276 A | 9/2007 |
| JP | 2008-534496 A | 8/2008 |
| JP | 2009-502959 A | 1/2009 |
| JP | 2009-524676 A | 7/2009 |
| JP | 2010-531344 A | 9/2010 |
| JP | 2011-500855 A | 1/2011 |
| RU | 2 140 417 C1 | 10/1999 |
| RU | 2007/139634 A | 4/2009 |
| WO | WO-03/061657 A1 | 7/2003 |
| WO | WO-2005/005951 A3 | 6/2005 |
| WO | WO-2005/055951 A2 | 6/2005 |
| WO | WO-2005/095397 A1 | 10/2005 |
| WO | WO-2006/101434 A1 | 9/2006 |
| WO | WO-2007/016353 A2 | 2/2007 |
| WO | WO-2007/016353 A3 | 2/2007 |
| WO | WO-2007/022502 A2 | 2/2007 |
| WO | WO-2007/022502 A3 | 2/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO 2008/051599 A3 | 5/2008 |
| WO | WO-2008-060190 A2 | 5/2008 |
| WO | WO-2008-060190 A3 | 5/2008 |
| WO | WO-2008/069963 A1 | 6/2008 |
| WO | WO-2008/073231 A1 | 6/2008 |
| WO | WO-2008/115098 A2 | 9/2008 |
| WO | WO-2008/115098 A3 | 9/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/001129 A1 | 12/2008 |
| WO | WO-2009/001129 A9 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/036998 A2 | 4/2010 |
| WO | WO-2010/036998 A3 | 4/2010 |
| WO | WO-2010/051501 A1 | 5/2010 |
| WO | WO-2010/051503 A1 | 5/2010 |
| WO | WO-2010/081115 A1 | 7/2010 |
| WO | WO-2010/127177 A1 | 11/2010 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/006419 A2 | 1/2012 |
| WO | WO-2012-006419 A3 | 1/2012 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112964 A3 | 8/2012 |
| WO | WO-2012/112965 A1 | 8/2012 |
| WO | WO-2012/112966 A1 | 8/2012 |
| WO | WO-2012/154261 A1 | 11/2012 |
| WO | WO-2014/031125 A1 | 2/2014 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.

Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.

Brown, C.M. et al. (1990). "$\alpha_2$-Adrenoceptor Subtypes and Imidazoline-Like Binding Sites in the Rat Brain," *Br. J. Pharmacol.* 99:803-809.

(56) References Cited

OTHER PUBLICATIONS

Bubber, P. et al. (May 2005, e-pub. Apr. 25, 2005). "Mitochondrial Abnormalities in Alzheimer Brain: Mechanistic Implications," *Ann Neurol.* 57(5):695-703.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Ennaceur, A. et al. (1988). "A New One-Trial Test for Neurobiological Studies of Memory in Rats. 1: Behavioral Data," *Behav. Brain. Res.* 31:47-59.

Garcïa-Sä inz, J.A. et al. (Jul. 31, 1992). "Species Heterogeneity of Hepatic $\alpha_1$- Adrenoceptors: $\alpha_{1A}$-, $\alpha_{1B\text{-}and\ \alpha1C}$-Subtypes," *Biochemical and Biophysical Research Communications* 186(2):760-767.

Gilliland, S.L. et al. (2000, e-pub. Feb. 29, 2000). "Characterization of Dopaminergic Compounds at $hD_{2short}$, $hD_{4.2}$ and $hD_{4.7}$ Receptors in Agonist-Stimulated [$^{35}$S]GTPyS Binding Assays," *Naunyn-Schmiedeberg's Archives of Pharmacology* 361:498-504.

Grandy, D.K. et al. (Dec. 1989). "Cloning of the cDNA and Gene for a Human $D_2$ Dopamine Receptor," *Proc. Natl. Acad. Sci. USA* 86:9762-9766.

Grossman, C.J. et al. (1993). "Development of a Radioligand Binding Assay for 5-HT$_4$ Receptors in Guinea-Pig and Rat Brain," *Br. J. Pharmacol.* 109:618-624.

Hardy, J. (1996). "New Insights Into the Genetics of Alzheimer's Disease," *Annals of Medicine* 28:255-258.

Hardy, J. (1997). "Amyloid, the Presenilins and Alzheimer's Disease," *Trends Neurosci.* 20(4):154-159.

Hayes, G. et al. (1992). "Structural Subtypes of the Dopamine D2 Receptor are Functionally Distinct: Expression of the Cloned $D2_A$ and $D2_B$ Subtypes in a Heterologous Cell Line," *Mol. Endocrinol.* 6(6):920-926.

Hoyer, D. et al. (1985). "Characterization of the 5-HT$_{1B}$ Recognition Site in Rat Brain: Binding Studies with (-)[$^{125}$I]Iodocyanopindolol," *European Journal of Pharmacology* 118:1-12.

International Search Report mailed on Apr. 17, 2009, for PCT Patent Application No. PCT/US2009/32065, filed on Jan. 26, 2009, 1 page.

Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.

Jerman, J.C. et al. (2001). "Pharmacological Characterisation of Human 5-HT$_2$ Receptor Subtypes," *European Journal of Pharmacology* 414:23-30.

Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.

Kohen, R. et al. (1996). "Cloning, Characterization, and Chromosomal Localization of a Human 5-HT$_6$ Serotonin Receptor," *J. Neurochem.* 66(1):47-56.

Martin, G.R. (1994). "Receptors for 5-Hydroxytryptamine: Current Perspectives on Classification and Nomenclature," *Neuropharmacology* 33(3/4):261-273.

May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.

Michel, A.D. et al. (1989). "Identification of a Single $\alpha_1$-Adrenoceptor Corresponding to the $\alpha_{1A}$-Subtype in Rat Submaxillary Gland," *Br. J. Pharmacol.* 98:883-889.

Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.

Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.

Monsma, F.J. Jr. et al. (1993). "Cloning and Expression of a Novel Serotonin Receptor with High Affinity for Tricyclic Psychotropic Drugs," *Molecular Pharmacology* 43:320-327.

Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.

Piercey, M.F. et al. (1988). "Dramatic Limbic and Cortical Effects Mediated by High Affinity PCP Receptors," *Life Sciences* 43(4):379-385.

Prichep, L.S. et al. (1994). "Quantitative EEG Correlates of Cognitive Deterioration in the Elderly," *Neurobiology of Aging* 15(1):85-90.

Reddy, P.H. et al. (2005, e-pub. Apr. 19, 2005). "Are Mitochondria Critical in the Pathogenesis of Alzheimer's Disease?" *Brain Res Rev.* 49(3):618-632.

Rees, S. et al. (Oct. 11, 1994). "Cloning and Characterisation of the Human 5-HT$_{5A}$ Serotonin Receptor," *FEBS Letters* 355:242-246.

Reisberg, B. et al. (Sep. 1982). "The Global Deterioration Scale for Assessment of Primary Degenerative Dementia," *Am. J. Psychiatry* 139(9):1136-1139.

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

Ruat, M. et al. (Mar. 1990). "Reversible and Irreversible Labeling and Autoradiographic Localization of the Cerebral Histamine H$_2$ Receptor Using [$^{125}$I]Iodinated Probes," *Proc. Natl. Acad. Sci. USA* 87(5):1658-1662.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of G$_i$Subtypes by the D$_2$ Dopamine Receptor in a Reconstituted System," *Journal of Biological Chemistry* 265(8):4507-4514.

Setola, V. et al. (2005). "Molecular Determinants for the Interaction of the Valvulopathic Anorexigen Norfenfluramine with the 5-HT$_{2B}$ Receptor," *Mol. Pharmacology* 68(1):20-33.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Uhlén, S. et al. (1994). "The Novel Alpha-2 Adrenergic RadioLigand [$^3$H]-MK912 is *Alpha-2C* Selective Among Human *Alpha-2A, Alpha-2B* and *Alpha-2C* Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-,$\alpha_{2B}$- and $\alpha_{2C}$-Adrenoceptors. Comparison with MK912, RX821002, Rauwolscine and Yohimbine," *European Journal of Pharmacology* 343:93-101.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion of the International Searching Authority mailed on Apr. 17, 2009, for PCT Patent Application No. PCT/US2009/32065, filed on Jan. 26, 2009, 6 pages.

(56) References Cited

OTHER PUBLICATIONS

Yanai, K. et al. (1994). "Binding Characteristics of a Histamine $H_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

Chemical Abstracts 1955, 49, 13251 a-13252g.

Chemical Abstracts 1961, 55, 10681 c-f.

Chern, M-S et al. (Nov.-Dec. 2004, e-published Oct. 21, 2004). "Traceless Solid-Phase Synthesis of Carbolinones," *J Comb Chem* 6(6):855-858.

U.S. Appl. No. 14/000,171, filed on Aug. 16, 2013, by Protter et al.

U.S. Appl. No. 14/000,179, filed on Aug. 16, 2013, by Chakravarty et al.

U.S. Appl. No. 14/000,184, filed on Aug. 16, 2013, by Protter et al.

U.S. Appl. No. 14/000,197, filed on Aug. 16, 2013, by Protter et al.

U.S. Appl. No. 14/048,656, filed on Oct. 8, 2013, by Hung et al.

Lohr, J.B. et al. (Aug. 28, 1995). "Motor Asymmetry, a Neurobiologic Abnormality in the Major Psychoses," *Psychiatry Research* 57(3):279-282.

Extended European Search Report mailed on Dec. 6, 2011, for EP Patent Application No. 09704753.4, filed on Jan. 26, 2009, 6 pages.

U.S. Appl. No. 13/318,123, internationally filed on Apr. 29, 2010, by Jain et al.

U.S. Appl. No. 13/318,124, international filed on Apr. 29, 2010, by Jain et al.

U.S. Appl. No. 13/498,097, international filed on Sep. 23, 2010, by Jain et al.

U.S. Appl. No. 13/498,099, international filed on Sep. 23, 2010, by Jain et al.

U.S. Appl. No. 14/531,915, filed on Nov. 3, 2014, by Hung et al.

Final Office Action mailed on Jul. 25, 2013, for U.S. Appl. No. 12/610,217, filed on Oct. 30, 2009, 11 pages.

Non-Final Office Action mailed on Apr. 16, 2013, for U.S. Appl. No. 12/610,217, filed on Oct. 30, 2009, 10 pages.

Non-Final Office Action mailed on Apr. 7, 2015, for U.S. Appl. No. 13/789,604, filed on Mar. 7, 2013, 20 pages.

U.S. Appl. No. 14/423,027, filed on Feb. 20, 2015, by Protter et al.

U.S. Appl. No. 14/631,615, filed on Feb. 25, 2015, by Hung et al.

U.S. Appl. No. 14/641,232, filed on Mar. 6, 2015, by Protter et al.

\* cited by examiner

2,3,4,5-TETRAHYDRO-1H-PYRIDO[4,3-B]INDOLE COMPOUNDS AND METHODS OF USE THEREOF

CROSS-REFERENCE TO RELATED APPLICATIONS

This application claims priority to U.S. Provisional Patent Application No. 61/062,430 filed Jan. 25, 2008 and U.S. Provisional Patent Application No. 61/062,394 filed Jan. 25, 2008, the disclosures of each of which are incorporated herein by reference in their entireties.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121.

All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Compounds of the general formula (I) are described as new histamine receptor modulators. Other compounds are also detailed herein. Compositions comprising the compounds are provided, as are kits comprising the compound as well as methods of using and making the compounds. Other compounds are also provided. Compounds of the invention may also find use in treating neurodegenerative diseases. Compounds of the invention may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

The invention embraces compounds of the formula (I):

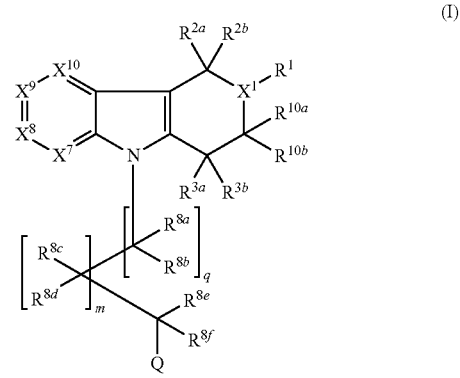

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano or nitro or $R^{3a}$ and $R^{3b}$ are taken together to form a carbonyl moiety;

each $X^7$, $X^8$, $X^9$ and $X^{10}$ is independently N or $CR^4$;

m and q are independently 0 or 1;

$X^1$ is N or CH;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^8$, $R^{8b}$, $R^{8c}$, $R^{8d}$, $R^{8e}$ and $R^{8f}$ is independently H, hydroxyl, $C_1$-$C_8$ alkyl or is taken together with the carbon to which it is attached and a geminal $R^{8(e-f)}$ to form a cycloalkyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is acylamino, carbonylalkoxy, acyloxy, aminoacyl or aminocarbonylalkoxy;

provided that: (1) when X is N, the compound is other than a compound in Table 1, and (2) when $X^1$ is CH, the compound is other than any of 9H-Carbazole-9-acetamide, 5,6,7,8-tetrahydro-3-[[[5-[[(1-methylethyl)sulfonyl]amino]pentyl]amino]carbonyl]-; 9H-Carbazole-9-acetamide, N-ethyl-1,2,3,4-tetrahydro-7-methoxy-2,2-dimethyl-N-2-thiazolyl-; 3,5-Pyridinedicarboxylic acid, 4-(2-chlorophenyl)-2-[[2-[[3-[3-[[(4-fluorophenyl)sulfonyl]amino]-1,2,3,4-tetrahydro-9H-carbazol-9-yl]-1-oxopropyl]amino]ethoxy]methyl]-1,4-dihydro-6-methyl-, 3-methyl5-(1-methylethyl)ester; 9H-Carbazole-9-acetamide, 1,2,3,4-tetrahydro-N-(2-methoxyphenyl)-; 9H-Carbazole-9-acetamide, 1,2,3,4-tetrahydro-7-methoxy-2,2-dimethyl-N,N-bis(3-methylbutyl)-; 3,5-Pyridinedicarboxylic acid, 4-(2,3-dichlorophenyl)-1,4-dihydro-2,6-dimethyl-, 2-[[3-[3-[[(4-fluorophenyl)sulfonyl]amino]-1,2,3,4-tetrahydro-9H-carbazol-9-yl]-1-oxopropyl]amino]ethyl methyl ester; 9H-Carbazole-9-butanamide, N-[4-[(4-aminophenyl)sulfonyl]phenyl]-1,2,3,4-tetrahydro-; Carbamic acid, [(1,2,3,4-tetrahydro-3-methyl-9H-carbazol-9-yl)acetyl]-, ethyl ester; 9H-Carbazole-9-acetamide, 1,2,3,4-tetrahydro-7-methoxy-2,2-dimethyl-N-(2-methylpropyl)-N-propyl-; 9H-Carbazole-9-butanamide, N-(9,10-dihydro-9,10-dioxo-1-anthracenyl)-1,2,3,4-tetrahydro-; 9H-Carbazole-9-acetamide, 1,2,3,4-tetrahydro-7-methoxy-2,2-dimethyl-N,N-dipropyl-; 3,5-Pyridinedicarboxylic acid, 1,4-dihydro-2,6-dimethyl-4-[2-(trifluoromethyl)phenyl]-, 2-[[3-[3-[[(4-fluorophenyl)sulfonyl]amino]-1,2,3,4-tetrahydro-9H-carbazol-9-yl]-1-oxopropyl]amino]ethyl 1-methylethylester; 1H-Carbazole-8-carboxylic acid, 2,3,4,9-tetrahydro-9-[2-[(2-hydroxyethyl)amino]-2-oxoethyl]-; 9H-Carbazole-9-acetamide, N-(cyclopropylmethyl)-1,2,3,4-tetrahydro-7-methoxy-2,2-dimethyl-N-propyl-; 3,5-Pyridinedicarboxylic acid, 1,4-dihydro-2,6-dimethyl-4-(3-nitrophenyl)-, 2-[[3-[3-[[(4-fluorophenyl)sulfonyl]amino]-1,2,3,4-tetrahydro-9H-carbazol-9-yl]-1-oxopropyl]amino]ethyl 1-methylethyl ester; 1H-Carbazole-8-carboxylic acid, 9-[2-(diethylamino)-2-oxoethyl]-2,3,4,9-tetrahydro-; 9H-Carbazole-9-acetamide, N,N-dibutyl-1,2,3,4-tetrahydro-7-methoxy-2,2-dimethyl-; 9H-Carbazole-9-acetamide, 5,6,7,8-tetrahydro-4-methoxy-N,N-dipropyl-; 9H-Carbazole-9-acetamide, N-(3,3-dimethylbutyl)-5,6,7,8-tetrahydro-2-methoxy-5-oxo-N-propyl-; 9H-Carbazole-9-acetamide, N-(2,2-dimethylpropyl)-N-ethyl-5,6,7,8-tetrahydro-2-methoxy-; 9H-Carbazole-9-propanamide, 3-[[(4-chlorophenyl)sulfonyl]amino]-6-fluoro-1,2,3,4-tetrahydro-N,N-dimethyl-; 9H-Carbazole-9-acetamide, N-(3,3-dimethylbutyl)-N-ethyl-5,6,7,8-tetrahydro-2-methoxy-5-oxo-; 9H-Carbazole-9-acetamide, N-(3,3-dimethylbutyl)-N-ethyl-5,6,7,8-tetrahydro-2-methoxy-; Benzamide, N-[1-methyl-3-(1,2,3,4-tetrahydro-9H-carbazol-9-yl)propyl]-3,5-dinitro-; 9H-Carbazole-9-acetamide, N-ethyl-5,6,7,8-tetrahydro-2-methoxy-N-(3-methylbutyl)-5-oxo-; 9H-Carbazole-9-acetamide, N-butyl-N-ethyl-5,6,7,8-tetrahydro-2-methoxy-; 9H-Carbazole-9-acetamide, 1,2,3,4-tetrahydro-1-hydroxy-; 9H-Carbazole-9-acetamide, N-ethyl-5,6,7,8-tetrahydro-2-methoxy-N-(2-methylpropyl)-5-oxo-; 9H-Carbazole-9-acetamide, N-(cyclopropylmethyl)-5,6,7,8-tetrahydro-2-methoxy-N-propyl-; Acetamide, N-[3-(1,2,3,4-tetrahydro-1-oxo-9H-carbazol-9-yl)propyl]-; 9H-Carbazole-9-acetamide, N-cyclohexyl-N-ethyl-5,6,7,8-tetrahydro-2-methoxy-5-oxo-; 9H-Carbazole-9-acetamide, N-ethyl-5,6,7,8-tetrahydro-2-methoxy-N-(3-methylbutyl)-; Carbamic acid, [(1S)-2-(6-chloro-1,2,3,4-tetrahydro-9H-carbazol-9-yl)-1-methylethyl]-, 1,1-dimethylethyl ester; 9H-Carbazole-9-acetamide, 5,6,7,8-tetrahydro-2-methoxy-N,N-bis(2-methylpropyl)-5-oxo-; 3,5-Pyridinedicarboxylic acid, 4-(2-chlorophenyl)-2-[[2-[[3-[3-[[(4-fluorophenyl)sulfonyl]amino]-1,2,3,4-tetrahydro-9H-carbazol-9-yl]-1-oxopropyl]amino]ethoxy]methyl]-1,4-dihydro-6-methyl-, 3-ethyl5-(1-methylethyl) ester; 9H-Carbazole-9-acetamide, 5,6,7,8-tetrahydro-2-methoxy-N,N-dipropyl-; Benzamide, 3,5-dinitro-N-[3-(1,2,3,4-tetrahydro-9H-carbazol-9-yl)propyl]-; Carbamic acid, [(1S)-2-(7-chloro-1,2,3,4-tetrahydro-9H-carbazol-9-yl)-1-methylethyl]-, 1,1-dimethylethyl ester; 9H-Carbazole-9-acetamide, N-(3,3-dimethylbutyl)-1,2,3,4-tetrahydro-7-methoxy-2,2-dimethyl-N-propyl-; 3,5-Pyridinedicarboxylic acid, 2-[[2-[[3-[3-[[(4-fluorophenyl)sulfonyl]amino]-1,2,3,4-tetrahydro-9H-carbazol-9-yl]-1-oxopropyl]amino]ethoxy]methyl]-1,4-dihydro-6-methyl-4-[2-(phenylmethoxy)phenyl]-, 3-ethyl 5-methyl ester; 9H-Carbazole-9-acetamide, N-(4-ethoxyphenyl)-1,2,3,4-tetrahydro-; 9H-Carbazole-9-acetamide, 1,2,3,4-tetrahydro-6-methyl-1-oxo-; 9H-Carbazole-9-acetamide, N-(3,3-dimethylbutyl)-N-ethyl-1,2,3,4-tetrahydro-7-methoxy-2,2-dimethyl-; 9H-Carbazole-9-propanamide, 3-[[(4-fluorophenyl)sulfonyl]amino]-1,2,3,4-tetrahydro-N-(2-hydroxyethyl)-, (R)-; Glycine, N-[(1,2,3,4-tetrahydro-3-methyl-9H-carbazol-9-yl)acetyl]-, ethyl ester; 9H-Carbazole-9-acetamide, N-ethyl-1,2,3,4-tetrahydro-7-methoxy-2,2-dimethyl-N-(3-methylbutyl)-; 3,5-Pyridinedicarboxylic acid, 4-(2-chlorophenyl)-1,4-dihydro-2,6-dimethyl-, 2-[[3-[3-[[(4-fluorophenyl)sulfonyl]amino]-1,2,3,4-tetrahydro-9H-carbazol-9-yl]-1-oxopropyl]amino]ethyl methyl ester; 9H-Carbazole-9-butanamide, N-(2-benzoyl-4-chlorophenyl)-1,2,3,4-tetrahydro-; 9H-Carbazole-9-acetamide, N-ethyl-1,2,3,4-tetrahydro-7-methoxy-2,2-dimethyl-N-(2-methylpropyl)-; 3,5-Pyridinedicarboxylic acid, 1,4-dihydro-2,6-dimethyl-4-(3-nitrophenyl)-, 2-[[3-[3-[[(4-fluorophenyl)sulfonyl]amino]-1,2,3,4-tetrahydro-9H-carbazol-9-yl]-1-oxopropyl]amino]ethyl methyl ester; 9H-Carbazole-9-butanamide, N-(9,10-dihydro-9,10-dioxo-2-anthracenyl)-1,2,3,4-tetrahydro-; 9H-Carbazole-9-acetamide, N-cyclohexyl-N-ethyl-1,2,3,4-tetrahydro-7-methoxy-2,2-dimethyl-; 3,5-Pyridinedicarboxylic acid, 4-(3-chlorophenyl)-1,4-dihydro-2,6-dimethyl-, 2-[[3-[3-[[(4-fluorophenyl)sulfonyl]amino]-1,2,3,4-tetrahydro-9H-carbazol-9-yl]-1-oxopropyl]amino]ethyl 1-methylethyl ester; 1H-Carbazole-8-carboxylic acid, 9-(2-amino-2-oxoethyl)-2,3,4,9-tetrahydro-; 9H-Carbazole-9-propanamide, 1,2,3,4-tetrahydro-6-methyl-1-oxo-; 9H-Carbazole-9-acetamide, 1,2,3,4-tetrahydro-7-methoxy-2,2-dimethyl-N,N-bis(2-methylpropyl)-; 9H-Carbazole-9-propanamide, 3-[[(4-fluorophenyl)sulfonyl]amino]-1,2,3,4-tetrahydro-; 1H-Carbazole-8-carboxylic acid, 9-[2-(dimethylamino)-2-oxoethyl]-2,3,4,9-tetrahydro-; 9H-Carbazole-9-acetamide, N-ethyl-5,6,7,8-tetrahydro-4-methoxy-N-(3-methylbutyl)-; 9H-Carbazole-9-propanamide, 3-[[(4-fluorophenyl)sulfonyl]amino]-1,2,3,4-tetrahydro-N-(methylsulfonyl)-, (R)-; 9H-Carbazole-9-acetamide, N,N-dibutyl-5,6,7,8-tetrahydro-4-methoxy-; 9H-Carbazole-9-propanamide, 3-[[(4-chlorophenyl)sulfonyl]amino]-6-fluoro-1,2,3,4-tetrahydro-; 9H-Carbazole-9-acetamide, N-ethyl-5,6,7,8-tetrahydro-2-methoxy-5-oxo-N-2-thiazolyl-; 9H-Carbazole-9-acetamide, N-ethyl-5,6,7,8-tetrahydro-2-methoxy-N-2-thiazolyl-; 9H-Carbazole-9-propanamide, 1,2,3,4-tetrahydro-1-oxo-; 9H-Carbazole-9-acetamide, 5,6,7,8-tetrahydro-2-methoxy-N,N-bis(3-methylbutyl)-5-oxo-; 9H-Carbazole-9-acetamide, N-butyl-5,6,7,8-tetrahydro-2-methoxy-N-propyl-; 9H-Carbazole-9-acetamide, 5,6,7,8-tetrahydro-2-methoxy-N-(2-methylpropyl)-5-oxo-N-propyl-; 9H-Carbazole-9-acetamide, N-cyclohexyl-N-ethyl-5,6,7,8-tetrahydro-2-methoxy-; 9H-Carbazole-9-acetamide, 1,2,3,4-tetrahydro-1-oxo-; 9H-Carbazole-9-acetamide, 5,6,7,8-tetrahydro-2-methoxy-5-oxo-N,N-dipropyl-; 9H-Carbazole-9-acetamide, 5,6,7,8-tetrahydro-2-methoxy-N,N-bis(2-methylpropyl)-; Acetamide, N-[2-(1,2,3,4-tetrahydro-1-oxo-9H-carbazol-9-yl)ethyl]-; 9H-Carbazole-9-acetamide, N-(cyclopropylmethyl)-5,6,7,8-tetrahydro-2-methoxy-5-oxo-N-propyl-; 3,5-Pyridinedicarboxylic acid, 4-(2,1,3-benzoxadiazol-4-yl)-2-[[2-[[3-[3-[[(4-fluorophenyl)sulfonyl]amino]-1,2,3,4-tetrahydro-9H-carbazol-9-yl]-1-oxopropyl]amino]ethoxy]methyl]-1,4-dihydro-6-methyl-, 3-ethyl5-(1-methylethyl) ester; 9H-Carbazole-9-acetamide, 5,6,7,8-tetrahydro-2-methoxy-N,N-bis(3-methylbutyl)-; Carbamic acid, [(1S)-2-(7-bromo-1,2,3,4-tetrahydro-9H-carbazol-9-yl)-1-methylethyl]-, 1,1-dimethylethyl ester; 9H-Carbazole-9-acetamide, N,N-dibutyl-5,6,7,8-tetrahydro-2-methoxy-5-oxo-; 3,5-Pyridinedicarboxylic acid, 2-[[2-[[3-[3-[[(4-fluorophenyl)sulfonyl]amino]-1,2,3,4-tetrahydro-9H-carbazol-9-yl]-1-oxopropyl]amino]ethoxy]methyl]-1,4-dihydro-6-methyl-4-(3-nitrophenyl)-, 3-ethyl 5-methyl ester; 9H-Carbazole-9-acetamide, N,N-dibutyl-5,6,7,8-tetrahydro-2-methoxy-; Carbazole-9-acetanilide, 1,2,3,4-tetrahydro-6-methyl-1-oxo-; and 3,5-Pyridinedicarboxylic acid, 4-(3-chlorophenyl)-1,4-dihydro-2,6-dimethyl-, 2-[[3-[3-[[(4-fluorophenyl)sulfonyl]amino]-1,2,3,4-tetrahydro-9H-carbazol-9-yl]-1-oxopropyl]amino]ethyl methyl ester.

TABLE 1

| Compound No. | Compound Name |
|---|---|
| 1x | 2H-Pyrido[4,3-b]indole-2-carboxylic acid, 5-[2-(dimethylamino)-2-oxoethyl]-1,3,4,5-tetrahydro-8-[(4-methyl-1-piperidinyl)carbonyl]-, 1,1-dimethylethyl ester |
| 2x | 5H-Pyrido[4,3-b]indole-5-acetamide, 1,2,3,4-tetrahydro-N,N-dimethyl-8-[(4-methyl-1-piperidinyl)carbonyl]- |
| 3x | 5H-Pyrido[4,3-b]indole-5-acetamide, 2-cyclobutyl-1,2,3,4-tetrahydro-N,N-dimethyl-8-[(4-methyl-1-piperidinyl)carbonyl]- |
| 4x | 5H-Pyrido[4,3-b]indole-5-acetamide, 2-cyclohexyl-1,2,3,4-tetrahydro-N,N-dimethyl-8-[(4-methyl-1-piperidinyl)carbonyl]- |
| 5x | 5H-Pyrido[4,3-b]indole-5-acetamide, 2-cyclopentyl-1,2,3,4-tetrahydro-N,N-dimethyl-8-[(4-methyl-1-piperidinyl)carbonyl]- |
| 6x | 5H-Pyrido[4,3-b]indole-5-acetamide, 8-formyl-1,2,3,4-tetrahydro-2-(1-methylethyl)- |
| 7x | 1H-Pyrido[4,3-b]indole-2,5-dipropanoic acid, 3,4-dihydro-8-methyl-, 2,5-diethyl ester |
| 8x | 1H-Pyrido[4,3-b]indole-2-butanoic acid, 5-(2-ethoxy-2-oxoethyl)-8-fluoro-3,4-dihydro-, ethyl ester |
| 9x | 1H-Pyrido[4,3-b]indole-2-propanoic acid, 5-(2-ethoxy-2-oxoethyl)-8-fluoro-3,4-dihydro-, ethyl ester |
| 10x | 2H-Pyrido[4,3-b]indole-2-butanoic acid, 5-(3-ethoxy-3-oxopropyl)-1,3,4,5-tetrahydro-8-methyl-, ethyl ester |
| 11x | 5H-Pyrido[4,3-b]indole-5-acetamide, 1,2,3,4-tetrahydro-2-(1-methylethyl)- |
| 12x | 5H-Pyrido[4,3-b]indole-5-acetamide, 1,2,3,4-tetrahydro-2,8-bis(1-methylethyl)- |
| 13x | 5H-Pyrido[4,3-b]indole-5-acetamide, 1,2,3,4-tetrahydro-8-methyl-2-(1-methylethyl)- |
| 14x | 5H-Pyrido[4,3-b]indole-5-acetamide, N-cyclohexyl-1,2,3,4-tetrahydro-2-(1-methylethyl)- |
| 15x | 5H-Pyrido[4,3-b]indole-5-acetamide, N-cyclopentyl-1,2,3,4-tetrahydro-2-(1-methylethyl)- |
| 16x | 5H-Pyrido[4,3-b]indole-5-acetic acid, 1,2,3,4-tetrahydro-, ethyl ester |
| 17x | 5H-Pyrido[4,3-b]indole-5-acetic acid, 1,2,3,4-tetrahydro-2-(1-naphthalenylcarbonyl)-, ethyl ester |
| 18x | 5H-Pyrido[4,3-b]indole-5-acetic acid, 1,2,3,4-tetrahydro-2-(2-phenylethyl)-, ethyl ester |
| 19x | 5H-Pyrido[4,3-b]indole-5-acetic acid, 1,2,3,4-tetrahydro-2-(4-pyridinylmethyl)-, ethyl ester |
| 20x | 5H-Pyrido[4,3-b]indole-5-acetic acid, 1,2,3,4-tetrahydro-2,8-dimethyl-, ethyl ester |

TABLE 1-continued

| Compound No. | Compound Name |
|---|---|
| 21x | 5H-Pyrido[4,3-b]indole-5-acetic acid, 1,2,3,4-tetrahydro-2-[(phenylamino)carbonyl]-, ethyl ester |
| 22x | 5H-Pyrido[4,3-b]indole-5-acetic acid, 1,2,3,4-tetrahydro-2-[(phenylmethoxy)carbonyl]-, ethyl ester |
| 23x | 5H-Pyrido[4,3-b]indole-5-acetic acid, 1,2,3,4-tetrahydro-2-[2-(3-pyridinyl)ethyl]-, ethyl ester |
| 24x | 5H-Pyrido[4,3-b]indole-5-acetic acid, 1,2,3,4-tetrahydro-2-methyl-, ethyl ester |
| 25x | 5H-Pyrido[4,3-b]indole-5-acetic acid, 1,2,3,4-tetrahydro-2-methyl-6-(trifluoromethyl)-, ethyl ester |
| 26x | 5H-Pyrido[4,3-b]indole-5-acetic acid, 1,2,3,4-tetrahydro-2-methyl-8-(trifluoromethyl)-, ethyl ester |
| 27x | 5H-Pyrido[4,3-b]indole-5-acetic acid, 1,2,3,4-tetrahydro-6-(trifluoromethyl)-, ethyl ester |
| 28x | 5H-Pyrido[4,3-b]indole-5-acetic acid, 1,2,3,4-tetrahydro-7-methyl-, ethyl ester |
| 29x | 5H-Pyrido[4,3-b]indole-5-acetic acid, 1,2,3,4-tetrahydro-8-(trifluoromethyl)-, ethyl ester |
| 30x | 5H-Pyrido[4,3-b]indole-5-acetic acid, 1,2,3,4-tetrahydro-8-[(4-methyl-1-piperidinyl)carbonyl]-, ethyl ester |
| 31x | 5H-Pyrido[4,3-b]indole-5-acetic acid, 1,2,3,4-tetrahydro-8-methyl-, ethyl ester |
| 32x | 5H-Pyrido[4,3-b]indole-5-acetic acid, 1,2,3,4-tetrahydro-8-methyl-2-(4-pyridinylmethyl)-, ethyl ester |
| 33x | 5H-Pyrido[4,3-b]indole-5-acetic acid, 1,2,3,4-tetrahydro-8-methyl-2-[2-(3-pyridinyl)ethyl]-, ethyl ester |
| 34x | 5H-Pyrido[4,3-b]indole-5-acetic acid, 2-(2-cyclohexyl-2-phenylacetyl)-1,2,3,4-tetrahydro-, ethyl ester |
| 35x | 5H-Pyrido[4,3-b]indole-5-acetic acid, 2-(ethoxycarbonyl)-1,2,3,4-tetrahydro-, methyl ester |
| 36x | 5H-Pyrido[4,3-b]indole-5-acetic acid, 2-[(1,1-dimethylethoxy)carbonyl]-1,2,3,4-tetrahydro-, ethyl ester |
| 37x | 5H-Pyrido[4,3-b]indole-5-acetic acid, 2-[(1,1-dimethylethoxy)carbonyl]-1,2,3,4-tetrahydro-, methyl ester |
| 38x | 5H-Pyrido[4,3-b]indole-5-acetic acid, 2-[(1,1-dimethylethoxy)carbonyl]-1,2,3,4-tetrahydro-6-(trifluoromethyl)-, ethyl ester |
| 39x | 5H-Pyrido[4,3-b]indole-5-acetic acid, 2-[(1,1-dimethylethoxy)carbonyl]-1,2,3,4-tetrahydro-8-(trifluoromethyl)-, ethyl ester |
| 40x | 5H-Pyrido[4,3-b]indole-5-acetic acid, 2-[(1,1-dimethylethoxy)carbonyl]-1,2,3,4-tetrahydro-8-[(4-methyl-1-piperidinyl)carbonyl]-, ethyl ester |
| 41x | 5H-Pyrido[4,3-b]indole-5-acetic acid, 2-[(1,1-dimethylethoxy)carbonyl]-1,2,3,4-tetrahydro-8-methyl-, ethyl ester |
| 42x | 5H-Pyrido[4,3-b]indole-5-acetic acid, 2-[(1,1-dimethylethoxy)carbonyl]-6-fluoro-1,2,3,4-tetrahydro-, ethyl ester |
| 43x | 5H-Pyrido[4,3-b]indole-5-acetic acid, 2-[(1,1-dimethylethoxy)carbonyl]-8-fluoro-1,2,3,4-tetrahydro-, ethyl ester |
| 44x | 5H-Pyrido[4,3-b]indole-5-acetic acid, 2-[(2-ethoxy-1-naphthalenyl)carbonyl]-1,2,3,4-tetrahydro-, ethyl ester |
| 45x | 5H-Pyrido[4,3-b]indole-5-acetic acid, 2-benzoyl-1,2,3,4-tetrahydro-8-methoxy-, ethyl ester |
| 46x | 5H-Pyrido[4,3-b]indole-5-acetic acid, 2-cyclobutyl-1,2,3,4-tetrahydro-8-[(4-methyl-1-piperidinyl)carbonyl]-, methyl ester |
| 47x | 5H-Pyrido[4,3-b]indole-5-acetic acid, 2-cyclohexyl-1,2,3,4-tetrahydro-8-[(4-methyl-1-piperidinyl)carbonyl]-, methyl ester |
| 48x | 5H-Pyrido[4,3-b]indole-5-acetic acid, 2-cyclopentyl-1,2,3,4-tetrahydro-8-[(4-methyl-1-piperidinyl)carbonyl]-, methyl ester |
| 49x | 5H-Pyrido[4,3-b]indole-5-acetic acid, 6-chloro-1,2,3,4-tetrahydro-, ethyl ester |
| 50x | 5H-Pyrido[4,3-b]indole-5-acetic acid, 6-fluoro-1,2,3,4-tetrahydro-, ethyl ester |
| 51x | 5H-Pyrido[4,3-b]indole-5-acetic acid, 6-fluoro-1,2,3,4-tetrahydro-2-methyl-, ethyl ester |
| 52x | 5H-Pyrido[4,3-b]indole-5-acetic acid, 7-chloro-1,2,3,4-tetrahydro-, ethyl ester |
| 53x | 5H-Pyrido[4,3-b]indole-5-acetic acid, 8-bromo-1,2,3,4-tetrahydro-, ethyl ester |
| 54x | 5H-Pyrido[4,3-b]indole-5-acetic acid, 8-chloro-1,2,3,4-tetrahydro-, ethyl ester |
| 55x | 5H-Pyrido[4,3-b]indole-5-acetic acid, 8-fluoro-1,2,3,4-tetrahydro-, ethyl ester |
| 56x | 5H-Pyrido[4,3-b]indole-5-acetic acid, 8-fluoro-1,2,3,4-tetrahydro-2-(2-phenylethyl)-, ethyl ester |
| 57x | 5H-Pyrido[4,3-b]indole-5-acetic acid, 8-fluoro-1,2,3,4-tetrahydro-2-(3-pyridinylmethyl)-, ethyl ester |
| 58x | 5H-Pyrido[4,3-b]indole-5-acetic acid, 8-fluoro-1,2,3,4-tetrahydro-2-(4-pyridinylmethyl)-, ethyl ester |
| 59x | 5H-Pyrido[4,3-b]indole-5-acetic acid, 8-fluoro-1,2,3,4-tetrahydro-2-(phenylmethyl)-, ethyl ester |
| 60x | 5H-Pyrido[4,3-b]indole-5-acetic acid, 8-fluoro-1,2,3,4-tetrahydro-2-[2-(3-pyridinyl)ethyl]-, ethyl ester |
| 61x | 5H-Pyrido[4,3-b]indole-5-acetic acid, 8-fluoro-1,2,3,4-tetrahydro-2-[2-(4-pyridinyl)ethyl]-, ethyl ester |
| 62x | 5H-Pyrido[4,3-b]indole-5-acetic acid, 8-fluoro-1,2,3,4-tetrahydro-2-methyl-, ethyl ester |

TABLE 1-continued

| Compound No. | Compound Name |
|---|---|
| 63x | 5H-Pyrido[4,3-b]indole-5-propanamide, 1,2,3,4-tetrahydro-2-methyl- |
| 64x | 5H-Pyrido[4,3-b]indole-5-propanoic acid, 1,2,3,4-tetrahydro-, ethyl ester |
| 65x | 5H-Pyrido[4,3-b]indole-5-propanoic acid, 1,2,3,4-tetrahydro-1,1,3,3-tetramethyl-, 2-(diethylamino)ethyl ester |
| 66x | 5H-Pyrido[4,3-b]indole-5-propanoic acid, 1,2,3,4-tetrahydro-1,1,3,3-tetramethyl-, 2-(dimethylamino)ethyl ester |
| 67x | 5H-Pyrido[4,3-b]indole-5-propanoic acid, 1,2,3,4-tetrahydro-1,1,3,3-tetramethyl-, ethyl ester |
| 68x | 5H-Pyrido[4,3-b]indole-5-propanoic acid, 1,2,3,4-tetrahydro-2-(2-phenylethyl)-6-(trifluoromethyl)-, ethyl ester |
| 69x | 5H-Pyrido[4,3-b]indole-5-propanoic acid, 1,2,3,4-tetrahydro-2-(3-pyridinylmethyl)-, ethyl ester |
| 70x | 5H-Pyrido[4,3-b]indole-5-propanoic acid, 1,2,3,4-tetrahydro-2-(4-pyridinylmethyl)-8-(trifluoromethyl)-, ethyl ester |
| 71x | 5H-Pyrido[4,3-b]indole-5-propanoic acid, 1,2,3,4-tetrahydro-2-(phenylmethyl)-6-(trifluoromethyl)-, ethyl ester |
| 72x | 5H-Pyrido[4,3-b]indole-5-propanoic acid, 1,2,3,4-tetrahydro-2-(phenylsulfonyl)-, ethyl ester |
| 73x | 5H-Pyrido[4,3-b]indole-5-propanoic acid, 1,2,3,4-tetrahydro-2,8-dimethyl-, ethyl ester |
| 74x | 5H-Pyrido[4,3-b]indole-5-propanoic acid, 1,2,3,4-tetrahydro-2-[2-(3-pyridinyl)ethyl]-, ethyl ester |
| 75x | 5H-Pyrido[4,3-b]indole-5-propanoic acid, 1,2,3,4-tetrahydro-2-[2-(3-pyridinyl)ethyl]-8-(trifluoromethyl)-, ethyl ester |
| 76x | 5H-Pyrido[4,3-b]indole-5-propanoic acid, 1,2,3,4-tetrahydro-2-methyl-, ethyl ester |
| 77x | 5H-Pyrido[4,3-b]indole-5-propanoic acid, 1,2,3,4-tetrahydro-2-methyl-6-(trifluoromethyl)-, ethyl ester |
| 78x | 5H-Pyrido[4,3-b]indole-5-propanoic acid, 1,2,3,4-tetrahydro-2-methyl-8-(trifluoromethyl)-, ethyl ester |
| 79x | 5H-Pyrido[4,3-b]indole-5-propanoic acid, 1,2,3,4-tetrahydro-6-(trifluoromethyl)-, ethyl ester |
| 80x | 5H-Pyrido[4,3-b]indole-5-propanoic acid, 1,2,3,4-tetrahydro-8-(trifluoromethyl)-, ethyl ester |
| 81x | 5H-Pyrido[4,3-b]indole-5-propanoic acid, 1,2,3,4-tetrahydro-8-methyl-, ethyl ester |
| 82x | 5H-Pyrido[4,3-b]indole-5-propanoic acid, 1,2,3,4-tetrahydro-8-methyl-2-(phenylsulfonyl)-, ethyl ester |
| 83x | 5H-Pyrido[4,3-b]indole-5-propanoic acid, 2-(ethoxycarbonyl)-1,2,3,4-tetrahydro-6-(trifluoromethyl)-, ethyl ester |
| 84x | 5H-Pyrido[4,3-b]indole-5-propanoic acid, 2-(ethoxycarbonyl)-1,2,3,4-tetrahydro-8-(trifluoromethyl)-, ethyl ester |
| 85x | 5H-Pyrido[4,3-b]indole-5-propanoic acid, 2-(ethoxycarbonyl)-6-fluoro-1,2,3,4-tetrahydro-, ethyl ester |
| 86x | 5H-Pyrido[4,3-b]indole-5-propanoic acid, 2-[(1,1-dimethylethoxy)carbonyl]-1,2,3,4-tetrahydro-, ethyl ester |
| 87x | 5H-Pyrido[4,3-b]indole-5-propanoic acid, 2-[(1,1-dimethylethoxy)carbonyl]-1,2,3,4-tetrahydro-8-methyl-, ethyl ester |
| 88x | 5H-Pyrido[4,3-b]indole-5-propanoic acid, 2-[(1,1-dimethylethoxy)carbonyl]-8-fluoro-1,2,3,4-tetrahydro-, ethyl ester |
| 89x | 5H-Pyrido[4,3-b]indole-5-propanoic acid, 2-[(3,4-dimethylphenyl)methyl]-8-fluoro-1,2,3,4-tetrahydro-, ethyl ester |
| 90x | 5H-Pyrido[4,3-b]indole-5-propanoic acid, 2-[(4-chlorophenyl)methyl]-8-fluoro-1,2,3,4-tetrahydro-, ethyl ester |
| 91x | 5H-Pyrido[4,3-b]indole-5-propanoic acid, 2-[(4-fluorophenyl)sulfonyl]-1,2,3,4-tetrahydro-, ethyl ester |
| 92x | 5H-Pyrido[4,3-b]indole-5-propanoic acid, 2-[(4-fluorophenyl)sulfonyl]-1,2,3,4-tetrahydro-8-methyl-, ethyl ester |
| 93x | 5H-Pyrido[4,3-b]indole-5-propanoic acid, 6-fluoro-1,2,3,4-tetrahydro-, ethyl ester |
| 94x | 5H-Pyrido[4,3-b]indole-5-propanoic acid, 6-fluoro-1,2,3,4-tetrahydro-2-[2-(4-pyridinyl)ethyl]-, ethyl ester |
| 95x | 5H-Pyrido[4,3-b]indole-5-propanoic acid, 6-fluoro-1,2,3,4-tetrahydro-2-methyl-, ethyl ester |
| 96x | 5H-Pyrido[4,3-b]indole-5-propanoic acid, 8-(ethoxycarbonyl)-1,2,3,4-tetrahydro-1,1,3,3-tetramethyl-, ethyl ester |
| 97x | 5H-Pyrido[4,3-b]indole-5-propanoic acid, 8-fluoro-1,2,3,4-tetrahydro-, ethyl ester |
| 98x | 5H-Pyrido[4,3-b]indole-5-propanoic acid, 8-fluoro-1,2,3,4-tetrahydro-2-(2-thienylmethyl)-, ethyl ester |
| 99x | 5H-Pyrido[4,3-b]indole-5-propanoic acid, 8-fluoro-1,2,3,4-tetrahydro-2-(3-pyridinylmethyl)-, ethyl ester |
| 100x | 5H-Pyrido[4,3-b]indole-5-propanoic acid, 8-fluoro-1,2,3,4-tetrahydro-2-(4-pyridinylmethyl)-, ethyl ester |
| 101x | 5H-Pyrido[4,3-b]indole-5-propanoic acid, 8-fluoro-1,2,3,4-tetrahydro-2-(phenylmethyl)-, ethyl ester |

TABLE 1-continued

| Compound No. | Compound Name |
|---|---|
| 102x | 5H-Pyrido[4,3-b]indole-5-propanoic acid, 8-fluoro-1,2,3,4-tetrahydro-2-(phenylsulfonyl)-, ethyl ester |
| 103x | 5H-Pyrido[4,3-b]indole-5-propanoic acid, 8-fluoro-1,2,3,4-tetrahydro-2-[2-(3-pyridinyl)ethyl]-, ethyl ester |
| 104x | 5H-Pyrido[4,3-b]indole-5-propanoic acid, 8-fluoro-1,2,3,4-tetrahydro-2-methyl-, ethyl ester |
| 105x | 5H-Pyrido[4,3-b]indole-5-propanoic acid, 8-fluoro-2-(2-furanylmethyl)-1,2,3,4-tetrahydro-, ethyl ester |
| 106x | 5H-Pyrido[4,3-b]indole-5-propanoic acid, 8-fluoro-2-[(4-fluorophenyl)sulfonyl]-1,2,3,4-tetrahydro-, ethyl ester |
| 107x | 5H-Pyrrolo[2,3-c:4,5-c']dipyridine-5-acetamide, 1,2,3,4-tetrahydro-2-(1-methylethyl)- |
| 108x | 5H-Pyrrolo[2,3-c:4,5-c']dipyridine-5-acetamide, N-cyclohexyl-1,2,3,4-tetrahydro-2-(1-methylethyl)- |
| 109x | 5H-Pyrrolo[3,2-c:4,5-c']dipyridine-5-acetamide, 1,2,3,4-tetrahydro-2-(1-methylethyl)- |
| 110x | 5H-Pyrrolo[3,2-c:4,5-c']dipyridine-5-acetamide, N-cyclohexyl-1,2,3,4-tetrahydro-2-(1-methylethyl)- |

The listing under proviso (1) above is also referred to herein as "proviso 1." The listing under proviso (2) above is also referred to herein as "proviso 2."

In one variation, the compound is of the formula (I) wherein the compound further is a type 1 compound. In another variation, the compound is of the formula (I) wherein the compound further is a type 2 compound. In yet another variation, the compound is of the formula (I) wherein the compound further is a type 3 compound. In a further variation, the compound is of the formula (I) wherein the compound further is a type 4 compound.

Other compounds are also detailed herein, including but not limited to compounds of the Formula (E):

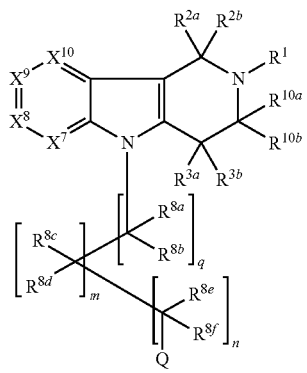

(E)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano hydroxyl, alkoxy, nitro or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

m and q are independently 0 or 1;

n is 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, substituted or unsubstituted alkyl or is taken together with the carbon to which it is attached and a geminal $R^{8(a-f)}$ to form a cycloalkyl moiety;

each $R^{10a}$ and $R^{10b}$ is independently H, substituted or unsubstituted $C_1$-$C_8$ alkyl, halo, hydroxyl, alkoxyl or $R^{10a}$ and $R^{10b}$ are taken together with the carbon to which they are attached to form a cycloalkyl moiety or a carbonyl moiety; and Q is acyclic or cyclic acylamino, carbonylalkoxy, acyloxy, aminoacyl, aminocarbonylalkoxy, substituted or unsubstituted lactam or substituted or unsubstituted cycloalkyl;

provided that: (ia) Q is substituted or unsubstituted cycloalkyl or a lactam moiety when each of m, n and q is 0 and (ib) m, n and q are 0 when Q is a substituted or unsubstituted cycloalkyl or a lactam moiety, (ii) Q is cyclic acylamino only when each of m, n and q is 1, (iii) when Q is carbonylalkoxy, each $R^{8a}$, $R^{8b}$, $R^{8c}$, $R^{8d}$, $R^{8e}$ and $R^{8f}$ is other than cycloalkyl and substituted alkyl; (iv) the compound is other than a compound in Table 1, and (v) the compound is other than 5-cyclohexyl-2,3,4,5-tetrahydro-2-methyl-1H-pyrido[4,3-b]indole and 5-cyclopentyl-2,3,4,5-tetrahydro-2-[(4-methyl-1H-imidazol-5-yl)methyl]-1H-pyrido[4,3-b]indol-1-one;

or a salt thereof.

Compounds of the formula (Vc) are also detailed herein:

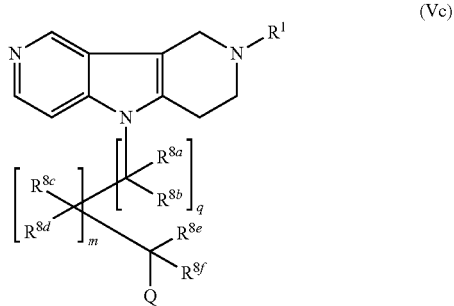

(Vc)

wherein: $R^1$ is methyl; m and q are independently 0 or 1; each $R^{8a}$, $R^{8b}$, $R^{8c}$, $R^{8d}$, $R^{8e}$ and $R^{8f}$ is independently H, hydroxyl, substituted or unsubstituted alkyl or is taken together with the carbon to which it is attached and a geminal $R^{8(a-f)}$ to form a cycloalkyl moiety; and Q is acyclic or cyclic acylamino, carbonylalkoxy, acyloxy, aminoacyl or aminocarbonylalkoxy, or a salt thereof.

Compounds of the formula (Vf) are also detailed herein:

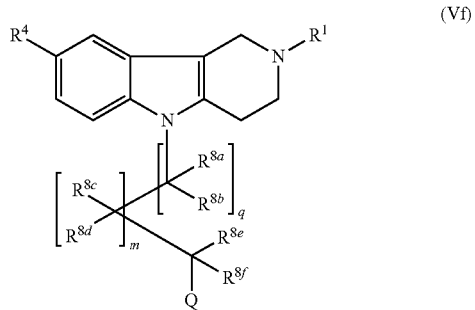

(Vf)

wherein: $R^1$ is methyl; $R^4$ is chloro or methyl; m and q are independently 0 or 1; each $R^{8a}$, $R^{8b}$, $R^{8c}$, $R^{8d}$, $R^{8e}$ and $R^{8f}$ is independently H, hydroxyl, substituted or unsubstituted alkyl or is taken together with the carbon to which it is attached and a geminal $R^{8(a-f)}$ to form a cycloalkyl moiety; and Q is acyclic or cyclic acylamino, carbonylalkoxy, acyloxy, aminoacyl or aminocarbonylalkoxy; provided that when $R^4$ is methyl, Q is acyclic or cyclic acylamino, acyloxy, aminoacyl or aminocarbonylalkoxy, or a salt thereof.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, Huntington's disease, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least two of the following receptors are modulated: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least three of the following receptors are modulated: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, each of the following receptors is modulated: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least one of the following receptors is modulated: α1D, α2A, α2B, 5-HT2A, 5-HT2C, 5-HT6,5-HT7, D2L, H1, H2 and H3. In another variation, at least two or three or four or five or six or seven or eight or nine or ten or eleven of the following receptors are modulated: α1D, α2A, α2B, 5-HT2A, 5-HT2C, 5-HT6, 5-HT7, D2L, H1, H2 and H3. In a particular variation, at least dopamine receptor D2L is modulated. In another particular variation, at least dopamine receptor D2L and serotonin receptor 5-HT2A are modulated. In a further particular variation, at least adrenergic receptors α1D, α2A, α2B and serotonin receptor 5-HT6 are modulated. In another particular variation, at least adrenergic receptors α1D, α2A, α2B, serotonin receptor 5-HT6 and one or more of serotonin receptor 5-HT7, 5-HT2A, 5-HT2C and histamine receptor H1 and H2 are modulated. In a further particular variation, histamine receptor H1 is modulated. In another variation, compounds of the invention exhibit any receptor modulation activity detailed herein and further stimulate neurite outgrowth and/or neurogenesis and/or enhance neurotrophic effects.

The invention is also directed to pharmaceutical compositions comprising a compound of the invention and a pharmaceutically acceptable carrier or excipient. Kits comprising a compound of the invention and instructions for use are also embraced by this invention.

DETAILED DESCRIPTION OF THE INVENTION

Definitions

For use herein, unless clearly indicated otherwise, use of the terms "a", "an" and the like refers to one or more.

The term "about" as used herein refers to the usual range of variation for the respective value readily known to the skilled person in this technical field. Reference to "about" a value or parameter herein includes (and describes) embodiments that are directed to that value or parameter per se.

As used herein, the term "aminergic G protein-coupled receptors" refers to a family of transmembrane proteins involved in cellular communication. Aminergic G protein coupled receptors are activated by biogenic amines and represent a subclass of the superfamily of G protein coupled receptors, which are structurally characterized by seven transmembrane helices. Aminergic G protein-coupled receptors include but are not limited to adrenergic receptors, serotonin receptors, dopamine receptors, histamine receptors and imidazoline receptors.

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an α1-adrenergic receptor (e.g., α1A, α1B and/or α1D) and/or a α2-adrenergic receptor (e.g., α2A, α2B and/or α2C) and/or reduces or eliminates or increases or enhances or mimics an activity of a α1-adrenergic receptor (e.g., α1A, α1B and/or α1D) and/or a α2-adrenergic receptor (e.g., α2A, α2B and/or α2C) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 (D1) and/or a dopamine-2 (D2) receptor or reduces or eliminates or increases or enhances or mimics an activity of a dopamine-1 (D1) and/or a dopamine-2 (D2) receptor in a reversible or irreversible manner. Dopamine D2 receptors are divided into two categories, D2L and D2S, which are formed from a single gene by differential splicing. D2L receptors have a longer intracellular domain than D2S. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor or reduces or eliminates or increases or enhances or mimics an activity of a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine H1 and/or H2 and/or H3 receptor or reduces or eliminates or increases or enhances or mimics an activity of a histamine H1 and/or H2 and/or H3 receptor in a reversible or irreversible manner. In some embodiments, the histamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the histamine receptor modulator reduces an activity of a histamine receptor by at least about or about any of 10%, 20%, 30%, 40%, 50%, 60%, 70%, 80%, 90%, 95% or 100% as compared to the corresponding activity in the same subject prior to treatment with the histamine receptor modulator or compared to the corresponding activity in other subjects not receiving the histamine receptor modulator. In some embodiments, the histamine receptor modulator enhances an activity of a histamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the histamine receptor modulator or compared to the corresponding activity in other subjects not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining beneficial or desired results, including clinical results. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, amyotrophic lateral sclerosis (ALS), autism, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic, and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. Aβ appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 1996, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: Mechanistic Implications, *Ann Neurol.*, 2005, 57(5), 695-703; Wang et al., Insights into amyloid-β-induced mitochondrial dysfunction in Alzheimer disease, *Free Radical Biology & Medicine*, 2007, 43, 1569-1573; Swerdlow et al., Mitochondria in Alzheimer's disease, *Int. Rev. Neurobiol.*, 2002, 53, 341-385; and Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" are used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) Am. J. Psychiatry 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep, John, Ferris, Reisberg, et al. (1994) Neurobiol. Aging 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time.

Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. A pharmaceutically acceptable salt intends ionic interactions and not a covalent bond. As such, an N-oxide is not considered a salt. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. In fused ring systems, one or more of the rings can be aryl or heteroaryl. A cycloalkyl having more than one ring where at least one ring is aromatic may be connected to the parent structure at either a non-aromatic ring position or at an aromatic ring position. In one variation, a cycloalkyl having more than one ring where at least one ring is aromatic is connected to the parent structure at a non-aromatic ring position. A preferred cycloalkyl is a saturated cyclic hydrocarbon having from 3 to 13 annular carbon atoms. A more preferred cycloalkyl is a saturated cyclic hydrocarbon having from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Alkylene" refers to the same residues as alkyl, but having bivalency. Examples of alkylene include ethylene (—$CH_2CH_2$—) and propylene (—$CH_2CH_2CH_2$—).

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the later example can be attached to the cyclohexenyl moiety at any available position on the ring.

"Alkynyl" refers to an unsaturated hydrocarbon group having at least one site of acetylenic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents s including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —C(O)$NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic, or $R_a$ and $R_b$ groups can be joined together with the nitrogen atom to form a heterocyclic or substituted heterocyclic ring.

"Acyclic acylamino" refers to the group —C(O)$NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic.

"Cyclic acylamino" refers to the group —C(O)$NR_aR_b$ where $R_a$ and $R_b$ groups are joined together with the nitrogen atom to form a heterocyclic or substituted heterocyclic ring. Examples of cyclic acylamino group include but are not limited to —C(O)(1-piperidinyl), —C(O)(1-piperazinyl), —C(O)(4-methyl-1-piperazinyl) and —C(O)(1-pyrrolidinyl).

"Aminocarbonylalkoxy" refers to the group —$NR_aC(O)OR_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic. Preferably, $R_a$ is H or alkyl.

"Aminosulfonyl" refers to the groups —$NRSO_2$-alkyl, —$NRSO_2$ substituted alkyl, —$NRSO_2$-alkenyl, —$NRSO_2$-substituted alkenyl, —$NRSO_2$-alkynyl, —$NRSO_2$-substituted alkynyl, —$NRSO_2$-aryl, —$NRSO_2$-substituted aryl, —$NRSO_2$-heteroaryl, —$NRSO_2$-substituted heteroaryl, —$NRSO_2$-heterocyclic, and —$NRSO_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —$SO_2NH_2$, —$SO_2$NR-alkyl, —$SO_2$NR-substituted alkyl, —$SO_2$NR-alkenyl, —$SO_2$NR-substituted alkenyl, —$SO_2$NR-alkynyl, —$SO_2$NR-substituted alkynyl, —$SO_2$NR-aryl, —$SO_2$NR-substituted aryl, —$SO_2$NR-heteroaryl, —$SO_2$NR-substituted heteroaryl, —$SO_2$NR-heterocyclic, and —$SO_2$NR-substituted heterocyclic, where R is H or alkyl, or —$SO_2NR_2$, where the two R groups are taken together and with the nitrogen atom to which they are attached to form a heterocyclic or substituted heterocyclic ring.

"Sulfonyl" refers to the groups —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic.

"Carbonylalkylenealkoxy" refers to the group —C(=O)—$(CH_2)_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Cyano" refers to the group —CN.

"Oxo" refers to the moiety =O.

"Nitro" refers to the group —$NO_2$.

"Thioalkyl" refers to the groups —S-alkyl.

"Alkylsulfonylamino" refers to the groups —$R^1SO_2NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the $R_a$ and $R_b$ groups can be joined together with the nitrogen atom to form a heterocyclic or substituted heterocyclic ring and $R^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure S compound means that the composition contains no more than 15% or no more than 10% or no more than 5% or no more than 3% or no more than 1% of the R form of the compound.

Compounds of the Invention

Compounds according to the invention are detailed herein, including in the Brief Summary of the Invention and the appended claims. Thus, compounds of the invention include any compounds detailed herein. The invention includes the use of all of the compounds described herein, including any and all stereoisomers, salts and solvates of the compounds described as histamine receptor modulators. Further methods of using the compounds of the invention are detailed throughout.

The invention embraces compounds of the formula (I):

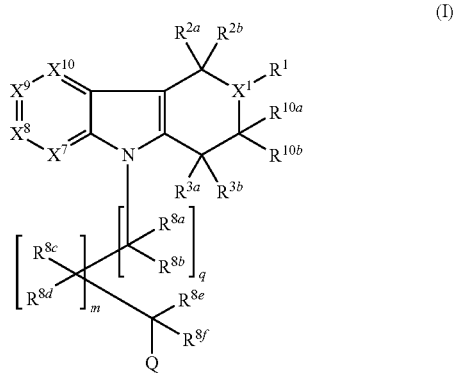

(I)

where:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$ and R$^{2b}$ is independently H, substituted or unsubstituted C$_1$-C$_8$ alkyl, halo, hydroxyl, alkoxy, cyano, nitro or R$^{2a}$ and R$^{2b}$ are taken together to form a carbonyl moiety;

each R$^{3a}$ and R$^{3b}$ is independently H, substituted or unsubstituted C$_1$-C$_8$ alkyl, halo, cyano or nitro or R$^{3a}$ and R$^{3b}$ are taken together to form a carbonyl moiety;

each X$^7$, X$^8$, X$^9$ and X$^{10}$ is independently N or CR$^4$;

m and q are independently 0 or 1;

X$^1$ is N or CH;

each R$^4$ is independently H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$ and R$^{8f}$ is independently H, hydroxyl, C$_1$-C$_8$ alkyl or is taken together with the carbon to which it is attached and a geminal R$^{8(e-f)}$ to form a cycloalkyl moiety;

each R$^{10a}$ and R$^{10b}$ is independently H, halo, a substituted or unsubstituted C$_1$-C$_8$ alkyl, hydroxyl, alkoxyl or R$^{10a}$ and R$^{10b}$ are taken together to form a carbonyl;

Q is acylamino, carbonylalkoxy, acyloxy, aminoacyl or aminocarbonylalkoxy;

provided that the compound is other than a compound according to proviso 1 and proviso 2. In one variation, the compound is of the formula (I) provided that the compound is other than any of compounds 1x-6x and a compound of proviso 2. In another variation, the compounds of the invention, and methods of using the compounds detailed herein, encompass any of the compounds of Formula (I), including those listed in proviso 1 or proviso 2 or a salt thereof. In one variation, the compound is of the formula (I) provided that the compound is other than a compound of the formula (X):

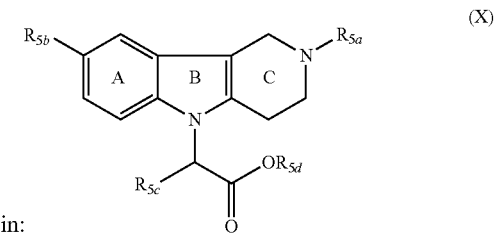

(X)

wherein:
R$_{5c}$ is selected from alkyl, substituted alkyl, and aralkyl;
R$_{5b}$ is selected from alkyl, aryl, and substituted aryl;
R$_{5a}$ is alkyl; and
R$_{5d}$ is alkyl.

In another variation, the compound is of the formula (I) and includes compounds of the formula (X).

In another variation, the invention embraces compounds of the formula (A):

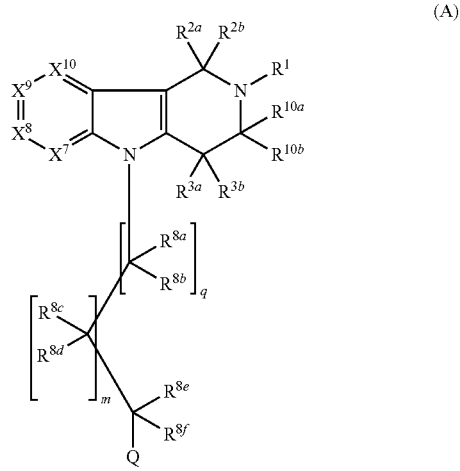

(A)

wherein $X^7$, $X^8$, $X^9$ and $X^{10}$; $R^1$, $R^{2a}$, $R^{2b}$, $R^{3a}$, $R^{3b}$, $R^4$, $R^{8a}$, $R^{8b}$, $R^{8c}$, $R^{8d}$, $R^{8e}$, $R^{8f}$, $R^{10a}$ and $R^{10b}$; and m and q are as defined in formula (I), provided that the compound is other than a compound in Table 1, or a salt thereof. In another variation, the compounds of the invention, and methods of using the compounds detailed herein, encompass any of the compounds of formula (A), including those listed in Table 1 or a salt thereof. In another variation, the invention embraces compounds of the formula (A) provided that at least one of $X^7$, $X^8$, $X^9$ and $X^{10}$ is other than CH. In another variation, the invention embraces compounds of the formula (A) where $X^9$ is other than $CR^4$ where $R^4$ is H, 4-methyl-1-piperidinylcarbonyl or formyl group.

The invention also embraces compounds of the formula (B):

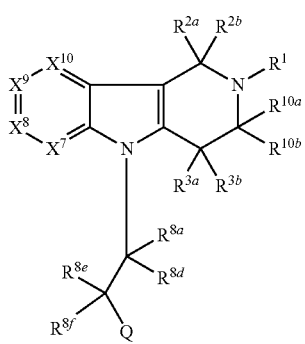

(B)

wherein $X^7$, $X^8$, $X^9$ and $R^1$, $R^{2a}$, $R^{2b}$, $R^{3a}$, $R^{3b}$, $R^4$, $R^{8c}$, $R^{8d}$, $R^{8e}$, $R^{8f}$, $R^{10a}$ and $R^{10b}$ are as defined in formula (I), provided that the compound is other than any of compounds 7x, 10x, 63x, 64x, 65x, 66x, 67x, 68x, 69x, 70x, 71x, 72x, 73x, 74x, 75x, 76x, 77x, 78x, 79x, 80x, 81x, 82x, 83x, 84x, 85x, 86x, 87x, 88x, 89x, 90x, 91x, 92x, 93x, 94x, 95x, 96x, 97x, 98x, 99x, 100x, 101x, 102x, 103x, 104x, 105x and 106x, or a salt thereof. In another variation, the compounds of the invention, and methods of using the compounds detailed herein, encompass any of the compounds of formula (B), including compounds 7x, 10x, 63x, 64x, 65x, 66x, 67x, 68x, 69x, 70x, 71x, 72x, 73x, 74x, 75x, 76x, 77x, 78x, 79x, 80x, 81x, 82x, 83x, 84x, 85x, 86x, 87x, 88x, 89x, 90x, 91x, 92x, 93x, 94x, 95x, 96x, 97x, 98x, 99x, 100x, 101x, 102x, 103x, 104x, 105x or 106x or a salt thereof.

The invention also embraces compounds of the formula (C):

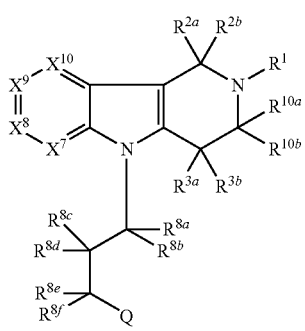

(C)

wherein $X^7$, $X^8$, $X^9$ and $X^{10}$; $R^1$, $R^{2a}$, $R^{2b}$, $R^{3a}$, $R^{3b}$, $R^4$, $R^{8a}$, $R^{8b}$, $R^{8c}$, $R^{8d}$, $R^{8e}$, $R^{8f}$, $R^{10a}$ and $R^{10b}$ are as defined in formula (I) or a salt thereof.

In one variation, the compound is of the formula (C) where one of $X^7$, $X^8$, $X^9$ and $X^{10}$ is N. In one such variation, $X^9$ is N and $X^7$, $X^8$ and $X^{10}$ are CH. In one variation, the compound is of the formula (C) where $X^9$ is N, $X^7$, $X^8$ and $X^{10}$ are CH and $R^1$ is alkyl e.g. methyl. In another variation, the compound is of the formula (C) where $X^9$ is N, $R^1$ is alkyl and Q is carbonylalkoxy, acylamino or aminoacyl. In yet another variation, the compound is of the formula (C) where $X^7$, $X^8$ and $X^{10}$ are CH, $X^9$ is N, $R^1$ is alkyl, each $R^{2a}$, $R^{2b}$, $R^{3a}$, $R^{3b}$, $R^{10a}$ and $R^{10b}$ is H and Q is carbonylalkoxy, acylamino or aminoacyl. In one specific variation, the compound is of the formula (C) where $X^7$, $X^8$ and $X^{10}$ are CH, $X^9$ is N, $R^1$ is methyl, each $R^{2a}$, $R^{2b}$, $R^{3a}$, $R^{3b}$, $R^{10a}$, $R^{10b}$, $R^{8a}$, $R^{8b}$, $R^{8c}$, $R^{8d}$, $R^{8e}$ and $R^{8f}$ is H and Q is carbonylalkoxy, acylamino or aminoacyl. In one such specific variation, Q is acylamino, e.g. —C(O)NHR' where R' is substituted or unsubstituted alkyl or cycloalkyl.

In one variation, the compound is of the formula (C) where each of $X^7$, $X^8$, $X^9$ and $X^{10}$ is $CR^4$ where $R^4$ is as defined in formula (I) or any variation thereof. In one such variation, $X^7$, $X^8$ and $X^{10}$ are CH and $X^9$ is $CR^4$ where $R^4$ is alkyl. In another variation, the compound is of the formula (C) where $X^7$, $X^8$ and $X^{10}$ are CH, $X^9$ is $CR^4$ where $R^4$ is alkyl and $R^1$ is alkyl. In yet another variation, the compound is of the formula (C) where $X^7$, $X^8$ and $X^{10}$ are CH, $X^9$ is $CR^4$ where $R^4$ is alkyl, $R^1$ is alkyl, each $R^{2a}$, $R^{2b}$, $R^{3a}$, $R^{3b}$, $R^{10a}$ and $R^{10b}$ is H and Q is acylamino or carbonylalkoxy. In one specific variation, the compound is of the formula (C) where $X^7$, $X^8$ and $X^{10}$ are CH and $X^9$ is $CR^4$ where $R^4$ is methyl, $R^1$ is methyl each $R^{2a}$, $R^{2b}$, $R^{3a}$, $R^{3b}$, $R^{10a}$, $R^{10b}$, $R^{8a}$, $R^{8b}$, $R^{8c}$, $R^{8d}$, $R^{8e}$ and $R^{8f}$ is H and Q is acylamino or carbonylalkoxy. In one such specific variation, Q is acylamino, e.g. —C(O)NHR' where R' is substituted or unsubstituted alkyl.

The invention also embraces compounds of the formula (D):

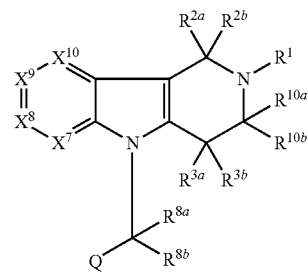

(D)

wherein $X^7$, $X^8$, $X^9$ and $X^{10}$; $R^1$, $R^{2a}$, $R^{2b}$, $R^{3a}$, $R^{3b}$, $R^4$, $R^{8e}$, $R^{8f}$, $R^{10a}$ and $R^{10b}$ are as defined in formula (I), provided that the compound is other than any of compounds 1x, 2x, 3x, 4x, 5x, 6x, 8x, 9x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 52x, 53x, 54x, 55x, 56x, 57x, 58x, 59x, 60x, 61x, 62x, 107x, 108x, 109x and 110x, or a salt thereof. In another variation, the compounds of the invention, and methods of using the compounds detailed herein, encompass any of the compounds of formula (D), including compounds 1x, 2x, 3x, 4x, 5x, 6x, 8x, 9x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 52x, 53x, 54x, 55x, 56x, 57x, 58x, 59x, 60x, 61x, 62x, 107x, 108x, 109x or 110x or a salt thereof.

In one variation, a compound of the invention is of the formula (I) where: $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; and each $R^{10a}$ and $R^{10b}$ is independently H, halo, hydroxyl or methyl or $R^{10a}$ and $R^{10b}$ are taken together to form a carbonyl. This variation of formula (I) is referred to herein as formula "(Ia)". All variations referring to formula (I), where applicable, may apply equally to any of formula (A)-(D) the same as if each and every variation were specifically and individually listed.

In a particular embodiment, the compound is of the formula (I) or (Ia) where $X^7$, $X^8$, $X^9$ and $X^{10}$ are $CR^4$. In another embodiment, the compound is of the formula (I) or (Ia) where at least one of $X^7$, $X^8$, $X^9$ and $X^{10}$ is N. Another variation provides a compound of the formula (I) or (Ia) where at least two of $X^7$, $X^8$, $X^9$ and $X^{10}$ are N. A further variation provides a compound of the formula (I) or (Ia) where 2 of $X^7$, $X^8$, $X^9$ and $X^{10}$ are N and 2 of $X^7$, $X^8$, $X^9$ and $X^{10}$ are $CR^4$. A compound of the formula (I) or (Ia) where 1 of $X^7$, $X^8$, $X^9$ and $X^{10}$ is N and 3 of $X^7$, $X^8$, $X^9$ and $X^{10}$ are $CR^4$ is also embraced by this invention.

The invention further embraces compounds of the formula (E):

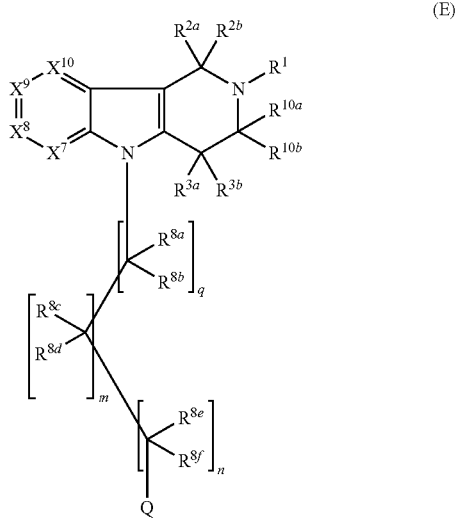

(E)

where:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano hydroxyl, alkoxy, nitro or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

m and q are independently 0 or 1;

n is 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, substituted or unsubstituted alkyl or is taken together with the carbon to which it is attached and a geminal $R^{8(a-f)}$ to form a cycloalkyl moiety;

each $R^{10a}$ and $R^{10b}$ is independently H, substituted or unsubstituted $C_1$-$C_8$ alkyl, halo, hydroxyl, alkoxyl or $R^{10a}$ and $R^{10b}$ are taken together with the carbon to which they are attached to form a cycloalkyl moiety or a carbonyl moiety; and Q is acyclic or cyclic acylamino, carbonylalkoxy, acyloxy, aminoacyl, aminocarbonylalkoxy, substituted or unsubstituted lactam or substituted or unsubstituted cycloalkyl;

provided that: (ia) Q is substituted or unsubstituted cycloalkyl or a lactam moiety when each of m, n and q is 0 and (ib) m, n and q are 0 when Q is a substituted or unsubstituted cycloalkyl or a lactam moiety, (ii) Q is cyclic acylamino only when each of m, n and q is 1, (iii) when Q is carbonylalkoxy, each $R^{8a}$, $R^{8b}$, $R^{8c}$, $R^{8d}$, $R^{8e}$ and $R^{8f}$ is other than cycloalkyl and substituted alkyl; (iv) the compound is other than a compound in Table 1, and (v) the compound is other than 5-cyclohexyl-2,3,4,5-tetrahydro-2-methyl-1H-pyrido[4,3-b]indole and 5-cyclopentyl-2,3,4,5-tetrahydro-2-[(4-methyl-1H-imidazol-5-yl)methyl]-1H-pyrido[4,3-b]indol-1-one;

or a salt thereof. In another variation, the compounds of the invention, and methods of using the compounds detailed herein, encompass any of the compounds of formula (E), including those listed in Table 1, 5-cyclohexyl-2,3,4,5-tetrahydro-2-methyl-1H-pyrido[4,3-b]indole or 5-cyclopentyl-2,3,4,5-tetrahydro-2-[(4-methyl-1H-imidazol-5-yl)methyl]-1H-pyrido[4,3-b]indol-1-one or a salt thereof.

In one variation, the compound is of the formula (E) where $X^9$ is N provided that the compound is other than compounds 109x and 110x. In another variation, the compound is of the formula (E) where $X^9$ is N and $R^1$ is a substituted alkyl or unsubstituted alkyl other than isopropyl. In another variation, the compound is of the formula (E) where $X^9$ is N and $R^1$ is methyl. In one variation, the compound is of the formula (E) where $X^9$ is N, n is 1 and at least one of m and q are 1. In another variation, the compound is of the formula (E) where $X^9$ is N and Q is other than acylamino. In yet another variation, the compound is of the formula (E) where $X^9$ is N and Q is aminoacyl, carbonylalkoxy or acyloxy. In one variation, the compound is of the formula (E) where each $X^7$, $X^8$ and $X^{10}$ is CH, $X^9$ is N and $R^1$ is methyl. In another variation, the compound is of the formula (E) where each $X^7$, $X^8$ and $X^{10}$ is CH, $X^9$ is N, $R^1$ is methyl and each $R^{2a}$, $R^{2b}$, $R^{3a}$, $R^{3b}$, $R^{10a}$ and $R^{10b}$ is H. In another variation, the compound is of the formula (E) where each $X^7$, $X^8$ and $X^{10}$ is CH, $X^9$ is N, $R^1$ is methyl, each $R^{2a}$, $R^{2b}$, $R^{3a}$, $R^{3b}$, $R^{10a}$ and $R^{10b}$ is H and each $R^{8a}$, $R^{8b}$, $R^{8c}$, $R^{8d}$, $R^{8e}$ and $R^{8f}$ is H when present. In another variation, the compound is of the formula (E) where each $X^7$, $X^8$ and $X^{10}$ is CH, $X^9$ is N, $R^1$ is methyl, each $R^{2a}$, $R^{2b}$, $R^{3a}$, $R^{3b}$, $R^{10a}$ and $R^{10b}$ is H, each m, n and q is 1 and each $R^{8a}$, $R^{8b}$, $R^{8c}$, $R^{8d}$, $R^{10a}$ and $R^{10b}$ is H. In yet another variation, the compound is of the formula (E) where each $X^7$, $X^8$ and $X^{10}$ is CH, $X^9$ is N, $R^1$ is methyl, each $R^{2a}$, $R^{2b}$, $R^{3a}$, $R^{3b}$, $R^{10a}$ and $R^{10b}$ is H, q is 0, m and n are 1 and each $R^{8c}$, $R^{8d}$, $R^{8e}$ and $R^{8f}$ is H. In one particular variation, the compound is of the formula (E) where each $X^7$, $X^8$ and $X^{10}$ is CH, $X^9$ is N, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino, aminoacyl or carbonylalkoxy.

In one variation, the compound is of the formula (E) where $X^9$ is $CR^4$ where $R^4$ is chloro. In another variation, the compound is of the formula (E) where $X^9$ is $CR^4$ where $R^4$ is chloro and n is 1. In another variation, the compound is of the formula (E) where $X^9$ is $CR^4$ where $R^4$ is chloro, n is 1 and one of m and q is 1 and the other is 0. In yet another variation, the compound is of the formula (E) where $X^9$ is $CR^4$ where $R^4$ is chloro, n is 1 and m and q are 0. In one variation, the compound is of the formula (E) where $X^9$ is $CR^4$ where $R^4$ is chloro and $R^1$ is alkyl, e.g. methyl. In another variation, the compound is of the formula (E) where $X^9$ is $CR^4$ where $R^4$ is chloro and Q is acylamino or carbonylalkoxy. In one variation, the compound is of the formula (E) where each $X^7$, $X^8$ and $X^{10}$ is CH, $X^9$ is $CR^4$ where $R^4$ is halo, $R^1$ is methyl and Q is other than ethoxycarbonyl. In another variation, the compound is of the formula (E) where each $X^7$, $X^8$ and $X^{10}$ is CH, $X^9$ is $CR^4$ where $R^4$ is halo, $R^1$ is methyl, each $R^{2a}$, $R^{2b}$, $R^{3a}$, $R^{3b}$, $R^{10a}$ and $R^{10b}$ is H and Q is other than ethoxycarbonyl. In another variation, the compound is of the formula (E) where each $X^7$, X and $X^{10}$ is CH, $X^9$ is $CR^4$ where $R^4$ is halo, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is other than ethoxycarbonyl. In another variation, the compound is of the formula (E) where each $X^7$, $X^8$ and $X^{10}$ is CH, $X^9$ is $CR^4$ where $R^4$ is halo, $R^1$ is methyl, each $R^{2a}$, $R^{2b}$, $R^{3a}$, $R^{3b}$, $R^{10a}$ and $R^{10b}$ is H, q is 0, m and n are 1, each $R^{8c}$, $R^{8d}$, $R^{8e}$ and $R^{8f}$ is H and Q is other than ethoxycarbonyl. In yet another variation, the compound is of the formula (E) where each $X^7$, $X^8$ and $X^{10}$ is CH, $X^9$ is $CR^4$ where $R^4$ is halo, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino or aminoacyl. In one variation, the compound is of the formula (E) where each $X^7$, $X^8$ and $X^{10}$ is CH, $X^9$ is $CR^4$ where $R^4$ is chloro and $R^1$ is alkyl. In another variation, the compound is of the formula (E) where each $X^7$, $X^8$ and $X^{10}$ is CH, $X^9$ is $CR^4$ where $R^4$ is chloro, $R^1$ is alkyl and each $R^{2a}$, $R^{2b}$, $R^{3a}$, $R^{3b}$, $R^{10a}$ and $R^{10b}$ is H. In another variation, the compound is of the formula (E) where each $X^7$, $X^8$ and $X^{10}$ is CH, $X^9$ is $CR^4$ where $R^4$ is chloro, $R^1$ is alkyl, each $R^{2a}$, $R^{2b}$, $R^{3a}$, $R^{3b}$, $R^{10a}$ and $R^{10b}$ is H and each $R^{8a}$, $R^{8b}$, $R^{8c}$, $R^{8d}$, $R^{8e}$ and $R^{8f}$ is H when present. In another variation, the compound is of the formula (E) where each $X^7$, $X^8$ and $X^{10}$ is CH, $X^9$ is $CR^4$ where $R^4$ is chloro, $R^1$ is alkyl, each $R^{2a}$, $R^{2b}$, $R^{3a}$, $R^{3b}$, $R^{10a}$ and $R^{10b}$ is H, each m, n and q is 1 and each $R^{8a}$, $R^{8b}$, $R^{8c}$, $R^{8d}$, $R^{8e}$ and $R^{8f}$ is H. In yet another variation, the compound is of the formula (E) where each $X^7$, $X^8$ and $X^{10}$ is CH, $X^9$ is $CR^4$ where $R^4$ is chloro, $R^1$ is alkyl, each $R^{2a}$, $R^{2b}$, $R^{3a}$, $R^{3b}$, $R^{10a}$ and $R^{10b}$ is H, q is 0, m and n are 1 and each $R^{8c}$, $R^{8d}$, $R^{8e}$ and $R^{8f}$ is H. In one particular variation, the compound is of the formula (E) where each $X^7$, $X^8$ and $X^{10}$ is CH, $X^9$ is $CR^4$ where $R^4$ is chloro, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino, aminoacyl or carbonylalkoxy.

In one variation, the compound is of the formula (E) where $X^9$ is $CR^4$ where $R^4$ is alkyl and each n, m and q is 1. In another variation, the compound is of the formula (E) where $X^9$ is $CR^4$ where $R^4$ is alkyl and $R^1$ is alkyl provided that the compound is other than any of compounds 13x, 20x and 73x. In another variation, the compound is of the formula (E) where $X^9$ is $CR^4$ where $R^4$ is alkyl, $R^1$ is methyl and Q is other than —C(O)OCH$_2$CH$_3$. In one variation, the compound is of the formula (E) where $X^9$ is $CR^4$ where $R^4$ is alkyl and Q is substituted acylamino. In another variation, the compound is of the formula (E) where $X^9$ is $CR^4$ where $R^4$ is alkyl, Q is acyclic acylamino and $R^1$ is a substituted alkyl or unsubstituted alkyl other than isopropyl. In yet another variation, the compound is of the formula (E) where $X^9$ is $CR^4$ where $R^4$ is alkyl, $R^1$ is methyl and Q is acyclic acylamino, aminoacyl or aminocarbonylalkoxy. In one variation, the compound is of the formula (E) where each $X^7$, $X^8$ and $X^{10}$ is CH, $X^9$ is $CR^4$ where $R^4$ is alkyl, $R^1$ is methyl and Q is other than ethoxycarbonyl. In another variation, the compound is of the formula (E) where each $X^7$, $X^8$ and $X^{10}$ is CH, $X^9$ is $CR^4$ where $R^4$ is alkyl, $R^1$ is methyl, each $R^{2a}$, $R^{2b}$, $R^{3a}$, $R^{3b}$, $R^{10a}$ and $R^{10b}$ is H and Q is other than ethoxycarbonyl. In another variation, the compound is of the formula (E) where each $X^7$, $X^8$ and $X^{10}$ is CH, $X^9$ is $CR^4$ where $R^4$ is alkyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is other than ethoxycarbonyl. In another variation, the compound is of the formula (E) where each $X^7$, $X^8$ and $X^{10}$ is CH, $X^9$ is $CR^4$ where $R^4$ is alkyl, $R^1$ is methyl, each $R^{2a}$, $R^{2b}$, $R^{3a}$, $R^{3b}$, $R^{10a}$ and $R^{10b}$ is H, q is 0, m and n are 1, each $R^{8c}$, $R^{8d}$, $R^{8e}$ and $R^{8f}$ is H and Q is other than ethoxycarbonyl. In yet another variation, the compound is of the formula (E) where each $X^7$, $X^8$ and $X^{10}$ is CH, $X^9$ is $CR^4$ where $R^4$ is alkyl, $R^1$ is methy, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino or aminoacyl. In one particular variation, the compound is of the formula (E) where each $X^7$, $X^8$ and $X^{10}$ is CH, $X^9$ is $CR^4$ where $R^4$ is methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino or aminoacyl.

In one variation, the compound is of the formula (E) where $R^1$ is a substituted alkyl or unsubstituted alkyl other than isopropyl and Q is acyclic acylamino other than —C(O)NMe$_2$ and —C(O)NH$_2$. In another variation, the compound is of the formula (E) where $R^1$ is a substituted alkyl or unsubstituted alkyl other than isopropyl and Q is acylamino of the formula —C(O)NHR' where R' is other than H. In yet another variation, the compound is of the formula (E) where $R^1$ is methyl and Q is acylamino of the formula —C(O)NHR' where R' is unsubstituted or substituted alkyl, unsubstituted or substituted cycloalkyl, unsubstituted or substituted aryl, unsubstituted or substituted heteroaryl or unsubstituted or substituted heterocyclyl. In one variation, the compound is of the formula (E) where each $X^7$, $X^8$ and $X^{10}$ is CH, $X^9$ is N or $CR^4$ where $R^4$ is chloro or methyl, $R^1$ is methyl and Q is acyclic acylamino. In another variation, the compound is of the formula (E) where each $X^7$, $X^8$ and $X^{10}$ is CH, $X^9$ is N or $CR^4$ where $R^4$ is chloro or methyl, $R^1$ is methyl, each $R^{2a}$, $R^{2b}$, $R^{3a}$, $R^{3b}$, $R^{10a}$ and $R^{10b}$ is H and Q is acyclic acylamino. In another variation, the compound is of the formula (E) where each $X^7$, $X^8$ and $X^{10}$ is CH, $X^9$ is N or $CR^4$ where $R^4$ is chloro or methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino. In one particular variation, the compound is of the formula (E) where each $X^7$, $X^8$ and $X^{10}$ is CH, $X^9$ is N or $CR^4$ where $R^4$ is chloro or methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acylamino of the formula —C(O)NHR' where R' is unsubstituted or substituted alkyl, unsubstituted or substituted cycloalkyl, unsubstituted or substituted aryl, unsubstituted or substituted heteroaryl or unsubstituted or substituted heterocyclyl.

In one variation, the compound is of the formula (E) where Q is aminoacyl. In another variation, the compound is of the formula (E) where Q is aminocarbonylalkoxy. In one variation, the compound is of the formula (E) where Q is acylamino of the formula —C(O)NHR' where R' is unsubstituted or substituted alkyl, substituted cycloalkyl, unsubstituted or substituted aryl, unsubstituted or substituted heteroaryl or unsubstituted or substituted heterocyclyl. In another variation, the compound is of the formula (E) where Q is carbonylalkoxy other than —C(O)OCH$_2$CH$_3$. In yet another variation, the compound is of the formula (E) where Q is carbonylalkoxy of the formula —C(O)OR' where R' is unsubstituted C$_3$-C$_8$ alkyl, substituted alkyl, unsubstituted or substituted aryl, unsubstituted or substituted heteroaryl or unsubstituted or substituted heterocyclyl. In one variation, the compound is of the formula (E) where Q is —C(O)NH$_2$, $R^1$ is methyl and at least one of $X^7$, $X^8$, $X^9$ and $X^{10}$ is other than CH. In another variation, the compound is of the formula (E) where Q is —C(O)NMe$_2$ and $R^1$ is methyl. In another variation, the compound is of the formula (E) where Q is —C(O)NMe$_2$ and at least one of $X^7$, $X^8$, $X^9$ and $X^{10}$ is CR$^4$ where $R^4$ is halo or alkyl. In one variation, the compound is of the formula (E) where each $X^7$, $X^8$ and $X^{10}$ is CH, $X^9$ is N or CR$^4$ where $R^4$ is chloro or methyl, $R^1$ is methyl and Q is aminoacyl or aminocarbonylalkoxy. In another variation, the compound is of the formula (E) where each $X^7$, $X^8$ and $X^{10}$ is CH, $X^9$ is N or CR$^4$ where $R^4$ is chloro or methyl, $R^1$ is methyl, each $R^{2a}$, $R^{2b}$, $R^{3a}$, $R^{3b}$, $R^{10a}$ and $R^{10b}$ is H and Q is aminoacyl or aminocarbonylalkoxy. In another variation, the compound is of the formula (E) where each $X^7$, $X^8$ and $X^{10}$ is CH, $X^9$ is N or CR$^4$ where $R^4$ is chloro or methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is aminoacyl or aminocarbonylalkoxy. In another variation, the compound is of the formula (E) where each $X^7$, $X^8$ and $X^{10}$ is CH, $X^9$ is N or CR$^4$ where $R^4$ is methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is aminoacyl or aminocarbonylalkoxy. In yet another variation, the compound is of the formula (E) where each $X^7$, $X^8$ and $X^{10}$ is CH, $X^9$ is N or CR$^4$ where $R^4$ is methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is aminoacyl of the formula —NHC(O)R' where R' is H, alkyl, substituted alkyl, alkenyl, substituted alkenyl, alkynyl, substituted alkynyl, aryl, substituted aryl, heteroaryl, substituted heteroaryl, heterocyclyl or substituted heterocyclyl. In a particular variation, the compound is of the formula (E) where each $X^7$, $X^8$ and $X^{10}$ is CH, $X^9$ is N or CR$^4$ where $R^4$ is methy $R^1$ is methy each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is of the formula —NHC(O)R' where R' is alkyl, substituted alkyl, aryl, substituted aryl, heteroaryl, substituted heteroaryl, heterocyclyl, substituted heterocyclyl, alkoxy or substituted alkoxy.

In one variation, the invention embraces the compound of formula (F):

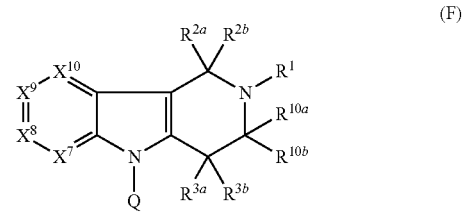

(F)

or a salt thereof, where $R^1$, $X^7$, $X^8$, $X^9$, $X^{10}$, $R^{2a}$, $R^{2b}$, $R^{3a}$, $R^{3b}$, $R^{10a}$, $R^{10b}$ and $R^4$ are as defined in formula (E) or any applicable variation thereof and Q is substituted or unsubstituted cycloalkyl or a lactam moiety, provided that the compound is other than any of 5-cyclohexyl-2,3,4,5-tetrahydro-2-methyl-1H-pyrido[4,3-b]indole and 5-cyclopentyl-2,3,4,5-tetrahydro-2-[(4-methyl-1H-imidazol-5-yl)methyl]-1H-pyrido[4,3-b]indol-1-one. In another variation, the compounds of the invention, and methods of using the compounds detailed herein, encompass any of the compounds of formula (F), including 5-cyclohexyl-2,3,4,5-tetrahydro-2-methyl-1H-pyrido[4,3-b]indole and 5-cyclopentyl-2,3,4,5-tetrahydro-2-[(4-methyl-1H-imidazol-5-yl)methyl]-1H-pyrido[4,3-b]indol-1-one or a salt thereof.

In one variation, the compound is of the formula (F) where Q is substituted cycloalkyl or a lactam moiety. The lactam moiety may be a substituted or unsubstituted lastam moiety. When the lactam is substituted, in one variation, the substituent is attached to the nitrogen of the lactam ring (e.g. N-methyl lactam). In another variation, the compound is of the formula (F) where at least one of $X^7$, $X^8$, $X^9$ and $X^{10}$ is other than CH. In another variation, the compound is of the formula (F) where Q is a moiety selected from the structures:

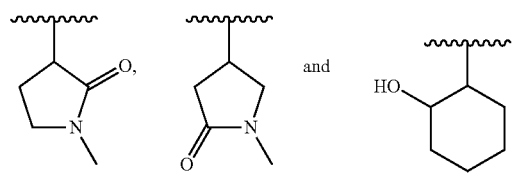

In another variation, a compound of the invention is of the formula (I) or (Ia) where $X^7$, $X^8$, $X^9$ and $X^{10}$ are taken together to provide an aromatic moiety selected from the following structures:

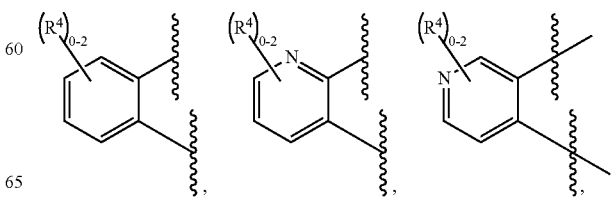

-continued

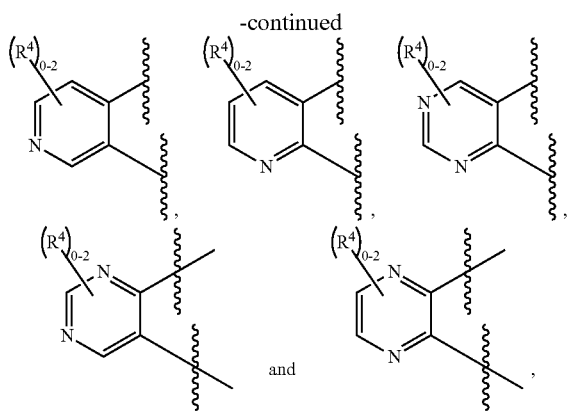

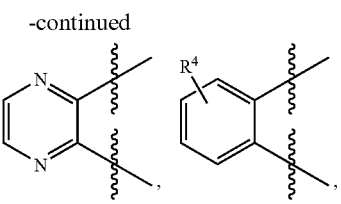

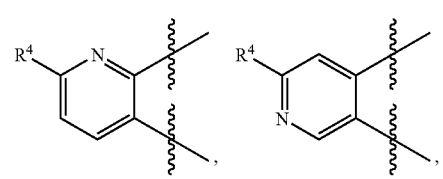

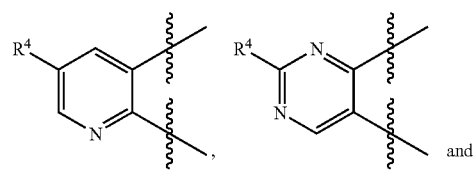

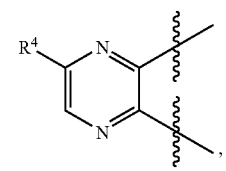

where each $R^4$ is as defined for formula (I) or (Ia); or in a particular variation, where each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where $R^4$ is independently halo, unsubstituted $C_1$-$C_4$ alkyl or $C_1$-$C_4$ perhaloalkyl.

In another variation, a compound of the invention is of the formula (I) or (Ia) where $X^7$, $X^8$, $X^9$ and $X^{10}$ are taken together to provide an aromatic moiety of the structure:

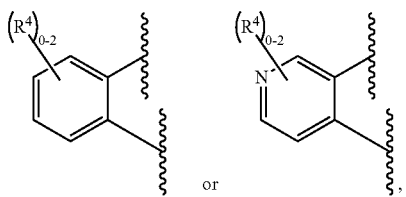

where each $R^4$ is as defined for formula (I) or (Ia); or in a particular variation, where each $R^4$ is independently alkyl or halo or in an even more particular variation, where each $R^4$ is independently methyl or chloro.

In still a further variation, a compound of the invention is of the formula (I) or (Ia) where $X^7$, $X^8$, $X^9$ and $X^{10}$ are taken together provide an aromatic moiety selected from the following structures:

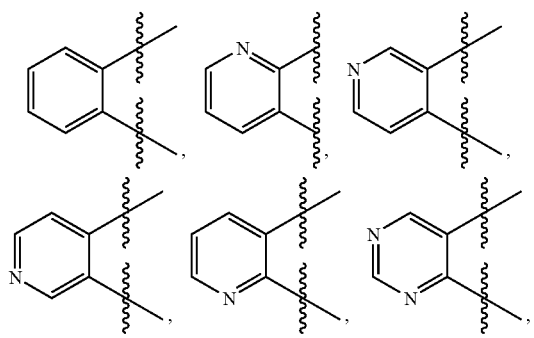

wherein $R^4$ is as defined in formula (I); or in a particular variation, where $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where each $R^4$ is independently halo, unsubstituted $C_1$-$C_4$ alkyl or $C_1$-$C_4$ perhaloalkyl.

In still a further variation, a compound of the invention is of the formula (I) or (Ia) where $X^7$, $X^8$, $X^9$ and $X^{10}$ are taken together provide an aromatic moiety of the structure:

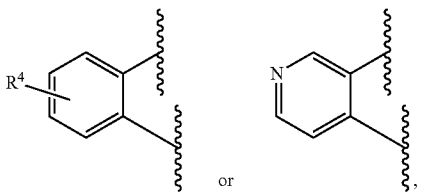

wherein $R^4$ is as defined in formula (I) or in any particular variation herein, such as when each $R^4$ is independently alkyl or halo or in an even more particular variation, where each $R^4$ is independently methyl or chloro. In yet another variation, a compound of the invention is of the formula (I) or (Ia) where $X^7$, $X^8$, $X^9$ and $X^{10}$ are taken together provide an aromatic moiety of the structure:

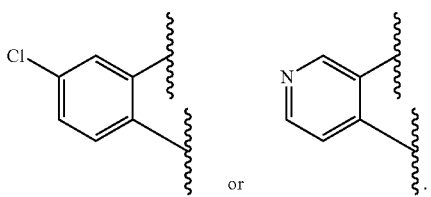 [SMILES: *c1ccc(Cl)cc1* ; *c1ccncc1*]

In another embodiment, a compound of the invention is of the formula (I), wherein $X^7$-$X^{10}$ are as defined in formula (I) or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is of the formula (I), wherein $X^7$-$X^{10}$ are as defined in formula (I) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is of the formula (I), wherein $X^7$-$X^{10}$ are as defined in formula (I) or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl. In another particular variation, a compound of the invention is of the formula (I), wherein $X^7$-$X^{10}$ are as defined in formula (I) or as detailed in any variation herein, where $R^1$ is methyl, ethyl, cyclopropyl, propyl, trifluoromethyl, isopropyl, tert-butyl, sec-butyl, 2-methylbutyl, propanoyl, 1-methyl-2-hydroxyethyl, 2-hydroxyethanoyl, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In another variation, the compound of the invention is of the formula (I), where $X^7$-$X^{10}$ and $R^1$ are as defined in formula (I) or as detailed in any variation herein, where $R^{2a}$ and $R^{2b}$ are independently H, substituted or unsubstituted $C_1$-$C_8$ alkyl, halo, cyano, nitro or $R^{2a}$ and $R^{2b}$ are taken together to form a carbonyl moiety and each $R^{3a}$ and $R^{3b}$ is independently H, substituted or unsubstituted $C_1$-$C_8$ alkyl, halo, cyano or nitro. In another variation, the compound of the invention is of the formula (I), where $X^7$-$X^{10}$ and $R^1$ are as defined in formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is of the formula (I), where $X^7$-$X^{10}$ and $R^1$ are as defined in formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention according to formula (I), where $X^7$-$X^{10}$ and $R^1$ are as defined in formula (I) or as detailed in any variation herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety. The invention further embraces compounds of the invention according to formula (I), where $X^7$-$X^{10}$ and $R^1$ are as defined in formula (I) or as detailed in any variation herein, where each of $R^{2a}$, $R^{2b}$, $R^{3a}$ and $R^{3b}$ is H. In one variation, a compound of the invention is of the formula (I) where $X^7$-$X^{10}$ and $R^1$ are as defined in formula (I) or as detailed in any variation herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In another variation, a compound of the invention is of the formula (I) where $X^7$-$X^{10}$ and $R^1$ are as defined in formula (I) or as detailed in any variation herein, where at least two of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, a compound of the invention is of the formula (I) where $X^7$-$X^{10}$ and $R^1$ are as defined in formula (I) or as detailed in any variation herein, where at least one of $R^{2a}$, $R^{2b}$, $R^{3a}$ and $R^{3b}$ is fluoro or methyl or is taken together with a geminal $R^2$ or $R^3$ to form a carbonyl moiety. In still another variation, a compound of the invention is of the formula (I) where $X^7$-$X^{10}$ and $R^1$ are as defined in formula (I) or as detailed in any variation herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl. In another variation, when $X^1$ is N, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl.

The invention also embraces compounds according to formula (I), where $X^7$-$X^{10}$, $R^1$, $R^{2a}$, $R^{2b}$, $R^{3a}$ and $R^{3b}$ are as defined in formula (I) or as detailed in any variation herein, where each $R^{10a}$ and $R^{10b}$ is independently H, halo, an unsubstituted $C_1$-$C_8$ alkyl, hydroxyl or $R^{10a}$ and $R^{10b}$ are taken together to form a carbonyl. Also embraced are compounds according to formula (I), where $X^7$-$X^{10}$, $R^1$, $R^{2a}$, $R^{2b}$, $R^{3a}$ and $R^{3b}$ are as defined in formula (I) or as detailed in any variation herein, where each $R^{10a}$ and $R^{10b}$ is independently H, halo, an unsubstituted $C_1$-$C_4$ alkyl, hydroxyl or $R^{10a}$ and $R^{10b}$ are taken together to form a carbonyl. In another variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where each $R^{10a}$ and $R^{10b}$ is independently H, bromo, methyl, hydroxyl or $R^{10a}$ and $R^{10b}$ are taken together to form a carbonyl. In yet another variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where at least one of $R^{10a}$ and $R^{10b}$ is an unsubstituted $C_1$-$C_8$ alkyl, hydroxyl, halo or $R^{10a}$ and $R^{10b}$ are taken together to form a carbonyl. In still a further variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where at least one of $R^{10a}$ and $R^{10b}$ is methyl, bromo, hydroxyl or $R^{10a}$ and $R^{10b}$ are taken together to form a carbonyl. In another variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where both $R^{10a}$ and $R^{10b}$ are methyl. In another variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where $R^{10a}$ and $R^{10b}$ are taken together to form a carbonyl. In another variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where $R^{10a}$ is H and $R^{10b}$ is methyl. In another variation, a compound of the invention is of the formula (I), where $X^7$-$X^{10}$, $R^1$, $R^{2a}$, $R^{2b}$, $R^{3a}$ and $R^{3b}$ are as defined in formula (I) or as detailed in any variation herein, where $R^{10a}$ is H and $R^{10b}$ is bromo. When the carbon of formula (I) bearing $R^{10a}$ and $R^{10b}$ is optically active, it may be in the S or R configuration and compositions comprising substantially pure R or S compound or mixtures thereof in any amount are embraced by this invention.

In a particular variation, a compound of the invention is of the formula (I) where $R^{2a}$, $R^{2b}$, $X^1$, $R^{10a}$, $R^{10b}$, $R^{3a}$ and $R^{3b}$ are taken together to form a ring selected from the structures:

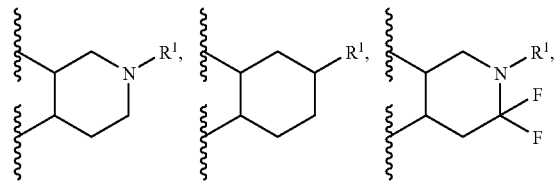

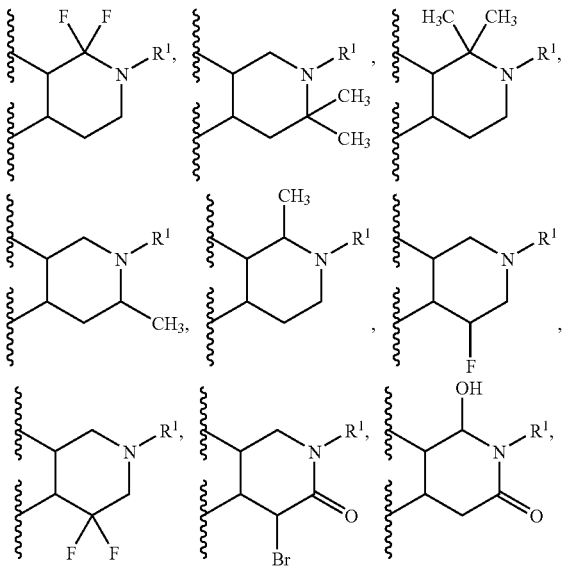

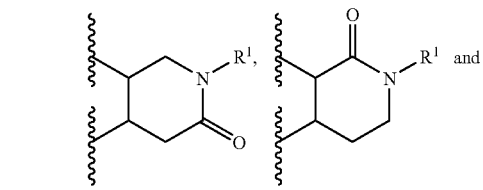

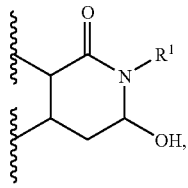

where $R^1$ in the structures above is as defined for formula (I) or any particular variation detailed herein.

In another variation, a compound of the invention is of the formula (I) where $R^{2a}$, $R^{2b}$, $X^1$, $R^{10a}$, $R^{10b}$, $R^{3a}$ and $R^{3b}$ are taken together to form a ring of the formula:

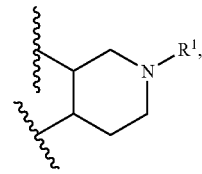

where $R^1$ is as defined in formula (I) or any variation detailed herein. In yet another variation, a compound of the invention is of the formula (I) where $R^{2a}$, $R^{2b}$, $X^1$, $R^{10a}$, $R^{10b}$, $R^{3a}$ and $R^{3b}$ are taken together to form a ring of the formula:

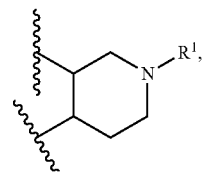

and where $X^7$, $X^8$, $X^9$ and $X^{10}$ are taken together provide an aromatic moiety of the structure:

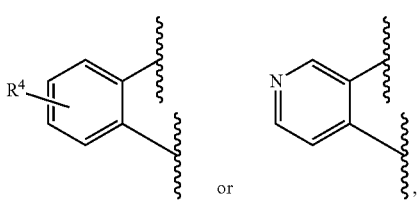

where $R^1$ is as defined in formula (I) or any variation detailed herein, such as when $R^1$ is an alkyl group or in a more particular variation when $R^1$ is methyl, and $R^4$ is as defined in formula (I) or in any particular variation herein, such as when each $R^4$ is independently alkyl or halo or in an even more particular variation, where each $R^4$ is independently methyl or chloro.

Compounds of the formulae (IIa), (IIb), (IIc), (IId), (IIe), (IIf), (IIg) and (IIh) are also embraced by this invention:

(IIa)

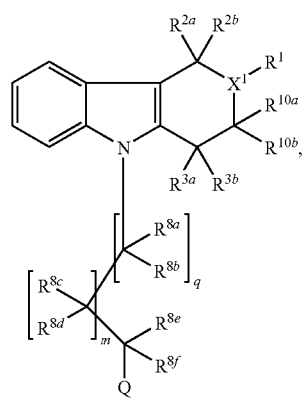

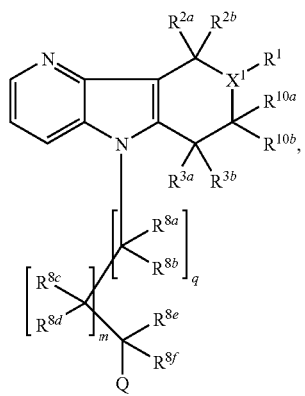
(IIb)

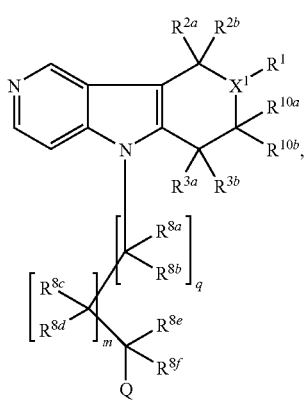
(IIc)

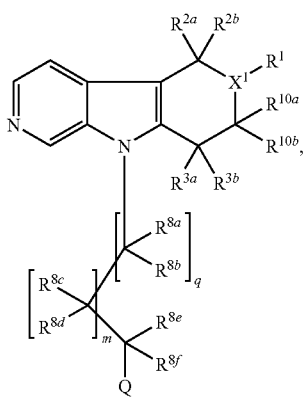
(IId)

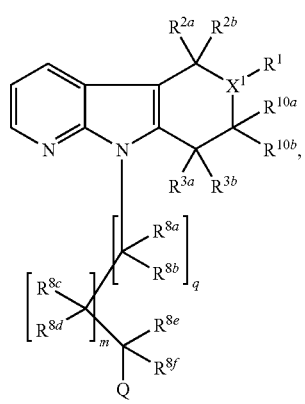
(IIe)

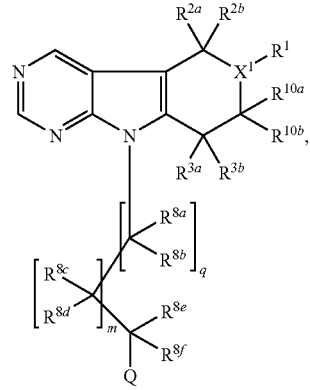
(IIf)

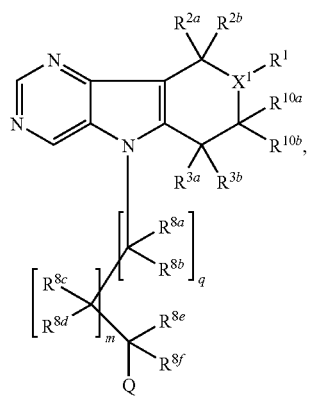
(IIg)

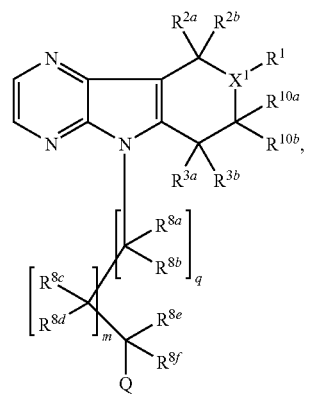
(IIh)

where in each of (IIa), (IIb), (IIc), (IId), (IIe), (IIf), (IIg) and (IIh), $R^1$, $R^{2a}$, $R^{2b}$, $R^{3a}$, $R^{3b}$, $R^{10a}$, $R^{10b}$, $R^{8a}$-$R^{8f}$, m, q and Q are as described for formula (I) or any applicable variation thereof. In one variation the invention relates to a compound of the formula (IIa). In another variation the invention relates to a compound of the formula (IIc). Where applicable, in each of (IIa), (IIb), (IIc), (IId), (IIe), (IIf), (IIg), and (IIh), $R^1$, $R^{2a}$, $R^{2b}$, $R^{3a}$, $R^{3b}$, $R^{10a}$, $R^{10b}$, $R^{8a}$-$R^{8f}$, m, q and Q may also be as described for any formulae or any application variation thereof detailed herein, including but not limited to formulae (A)-(G).

In one variation, the compound is of the formula (IIa), provided that when $X^1$ is N, the compound is other than any of compounds 11x, 14x, 15x, 16x, 17x, 18x, 19x, 21x, 22x, 23x, 24x, 34x, 35x, 36x, 37x, 44x, 63x, 64x, 65x, 66x, 67x, 69x, 72x, 74x, 76x, 86x and 91x, or a salt thereof. In one variation, the compound is of formula (IIa) wherein $X^1$ is N, $R^1$ is methyl and Q is cyclic acylamino, acyloxy, aminoacyl or aminocarbonylalkoxy. In another variation, the compounds of the invention, and methods of using the compounds detailed herein, encompass any of the compounds of formula (IIa), including those listed in Table 1, such as 11x, 14x, 15x, 16x, 17x, 18x, 19x, 21x, 22x, 23x, 24x, 34x, 35x, 36x, 37x, 44x, 63x, 64x, 65x, 66x, 67x, 69x, 72x, 74x, 76x, 86x or 91x or a salt thereof.

In one variation, the compound is of the formula (IIc), provided that when $X^1$ is N, the compound is other than any of compounds 109x and 110x, or a salt thereof. In one variation, the compound is of the formula (IIc) wherein $X^1$ is N and $R^1$ is methyl. In another variation, the compound is of the formula (IIc) wherein $X^1$ is N and Q is carbonylalkoxy, acyloxy, aminoacyl or aminocarbonylalkoxy. In one such variation, the compound is of the formula (IIc) where $X^1$ is N, $R^1$ is $C_1$-$C_8$ alkyl (e.g., methyl) and Q is carbonylalkoxy, acyloxy, aminoacyl or aminocarbonylalkoxy. In another variation, the compounds of the invention, and methods of using the compounds detailed herein, encompass any of the compounds of formula (IIc), including those listed in Table 1, such as 109x or 110x or a salt thereof.

In one variation, the compound is of the formula (IId), provided that when $X^1$ is N, the compound is other than any of compounds 107x and 108x, or a salt thereof. In another variation, the compound is of the formula (IId) wherein $X^1$ is N and $R^1$ is methyl. In a further variation, the compound is of the formula (IId) wherein $X^1$ is N and Q is carbonylalkoxy, acyloxy, aminoacyl or aminocarbonylalkoxy. In another variation, the compounds of the invention, and methods of using the compounds detailed herein, encompass any of the compounds of formula (IId), including those listed in Table 1, such as 107x or 108x or a salt thereof.

Compounds of the formulae (IIIa), (IIIb), (IIIc), (IIId), (IIIe), (IIIf), (IIIg), (IIIh), (IIIi), (IIIj), (IIIk), (IIIl) and (IIIm) are further embraced by this invention:

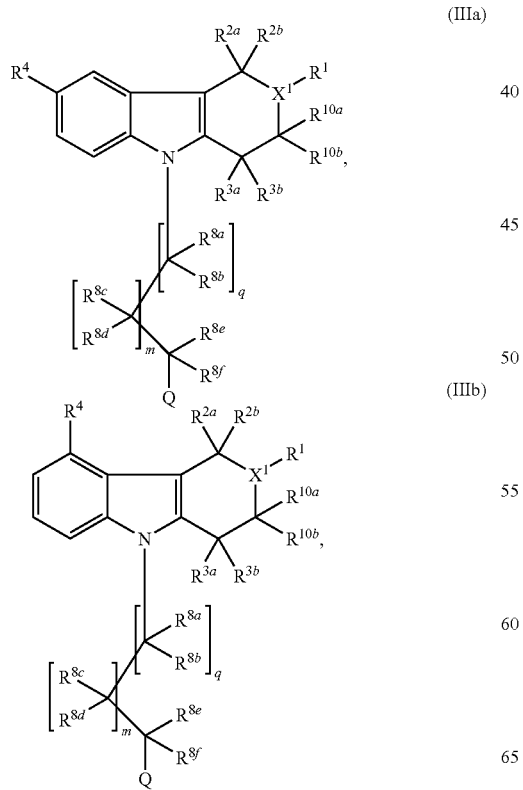

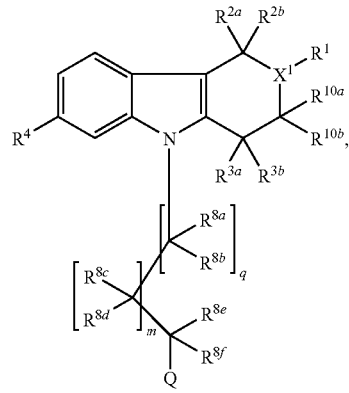

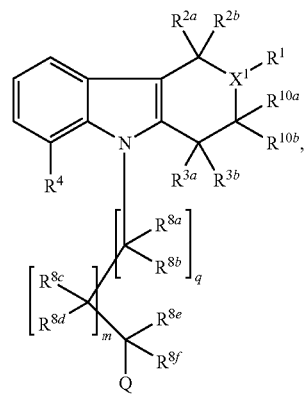

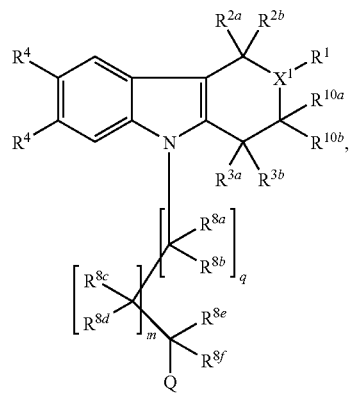

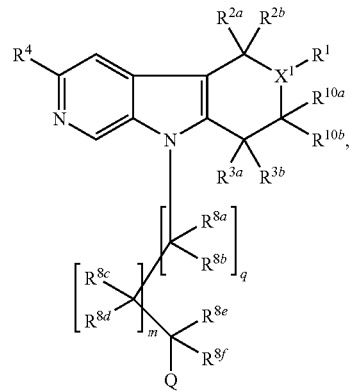

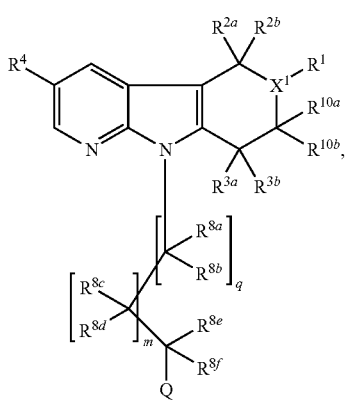 (IIIg)

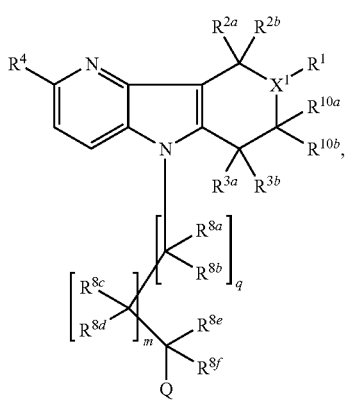 (IIIh)

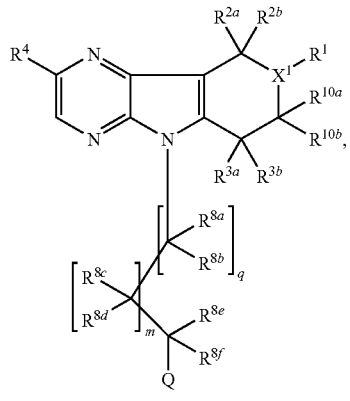 (IIIi)

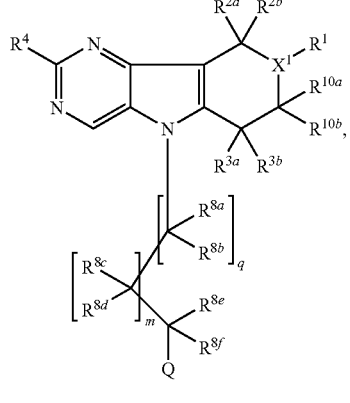 (IIIj)

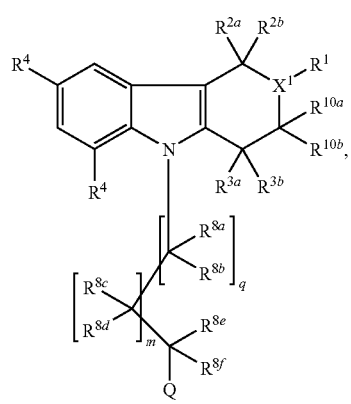 (IIIk)

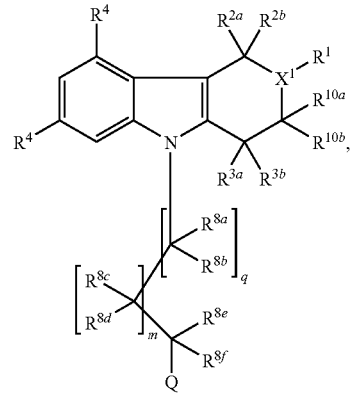 (IIIl)

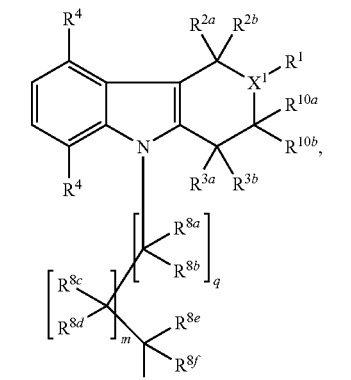 (IIIm)

where in each of (IIIa), (IIIb), (IIIc), (IIId), (IIIe), (IIIf), (IIIg), (IIIh), (IIIi), (IIIj), (IIIk), (IIIl) and (IIIm), $R^1$, $R^4$, $R^{2a}$, $R^{2b}$, $R^{3a}$, $R^{3b}$, $R^{10a}$, $R^{10b}$, $R^{8a}$-$R^{8f}$, m q and Q are as described for formula (I) or any applicable variation thereof. Where applicable, in each of (IIIa), (IIIb), (IIIc), (IIId), (IIIe), (IIIf), (IIIg), (IIIh), (IIIi), (IIIj), (IIIk), (IIIl) and (IIIm), $R^1$, $R^4$, $R^{2a}$, $R^{2b}$, $R^{3a}$, $R^{3b}$, $R^{10a}$, $R^{10b}$, $R^{8a}$-$R^{8f}$ m, q and Q may also be as described for any formulae or any applicable variation thereof detailed herein, including but not limited to formulae (A)-(G).

In one variation, the compound is of the formula (IIIa), provided that when $X^1$ is N, the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 29x, 30x, 31x, 32x, 33x, 34x, 35x, 36x, 37x, 39x, 40x, 41x, 43x, 44x, 45x, 46x, 47x, 48x, 53x, 54x, 55x, 56x, 57x, 58x, 59x, 60x, 61x, 62x, 63x, 64x, 65x, 66x, 67x, 69x, 70x, 72x, 73x, 74x, 75x, 76x, 78x, 80x, 81x, 82x, 84x, 86x, 87x, 88x, 89x, 90x, 91x, 92x, 96x, 97x, 98x, 99x, 100x, 101x, 102x, 103x, 104x, 105x and 106x, or a salt thereof. In another variation, the compound is of the formula (IIIa), wherein $X^1$ is N, $R^4$ is other than H and Q is acyclic or cyclic acylamino, acyloxy, aminoacyl or aminocarbonylalkoxy. In one such variation, the compound contains one or more of the following structural features: $R^4$ is a substituted or unsubstituted $C_1$-$C_8$ alkyl (e.g., methyl) or halo (e.g., chloro) and $R^{2a}$, $R^{3b}$, $R^{3a}$, $R^{3b}$, $R^{10a}$ and $R^{10b}$ are each H. In another variation, the compounds of the invention, and methods of using the compounds detailed herein, encompass any of the compounds of formula (IIIa), including those listed in Table 1, such as 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 29x, 30x, 31x, 32x, 33x, 34x, 35x, 36x, 37x, 39x, 40x, 41x, 43x, 44x, 45x, 46x, 47x, 48x, 53x, 54x, 55x, 56x, 57x, 58x, 59x, 60x, 61x, 62x, 63x, 64x, 65x, 66x, 67x, 69x, 70x, 72x, 73x, 74x, 75x, 76x, 78x, 80x, 81x, 82x, 84x, 86x, 87x, 88x, 89x, 90x, 91x, 92x, 96x, 97x, 98x, 99x, 100x, 101x, 102x, 103x, 104x, 105x or 106x or a salt thereof.

In one variation, the compound is of the formula (IIIb), provided that when $X^1$ is N, the compound is other than any of compounds 11x, 14x, 15x, 16x, 17x, 18x, 19x, 21x, 22x, 23x, 24x, 34x, 35x, 36x, 37x, 44x, 63x, 64x, 65x, 66x, 67x, 69x, 72x, 74x, 76x, 86x and 91x, or a salt thereof. In one variation, the compound is of the formula (IIIb) wherein $X^1$ is N and $R^4$ is chloro. In another variation, the compound is of the formula (IIIb) wherein $X^1$ is N, $R^4$ is chloro and $R^1$ is methyl. In still another variation, the compound is of the formula (IIIb) wherein $X^1$ is N, $R^4$ is chloro, $R^1$ is methyl and q is 0. In another variation, the compound is of the formula (IIIb) wherein $X^1$ is N, $R^4$ and $R^1$ are each methyl and Q is acyclic or cyclic acylamino, acyloxy, aminoacyl or aminocarbonylalkoxy. In yet another variation, the compound is of the formula (IIIb) wherein $X^1$ is N, $R^4$ and $R^1$ are each methyl and Q is acyclic or cyclic acylamino, aminoacyl or aminocarbonylalkoxy. In another variation, the compounds of the invention, and methods of using the compounds detailed herein, encompass any of the compounds of formula (IIIb), including those listed in Table 1, such as 11x, 14x, 15x, 16x, 17x, 18x, 19x, 21x, 22x, 23x, 24x, 34x, 35x, 36x, 37x, 44x, 63x, 64x, 65x, 66x, 67x, 69x, 72x, 74x, 76x, 86x or 91x or a salt thereof.

In one variation, the compound is of the formula (IIIc), provided that when $X^1$ is N, the compound is other than any of compounds 11x, 14x, 15x, 16x, 17x, 18x, 19x, 21x, 22x, 23x, 24x, 28x, 34x, 35x, 36x, 37x, 44x, 52x, 63x, 64x, 65x, 66x, 67x, 69x, 72x, 74x, 76x, 86x and 91x, or a salt thereof. In another variation, the compound is of the formula (IIIc) wherein $X^1$ is N, $R^4$ is other than H and $R^1$ is methyl. In another variation, the compounds of the invention, and methods of using the compounds detailed herein, encompass any of the compounds of formula (IIIc), including those listed in Table 1, such as 11x, 14x, 15x, 16x, 17x, 18x, 19x, 21x, 22x, 23x, 24x, 28x, 34x, 35x, 36x, 37x, 44x, 52x, 63x, 64x, 65x, 66x, 67x, 69x, 72x, 74x, 76x, 86x or 91x or a salt thereof.

In one variation, the compound is of the formula (IIId), provided that when $X^1$ is N, the compound is other than any of compounds 11x, 14x, 15x, 16x, 17x, 18x, 19x, 21x, 22x, 23x, 24x, 25x, 27x, 34x, 35x, 36x, 37x, 38x, 42x, 44x, 49x, 50x, 51x, 63x, 64x, 65x, 66x, 67x, 68x, 69x, 71x, 72x, 74x, 76x, 77x, 79x, 83x, 85x, 86x, 91x, 93x, 94x and 95x, or a salt thereof. In anther variation, the compound is of the formula (IIId) wherein $X^1$ is N, $R^4$ is other than hydrogen and Q is acyclic or cyclic acylamino, acyloxy, aminoacyl or aminocarbonylalkoxy. In another variation, the compounds of the invention, and methods of using the compounds detailed herein, encompass any of the compounds of formula (IIId), including those listed in Table 1, such as 11x, 14x, 15x, 16x, 17x, 18x, 19x, 21x, 22x, 23x, 24x, 25x, 27x, 34x, 35x, 36x, 37x, 38x, 42x, 44x, 49x, 50x, 51x, 63x, 64x, 65x, 66x, 67x, 68x, 69x, 71x, 72x, 74x, 76x, 77x, 79x, 83x, 85x, 86x, 91x, 93x, 94x or 95x or a salt thereof.

In one variation, the compound is of the formula (IIIe), provided that when $X^1$ is N, the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 28x, 29x, 30x, 31x, 32x, 33x, 34x, 35x, 36x, 37x, 39x, 40x, 41x, 43x, 44x, 45x, 46x, 47x, 48x, 52x, 53x, 54x, 55x, 56x, 57x, 58x, 59x, 60x, 61x, 62x, 63x, 64x, 65x, 66x, 67x, 69x, 70x, 72x, 73x, 74x, 75x, 76x, 78x, 80x, 81x, 82x, 84x, 86x, 87x, 88x, 89x, 90x, 91x, 92x, 96x, 97x, 98x, 99x, 100x, 101x, 102x, 103x, 104x, 105x and 106x, or a salt thereof. In another variation, the compound is of the formula (IIIe) wherein $X^1$ is N, $R^1$ is methyl and at least one of $R^4$ is chloro. In another variation, the compound is of the formula (IIIe) wherein $X^1$ is N, $R^1$ is methyl and Q is cyclic acylamino, acyloxy, aminoacyl or aminocarbonylalkoxy. In yet another variation, the compound is of the formula (IIIe) wherein $X^1$ is N, $R^1$ is methyl, at least one of $R^4$ is methyl and Q is acyclic or cyclic acylamino, acyloxy, aminoacyl or aminocarbonylalkoxy. In yet another variation, the compound is of the formula (IIIe) wherein $X^1$ is N, $R^1$ is methyl, at least one of $R^4$ is methyl and Q is acyclic or cyclic acylamino, aminocarbonylalkoxy, or acylamino. In another variation, the compounds of the invention, and methods of using the compounds detailed herein, encompass any of the compounds of formula (IIIe), including those listed in Table 1, such as 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 28x, 29x, 30x, 31x, 32x, 33x, 34x, 35x, 36x, 37x, 39x, 40x, 41x, 43x, 44x, 45x, 46x, 47x, 48x, 52x, 53x, 54x, 55x, 56x, 57x, 58x, 59x, 60x, 61x, 62x, 63x, 64x, 65x, 66x, 67x, 69x, 70x, 72x, 73x, 74x, 75x, 76x, 78x, 80x, 81x, 82x, 84x, 86x, 87x, 88x, 89x, 90x, 91x, 92x, 96x, 97x, 98x, 99x, 100x, 101x, 102x, 103x, 104x, 105x or 106x or a salt thereof.

In one variation, the compound is of the formula (IIIf), provided that when $X^1$ is N, the compound is other than any of compounds 107x and 108x, or a salt thereof. In yet another variation, the compound is of the formula (IIIf) wherein $X^1$ is N and $R^1$ is methyl. In yet another variation, the compound is of the formula (IIIf) wherein $X^1$ is N and at least one of m and q is 1. In another variation, the compounds of the invention, and methods of using the compounds detailed herein, encompass any of the compounds of formula (IIIf), including those listed in Table 1, such as 107x or 108x or a salt thereof.

In one variation, the compound is of the formula (IIIk), provided that when $X^1$ is N, the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 53x, 54x, 55x, 56x, 57x, 58x, 59x, 60x, 61x, 62x, 63x, 64x, 65x, 66x, 67x, 68x, 69x, 70x, 71x, 72x, 73x, 74x, 75x, 76x, 77x, 78x, 79x, 80x, 81x, 82x, 83x, 84x, 85x, 86x, 87x, 88x, 89x, 90x, 91x, 92x, 93x, 94x, 95x, 96x, 97x, 98x, 99x, 100x, 101x, 102x, 103x, 104x, 105x and 106x, or a salt thereof. In another variation, the compound is of the formula (IIIk) wherein $X^1$ is N, $R^1$ is methyl, at least one $R^4$ is methyl or chloro and Q is acyclic or cyclic acylamino, acyloxy, aminoacyl or aminocarbonylalkoxy. In yet another variation, the compound is of the formula (IIIk) wherein $X^1$ is N, $R^1$ is methyl, at least one $R^4$ is methyl or chloro and Q is acyclic or cyclic acylamino, aminoacyl or aminocarbonylalkoxy. In another variation, the compounds of the invention, and methods of using the compounds detailed herein, encompass any of the compounds of formula (IIIk), including those listed in Table 1, such as 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 53x, 54x, 55x, 56x, 57x, 58x, 59x, 60x, 61x, 62x, 63x, 64x, 65x, 66x, 67x, 68x, 69x, 70x, 71x, 72x, 73x, 74x, 75x, 76x, 77x, 78x, 79x, 80x, 81x, 82x, 83x, 84x, 85x, 86x, 87x, 88x, 89x, 90x, 91x, 92x, 93x, 94x, 95x, 96x, 97x, 98x, 99x, 100x, 101x, 102x, 103x, 104x, 105x or 106x or a salt thereof.

In one variation, the compound is of the formula (IIIl), provided that when $X^1$ is N, the compound is other than any of compounds 11x, 14x, 15x, 16x, 17x, 18x, 19x, 21x, 22x, 23x, 24x, 28x, 34x, 35x, 36x, 37x, 44x, 52x, 63x, 64x, 65x, 66x, 67x, 69x, 72x, 74x, 76x, 86x and 91x, or a salt thereof. In another variation, the compound is of the formula (IIIl) wherein $X^1$ is N, $R^1$ is methyl and at least one of $R^4$ is other than H. In another variation, the compounds of the invention, and methods of using the compounds detailed herein, encompass any of the compounds of formula (IIIl), including those listed in Table 1, such as 11x, 14x, 15x, 16x, 17x, 18x, 19x, 21x, 22x, 23x, 24x, 28x, 34x, 35x, 36x, 37x, 44x, 52x, 63x, 64x, 65x, 66x, 67x, 69x, 72x, 74x, 76x, 86x or 91x or a salt thereof.

In one variation, the compound is of the formula (IIIm), provided that when $X^1$ is N, the compound is other than any of compounds 11x, 14x, 15x, 16x, 17x, 18x, 19x, 21x, 22x, 23x, 24x, 25x, 27x, 34x, 35x, 36x, 37x, 38x, 42x, 44x, 49x, 50x, 51x, 63x, 64x, 65x, 66x, 67x, 68x, 69x, 71x, 72x, 74x, 76x, 77x, 79x, 83x, 85x, 86x, 91x, 93x, 94x and 95x, or a salt thereof. In another variation, the compound is of the formula (IIIm) wherein $X^1$ is N and each $R^4$ is other than H. In another variation, the compound is of the formula (IIIm) wherein $X^1$ is N, $R^1$ is methyl and Q is cyclic acylamino, acyloxy, aminoacyl or aminocarbonylalkoxy. In another variation, the compounds of the invention, and methods of using the compounds detailed herein, encompass any of the compounds of formula (IIIm), including those listed in Table 1, such as 1x, 14x, 15x, 16x, 17x, 18x, 19x, 21x, 22x, 23x, 24x, 25x, 27x, 34x, 35x, 36x, 37x, 38x, 42x, 44x, 49x, 50x, 51x, 63x, 64x, 65x, 66x, 67x, 68x, 69x, 71x, 72x, 74x, 76x, 77x, 79x, 83x, 85x, 86x, 91x, 93x, 94x or 95x or a salt thereof.

Compounds of the formulae (IVa), (IVb), (IVc), (IVd), (IVe), (IVf), (IVg), (IVh), (IVi), (IVj) and (IVk) are further embraced by this invention:

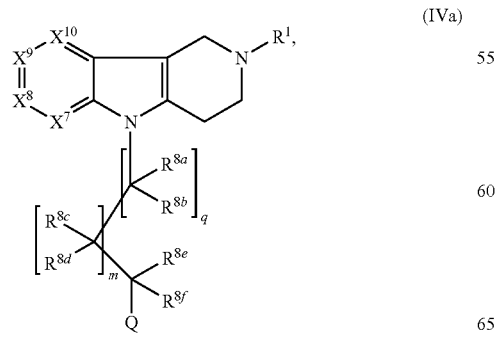
(IVa)

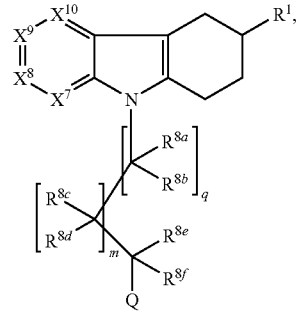
(IVb)

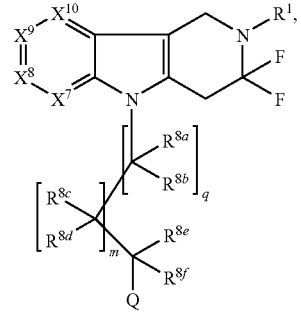
(IVc)

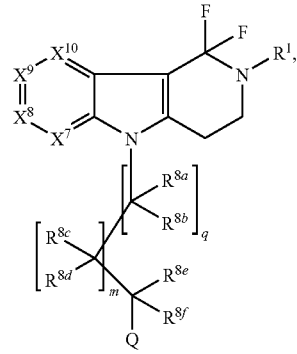
(IVd)

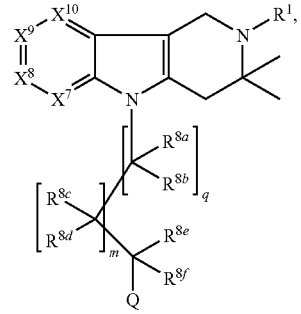
(IVe)

-continued

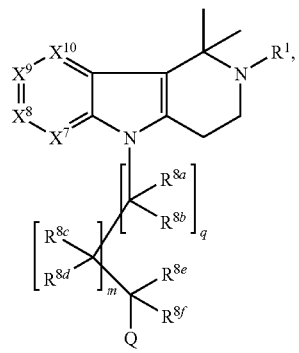
(IVf)

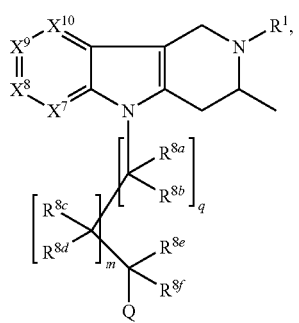
(IVg)

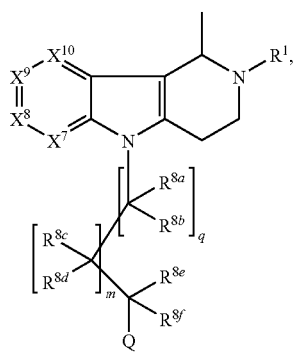
(IVh)

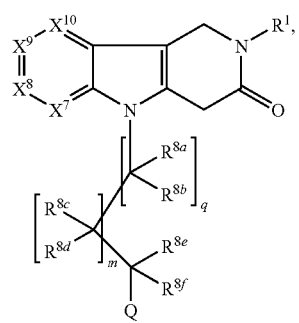
(IVi)

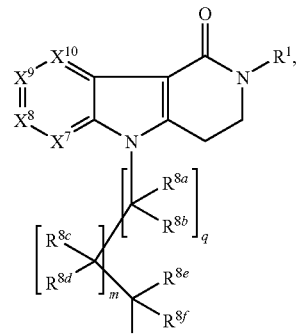
(IVj)

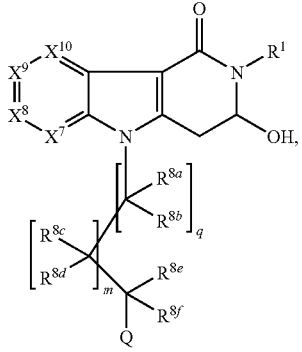
(IVk)

where in each of (IVa), (IVb), (IVc), (IVd), (IVe), (IVf), (IVg), (IVh), (IVi), (IVj) and (IVk), $R^1$, $X^7$, $X^8$, $X^9$, $X^{10}$, $R^{8a}$-$R^{8f}$, m, q and Q are as described for formula (I) or any applicable variation thereof. Where applicable, in each of (IVa), (IVb), (IVc), (IVd), (IVe), (IVf), (IVg), (IVh), (IVi), (IVj) and (IVk), $R^1$, $X^7$, $X^8$, $X^9$, $X^{10}$, $R^{8a}$-$R^{8f}$, m, q and Q may also be as described for any formulae or any applicable variation thereof detailed herein, including but not limited to formulae (A)-(G).

In one variation, the compound is of the formula (IVa), provided that the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 52x, 53x, 54x, 55x, 56x, 57x, 58x, 59x, 60x, 61x, 62x, 63x, 64x, 68x, 69x, 70x, 71x, 72x, 73x, 74x, 75x, 76x, 77x, 78x, 79x, 80x, 81x, 82x, 83x, 84x, 85x, 86x, 87x, 88x, 89x, 90x, 91x, 92x, 93x, 94x, 95x, 97x, 98x, 99x, 100x, 101x, 102x, 103x, 104x, 105x, 106x, 107x, 108x, 109x and 110x, or a salt thereof. In one variation, the compound is of the formula (IVa) wherein m and q are each 1. In one such variation, m and q are each 1 and $R^1$ is methyl. In another such variation, m and q are each 1 and $R^1$ is methyl and $X^9$ is N or $CR^4$ where $R^4$ is $C_1$-$C_8$alkyl (e.g., methyl) or halo (e.g., chloro). In another variation, the compound is of the formula (IVa) wherein $R^1$ is methyl and Q is cyclic acylamino, acyloxy, aminoacyl or aminocarbonylalkoxy. In another variation, the compound is of the formula (IVa) wherein $R^1$ is methyl and at least one of $X^7$-$X^{10}$ is $CR^4$ where $R^4$ is chloro. In another variation, the compounds of the invention, and methods of using the compounds detailed herein, encompass any of the compounds of formula (IVa), including those listed in Table 1, such as 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 25x, 26x, 27x, 28x, 29x, 30x, 31x, 32x, 33x, 34x, 35x, 36x, 37x, 38x, 39x, 40x, 41x, 42x, 43x, 44x, 45x, 46x, 47x, 48x, 49x, 50x, 51x, 52x, 53x, 54x, 55x, 56x, 57x, 58x, 59x, 60x, 61x, 62x, 63x, 64x, 68x, 69x, 70x, 71x, 72x, 73x, 74x, 75x, 76x, 77x, 78x, 79x, 80x, 81x, 82x, 83x, 84x, 85x, 86x, 87x, 88x, 89x, 90x, 91x, 92x, 93x, 94x, 95x, 97x, 98x, 99x, 100x, 101x, 102x, 103x, 104x, 105x, 106x, 107x, 108x, 109x or 110x or a salt thereof.
The invention also embraces compounds of the formulae (Va)-(Vzf):
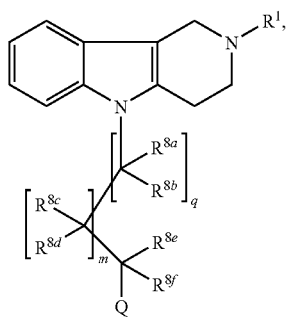
(Va)
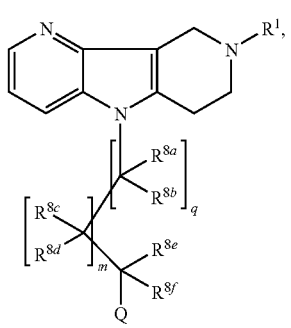
(Vb)
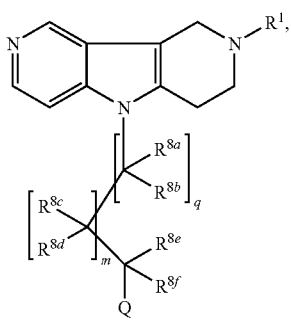
(Vc)
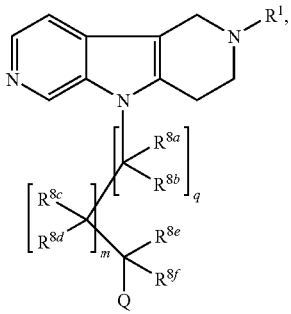
(Vd)
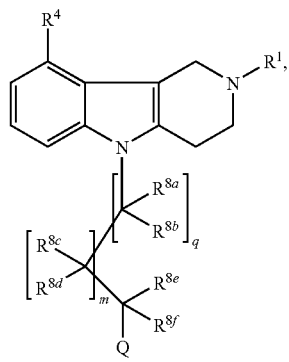
(Ve)
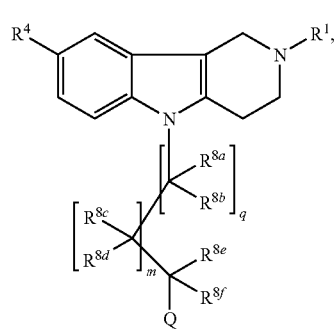
(Vf)
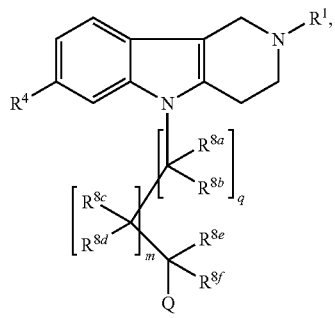
(Vg)
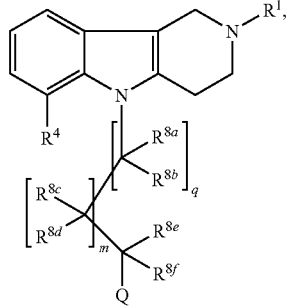
(Vh)
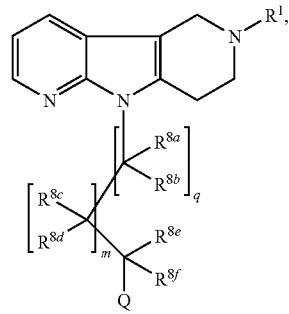
(Vi)

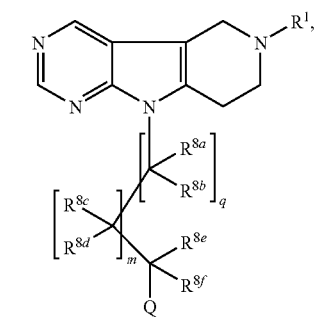
(Vj)
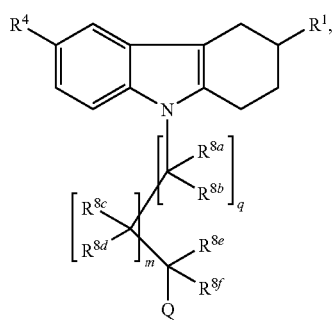
(Vk)
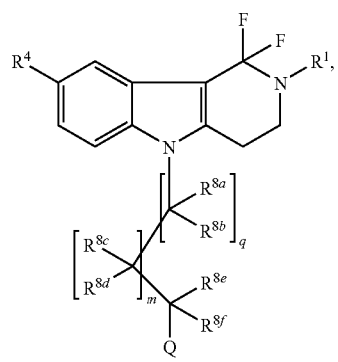
(Vl)
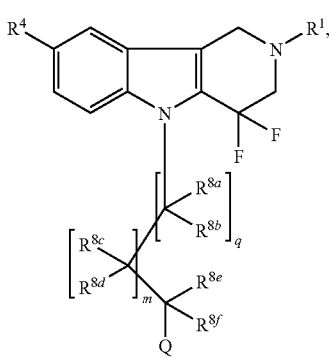
(Vm)
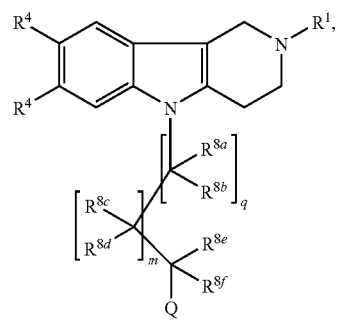
(Vn)
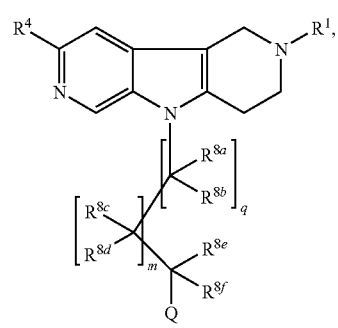
(Vo)
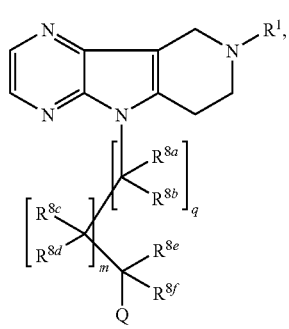
(Vp)
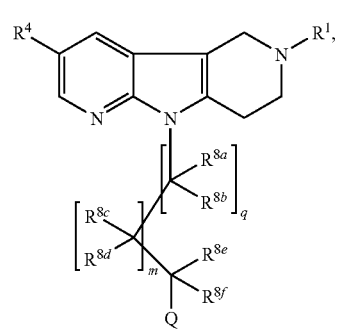
(Vq)
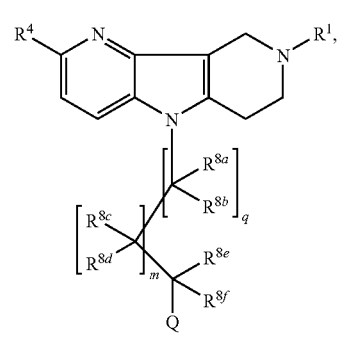
(Vr)

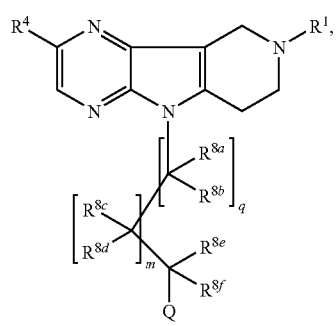 (Vs)
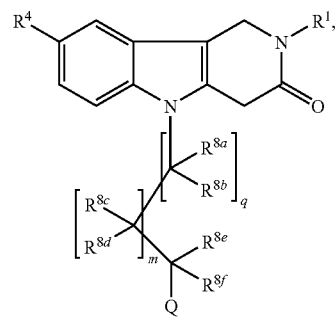 (Vx)
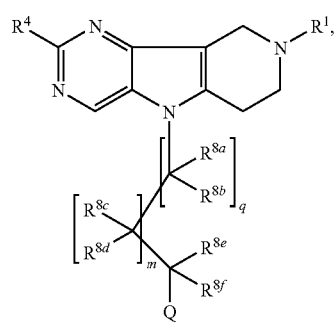 (Vt)
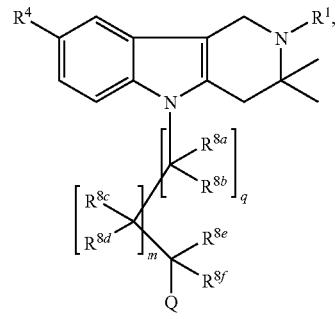 (Vy)
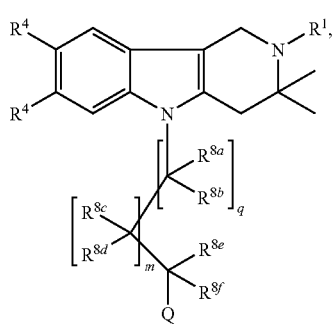 (Vu)
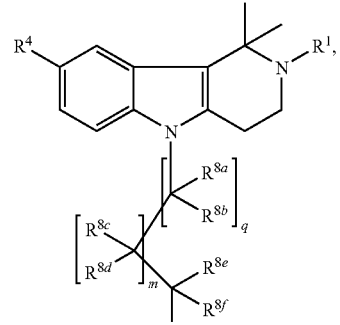 (Vz)
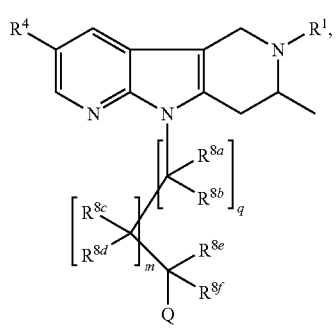 (Vv)
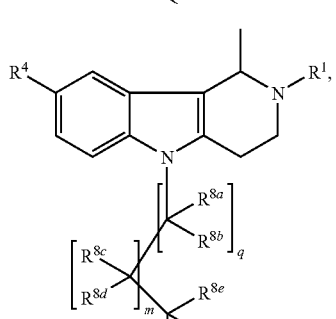 (Vza)
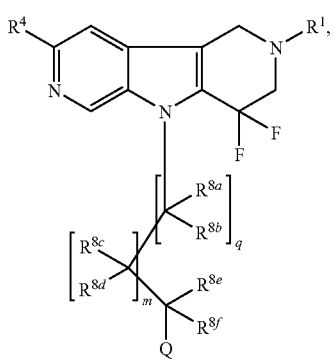 (Vw)
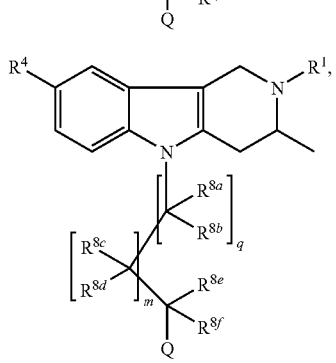 (Vzb)

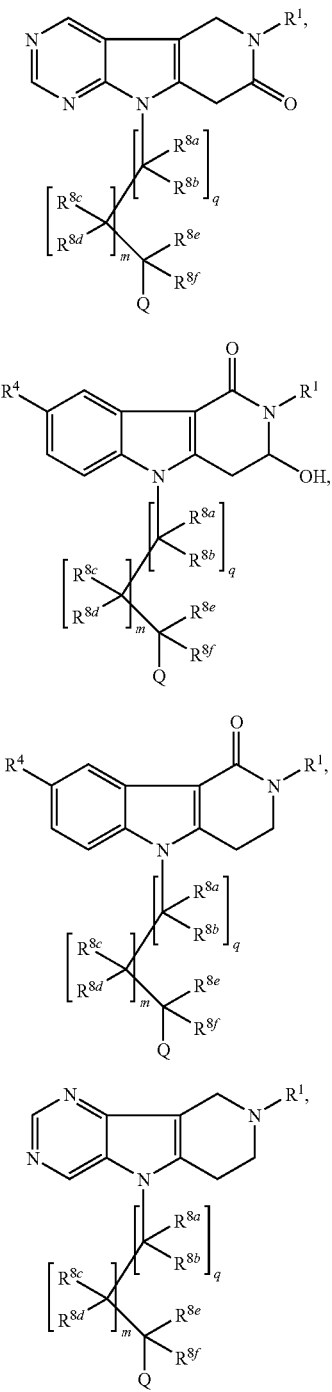

or a salt thereof. In one variation, the compound is of the formula (Va) wherein at least one of (i)-(iv) apply: (i) at least one of m and q is 1 and Q is cyclic acylamino, acyloxy, aminoacyl or aminocarbonylalkoxy; (ii) Q is aminoacyl or aminocarvonylalkoxy; (iii) $R^1$ is methyl and Q is cyclic acylamino, acyloxy, aminoacyl or aminocarbonylalkoxy; (iv) both m and q are 1. In one variation, at least two of (i)-(iv) apply. In another variation, the compounds of the invention, and methods of using the compounds detailed herein, encompass any of the compounds of formula (Va), including those listed in Table 1, such as 11x, 14x, 15x, 16x, 17x, 18x, 19x, 21x, 22x, 23x, 24x, 34x, 35x, 36x, 37x, 44x, 63x, 64x, 69x, 72x, 74x, 76x, 86x or 91x or a salt thereof.

In one variation, the compound is of the formula (Vc), provided that the compound is other than any of compounds 109x and 110x, or a salt thereof. In another variation, the compound is of the formula (Vc) wherein at least one of (i)-(iii) apply: (i) $R^1$ is methyl; (ii) at least one of m and q is 1; (iii) Q is carbonylalkoxy, acyloxy, aminoacyl or aminocarbonylalkoxy. In one such variation, at least two of (i)-(iii) apply. In yet another variation, the compound is of the formula (Vc) wherein Q is aminoacyl or carbonyl alkoxy. In still another variation, the compound is of the formula (Vc) wherein Q is aminoacyl or carbonyl alkoxy and $R^1$ is methyl. In one variation, the compound is of the formula (Vc) where $R^1$ is other than isopropyl. In another variation, the compounds of the invention, and methods of using the compounds detailed herein, encompass any of the compounds of formula (Vc), including those listed in Table 1, such as 109x or 110x or a salt thereof.

In one variation, the compound is of the formula (Vd), provided that the compound is other than any of compounds 107x and 108x, or a salt thereof. In anther variation, the compound is of the formula (Vd) wherein Q is carbonylalkoxy, acyloxy, aminoacyl or aminocarbonylalkoxy. In another variation, the compounds of the invention, and methods of using the compounds detailed herein, encompass any of the compounds of formula (Vd), including those listed in Table 1, such as 107x or 108x or a salt thereof.

In one variation, the compound is of the formula (Ve), provided that the compound is other than any of compounds 11x, 14x, 15x, 16x, 17x, 18x, 19x, 21x, 22x, 23x, 24x, 34x, 35x, 36x, 37x, 44x, 63x, 64x, 69x, 72x, 74x, 76x, 86x and 91x, or a salt thereof. In one variation, the compound is of the formula (Ve) wherein Q is aminoacyl or aminocarbonylalkoxy. In another variation, the compounds of the invention, and methods of using the compounds detailed herein, encompass any of the compounds of formula (Ve), including those listed in Table 1, such as 11x, 14x, 15x, 16x, 17x, 18x, 19x, 21x, 22x, 23x, 24x, 34x, 35x, 36x, 37x, 44x, 63x, 64x, 69x, 72x, 74x, 76x, 86x or 91x or a salt thereof.

In one variation, the compound is of the formula (Vf), provided that the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 29x, 30x, 31x, 32x, 33x, 34x, 35x, 36x, 37x, 39x, 40x, 41x, 43x, 44x, 45x, 46x, 47x, 48x, 53x, 54x, 55x, 56x, 57x, 58x, 59x, 60x, 61x, 62x, 63x, 64x, 69x, 70x, 72x, 73x, 74x, 75x, 76x, 78x, 80x, 81x, 82x, 84x, 86x, 87x, 88x, 89x, 90x, 91x, 92x, 97x, 98x, 99x, 100x, 101x, 102x, 103x, 104x, 105x and 106x, or a salt thereof. In one variation, the compound is of the formula (Vf) wherein $R^1$ is methyl and Q is cyclic acylamino, acyloxy, aminoacyl or aminocarbonylalkoxy. In another variation, the compound is of the formula (Vf) wherein m and q are each 1. In another variation, the compound is of the formula (Vf) wherein $R^1$ is methyl and $R^4$ is chloro. In yet another variation, the compound is of the formula (Vf) wherein $R^1$ is where in each of (Va)-(Vzf), $R^1$, $R^4$, $R^{8a}$-$R^{8f}$, m, q and Q are as described for formula (I) or any applicable variation thereof. In one variation the invention relates to a compound of the formula (Vc) or (Vf). Where applicable, in each of (Va)-(Vzf), $R^1$, $R^4$, $R^{8a}$-$R^{8f}$, m, q and Q may also be as described for any formulae or any applicable variation thereof detailed herein, including but not limited to formulae (A)-(G).

In one variation, the compound is of the formula (Va), provided that the compound is other than any of compounds 11x, 14x, 15x, 16x, 17x, 18x, 19x, 21x, 22x, 23x, 24x, 34x, 35x, 36x, 37x, 44x, 63x, 64x, 69x, 72x, 74x, 76x, 86x and 91x, methyl, $R^4$ is methyl and Q is acyclic or cyclic acylamino, acyloxy, aminoacyl or aminocarbonylalkoxy. In another variation, the compound is of the formula (Vf) wherein $R^1$ is methyl, $R^4$ is methyl and Q is acyclic or cyclic acylamino, acyloxy, aminoacyl or aminocarbonylalkoxy. In one variation, the compound is of the formula (Vf) where $R^1$ is methyl, $R^4$ is other than H and Q is other than —C(O)O-ethyl. In another variation, the compound is of the formula (Vf) where $R^1$ and $R^4$ are methyl and Q is other than —C(O)O-ethyl. In yet another variation, the compound is of the formula (Vf) where $R^1$ and $R^4$ are methyl and Q is acyclic acylamino, acyloxy, aminoacyl or aminocarbonylalkoxy. In another variation, the compounds of the invention, and methods of using the compounds detailed herein, encompass any of the compounds of formula (Vf), including those listed in Table 1, such as 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 29x, 30x, 31x, 32x, 33x, 34x, 35x, 36x, 37x, 39x, 40x, 41x, 43x, 44x, 45x, 46x, 47x, 48x, 53x, 54x, 55x, 56x, 57x, 58x, 59x, 60x, 61x, 62x, 63x, 64x, 69x, 70x, 72x, 73x, 74x, 75x, 76x, 78x, 80x, 81x, 82x, 84x, 86x, 87x, 88x, 89x, 90x, 91x, 92x, 97x, 98x, 99x, 100x, 101x, 102x, 103x, 104x, 105x or 106x or a salt thereof.

In one variation, the compound is of the formula (Vg), provided that the compound is other than any of compounds 11x, 14x, 15x, 16x, 17x, 18x, 19x, 21x, 22x, 23x, 24x, 28x, 34x, 35x, 36x, 37x, 44x, 52x, 63x, 64x, 69x, 72x, 74x, 76x, 86x and 91x, or a salt thereof. In one variation, the compound is of the formula (Vg) wherein at least one of (i)-(iii) applies: (1) both of m and q are 1; (2) when one of m and q is 1 and the other is 0, then $R^4$ is other than H; (3) Q is aminoacyl or aminocarbonylalkoxy. In another variation, the compounds of the invention, and methods of using the compounds detailed herein, encompass any of the compounds of formula (Vg), including those listed in Table 1, such as 11x, 14x, 15x, 16x, 17x, 18x, 19x, 21x, 22x, 23x, 24x, 28x, 34x, 35x, 36x, 37x, 44x, 52x, 63x, 64x, 69x, 72x, 74x, 76x, 86x or 91x or a salt thereof.

In one variation, the compound is of the formula (Vh), provided that the compound is other than any of compounds 11x, 14x, 15x, 16x, 17x, 18x, 19x, 21x, 22x, 23x, 24x, 25x, 27x, 34x, 35x, 36x, 37x, 38x, 42x, 44x, 49x, 50x, 51x, 63x, 64x, 68x, 69x, 71x, 72x, 74x, 76x, 77x, 79x, 83x, 85x, 86x, 91x, 93x, 94x and 95x, or a salt thereof. In one variation, the compound is of the formula (Vh) wherein at least one of (i)-(iii) applies: (1) both of m and q are 1; (2) when one of m and q is 1 and the other is 0, then Q cyclic acylamino, acyloxy, aminoacyl or aminocarbonylalkoxy; (3) Q is aminoacyl or aminocarbonylalkoxy. In another variation, the compounds of the invention, and methods of using the compounds detailed herein, encompass any of the compounds of formula (Vh), including those listed in Table 1, such as 11x, 14x, 15x, 16x, 17x, 18x, 19x, 21x, 22x, 23x, 24x, 25x, 27x, 34x, 35x, 36x, 37x, 38x, 42x, 44x, 49x, 50x, 51x, 63x, 64x, 68x, 69x, 71x, 72x, 74x, 76x, 77x, 79x, 83x, 85x, 86x, 91x, 93x, 94x and 95x or a salt thereof.

In one variation, the compound is of the formula (Vn), provided that the compound is other than any of compounds 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 28x, 29x, 30x, 31x, 32x, 33x, 34x, 35x, 36x, 37x, 39x, 40x, 41x, 43x, 44x, 45x, 46x, 47x, 48x, 52x, 53x, 54x, 55x, 56x, 57x, 58x, 59x, 60x, 61x, 62x, 63x, 64x, 69x, 70x, 72x, 73x, 74x, 75x, 76x, 78x, 80x, 81x, 82x, 84x, 86x, 87x, 88x, 89x, 90x, 91x, 92x, 97x, 98x, 99x, 100x, 101x, 102x, 103x, 104x, 105x and 106x, or a salt thereof. In one variation, the compound is of the formula (Vn) wherein $R^1$ is methyl and at least one of (i)-(iii) applies: (i) at least one of $R^4$ is chloro; (ii) m and q are each 1; and (iii) Q is cyclic acylamino, acyloxy, aminoacyl or aminocarbonylalkoxy. In one such variation, at least two of (i)-(iii) apply. In another variation, the compounds of the invention, and methods of using the compounds detailed herein, encompass any of the compounds of formula (Vn), including those listed in Table 1, such as 1x, 2x, 3x, 4x, 5x, 6x, 7x, 8x, 9x, 10x, 11x, 12x, 13x, 14x, 15x, 16x, 17x, 18x, 19x, 20x, 21x, 22x, 23x, 24x, 26x, 28x, 29x, 30x, 31x, 32x, 33x, 34x, 35x, 36x, 37x, 39x, 40x, 41x, 43x, 44x, 45x, 46x, 47x, 48x, 52x, 53x, 54x, 55x, 56x, 57x, 58x, 59x, 60x, 61x, 62x, 63x, 64x, 69x, 70x, 72x, 73x, 74x, 75x, 76x, 78x, 80x, 81x, 82x, 84x, 86x, 87x, 88x, 89x, 90x, 91x, 92x, 97x, 98x, 99x, 100x, 101x, 102x, 103x, 104x, 105x or 106x or a salt thereof.

In one variation, the compound is of the formula (Vo), provided that the compound is other than any of compounds 107x and 108x, or a salt thereof. In one variation, the compound is of the formula (Vo) wherein $R^1$ is methyl. In another variation, the compounds of the invention, and methods of using the compounds detailed herein, encompass any of the compounds of formula (Vo), including those listed in Table 1, such as 107x or 108x or a salt thereof.

In one variation, a compound of the invention is of the formula (I) or (Ia) or any variation of the foregoing detailed herein, or is of any one of the formulae (IIa)-(IIh), (IIIa)-(IIIm), (IVa)-(IVk) or (Va)-(Vzf), where each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R^{8(e-f)}$ to form a cycloalkyl moiety. Where applicable, such variations apply equally to any formulae detailed herein, such as formula (A)-(G). In another variation, a compound of the invention is of the formula (I) or (Ia) or any variation of the foregoing detailed herein, or is of any one of the formulae (IIa)-(IIh), (IIIa)-(IIIm), (IVa)-(IVk) or (Va)-(Vzf), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^{8(a-f)}$ to form a cyclopropyl moiety. Where applicable, such variations apply equally to any formulae detailed herein, such as formula (A)-(G). In yet another variation, a compound of the invention is of the formula (I) or (Ia) or any variation of the foregoing detailed herein, or is any one of the formulae (IIa)-(IIh), (IIIa)-(IIIm), (IVa)-(IVk) or (Va)-(Vzf), where wherein q is 0 and m is 1. Where applicable, such variations apply equally to any formulae detailed herein, such as formula (A)-(G). The invention also embraces a compound of the invention according to formula (I) or (Ia) or any variation of the foregoing detailed herein, or a compound according to any one of the formulae (IIa)-(IIh), (IIIa)-(IIIm), (IVa)-(IVk) or (Va)-(Vzf), where q and m are both 0. Where applicable, such variations apply equally to any formulae detailed herein, such as formula (A)-(G). The invention further embraces a compound according to formula (I) or (Ia) or any variation of the foregoing detailed herein, or a compound according to any one of the formulae (IIa)-(IIh), (IIa)-(IIIm), (IVa)-(IVk) or (Va)-(Vzf), where q, m, $R^{8a}$, $R^{8b}$, $R^{8c}$, $R^{8d}$, $R^{8e}$ and $R^{8f}$ are taken together to form a moiety selected from the group consisting of: —CH$_2$—, —CH$_2$CH$_2$—, —CH$_2$CH$_2$CH$_2$—, —CH$_2$—C(H)(OH)—, —C(H)(OH)—CH$_2$—, —CH$_2$—C(OH)(CH$_3$)—, —C(OH)(CH$_3$)—CH$_2$—, —CH$_2$—C(H)(CH$_3$)—, —C(H)(CH$_3$)—CH$_2$—, —CH$_2$—C(CH$_3$)(CH$_3$)—, —C(CH$_2$CH$_2$)—CH$_2$— and —CH$_2$—C(CH$_2$CH$_2$)—. Where applicable, such variations apply equally to any formulae detailed herein, such as formula (A)-(G).

In another variation, a compound of the invention is of the formula (I) or (Ia) or any variation of the foregoing detailed herein, or a compound according to any one of the formulae (IIIa)-(IIIm), (IVa)-(IVk) or (Va)-(Vzf), where each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl. In yet another variation, a compound of the invention is of the formula (I) or (Ia) or any variation of the foregoing detailed herein, or a compound according to any one of the formulae (IIIa)-(IIIm), (IVa)-(IVk) or (Va)-(Vzf), where each $R^4$ is independently H or a substituted or unsubstituted $C_1$-$C_8$ alkyl. In still another variation, a compound of the invention is of the formula (I) or (Ia) or any variation of the foregoing detailed herein, or a compound according to any one of the formulae (IIIa)-(IIIm), (IVa)-(IVk) or (Va)-(Vzf), where each $R^4$ is H. The invention also embraces compounds of the formula (I) or (Ia) or any variation of the foregoing detailed herein, or a compound according to any one of the formulae (IIIa)-(IIIm), (IVa)-(IVk) or (Va)-(Vzf), where each $R^4$ is independently H, halo, unsubstituted $C_1$-$C_4$ alkyl, $C_1$-$C_4$ perhaloalkyl or a substituted or unsubstituted aryl. The invention further embraces compounds of the formula (I) or (Ia) or any variation of the foregoing detailed herein, or a compound according to any one of the formulae (IIIa)-(IIIm), (IVa)-(IVk) or (Va)-(Vzf) where each $R^4$ is independently H, halo, methyl, perfluoromethyl or cyclopropyl.

The invention also embraces compounds of the formula (I), (E) or (Ia) or any variation of the foregoing detailed herein, or a compound according to any one of the formulae (IIa)-(IIh), (IIa)-(IIIm), (IVa)-(IVk) or (Va)-(Vzf) where Q is an aminoacyl moiety. In one variation, Q is an aminoacyl group where at least one of $R_a$ and $R_b$ is H, such as when Q is of the formula —NHC(O)$R_b$. In one variation, Q is an aminoacyl moiety selected from the group consisting of: —NHC(O)-heterocyclyl, —NHC(O)-substituted heterocyclyl, —NHC(O)-alkyl, —NHC(O)-cycloalkyl, —NHC(O)-alkaryl and —NHC(O)-substituted aryl. In another variation, Q is an aminoacyl moiety selected from the group consisting of: —NHC(O)—$C_5$-$C_7$heterocyclyl, —NHC(O)—$C_1$-$C_6$alkyl, —NHC(O)—$C_3$-$C_7$cycloalkyl, —NHC(O)—$C_1$-$C_3$alkaryl and —NHC(O)-substituted phenyl. In a particular is a moiety of the formula:

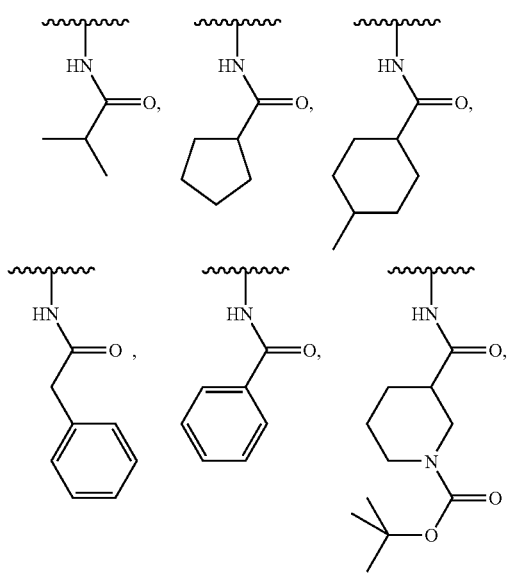

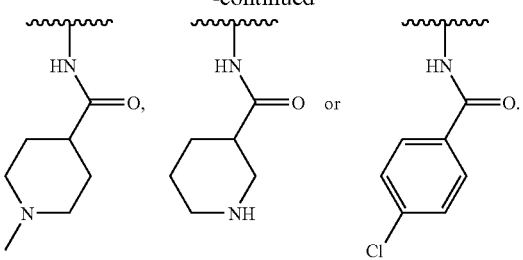

In one variation, a compound of the invention is of the formula (I), (E) or (Ia) or any variation of the foregoing detailed herein, or a compound according to any one of the formulae (IIa)-(IIh), (IIIa)-(IIIm), (IVa)-(IVk) or (Va)-(Vzf) where Q is acyloxy.

In one variation, a compound of the invention is of the formula (I), (E) or (Ia) or any variation of the foregoing detailed herein, or a compound according to any one of the formulae (IIa)-(IIh), (IIIa)-(IIIm), (IVa)-(IVk) or (Va)-(Vzf) where Q is a carbonylalkoxy moiety. In one variation, Q is a carbonylalkoxy moiety of the formula —C(O)—O—R where R is H, alkyl, substituted alkyl or alkaryl. In one variation, Q is carbonylalkoxy moiety of the formula —C(O)—O—$C_1$-$C_6$alkyl. In a particular variation, Q is a carbonylalkoxy moiety of the formula —C(O)—O—$C_2H_5$. In one variation, Q is a carbonylalkoxy moiety selected from the group consisting of: —C(O)—O—$C_1$-$C_{10}$alkyl, —C(O)—O—$C_1$-$C_3$alkaryl, —C(O)—O—$C_1$-$C_3$ substituted alkyl and —C(O)—OH. In another variation, Q is —C(O)—O—$C_1$-$C_6$alkyl. In a particular variation, Q is a moiety of the formula:

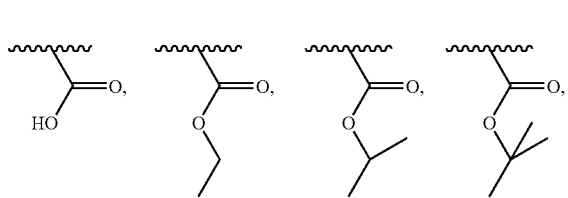

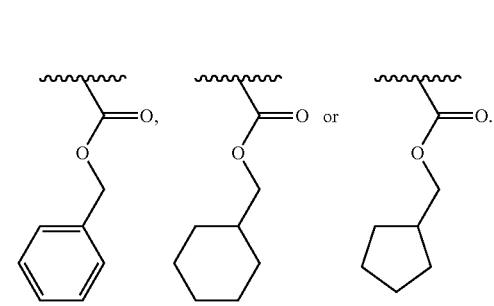

In another particular variation, Q is a moiety of the formula:

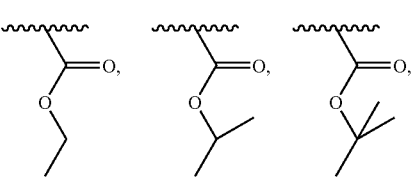

-continued

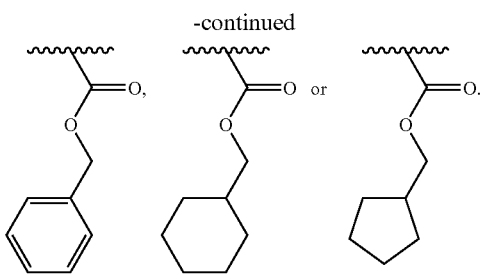

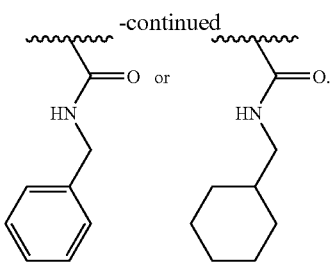

In another variation, a compound of the invention is of the formula (I), (E) or (Ia) or any variation of the foregoing detailed herein, or a compound according to any one of the formulae (IIa)-(IIh), (IIIa)-(IIIm), (IVa)-(IVk) or (Va)-(Vzf) where Q is an aminocarbonylalkoxy moiety. In one variation, Q is an aminocarbonylalkoxy moiety of the formula —NHC(O)—O—$R_b$. In another variation, Q is an aminocarbonylalkoxy moiety of the formula —NHC(O)—O—$R_b$ where $R_b$ is a substituted alkyl group. In a particular variation, Q is a moiety of the formula —NH—C(O)—O—$CH_2$—$C(Cl)_3$.

The invention also embraces compounds of the formula (I), (E) or (Ia) or any variation of the foregoing detailed herein, or a compound according to any one of the formulae (IIa)-(IIh), (IIa)-(IIIm), (IVa)-(IVk) or (Va)-(Vzf) where Q is an acylamino moiety. In one variation, Q is an acylamino group where at least one of $R_a$ and $R_b$ is H, such as when Q is of the formula —C(O)N(H)($R_b$). In another variation, Q is an acylamino group where both $R_a$ and $R_b$ are alkyl. In one variation, Q is an acylamino moiety selected from the group consisting of: —C(O)—N(H)(alkyl), —C(O)—N(alkyl)$_2$, —C(O)—N(H)(alkaryl) and —C(O)—N(H)(aryl). In another variation, Q is an acylamino moiety selected from the group consisting of: —C(O)—N(H)$_2$, —C(O)—N(H)($C_1$-$C_8$alkyl), —C(O)—N($C_1$-$C_6$alkyl)$_2$ and —C(O)—N(H)($C_1$-$C_3$alkaryl). In a particular variation, Q is a moiety of the formula:

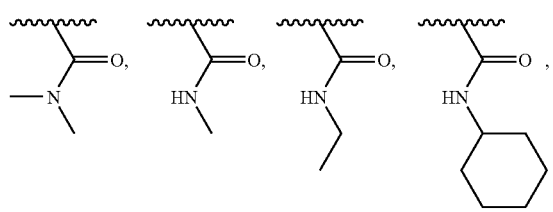

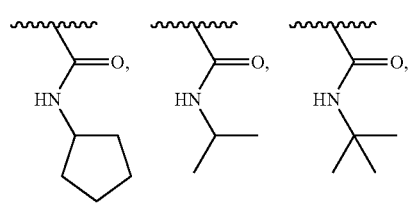

In yet a further variation, a compound of the invention is of the formula (I) where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$, where $R^4$ is as defined in formula (I) or in a particular variation, $R^4$ is H, halo, pyridyl, methyl or trifluoromethyl; $R^{10a}$ and $R^{10b}$ are both H. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl. In another variation, a compound of the variation detailed herein is provided wherein $R^1$ is propyl, methyl, ethyl, cyclopropyl, trifluoromethyl, isopropyl, tert-butyl, sec-butyl, 2-methylbutyl, propanoyl, 1-methyl-2-hydroxyethyl, 2-hydroxyethanoyl, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is of the formula (I) where $R^1$ is a substituted or unsubstituted $C_1$-$C_8$ alkyl; each $R^{2a}$, $R^{2b}$, $R^{3a}$ and $R^{3b}$ is independently H or halo; $X^1$ is N; each $R^4$ is independently H, halo, $C_1$-$C_8$ perhaloalkyl, substituted or a unsubstituted $C_1$-$C_8$ alkyl; each $R^{8a}$, $R^{8b}$, $R^{8c}$, $R^{8d}$, $R^{8e}$ and $R^{8f}$ is H. The invention also embraces a compound of the formula (I) where $R^1$ is a methyl; at least one of $X^7$, $X^8$, $X^9$ and $X^{10}$ is $CR^4$, and each $R^4$ is independently H, halo, methyl or trifluoromethyl.

In a particular variation, the compound is of the formula (I) where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; $X^1$ is N, each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl, provided that at least one of $R^{10a}$ and $R^{10b}$ is other than H. In yet another aspect of this variation, $X^7$, $X^8$, $X^9$ and $X^{10}$ are $CR^4$ and each $R^4$ is independently H, halo or methyl.

Examples of compounds according to the invention are depicted in Table 2. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2
Representative Compounds According to the Invention.
| Compound No. | Structure | CD# |
|---|---|---|
| 1 | 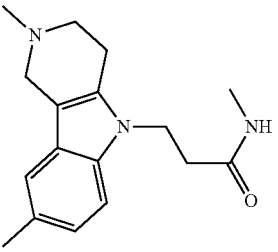 [SMILES: CNC(=O)CCn1c2c(c3cc(C)ccc31)CN(C)CC2] | CD2 |
| 2 | 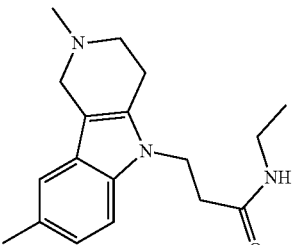 | CD3 |
| 3 | 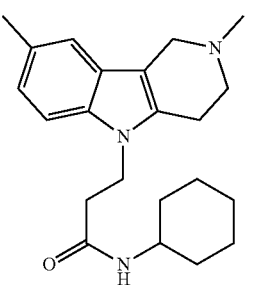 | CD4 |
| 4 | 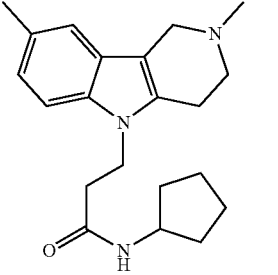 | CD5 |
| 5 | 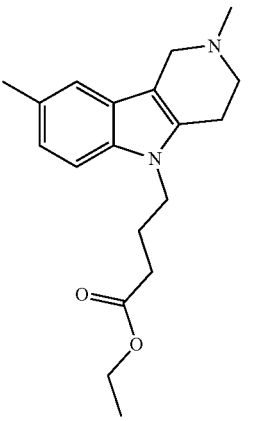 [SMILES: CCOC(=O)CCCn1c2c(c3cc(C)ccc31)CN(C)CC2] | CD6 |

TABLE 2-continued

Representative Compounds According to the Invention.

| Compound No. | Structure | CD# |
|---|---|---|
| 6 | 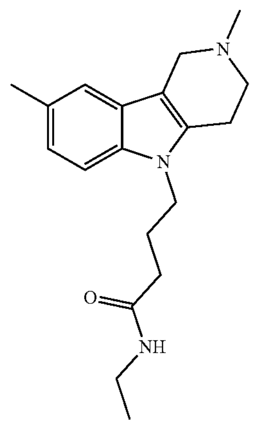 [SMILES: CCNC(=O)CCCn1c2c(c3cc(C)ccc31)CN(C)CC2] | CD7 |
| 7 | 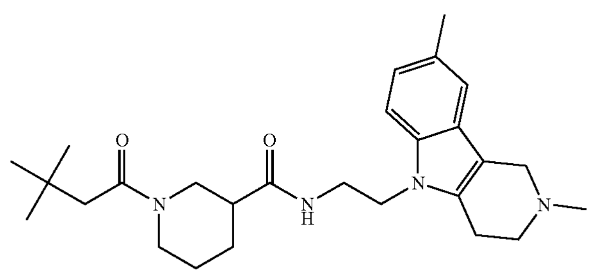 [SMILES: Cc1ccc2c(c1)c1c(n2CCNC(=O)C2CCCN(C(=O)CC(C)(C)C)C2)CCN(C)C1] | CD8 |
| 8 | 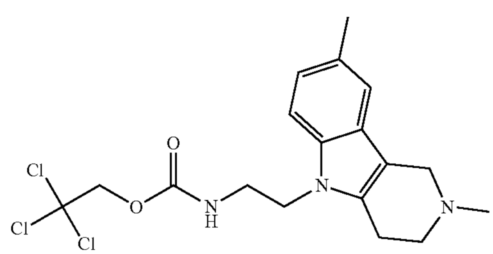 [SMILES: Cc1ccc2c(c1)c1c(n2CCNC(=O)OCC(Cl)(Cl)Cl)CCN(C)C1] | CD9 |
| 9 | 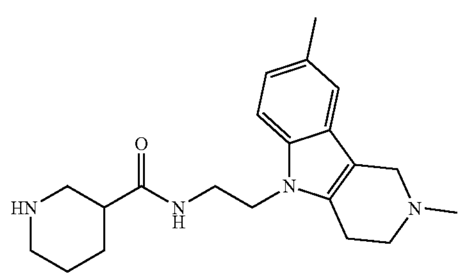 [SMILES: Cc1ccc2c(c1)c1c(n2CCNC(=O)C2CCCNC2)CCN(C)C1] | CD10 |
| 10 | 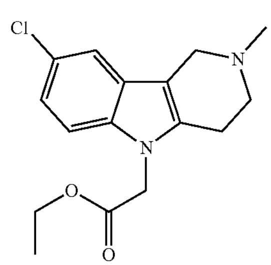 [SMILES: CCOC(=O)Cn1c2c(c3cc(Cl)ccc31)CN(C)CC2] | CD11 |

TABLE 2-continued

Representative Compounds According to the Invention.

| Compound No. | Structure | CD# |
|---|---|---|
| 11 | (8-Cl-2-methyl-2,3,4,5-tetrahydro-1H-pyrido[4,3-b]indol-5-yl)acetic acid isopropyl ester | CD12 |
| 12 | (8-Cl-2-methyl-2,3,4,5-tetrahydro-1H-pyrido[4,3-b]indol-5-yl)acetic acid tert-butyl ester | CD13 |
| 13 | (8-Cl-2-methyl-2,3,4,5-tetrahydro-1H-pyrido[4,3-b]indol-5-yl)acetic acid benzyl ester | CD14 |
| 14 | (8-Cl-2-methyl-2,3,4,5-tetrahydro-1H-pyrido[4,3-b]indol-5-yl)acetic acid cyclohexylmethyl ester | CD15 |
| 15 | (8-Cl-2-methyl-2,3,4,5-tetrahydro-1H-pyrido[4,3-b]indol-5-yl)acetic acid cyclopentyl ester | CD16 |

TABLE 2-continued
Representative Compounds According to the Invention.
| Compound No. | Structure | CD# |
|---|---|---|
| 16 | 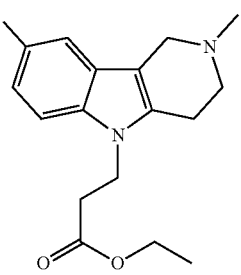 | CD17 |
| 17 | 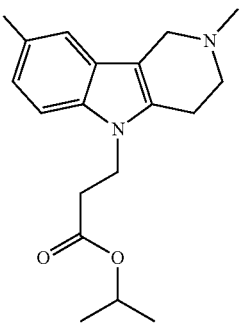 | CD18 |
| 18 | 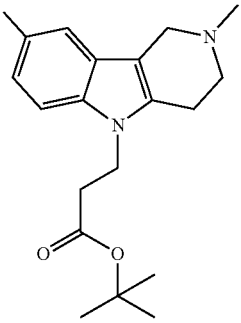 | CD19 |
| 19 | 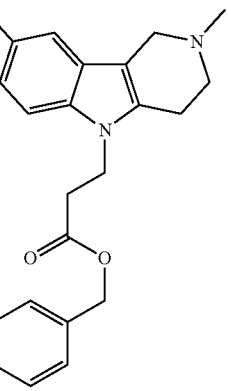 | CD20 |

TABLE 2-continued
Representative Compounds According to the Invention.
| Compound No. | Structure | CD# |
|---|---|---|
| 20 | 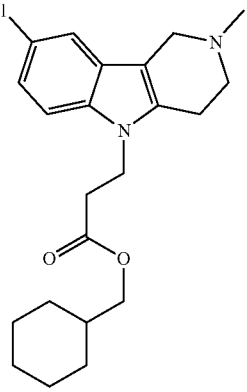 | CD21 |
| 21 | 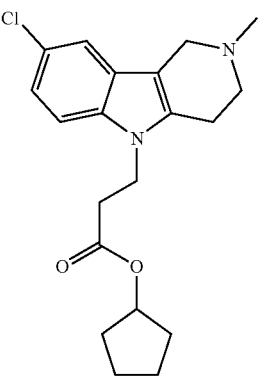 [SMILES: CN1CCc2c(c3cc(Cl)ccc3n2CCC(=O)OC2CCCC2)C1] | CD22 |
| 22 | 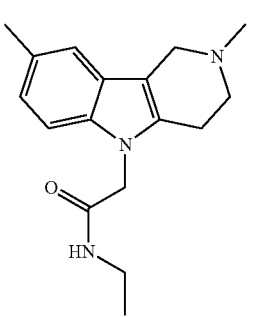 | CD23 |
| 23 | 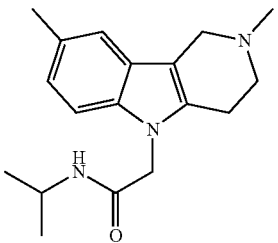 [SMILES: Cc1ccc2c(c1)c1c(n2CC(=O)NC(C)C)CCN(C)C1] | CD24 |

TABLE 2-continued

Representative Compounds According to the Invention.

| Compound No. | Structure | CD# |
|---|---|---|
| 24 | 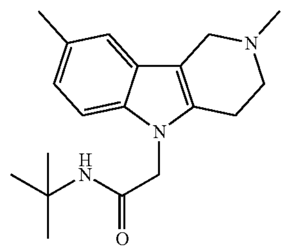 [SMILES: Cc1ccc2c(c1)c1c(n2CC(=O)NC(C)(C)C)CCN(C)C1] | CD25 |
| 25 | 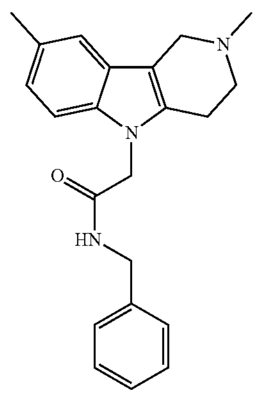 | CD26 |
| 26 | 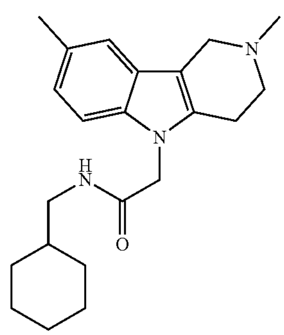 [SMILES: Cc1ccc2c(c1)c1c(n2CC(=O)NCC2CCCCC2)CCN(C)C1] | CD27 |
| 27 | 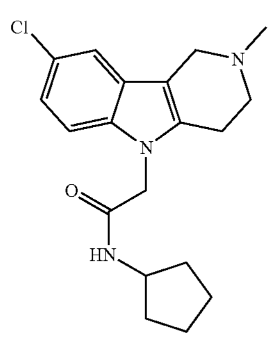 [SMILES: CN1CCc2c(c3cc(Cl)ccc3n2CC(=O)NC2CCCC2)C1] | CD28 |

TABLE 2-continued
Representative Compounds According to the Invention.
| Compound No. | Structure | CD# |
|---|---|---|
| 28 | 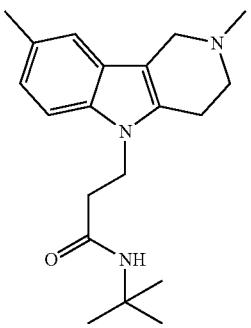 | CD29 |
| 29 | 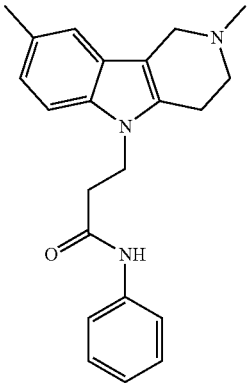 | CD30 |
| 30 | 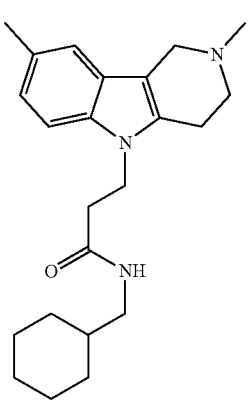 | CD31 |
| 31 | 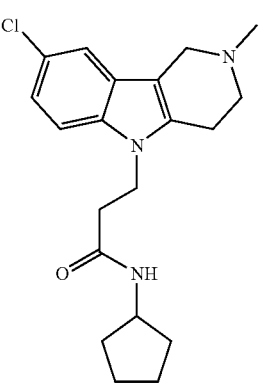 [SMILES: CN1CCc2c(c3cc(Cl)ccc3n2CCC(=O)NC2CCCC2)C1] | CD32 |

TABLE 2-continued
Representative Compounds According to the Invention.
| Compound No. | Structure | CD# |
|---|---|---|
| 32 | 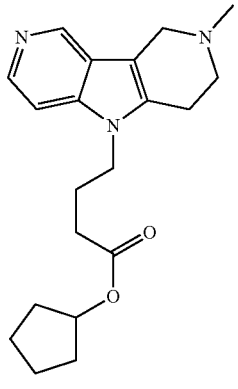 [SMILES: CN1CCc2c(c3cnccc3n2CCCC(=O)OC2CCCC2)C1] | CD33 |
| 33 | 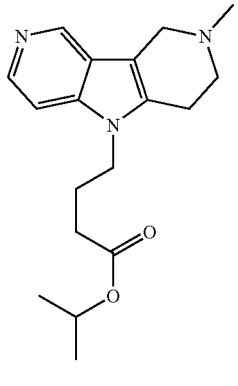 [SMILES: CC(C)OC(=O)CCCn1c2c(c3cnccc31)CN(C)CC2] | CD34 |
| 34 | 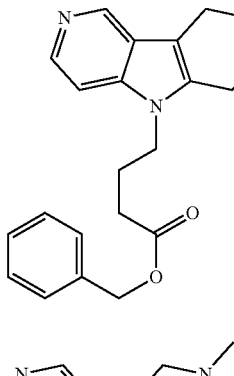 | CD35 |
| 35 | 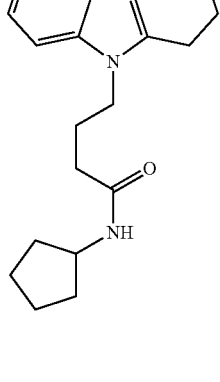 | CD36 |

TABLE 2-continued
Representative Compounds According to the Invention.
| Compound No. | Structure | CD# |
|---|---|---|
| 36 | 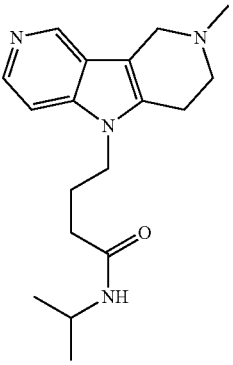 [SMILES: CC(C)NC(=O)CCCn1c2c(c3cnccc31)CN(C)CC2] | CD37 |
| 37 | 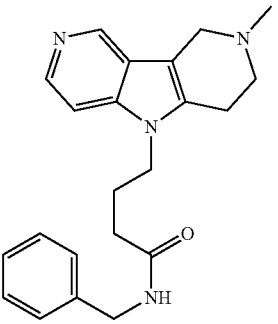 [SMILES: CN1CCc2c(c3cnccc3n2CCCC(=O)NCc2ccccc2)C1] | CD38 |
| 38 | 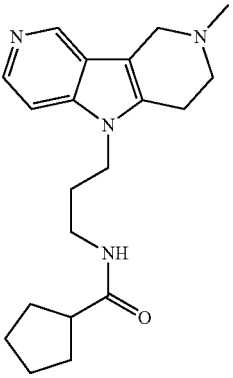 [SMILES: CN1CCc2c(c3cnccc3n2CCCNC(=O)C2CCCC2)C1] | CD39 |
| 39 | 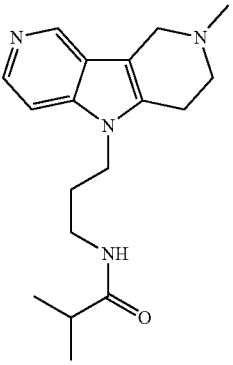 [SMILES: CC(C)C(=O)NCCCn1c2c(c3cnccc31)CN(C)CC2] | CD40 |

TABLE 2-continued

Representative Compounds According to the Invention.

| Compound No. | Structure | CD# |
|---|---|---|
| 40 | 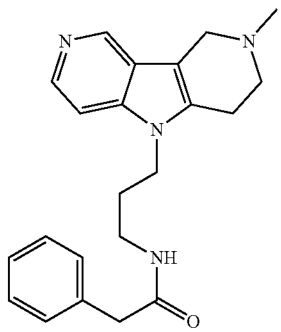 [SMILES: CN1CCc2c(c3cnccc3n2CCCNC(=O)Cc2ccccc2)C1] | CD41 |
| 41 | 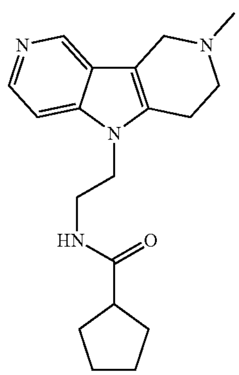 [SMILES: CN1CCc2c(c3cnccc3n2CCNC(=O)C2CCCC2)C1] | CD42 |
| 42 | 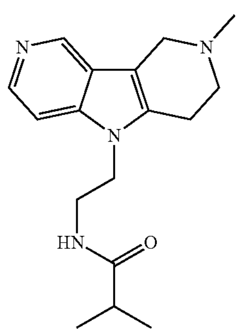 [SMILES: CC(C)C(=O)NCCn1c2c(c3cnccc31)CN(C)CC2] | CD43 |
| 43 | 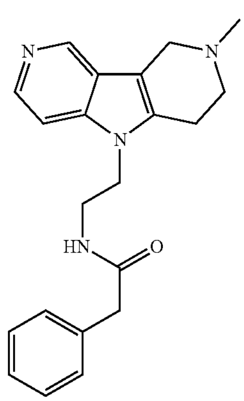 [SMILES: CN1CCc2c(c3cnccc3n2CCNC(=O)Cc2ccccc2)C1] | CD44 |

TABLE 2-continued

Representative Compounds According to the Invention.

| Compound No. | Structure | CD# |
|---|---|---|
| 44 | 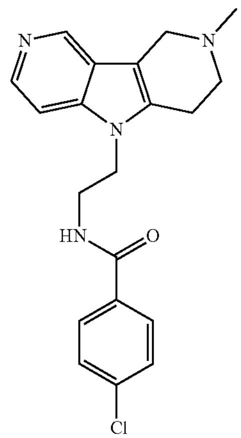 [SMILES: CN1CCc2c(c3cnccc3n2CCNC(=O)c2ccc(Cl)cc2)C1] | CD45 |
| 45 | 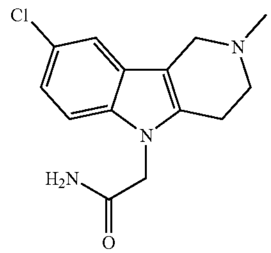 [SMILES: CN1CCc2c(c3cc(Cl)ccc3n2CC(N)=O)C1] | CD48 |
| 46 | 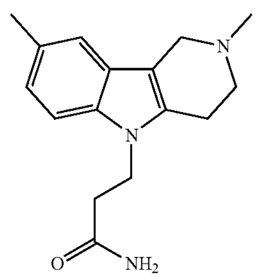 | CD49 |
| 47 | 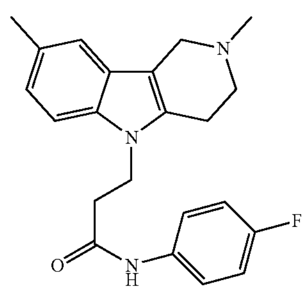 [SMILES: Cc1ccc2c(c1)c1c(n2CCC(=O)Nc2ccc(F)cc2)CCN(C)C1] | CD50 |
| 48 | 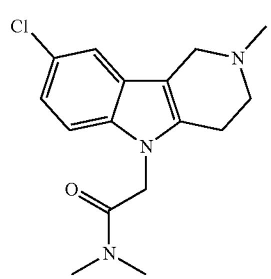 [SMILES: CN1CCc2c(c3cc(Cl)ccc3n2CC(=O)N(C)C)C1] | CD51 |

TABLE 2-continued

Representative Compounds According to the Invention.

| Compound No. | Structure | CD# |
|---|---|---|
| 49 | 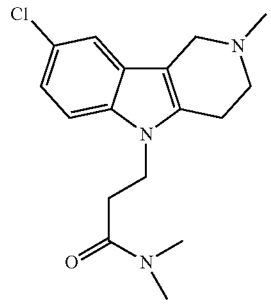 [SMILES: CN1CCc2c(c3cc(Cl)ccc3n2CCC(=O)N(C)C)C1] | CD52 |
| 50 | 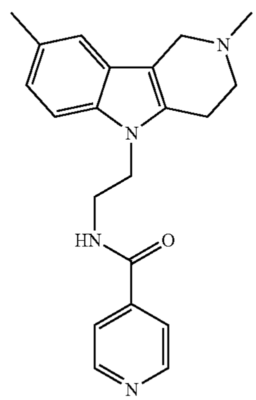 | CD53 |
| 51 | 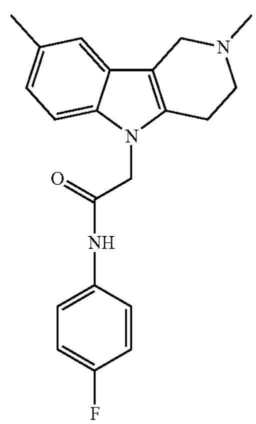 | CD54 |
| 52 | 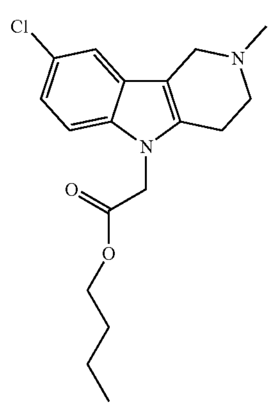 [SMILES: CCCCOC(=O)Cn1c2c(c3cc(Cl)ccc31)CN(C)CC2] | CD56 |

TABLE 2-continued
Representative Compounds According to the Invention.
| Compound No. | Structure | CD# |
|---|---|---|
| 53 | 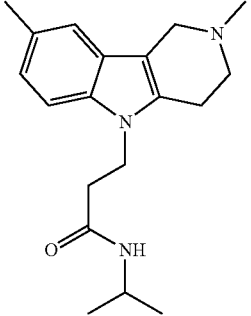 | CD60 |
| 54 | 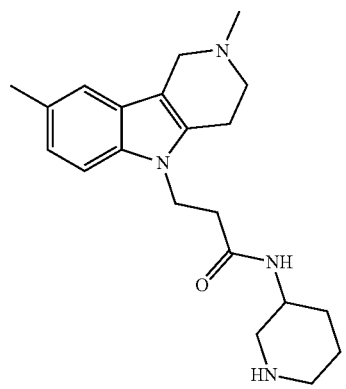 [SMILES: Cc1ccc2c(c1)c1c(n2CCC(=O)NC2CCCNC2)CCN(C)C1] | CD64 |
| 55 | 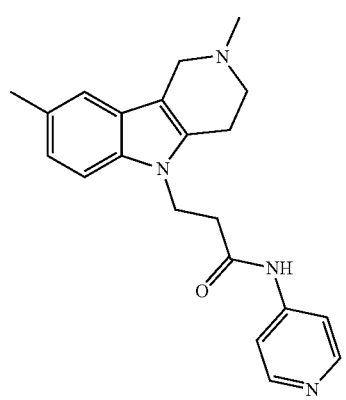 [SMILES: Cc1ccc2c(c1)c1c(n2CCC(=O)Nc2ccncc2)CCN(C)C1] | CD65 |
| 56 | 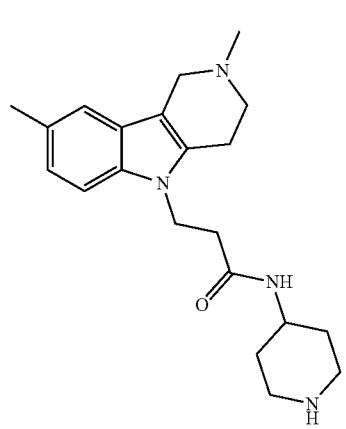 [SMILES: Cc1ccc2c(c1)c1c(n2CCC(=O)NC2CCNCC2)CCN(C)C1] | CD66 |

TABLE 2-continued
Representative Compounds According to the Invention.
| Compound No. | Structure | CD# |
|---|---|---|
| 57 | 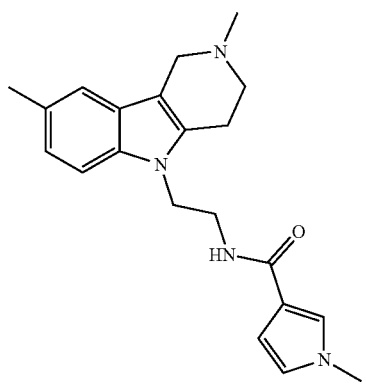 | CD67 |
| 58 | 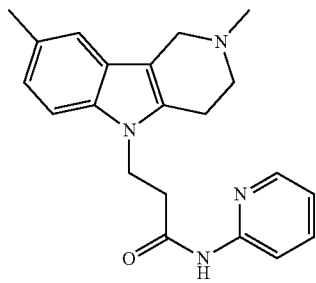 [SMILES: Cc1ccc2c(c1)c1c(n2CCC(=O)Nc2ccccn2)CCN(C)C1] | CD69 |
| 59 | 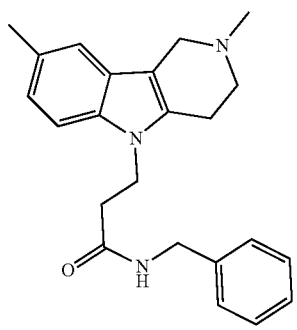 [SMILES: Cc1ccc2c(c1)c1c(n2CCC(=O)NCc2ccccc2)CCN(C)C1] | CD74 |
| 60 | 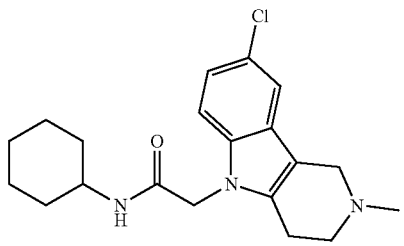 [SMILES: CN1CCc2c(c3cc(Cl)ccc3n2CC(=O)NC2CCCCC2)C1] | CD75 |

TABLE 2-continued

Representative Compounds According to the Invention.

| Compound No. | Structure | CD# |
|---|---|---|
| 61 | 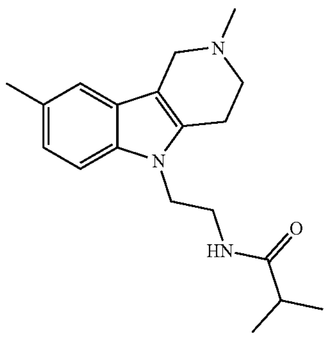 [SMILES: Cc1ccc2c(c1)c1c(n2CCNC(=O)C(C)C)CCN(C)C1] | CD76 |
| 62 | 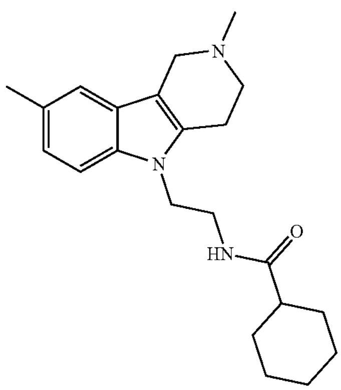 [SMILES: Cc1ccc2c(c1)c1c(n2CCNC(=O)C2CCCCC2)CCN(C)C1] | CD77 |
| 63 | 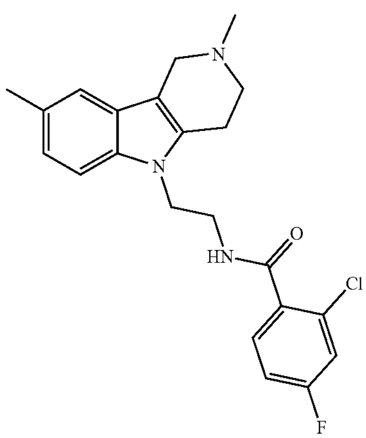 [SMILES: Cc1ccc2c(c1)c1c(n2CCNC(=O)c2ccc(F)cc2Cl)CCN(C)C1] | CD78 |
| 64 | 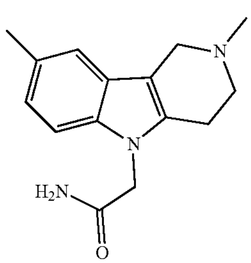 | CD79 |

105
106
TABLE 2-continued
Representative Compounds According to the Invention.
| Compound No. | Structure | CD# |
|---|---|---|
| 65 | 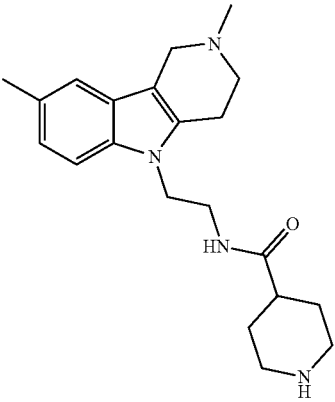 [SMILES: Cc1ccc2c(c1)c1c(n2CCNC(=O)C2CCNCC2)CCN(C)C1] | CD80 |
| 66 | 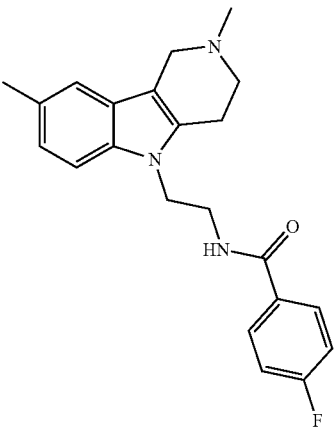 [SMILES: Cc1ccc2c(c1)c1c(n2CCNC(=O)c2ccc(F)cc2)CCN(C)C1] | CD81 |
| 67 | 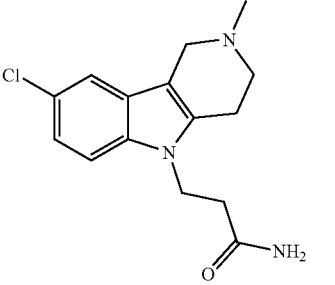 [SMILES: CN1CCc2c(c3cc(Cl)ccc3n2CCC(N)=O)C1] | CD82 |
| 68 | 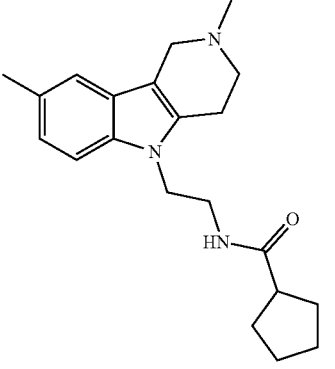 [SMILES: Cc1ccc2c(c1)c1c(n2CCNC(=O)C2CCCC2)CCN(C)C1] | CD83 |

TABLE 2-continued
Representative Compounds According to the Invention.
| Compound No. | Structure | CD# |
|---|---|---|
| 69 | 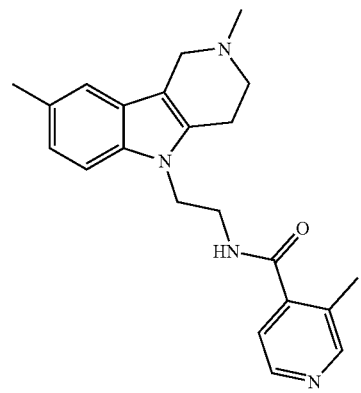 | CD84 |
| 70 | 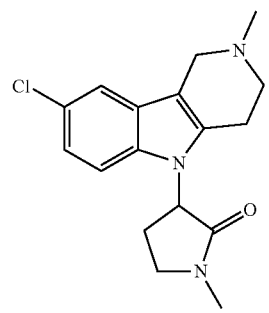 [SMILES: CN1CCc2c(c3cc(Cl)ccc3n2C2CCN(C)C2=O)C1] | CD72 |
| 71 | 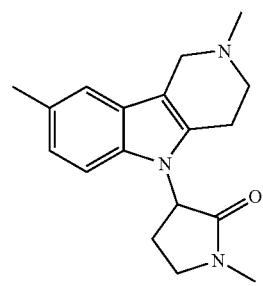 [SMILES: Cc1ccc2c(c1)c1c(n2C2CCN(C)C2=O)CCN(C)C1] | |
| 72 | 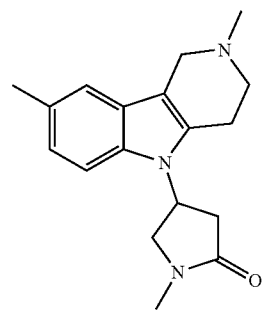 [SMILES: Cc1ccc2c(c1)c1c(n2C2CC(=O)N(C)C2)CCN(C)C1] | |

TABLE 2-continued

Representative Compounds According to the Invention.

| Compound No. | Structure | CD# |
|---|---|---|
| 73 | 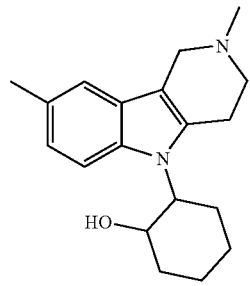 [SMILES: Cc1ccc2c(c1)c1c(n2C2CCCCC2O)CCN(C)C1] | |

Also embraced by the invention is a compound of the formula (G):

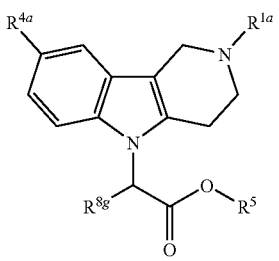

or a salt thereof,
where:
$R^{1a}$ is alkyl;
$R^{4a}$ is selected from alkyl, aryl, and substituted aryl;
$R^5$ is alkyl; and
$R^{8g}$ is selected from alkyl, substituted alkyl and aralkyl.

In one variation of the formula (G), $R^{8g}$ is alkyl, e.g. methyl or isopropyl. In another variation of the formula (G), $R^{8g}$ is substituted alkyl substituted with one or more alkyl or alkoxy groups. In yet another variation, of the formula (G), $R^{8g}$ is substituted alkyl substituted with an alkoxy group, e.g. methoxymethyl. In yet another variation, $R^{8g}$ is substituted aralkyl where the aryl moiety of the aralkyl is at least 3 carbon atoms removed from the carbon to which $R^{8g}$ is attached, e.g. 3-phenylpropyl.

In some embodiments, $R^{8g}$ is selected from alkyl, substituted alkyl, and alkyl-phenyl. In some embodiments, $R^{8g}$ is selected from $C_1$-$C_4$ alkyl, substituted $C_1$-$C_4$ alkyl, and $C_1$-$C_4$ alkyl-phenyl. In some embodiments, $R^{8g}$ is selected from methyl, isopropyl, methoxymethyl, and benzyl.

In some embodiments, $R^{4a}$ is selected from alkyl, phenyl, and substituted phenyl. In some embodiments, $R^{4a}$ is selected from $C_1$-$C_4$ alkyl, phenyl, and phenyl substituted with a $C_1$-$C_4$ alkoxy or $C_1$-$C_4$ alkyl moiety. In some embodiments, $R^{4a}$ is selected from methyl, phenyl, 4-methoxyphenyl, and 4-methylphenyl.

In some embodiments, $R^{1a}$ is $C_1$-$C_4$ alkyl. In some embodiments, $R^{1a}$ is methyl.

In some embodiments, $R^5$ is $C_1$-$C_4$ alkyl. In some embodiments, $R^5$ is ethyl.

In one variation, $R^{1a}$ is methyl, $R^5$ is ethyl and $R^{8g}$ and $R^{4a}$ are as defined by any variation herein.

In some embodiments, $R^{4a}$ is methyl, $R^{1a}$ is methyl, $R^5$ is ethyl, and $R^{8g}$ is selected from alkyl, substituted alkyl, and $C_1$-$C_4$ aralkyl, where the aralkyl group is attached to the parent residue via the alkyl moiety.

In some embodiments, $R^{4a}$ is methyl, $R^{1a}$ is methyl, $R^5$ is ethyl, and $R^{8g}$ is selected from $C_1$-$C_4$ alkyl, substituted $C_1$-$C_4$ alkyl, and $C_1$-$C_4$ alkyl-phenyl.

In some embodiments, $R^{4a}$ is methyl, $R^{1a}$ is methyl, $R^5$ is ethyl, and $R^{8g}$ is selected from methyl, isopropyl, methoxymethyl, and benzyl.

In some embodiments, $R^{8g}$ is methyl, $R^{1a}$ is methyl, $R^5$ is ethyl, and $R^{4a}$ is selected from alkyl, phenyl, and substituted phenyl.

In some embodiments, $R^{8g}$ is methyl, $R^{1a}$ is methyl, $R^5$ is ethyl, and $R^{4a}$ is selected from $C_1$-$C_4$ alkyl, phenyl, and phenyl substituted with a $C_1$-$C_4$ alkoxy or $C_1$-$C_4$ alkyl moiety.

In some embodiments, $R^{8g}$ is methyl, $R^{1a}$ is methyl, $R^5$ is ethyl, and $R^{4a}$ is selected from methyl, phenyl, 4-methoxyphenyl, and 4-methylphenyl.

In some embodiments, the compound is selected from ethyl 2-(2,8-dimethyl-3,4-dihydro-1H-pyrido[4,3-b]indol-5(2H)-yl)propanoate; ethyl 2-(2,8-dimethyl-3,4-dihydro-1H-pyrido[4,3-b]indol-5(2H)-yl)-3-methylbutanoate; ethyl 2-(2,8-dimethyl-3,4-dihydro-1H-pyrido[4,3-b]indol-5(2H)-yl)-3-phenylpropanoate; ethyl 2-(2,8-dimethyl-3,4-dihydro-1H-pyrido[4,3-b]indol-5(2H)-yl)-3-methoxypropanoate; ethyl 2-(2-methyl-8-phenyl-3,4-dihydro-1H-pyrido[4,3-b]indol-5(2H)-yl)propanoate; ethyl 2-(8-(4-methoxyphenyl)-2-methyl-3,4-dihydro-1H-pyrido[4,3-b]indol-5(2H)- and yl)propanoate; and ethyl 2-(2-methyl-8-p-tolyl-3,4-dihydro-1H-pyrido[4,3-b]indol-5(2H)-yl)propanate.

Certain examples of compounds according to the invention are depicted in Table 3. The compounds depicted may be present as salts even if salts are not depicted and it is understood that the invention embraces all salts, hydrates and solvates of the compounds depicted here, as well as the non-salt, non-hydrate, non-solvate form of the compound, as is well understood by the skilled artisan. It is thus understood that pharmaceutically acceptable salts of compounds according the invention are intended.

TABLE 3

Certain compounds of the invention.

| Compound No. | Name | Structure |
| --- | --- | --- |
| G1 | ethyl 2-(2,8-dimethyl-3,4-dihydro-1H-pyrido[4,3-b]indol-5(2H)-yl)propanoate | 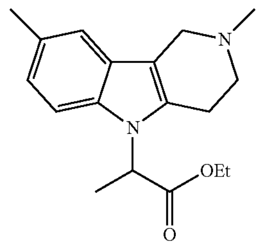 |
| G2 | ethyl 2-(2,8-dimethyl-3,4-dihydro-1H-pyrido[4,3-b]indol-5(2H)-yl)-3-methylbutanoate | 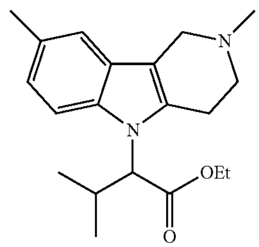 |
| G3 | ethyl 2-(2,8-dimethyl-3,4-dihydro-1H-pyrido[4,3-b]indol-5(2H)-yl)-3-phenylpropanoate | 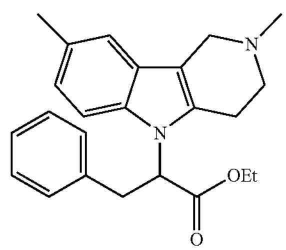 [SMILES: CCOC(=O)C(Cc1ccccc1)n1c2c(c3cc(C)ccc31)CN(C)CC2] |
| G4 | ethyl 2-(2,8-dimethyl-3,4-dihydro-1H-pyrido[4,3-b]indol-5(2H)-yl)-3-methoxypropanoate | 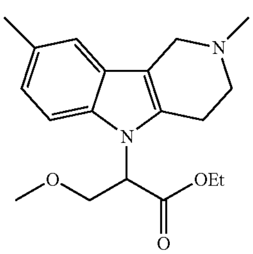 |
| G5 | ethyl 2-(2-methyl-8-phenyl-3,4-dihydro-1H-pyrido[4,3-b]indol-5(2H)-yl)propanoate | 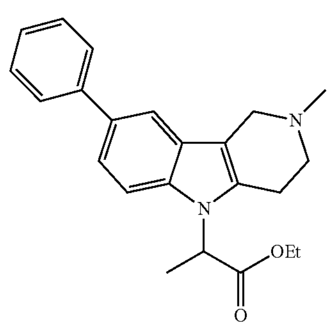 [SMILES: CCOC(=O)C(C)n1c2c(c3cc(-c4ccccc4)ccc31)CN(C)CC2] |

TABLE 3-continued

Certain compounds of the invention.

| Compound No. | Name | Structure |
|---|---|---|
| G6 | ethyl 2-(8-(4-methoxyphenyl)-2-methyl-3,4-dihydro-1H-pyrido[4,3-b]indol-5(2H)-yl)propanoate | 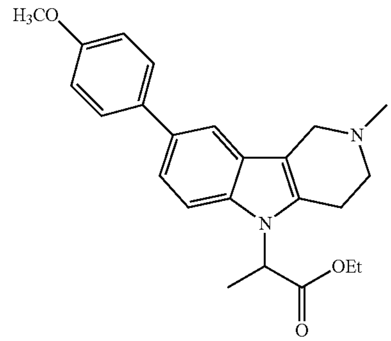 [SMILES: CCOC(=O)C(C)n1c2c(c3cc(-c4ccc(OC)cc4)ccc31)CN(C)CC2] |
| G7 | ethyl 2-(2-methyl-8-p-tolyl-3,4-dihydro-1H-pyrido[4,3-b]indol-5(2H)-yl)propanoate | 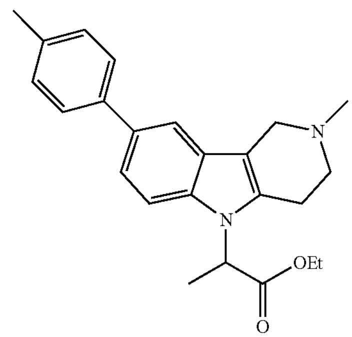 |

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. Pharmaceutical compositions according to the invention may take a form suitable for oral, buccal, parenteral, nasal, topical or rectal administration, or a form suitable for administration by inhalation.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha_{1D}$, $\alpha_{2A}$ and $\alpha_{2B}$), inhibition of binding of a ligand to a serotonin receptor (e.g., 5-HT$_{2A}$, 5-HT$_{2C}$, 5-HT$_{6}$ and 5-HT$_{7}$), inhibition of binding of a ligand to a dopamine receptor (e.g., D2L), and inhibition of binding of a ligand to a histamine receptor (e.g., $H_1$, $H_2$ and $H_3$); agonist/antagonist activity to a serotonin receptor (e.g., 5-HT$_{2A}$, 5-HT$_{6}$); agonist/antagonist activity to a dopamine receptor (e.g., $D_{2L}$, $D_{2S}$); agonist/antagonist activity to a histamine receptor (e.g., $H_1$); activity in a neurite outgrowth assay; efficacy in a preclinical model of memory dysfunction associated with cholinergic hyperfunction; and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85-95% or between about 90-100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha_{1D}$, $\alpha_{2A}$, $\alpha_{2B}$, 5-HT$_{2A}$, 5-HT$_{2C}$, 5-HT6, 5-HT$_{7}$, D$_{2L}$, $H_1$, $H_2$, $H_3$). In one variation, a compound of the invention inhibits binding of a ligand to at least one and as many as eleven receptors detailed herein and further displays agonist or antagonist activity to one or more receptors detailed herein (e.g., serotonin receptor 5-HT$_{2A}$, serotonin receptor 5-HT$_{6}$, dopamine receptor D$_{2L}$, and dopamine receptor D$_{2S}$, histamine receptor $H_1$) as measured in the assays described herein. In one variation, agonist response of serotonin receptor 5-HT$_{2A}$ is inhibited by compounds of the invention by at least about any one of 50%, 50%, 70%, 80%, 90%, 100%, 110%, 120%, 130%, 140%, 150% as determined in a suitable assay such as the assay described herein.

In one variation, a compound of the invention displays the above described neurotransmitter receptor binding profile i.e. inhibits binding of a ligand to at least one receptor and as many as eleven as detailed herein and further stimulates neurite outgrowth, e.g. as measured by the assays described herein. In one variation, a compound of the invention shows activity in neurite outgrowth assays using primary neurons in culture. In another variation, a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic hyperfunction, i.e. shows pro-cognitive effects in a preclinical model of memory dysfunction. In one variation, a compound of the invention is effective in a preclinical model of memory dysfunction associated with cholinergic hypofunction. As $H_1$ antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a $5\text{-}HT_6$ antagonist may have cognition-enhancing effects as serotonin acting through this receptor may impair memory.

In another variation, a compound of the invention inhibits at least one and as many as eleven receptors as detailed herein, further shows efficacy in a preclinical model of memory dysfunction associated with cholinergic hyperfunction i.e. shows pro-cognitive effects in a preclinical model of memory dysfunction and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic hyperfunction i.e. shows pro-cognitive effects in a preclinical model of memory dysfunction and further stimulates neurite outgrowth.

In another variation, a compound of the invention inhibits at least one and as many as eleven receptors as detailed herein, further shows efficacy in a preclinical model of memory dysfunction associated with cholinergic hyperfunction i.e. shows pro-cognitive effects in a preclinical model of memory dysfunction, further displays agonist or antagonist activity to one or more receptor detailed herein and further stimulates neurite outgrowth.

In a further variation, a compound of the invention inhibits binding of a ligand to at least one and as many as eleven receptors and further possess anti-psychotic effects as measured in a preclinical model of schizophrenia, i.e., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic hyperfunction and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic hyperfunction.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic hyperfunction.

In a further variation, a compound of the invention inhibits binding to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic hyperfunction.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic hyperfunction. In another variation, a compound of the invention shows efficacy in a preclinical model of schizophrenia, further stimulates neurite outgrowth and further shows efficacy in a preclinical model of memory dysfunction associated with cholinergic hyperfunction.

In one aspect, compounds of the invention inhibit binding of a ligand to adrenergic receptors $\alpha_{1D}$, $\alpha_{2A}$, $\alpha_{2B}$ and inhibit binding of a ligand to serotonin receptor 5-HT6. In another variation, compounds of the invention inhibit binding of a ligand to adrenergic receptors $\alpha_{1D}$, $\alpha_{2A}$, $\alpha_{2B}$, to serotonin receptor $5\text{-}HT_6$ and to any one or more of the following receptors: serotonin receptor $5\text{-}HT_7$, $5\text{-}HT_{2A}$ and $5\text{-}HT_{2C}$. In another variation, compounds of the invention inhibit binding of a ligand to adrenergic receptors $\alpha_{1D}$, α2A, $\alpha_{2B}$, to serotonin receptor $5\text{-}HT_6$ and to any one or more of the following receptors: serotonin receptor $5\text{-}HT_7$, $5\text{-}HT_{2A}$ and $5\text{-}HT_{2C}$ and further show weak inhibition of binding of a ligand to histamine receptor $H_1$ and/or $H_2$. In one variation, compounds of the invention that also display strong inhibition of binding of a ligand to the serotonin receptor 5-$HT_7$ are particularly desired. In another variation, compounds of the invention inhibit binding of a ligand to adrenergic receptors $\alpha_{1D}$, $\alpha_{2A}$, $\alpha_{2B}$, to serotonin receptor 5-$HT_6$ and further show weak inhibition of binding of a ligand to histamine receptor $H_1$ and/or $H_2$. Weak inhibition of binding of a ligand to the histamine $H_1$ receptor is permitted as agonists of this receptor have been implicated in stimulating memory as well as weight gain. In one variation, binding to histamine receptor $H_1$ is inhibited by less than about 80%. In another variation, binding of a ligand to histamine receptor $H_1$ is inhibited by less than about any of 75%, 70%, 65%, 60%, 55%, or 50% as determined by a suitable assay known in the art such as the assays described herein.

In another variation, compounds of the invention inhibit binding of a ligand to dopamine receptor $D_{2L}$. In another variation, compounds of the invention inhibit binding of a ligand to dopamine receptor D2L and to serotonin receptor 5-$HT_{2A}$. In another variation, compounds of the invention inhibit binding of a ligand to histamine receptor $H_1$. In certain aspects, compounds of the invention further show one or more of the following properties: strong inhibition of binding of a ligand to the serotonin 5-$HT_7$ receptor, strong inhibition of binding of a ligand to the serotonin 5-$HT_{2A}$ receptor, strong inhibition of binding of a ligand to the serotonin 5-$HT_{2C}$ receptor, weak inhibition of binding of a ligand to the histamine $H_1$ receptor, weak inhibition of binding of ligands to the histamine $H_2$ receptor, and antagonist activity to serotonin receptor 5-$HT_{2A}$.

In one variation, compounds of the invention show any of the receptor binding aspects detailed herein and further display agonist/antagonist activity to one or more of the following receptors: serotonin receptor 5-$HT_{2A}$, serotonin receptor 5-HT6, dopamine receptor D2L, dopamine receptor $D_{2S}$ and histamine receptor $H_1$. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic hyperfunction. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-$HT_{2A}$, 5-HT6, dopamine receptor $D_{2L}$, dopamine receptor $D_{2S}$ and histamine receptor $H_1$), neurite outgrowth, a preclinical model of memory dysfunction associated with cholinergic hyperfunction and a preclinical model of schizophrenia.

In some aspects, compounds of the invention inhibit binding of a ligand to adrenergic receptors α1D, α2A, α2B, serotonin receptor 5-$HT_6$ and dopamine receptor $D_{2L}$ by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85-95% or about 90-100% as determined in a suitable assay known in the art such as the assays described herein.

In some aspects, compounds of the invention display the above described neurotransmitter receptor binding profile and further show antipsychotic effects. In one variation, a compound of the invention has binding profiles similar to compounds with antipsychotic activity. In another variation, a compound of the invention is effective in a preclinical model of schizophrenia. In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction. In another variation, compounds of the invention display the above described neurotransmitter receptor binding profile and do not show pro-cognitive effects in a preclinical model of memory dysfunction.

In one variation, compounds of the invention demonstrate pro-cognitive effects in a preclinical model of memory dysfunction. In a further variation, compounds of the invention possess anti-psychotic effects in a preclinical model of schizophrenia. In a further variation, compounds of the invention demonstrate pro-cognitive effects in a preclinical model of memory dysfunction and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In another aspect, the compounds described herein may be used to treat, prevent, delay the onset and/or delay the development of a psychotic disorder. In yet another aspect, the compounds described herein may be used to treat, prevent, delay the onset and/or delay the development of a neurotransmitter-mediated disorders disorder. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis and depression. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha_{1D}$, $\alpha_{2A}$, $\alpha_{2B}$, serotonin receptor 5-HT$_{2A}$, 5-HT6, 5HT7, histamine receptor H$_1$ and/or H$_2$ is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$ and a serotonin receptor 5-HT$_6$ receptor is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$, and a serotonin receptor 5-HT$_6$ receptor and modulation of one or more of the following receptors serotonin 5-HT$_7$, 5-HT$_{2A}$, 5-HT$_{2C}$ and histamine H$_1$ and H$_2$ is expected to be or is beneficial for the cognitive disorders, psychotic disorders, neurotransmitter-mediated disorders and/or neuronal disorders. In some variations, modulation of dopamine receptor D$_{2L}$ is expected to be or is beneficial for the cognitive disorders, psychotic disorders, neurotransmitter-mediated disorders and/or neuronal disorders. In certain variations, modulation of a dopamine D$_{2L}$ receptor and serotonin receptor 5-HT$_{2A}$ is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor $\alpha_{1D}$, $\alpha_{2A}$, $\alpha_{2B}$, serotonin receptor 5-HT$_{2A}$, 5-HT6, 5HT7, histamine receptor H$_1$ and/or H$_2$ is desirable or expected to be desirable to improve cognitive functions. In some variations modulation of $\alpha_{1D}$, $\alpha_{2A}$, $\alpha_{2B}$ adrenergic receptors and a serotonin 5-HT$_6$ receptor is desirable or expected to be desirable to improve cognitive functions. In some variations, modulation of $\alpha_{1D}$, $\alpha_{2A}$, $\alpha_{2B}$ adrenergic receptors and serotonin receptor 5-HT$_6$ and modulation of one or more of the following receptors: serotonin receptor 5-HT$_7$, 5-HT$_{2A}$, 5-HT$_{2C}$ and histamine receptor H$_1$ and H$_2$, is desirable or expected to be desirable to improve cognitive functions. In another aspect, the invention encompasses methods to reduce psychotic effects by administering a compound of the invention to an individual in need thereof. In some embodiments, modulation of a dopamine D2L receptor is expected to be or is desirable to reduce psychotic effects. In some embodiments, modulation of a dopamine D$_{2L}$ receptor and a serotonin 5-HT$_{2A}$ receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a $\alpha_{1D}$, $\alpha_{2A}$, $\alpha_{2B}$ adrenergic receptor and a serotonin 5-HT$_6$ receptor. In some variations, the aminergic G protein-coupled receptor is a $\alpha_{1D}$, $\alpha_{2A}$, $\alpha_{2B}$ adrenergic receptor and a serotonin 5-HT$_6$ and 5-HT$_7$ receptor. In some variations, the aminergic G protein-coupled receptor is a $\alpha_{1D}$, $\alpha_{2A}$, $\alpha_{2B}$ adrenergic receptor, a serotonin 5-HT$_6$ and one or more of the following receptors: serotonin 5-HT-7, 5-HT$_{2A}$ and 5-HT$_{2C}$ and histamine H$_1$ and H$_2$ receptor. In some variations, the aminergic G protein-coupled receptor is a dopamine D$_{2L}$ receptor. In some variations, the aminergic G protein-coupled receptor is a dopamine D$_{2L}$ receptor and a serotonin 5-HT$_{2A}$ receptor. In some variations, the aminergic G protein-coupled receptor is a histamine H$_1$ receptor.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); Hour (h); Ethanol (EtOH); dimethylsulfoxide (DMSO); N,N-dimethylformamide (DMF); trifluoroacetic acid (TFA); teterahydrofuran (THF); Normal (N); aqueous (aq.); methanol (MeOH); dichloromethane (DCM); Retention factor (Rf).

Compounds made by General Methods 1 and 8 may also be used as intermediates for the synthesis of other compounds of the invention.

General Method 1

Scheme 1-A

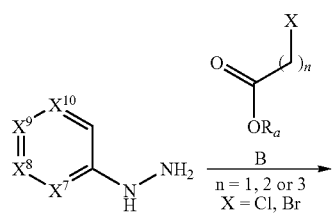

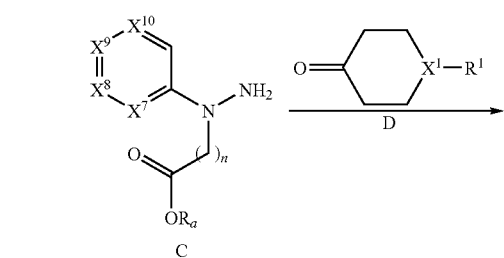

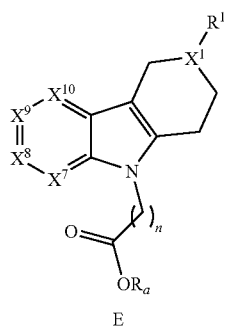

Scheme 1-B

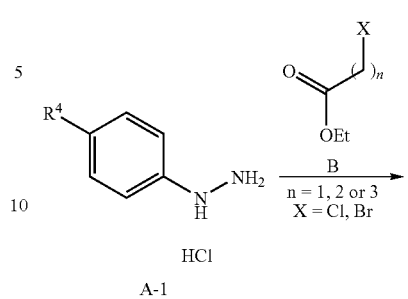

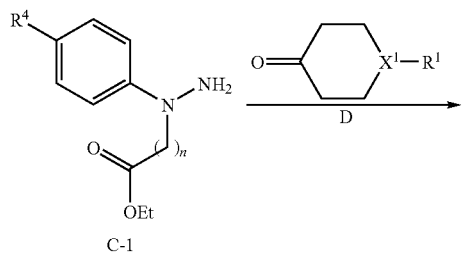

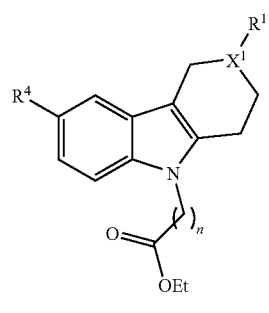

Compound A (1 equiv.), triethylamine (3 equiv) and compound B (1 equiv.) are dissolved in EtOH and stirred at 25° C. for 1 h and then at 90° C. for 3 h after which the contents are cooled to 25° C. and evaporated to dryness to obtain crude C. The residue is acidified with ethanolic HCl and the volatiles are removed under reduced pressure. Ethanol is added followed by compound D (1 to 1.5 equiv) and the contents are heated at 90° C. for additional 16 h. Solvent is removed in vacuo. The remaining residue is diluted with ethyl acetate and washed with saturated aq. NaHCO$_3$. The aqueous layer is extracted twice with ethyl acetate and the combined organic layer is dried over Na$_2$SO$_4$, and concentrated. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL). Similar synthetic details may be employed for compounds made according to Scheme 1-B. This procedure is exemplified by the synthesis of compounds CD11, CD17, CD19, CD27 and CD29.

General Method 2

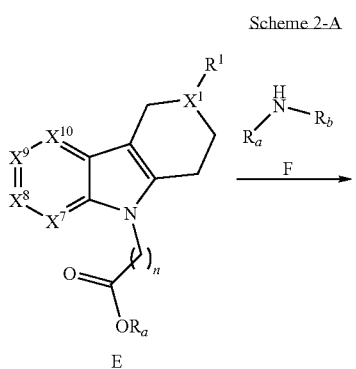

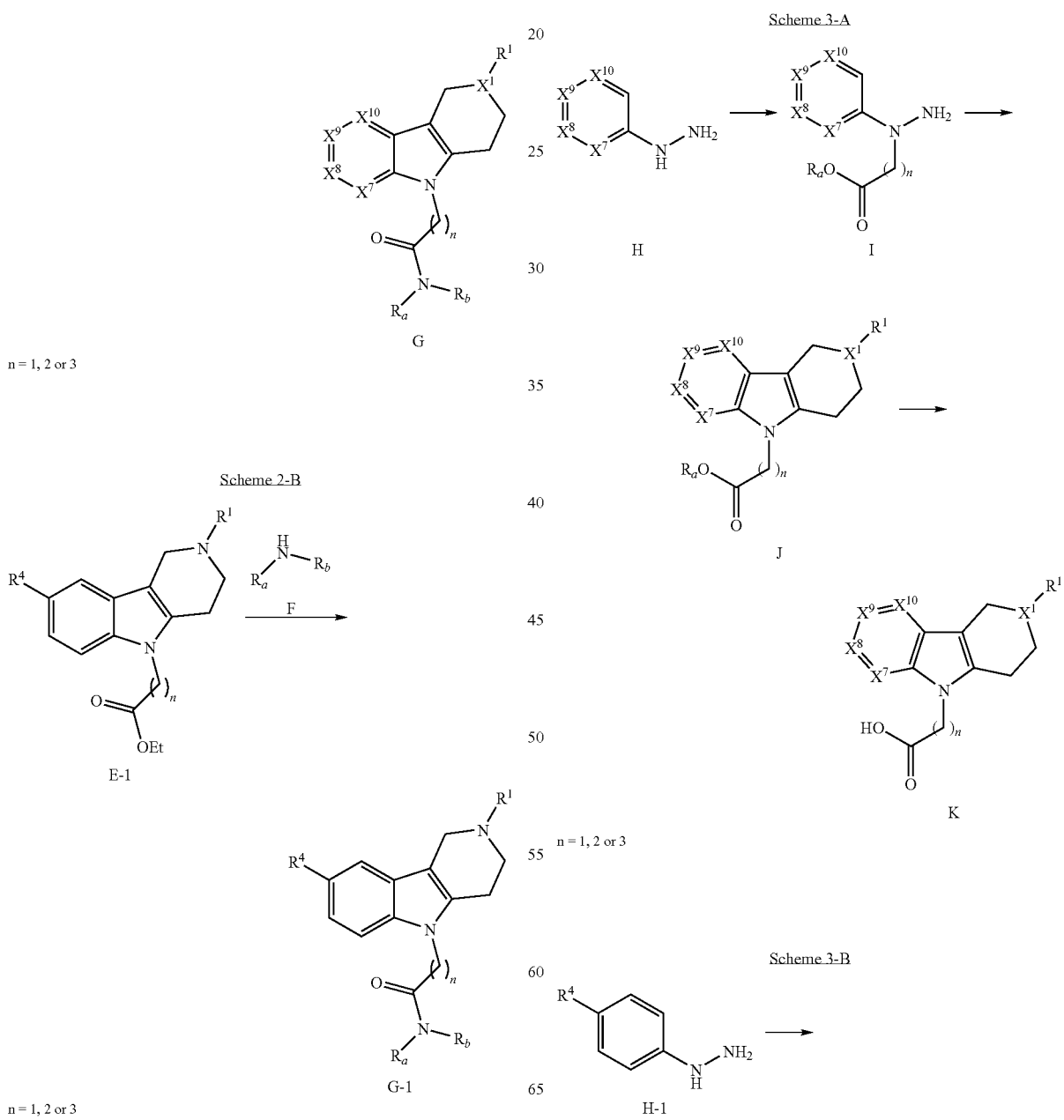

A mixture of compounds E (1 equiv.) and F (neat or aqueous, 10-25 folds w/v) is heated at 100-120° C. for 3-4 h after which the reaction mixture is evaporated to dryness. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL). Similar synthetic details may be employed for compounds made according to Scheme 2-B.

General Method 3

General methods according to Schemes 3-A and 3-B are exemplified below for the synthesis of CD63.

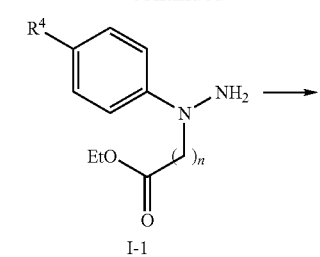

I-1

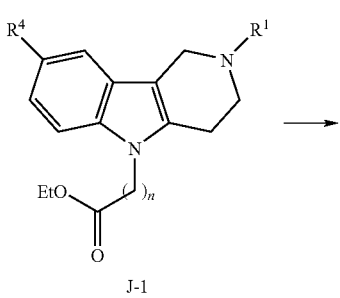

J-1

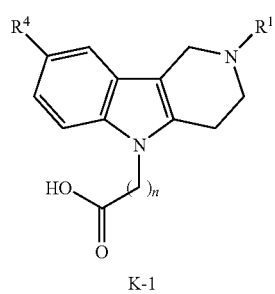

K-1 n = 1, 2 or 3

Scheme 3-C Synthesis of CD63

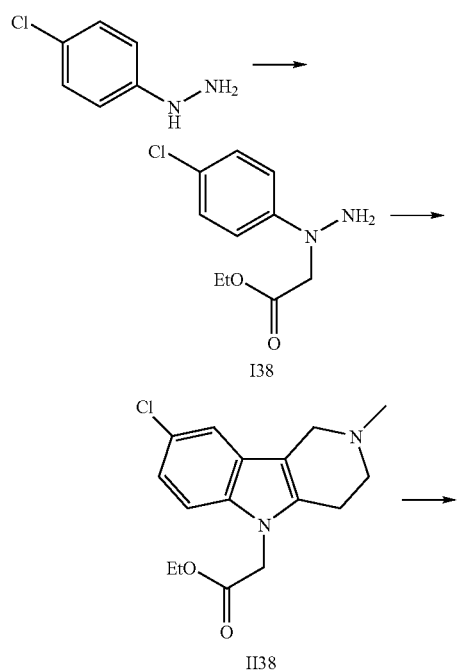

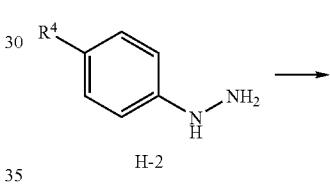

38
(CD63)

The reaction of described above for 4-chlorophenylhydrazine, which can be extended to any appropriately substituted phenyl hydrazine (such as H or H-1), with ethyl bromo (or chloro)acetate under appropriate alkylating conditions results in the formation of the internally substituted hydrazine (I38) The reaction of (I38) with N-methyl-4-piperidone results in the formation of the carboline (II38). The hydrolysis of (II38) gives the acid 38. Similar synthetic details may be employed in the reaction according to Scheme 3-A or 3-B.

General Method 4

General methods according to Schemes 4-A and 4-B are exemplified below for the synthesis of CD55.

Scheme 4-A

H-2

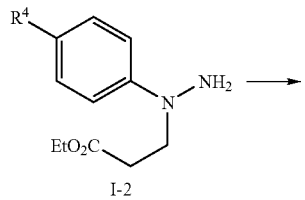

I-2

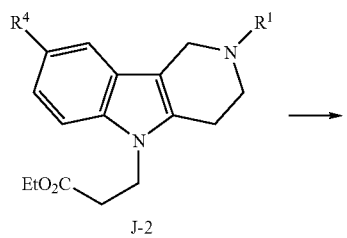

J-2

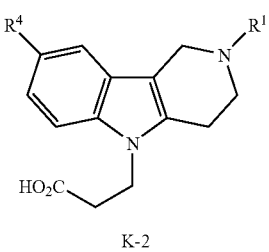

K-2

Scheme 4-B-Synthesis of CD55

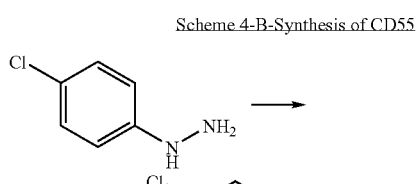

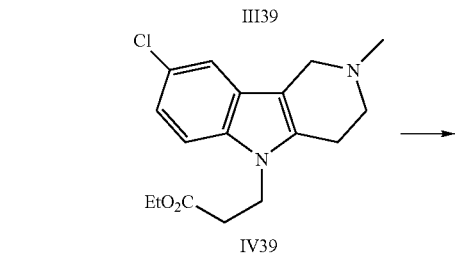

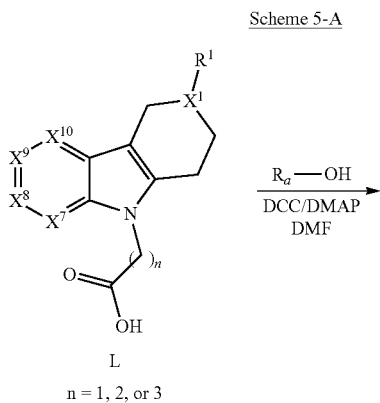

The reaction of 4-chlorophenylhydrazine, which can be extended to any appropriately substituted phenyl hydrazine (such as H-2), with ethyl 3-bromo (or chloro)propionate under appropriate alkylating conditions results in the formation of the internally substituted hydrazine (III39). The reaction of (III39) with N-methyl-4-piperidone results in the formation of the carboline (IV39). The hydrolysis of (IV39) gives the acid (39). Similar synthetic details may be employed in the reaction according to Scheme 4-A.

General Method 5

Certain compounds of the invention are synthesized according to Schemes 5-A and 5-B as exemplified by the methods according to Schemes 5-C and 5-D. Dichloromethan can be used as the solvent in place of or in addition to DMF as shown in Schemes 5-A to 5-D. For example, dichloromethane is used as solvent in the syntheses of compounds CD13 and CD15.

Scheme 5-A

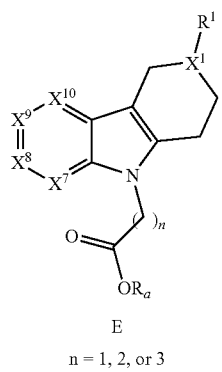

L n = 1, 2, or 3

Scheme 5-B

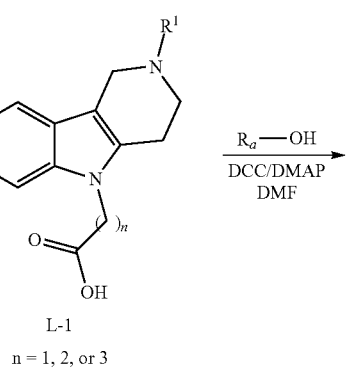

L-1 n = 1, 2, or 3

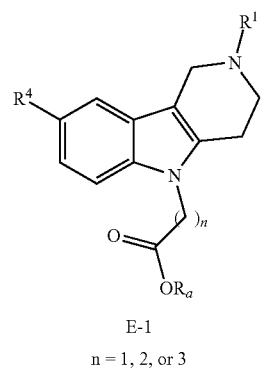

E-1 n = 1, 2, or 3

Scheme 5-C

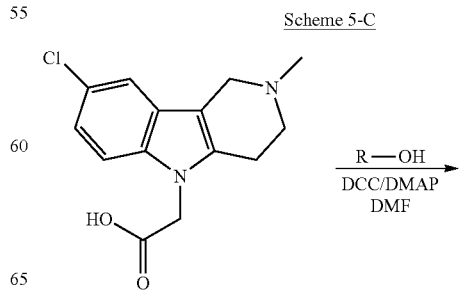

-continued

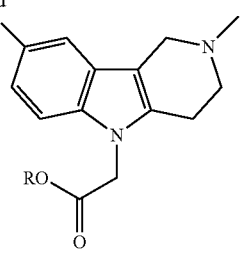

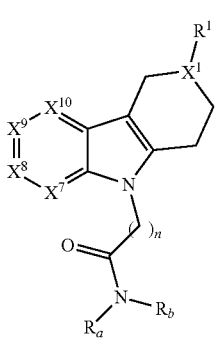

n = 1, 2, or 3

G

Scheme 5-D

Scheme 6-B

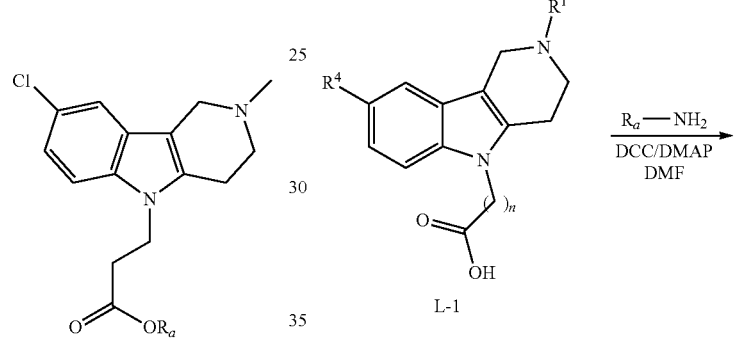

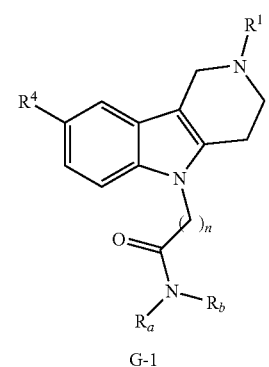

G-1 n = 1, 2, or 3

The carboxylic acids (exemplified above for 3-(8-chloro-1,2,3,4-tetrahydro-2-methylpyrido[4,3-b]indol-5-yl)propanoic acid) of the general structure described above can be treated with DCC/DMAP in an appropriate solvent, such as dimethylformamide or methylene chloride followed by treatment with a desired alcohol ($R_a$—OH) to provide the corresponding esters. Isolation and purification of these esters can be carried out using standard work up and normal phase or reverse phase chromatographic methods.

General Method 6

Certain compounds of the invention are synthesized according to Schemes 6-A and 6-B as exemplified by the methods according to Schemes 6-C and 6-D. Dichloromethan can be used as the solvent in place of or in addition to DMF as shown in Schemes 6-A to 6-D. For example, dichloromethane is used as solvent in the syntheses of compound CD25.

Scheme 6-A

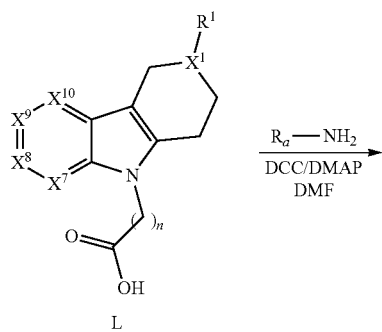

L

Scheme 6-C

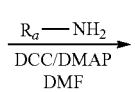

131

-continued

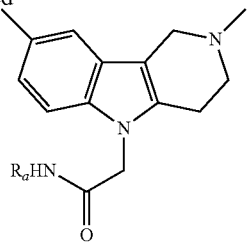

132

-continued

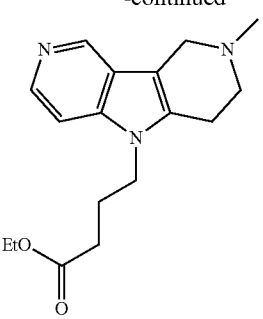

Scheme 6-D

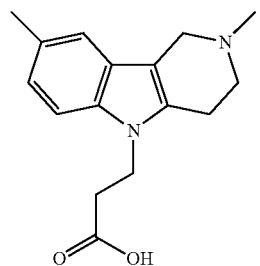

$\xrightarrow{\text{R}_a\text{—NH}_2}{\text{DCC/DMAP} \atop \text{DMF}}$

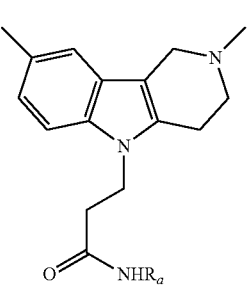

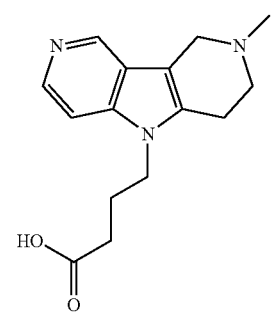

iii $\text{R}_a\text{—OH} \atop \text{DCC/DMAP} \atop \text{DMF}$

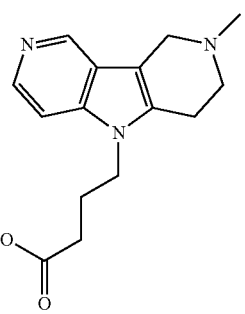

$\text{R}_a\text{—NH}_2 \atop \text{DCC/DMAP} \atop \text{DMF}$

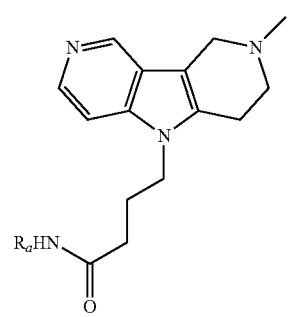

The carboxylic acids (exemplified above for 3-(2,8-dimethyl-3,4-dihydro-1H-pyrido[4,3-b]indol-5(2H)-yl)propanoic acid) of the general structure described above can be treated with DCC/DMAP in an appropriate solvent, such as dimethylformamide or methylene chloride followed by treatment with a desired amine ($\text{R}_a$—$\text{NH}_2$) to provide the corresponding amides. Isolation and purification of these amides can be carried out using standard work up and normal phase or reverse phase chromatographic methods.

General Method 7

General method according to Scheme 7-A is exemplified by the synthesis of CD33-CD35 (esters) and CD36-CD38 (amines).

Scheme 7-A

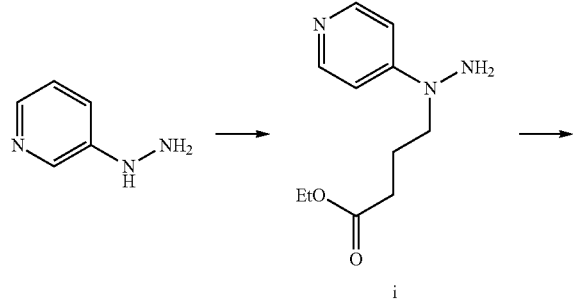

The reaction of 4-pyridylhydrazine with ethyl 4-bromo (or chloro)butanoate under appropriate alkylating conditions results in the formation of the internally substituted hydrazine (i) The reaction of (i) with N-methyl-4-piperidone results in the formation of the carboline (ii). The hydrolysis of (ii) gives the acid (iii). The carboxylic acids, including (iii) can be treated with DCC/DMAP in an appropriate solvent, such as dimethylformamide or methylene chloride followed by treatment with (a) a desired alcohol (R—OH) to provide the corresponding esters, or (b) a desired amine ($\text{R}_a$—$\text{NH}_2$) to provide the corresponding amides. Isolation and purification of these esters can be carried out using standard work up and normal phase or reverse phase chromatographic methods.

General Method 8

General method according to Scheme 8-A is exemplified by the synthesis of CD39-CD41.

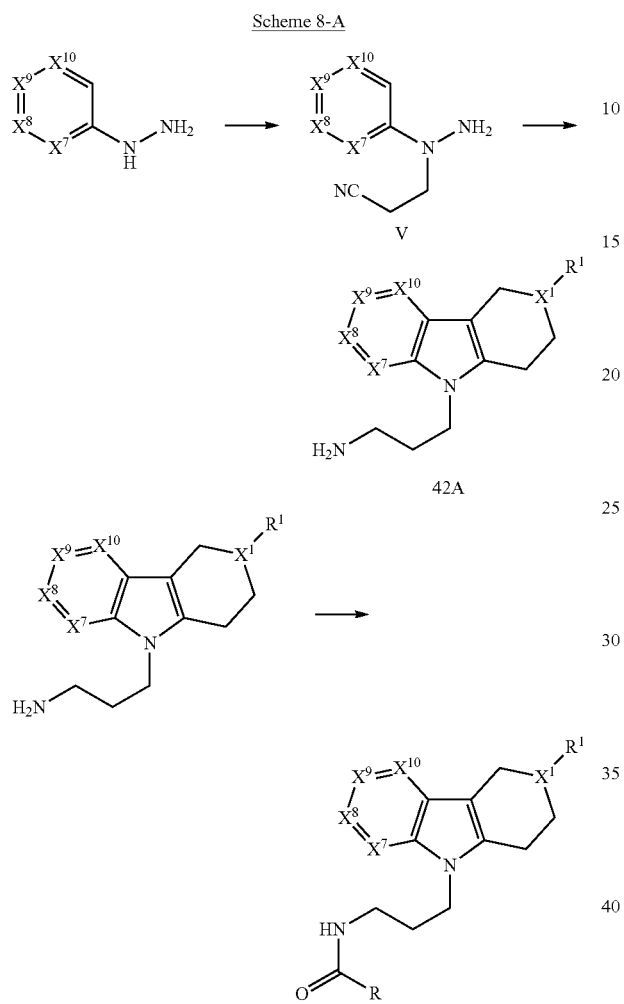

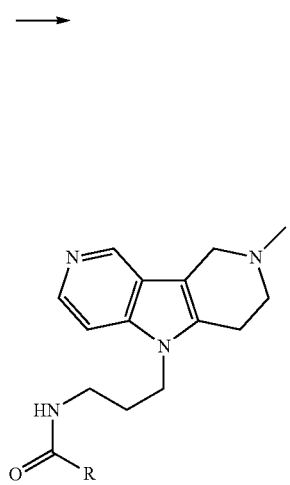

The reaction of a 4-pyridylhydrazine with 3-bromo (or chloro)propionitrile under appropriate alkylating conditions results in the formation of the internally substituted hydrazine (V) which upon treatment with N-methyl-4-piperidone and reduction of the corresponding carboline results in the formation of the amine (42). The conversion of the amine (42) to the amides described above can be carried out using standard peptide coupling conditions in an appropriate solvent, such as dimethylformamide or methylene chloride followed by treatment with desired acids, to provide the corresponding amides. Isolation and purification of these amides can be carried out using standard work up and normal phase or reverse phase chromatographic methods.

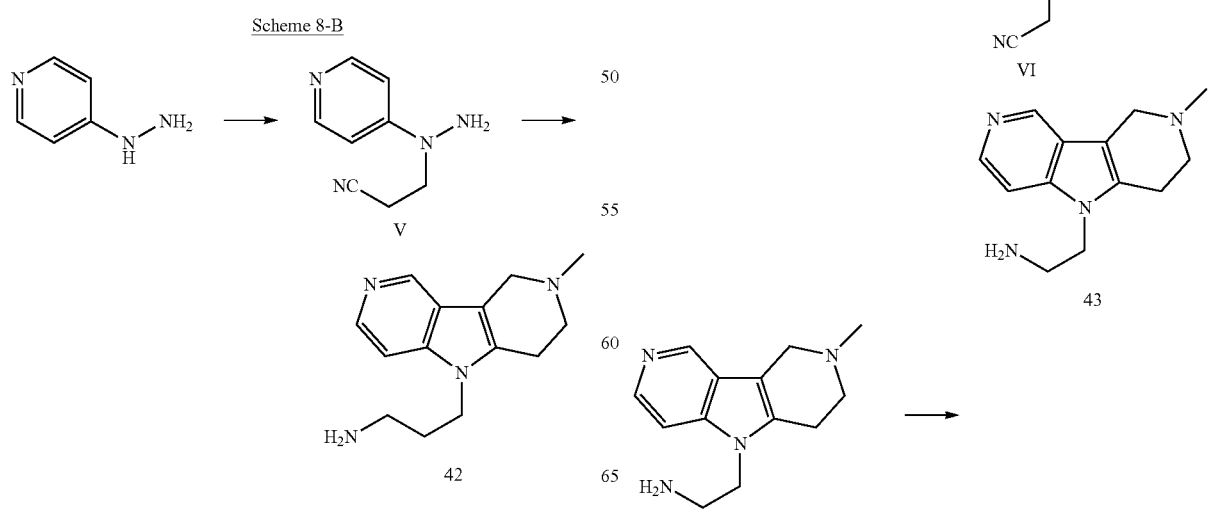

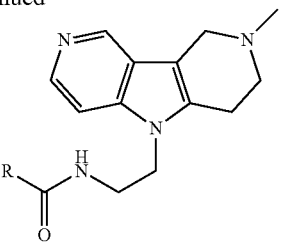

The reaction of a 4-pyridylhydrazine with bromo (or chloro)acetonitrile under appropriate alkylating conditions results in the formation of the internally substituted hydrazine (VI) which upon treatment with N-methyl-4-piperidone and reduction of the corresponding carboline results in the formation of the amine (43). The conversion of the amine (43) to the amides described above can be carried out using standard peptide coupling conditions in an appropriate solvent, such as dimethylformamide or methylene chloride followed by treatment with desired acids, to provide the corresponding amides. Isolation and purification of these amides can be carried out using standard work up and normal phase or reverse phase chromatographic methods.

General Method 9.

Scheme 9

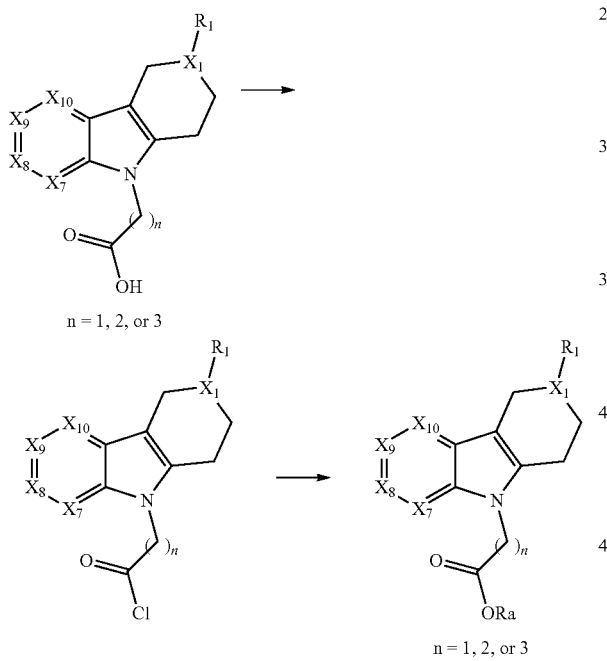

n = 1, 2, or 3

Certain compounds of the invention are synthesized using acid chloride intermediates as CD18 and CD20-CD22.

General Method 10.

Scheme 10

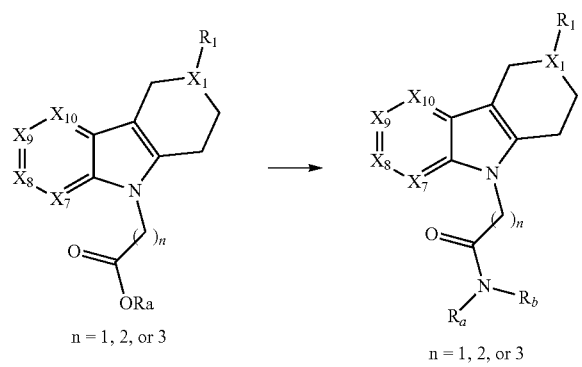

n = 1, 2, or 3

Certain compounds of the invention are synthesized using an acid amine transfer method as shown in Scheme 10. This general method is exemplified by the syntheses of compounds CD2, CD3, CD5, CD23 and CD24.

General Method 11.

Scheme 11

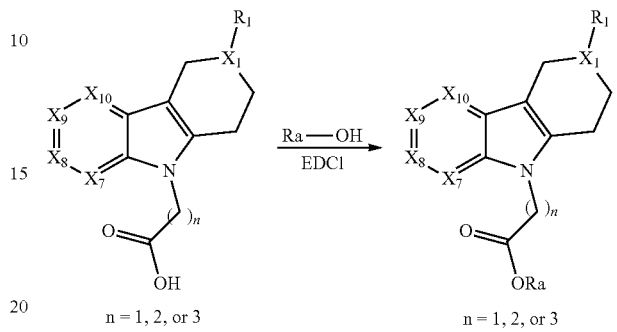

n = 1, 2, or 3

Certain compounds of the invention are synthesized using a EDCI as a coupling reagent as shown in Scheme. Solvents for the reaction, e.g. DMF or dichlormethane can be selected by one skilled in the art, for example, based on choice of starting materials. This general method is exemplified by the syntheses of compounds CD4, CD12, CD14, CD26, CD30, CD31 and CD54.

General Method 12.

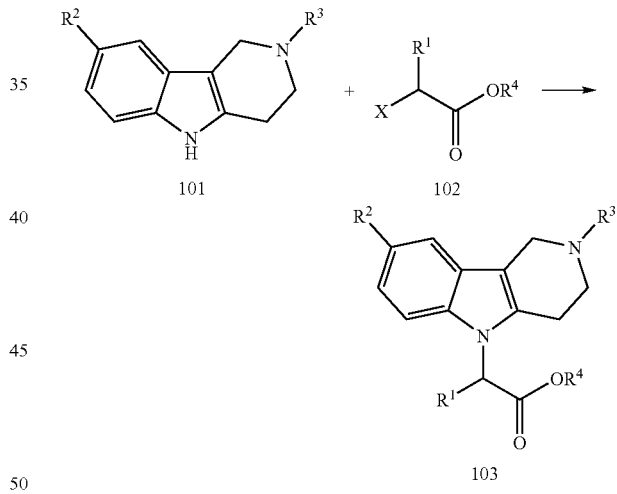

Compounds of structure 103 can be synthesized using the general synthetic protocol outlined in General Method 1. Appropriately substituted compounds of structure 101, wherein $R^2$ and $R^3$ are as described hereinabove, can be reacted under standard alkylating conditions with appropriately substituted compounds of structure 102, wherein $R^1$ and $R^4$ are as described hereinabove and X is a halogen selected from Cl, Br, and I, to give compounds of structure 103.

In one variation, sodium hydride (260 mmol) is added to a solution of 101 in DMF (150 ml) with stirring and cooling. After 30 minutes a solution of 102 (260 mmol) in DMF (20 ml) is added dropwise over 10-15 minutes to the reaction mixture. Obtained mixture is stirred at 70° C. for 10 h. The reaction mixture is evaporated to dryness under vacuum; the residue is poured into ice water (100 ml) and is extracted with methylene chloride (3×100 ml). The organic extract is dried with anhydrous sodium sulfate, the solvent is evaporated under vacuum, and the residue is recrystallized from benzene or it is chromatographed on dry column in the system petroleum ether-ethyl acetate with concentration gradient up to 15% of the latter to obtain 103.

General Method 13a.

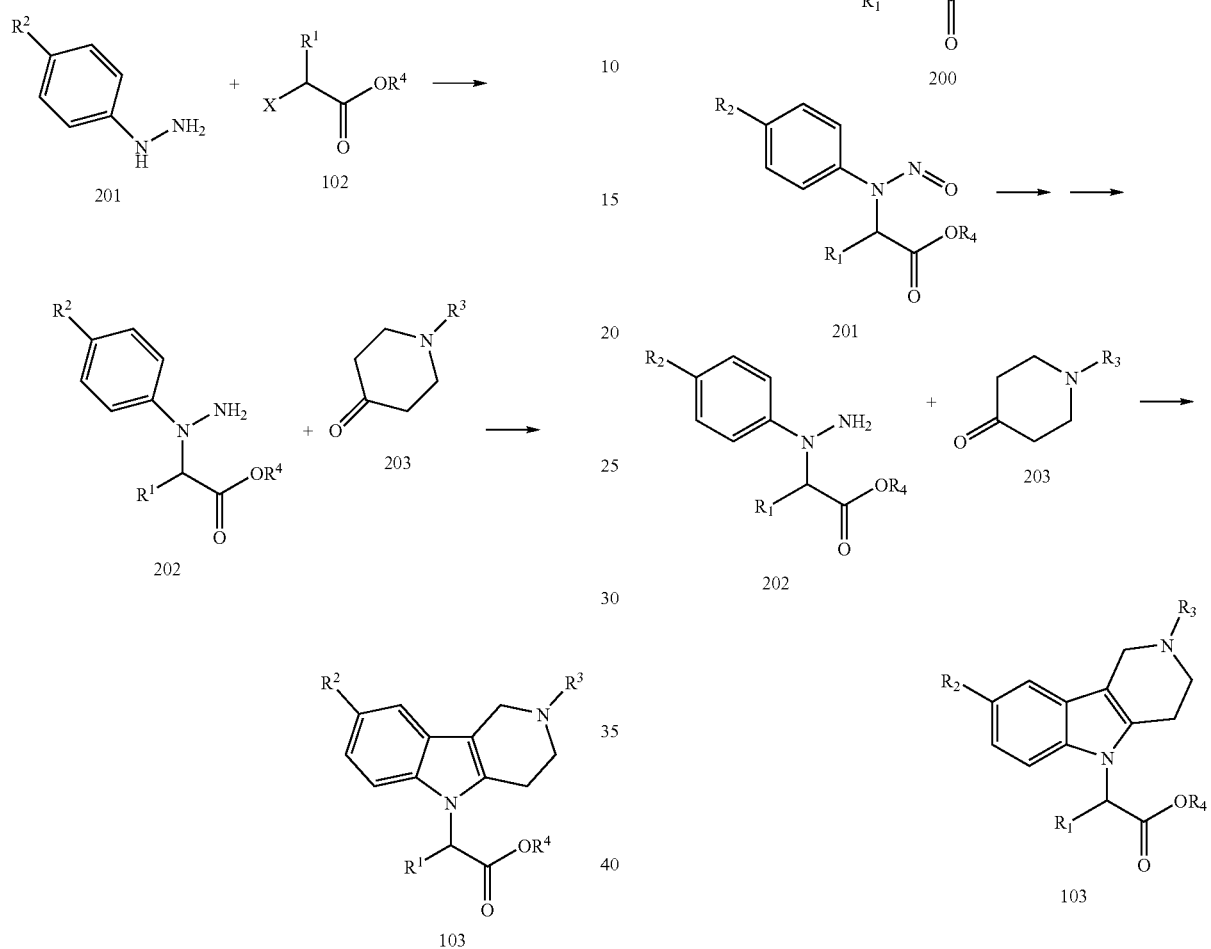

Compounds of structure 103 can also be synthesized using the general synthetic protocol outlined in General Method 2a. Appropriately substituted compounds of structure 201, wherein $R^2$ is as described hereinabove, may be reacted under standard alkylating conditions with appropriately substituted compounds of structure 102, wherein $R^1$ and $R^4$ are described hereinabove and X is selected from Cl, Br, and I, to give compounds of structure 202. Reaction of compounds of structure 202 under standard Fischer indole synthesis conditions with compounds of structure 203, wherein $R^3$ is as described hereinabove, gives compounds of structure 103.

General Method 13b.

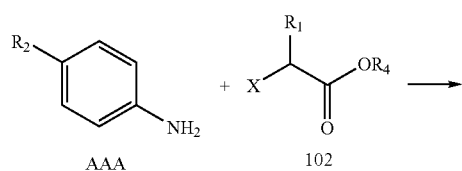

In another variation, the compounds of structure 103 can be synthesized according to the general synthetic protocol outlined in General Method 2b. Solution of aniline (10 mmol), ester of 102 (10 mmol) and diisopropylethylamine (10 mmol) in THF (40 ml) is reflux for 24 h. The reaction mixture is poured into ice water (100 ml) and is extracted with methylene chloride (4×50 ml). The organic extract is dried with anhydrous sodium sulfate, the solvent is evaporated under vacuum, and the residue is dissolved in ethanol and an excess of hydrogen chloride solution in ether is added. The volatile components are removed under vacuum, and the residue is recrystallized from ethanol-ether mixture to provide a compound of structure 200.

Hydrochloride of 200 (5.2 mmol) is added all at once with cooling and vigorous stirring to 50 ml of cold solution of potassium hydroxide (5.2 mmol) in water. Amine is extracted with ether (3×50 ml), is washed with water and a saturated sodium chloride solution, and the extract is dried with anhydrous sodium sulfate. The solvent is removed at reduced pressure, the residue is dissolved in anhydrous THF (10 ml), and 14% solution of ethyl nitrite in alcohol (~7.2 mmol) is added in portions with cooling and stirring to the solution obtained. The reaction mixture is held for 12 h at room temperature in the dark. The volatile components are removed under vacuum with bath temperature of 40° C., and a compound of formula 201 is obtained. This compound is used in later conversions without additional purification.

Concentrated HCl (72 ml) and (in portions with vigorous stirring) zinc dust (75 mmol) are added to a solution of nitrosamine of 201 (9 mmol) in absolute methanol (100 ml) with cooling down to −80° C. in argon atmosphere. The reaction mixture is stirred vigorously for 6-8 h at temperature from −80° C. to −70° C. in argon atmosphere. The completeness of reduction is monitored by TLC. The excess of zinc is filtered off, the residue is washed with methanol (20 ml), the filtrate is evaporated under vacuum at room temperature down to a volume of ~20 ml, is poured into ice water (100 ml) and is made alkaline by adding of 24% aqueous solution of ammonia (20 ml). This is extracted with methylene chloride (4×50 ml), the extract is washed with saturated sodium chloride solution (30 ml) and is dried with anhydrous sodium sulfate. After removing the solvent under vacuum, a compound of the formula 202 is obtained. This substance is used without additional purification.

Compound of structure 203 (4 mmol) and a catalytic amount of p-toluenesulfonic acid are added to a solution of compound 202 (4 mmol) in benzene (10 ml), and the mixture is boiled for 8 h with a Dean and Stark still head. The formation of hydrazone is confirmed by LC-MS. Benzene is removed under reduced pressure, the residue is dissolved in toluene (40 ml), Amberlist 15 (3 g) is added, and the mixture is stirred vigorously for 3 h at 90-100° C. The resin is filtered of, washed with ethyl acetate (60 ml), the filtrate is evaporated in vacuum, and the residue is chromatographed on a column of silica gel in the system petroleum ether-ethyl acetate with concentration gradient up to 15% of the latter, to provide a compound of the formula 103.

Compounds G1-G7 are synthesized using General Methods 12, 13a or 13b, or applicable general methods and synthetic procedures described herein. Compound 18 (CD19) is prepared according to General Method 1. Compounds 55 (CD65) and 58 (CD69) are prepared according to General Method 6. Compound 57 (CD67) is prepared according to General Method 8 where $X^9$ is $CR^4$.

The methods detailed above may be adapted as known by those of skill in the art. Particular examples of each General Method are provided in the Examples below.

The following Examples are provided to illustrate but not limit the invention.

All references disclosed herein are incorporated by reference in their entireties.

EXAMPLES

Example 1

Preparation of ethyl 3-(1,2,3,4-tetrahydro-2,8-dimethylpyrido[4,3-b]indol-5-yl)propanoate (CD1)

Preparation of the title compound was carried out according to General Method 1. p-Tolylhydrazine hydrochloride (20 g, 126 mmol), ethyl 3-bromopropionate (22.8 g, 126 mmol) and triethylamine (38.1 g, 378 mmol) in ethanol (200 ml) were stirred at 25° C. for 1 h after which the contents were heated at 90° C. for 3 h. The contents were cooled to 25° C. and evaporated to dryness. The residue was acidified with ethanolic HCl and the volatiles were removed under reduced pressure. Ethanol (200 mL) was added followed by N-methyl-4-piperidone hydrochloride (2.87 g, 18.9 mmol). Heating was continued at 90° C. for 16 h. The contents were concentrated in vacuo, basified by adding saturated aqueous NaHCO₃, and extracted with ethyl acetate. The organic layer was dried over anhydrous sodium sulfate and concentrated. The crude product was purified by chromatography on neutral alumina using methanol-dichloromethane gradient to obtain 1.5 g of ethyl 3-(1,2,3,4-tetrahydro-2,8-dimethylpyrido[4,3-b]indol-5-yl)propanoate.

Example 2

Preparation of ethyl 4-(1,2,3,4-tetrahydro-2,8-dimethylpyrido[4,3-b]indol-5-yl)butanoate (CD6)

Preparation of the title compound was carried out according to General Method 1 by using p-Tolylhydrazine hydrochloride (600 mg, 3.7 mmol), ethyl-4-chlorobutyrate (0.54 ml, 3.7 mmol), triethylamine (1.5 ml, 11.3 mmol) and N-methyl-4-piperidone hydrochloride (0.563 g, 3.7 mmol) in ethanol (10 ml) to obtain 130 mg of ethyl 4-(1,2,3,4-tetrahydro-2,8-dimethylpyrido[4,3-b]indol-5-yl)butanoate after purification on silica gel (230-400 mesh) chromatography eluting with methanol-dichloromethane gradient. The free base was converted into its oxalate salt by treatment of oxalic acid (1 equiv) in anhydrous THF.

Example 3

Preparation of ethyl 2-(8-chloro-1,2,3,4-tetrahydro-2-methylpyrido[4,3-b]indol-5-yl)acetate (CD11)

Preparation of the title compound was carried out according to General Method 1 by using 4-chlorophenylhydrazine hydrochloride (5 g, 27.9 mmol), ethyl bromoacetate (4.6 g, 27.9 mmol), triethylamine (11.6 mL, 83.2 mmol) and N-methyl-4-piperidone hydrochloride (5.2 g, 34.9 mmol) in ethanol (50 ml) to obtain 1.3 g of ethyl 2-(8-chloro-1,2,3,4-tetrahydro-2-methylpyrido[4,3-b]indol-5-yl)acetate after purification on neutral alumina chromatography eluting with dichloromethane-hexane gradient.

Example 4

Preparation of ethyl 3-(8-chloro-1,2,3,4-tetrahydro-2-methylpyrido[4,3-b]indol-5-yl)propanoate (CD59)

Preparation of the title compound was carried out according to General Method 1 by using 4-chlorophenylhydrazine hydrochloride (10 g, 55 mmol), ethyl 3-bromopropionate (7.2 mL, 55 mmol), triethylamine (23 mL, 165 mmol) and N-methyl-4-piperidone hydrochloride (8.3 g, 55 mmol) in ethanol (100 ml) to obtain 1.4 g of ethyl 3-(8-chloro-1,2,3,4-tetrahydro-2-methylpyrido[4,3-b]indol-5-yl)propanoate after purification on neutral alumina chromatography eluting with dichloromethane-hexane gradient.

Example 5

Preparation of 2-(1,2,3,4-tetrahydro-2,8-dimethylpyrido[4,3-b]indol-5-yl)acetonitrile (CD61)

Preparation of the title compound was carried out according to General Method 8 by using p-tolylhydrazine hydrochloride (10 g, 63 mmol), bromo acetonitrile (7.56 ml, 63 mmol), triethylamine (19.1 g, 189 mmol) and N-methyl-4-piperidone hydrochloride (2.54 g, 17 mmol) in ethanol (30 ml) to obtain 1.8 g of 2-(1,2,3,4-tetrahydro-2,8-dimethylpyrido[4,3-b]indol-5-yl)acetonitrile after purification on neutral alumina chromatography eluting with methanol-dichloromethane gradient. The TFA salt of this material was obtained by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 6

Preparation of 2,2,2-trichloroethyl 2-(1,2,3,4-tetrahydro-2,8-dimethylpyrido[4,3-b]indol-5-yl)ethylcarbamate (CD9)

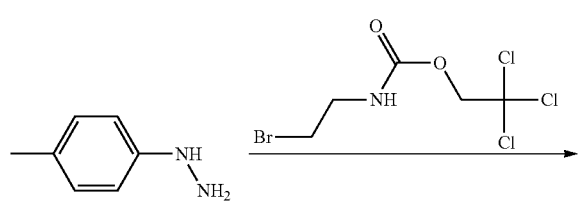

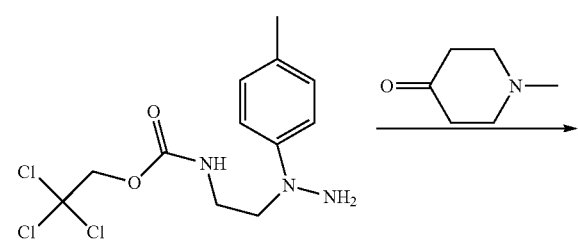

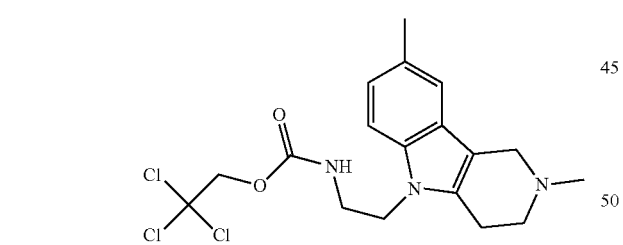

Preparation of the title compound was carried out using p-Tolylhydrazine hydrochloride (396 mg, 2.5 mmol), 2,2,2-trichloroethyl 2-bromoethylcarbamate (750 mg, 2.5 mmol), triethylamine (1 ml, 7.4 mmol) and N-methyl-4-piperidone hydrochloride (394 mg, 2.6 mmol) in ethanol-HCl (15 ml) to obtain 160 mg of 2,2,2-trichloroethyl 2-(1,2,3,4-tetrahydro-2,8-dimethylpyrido[4,3-b]indol-5-yl)ethylcarbamate as TFA salt after purification on silica gel (230-400 mesh) chromatography eluting with methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 7

Preparation of N-(4-fluorophenyl)-3-(1,2,3,4-tetrahydro-2,8-dimethylpyrido[4,3-b]indol-5-yl)propanamide (CD50)

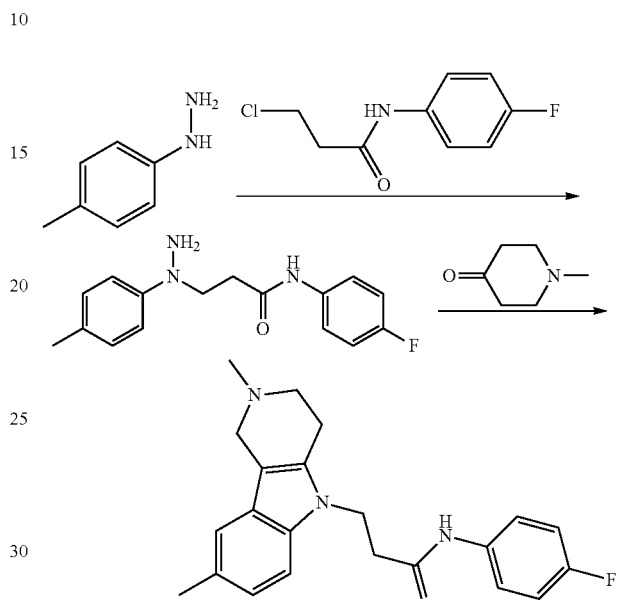

Preparation of the title compound was carried out using p-tolylhydrazine hydrochloride (1.1 g, 7.4 mmol), 3-chloro-N-(4-fluorophenyl)propanamide (1.5 g, 7.4 mmol), triethylamine (2.2 g, 22.3 mmol) and N-methyl-4-piperidone hydrochloride (1.1 g, 7.4 mmol) in ethanol-HCl (12 ml) to obtain N-(4-fluorophenyl)-3-(1,2,3,4-tetrahydro-2,8-dimethylpyrido[4,3-b]indol-5-yl)propanamide as TFA salt after purification on silica gel (230-400 mesh) chromatography eluting with methanol-dichloromethane gradient followed by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 8

Preparation of 3-(1,2,3,4-tetrahydro-2,8-dimethylpyrido[4,3-b]indol-5-yl)-N-methylpropanamide (CD2)

A mixture of ethyl 3-(1,2,3,4-tetrahydro-2,8-dimethylpyrido[4,3-b]indol-5-yl)propanoate (100 mg, 0.33 mmol) and methyl amine (40% aq, 2.5 ml) was heated at 100-120° C. for 3-4 h. The reaction mixture was evaporated to dryness and the residue was purified by on neutral alumina chromatography eluting with methanol-dichloromethane gradient to obtain 10 mg of 3-(1,2,3,4-tetrahydro-2,8-dimethylpyrido[4,3-b]indol-5-yl)-N-methylpropanamide.

Example 9

Preparation of N-ethyl-3-(1,2,3,4-tetrahydro-2,8-dimethylpyrido[4,3-b]indol-5-yl)propanamide (CD3)

A mixture of ethyl 3-(1,2,3,4-tetrahydro-2,8-dimethylpyrido[4,3-b]indol-5-yl)propanoate (100 mg, 0.33 mmol) and ethyl amine (40% aq, 2.5 ml) was heated at 100-120° C. for 3-4 h to obtain 19 mg of N-ethyl-3-(1,2,3,4-tetrahydro-2,8-dimethylpyrido[4,3-b]indol-5-yl)propanamide after purification on neutral alumina chromatography eluting with methanol-dichloromethane gradient.

Example 10

Preparation of N-cyclopentyl-3-(1,2,3,4-tetrahydro-2,8-dimethylpyrido[4,3-b]indol-5-yl)propanamide (CD5)

A mixture of ethyl 3-(1,2,3,4-tetrahydro-2,8-dimethylpyrido[4,3-b]indol-5-yl)propanoate (100 mg, 0.33 mmol) and cyclopentylamine (1 ml, 10 mmol) was heated at 100-120° C. for 3-4 h to obtain 17 mg of N-cyclopentyl-3-(1,2,3,4-tetrahydro-2,8-dimethylpyrido[4,3-b]indol-5-yl)propanamide after purification on neutral alumina chromatography eluting with methanol-dichloromethane gradient.

Example 11

Preparation of N-ethyl-4-(1,2,3,4-tetrahydro-2,8-dimethylpyrido[4,3-b]indol-5-yl)butanamide (CD7)

Ethyl 4-(1,2,3,4-tetrahydro-2,8-dimethylpyrido[4,3-b]indol-5-yl)butanoate (80 mg, 0.2 mmol) was stirred with ethylamine (0.8 ml) at 100-120° C. for 3-4 h to obtain 40 mg of N-ethyl-4-(1,2,3,4-tetrahydro-2,8-dimethylpyrido[4,3-b]indol-5-yl)butanamide after purification on neutral alumina chromatography eluting with methanol-dichloromethane gradient.

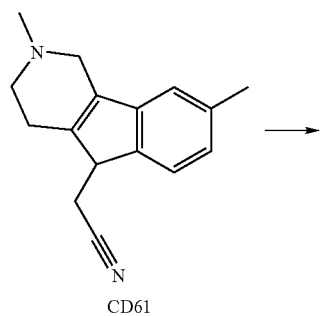

CD61

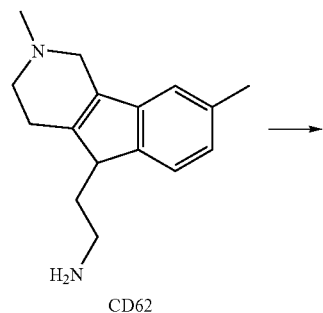

CD62

-continued

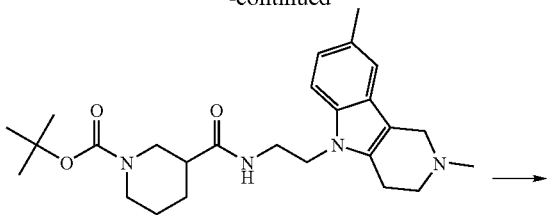

CD8

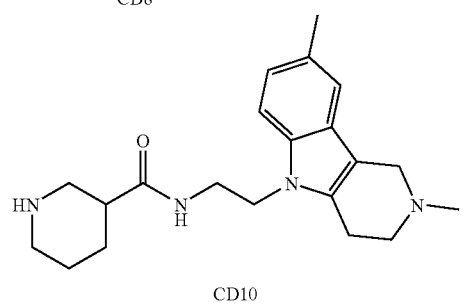

CD10

Example 12

Preparation of 2-(1,2,3,4-tetrahydro-2,8-dimethylpyrido[4,3-b]indol-5-yl)ethanamine (CD62)

2-(1,2,3,4-tetrahydro-2,8-dimethylpyrido[4,3-b]indol-5-yl)acetonitrile (500 mg, 2 mmol) was treated with diisobutylaluminum hydride (6.2 ml, 6.2 mmol) in toluene (10 ml) at 80° C. to obtain 250 mg of 2-(1,2,3,4-tetrahydro-2,8-dimethylpyrido[4,3-b]indol-5-yl)ethanamine after purification on silica gel (230-400 mesh) chromatography eluting with methanol-dichloromethane gradient.

Example 13

Preparation of tert-butyl 3-(2-(1,2,3,4-tetrahydro-2,8-dimethylpyrido[4,3-b]indol-5-yl)ethylcarbamoyl)piperidine-1-carboxylate (CD8)

2-(1,2,3,4-tetrahydro-2,8-dimethylpyrido[4,3-b]indol-5-yl)ethanamine (100 mg, 0.4 mmol) was mixed with EDCI (78 mg, 0.4 mmol) and N-Boc-(S)-nipecotic acid (94 mg, 0.4 mmol) in dichloromethane (3 ml) and the reaction mixture was stirred for 16 h to obtain tert-butyl 3-(2-(1,2,3,4-tetrahydro-2,8-dimethylpyrido[4,3-b]indol-5-yl)ethylcarbamoyl)piperidine-1-carboxylate as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

Example 14

Preparation of N-(2-(1,2,3,4-tetrahydro-2,8-dimethylpyrido[4,3-b]indol-5-yl)ethyl)piperidine-3-carboxamide (CD10)

tert-butyl 3-(2-(1,2,3,4-tetrahydro-2,8-dimethylpyrido[4,3-b]indol-5-yl)ethylcarbamoyl)piperidine-1-carboxylate (40 mg, 0.08 mmol) was stirred with trifluoroacetic acid (0.1 mL) in dichloromethane (2 ml) to obtain 10 mg of N-(2-(1,2,3,4-tetrahydro-2,8-dimethylpyrido[4,3-b]indol-5-yl)ethyl)piperidine-3-carboxamide as di-TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).
Example 14A
Preparation of Compound 54 (CD64)
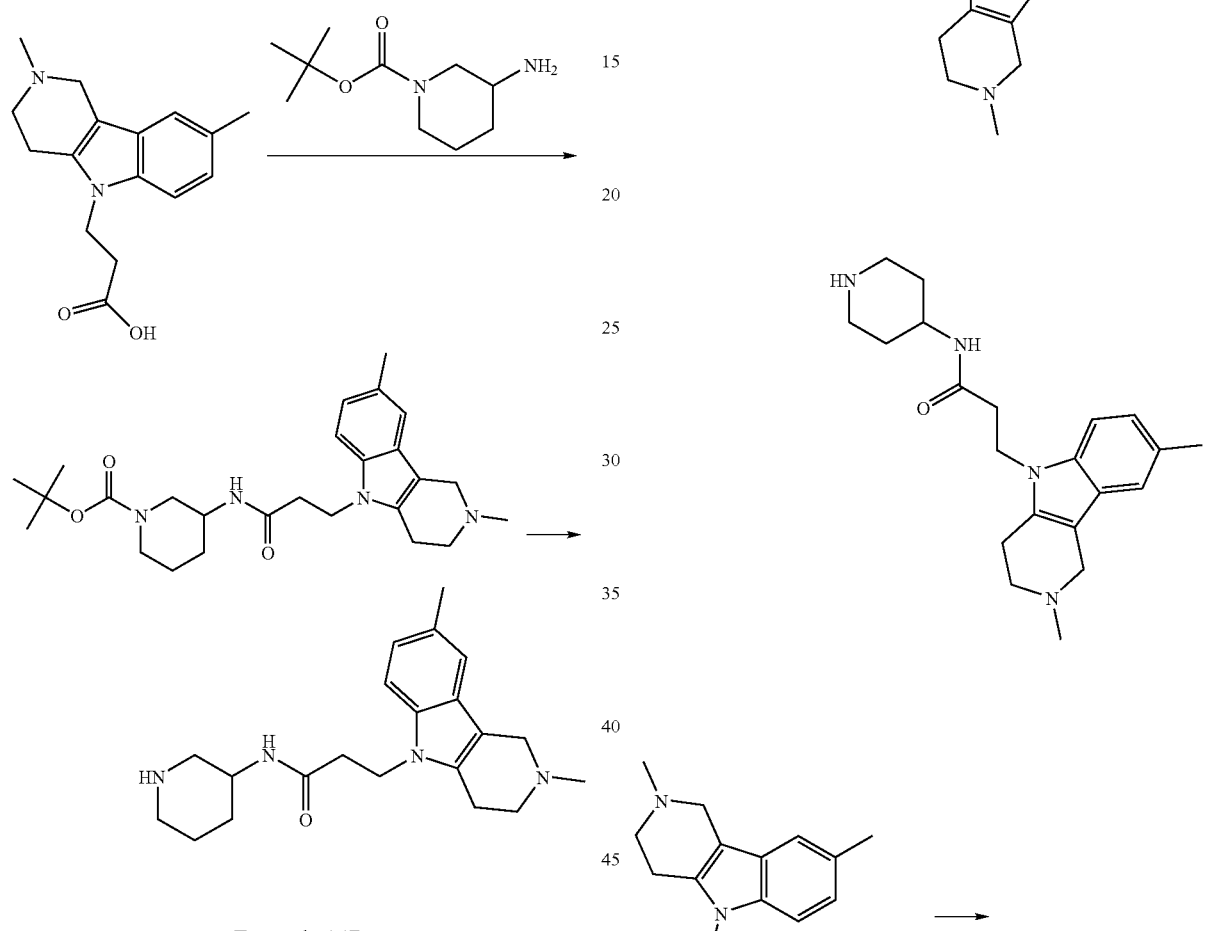
Example 14B
Preparation of Compound 56 (CD66)
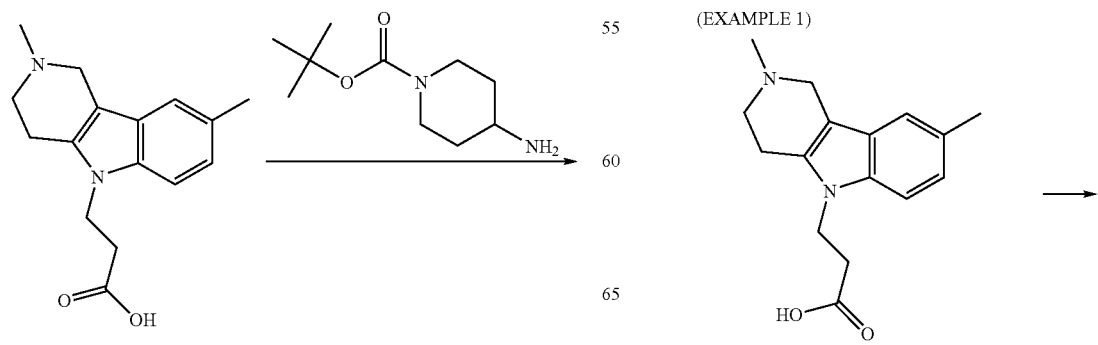
(EXAMPLE 1)

-continued

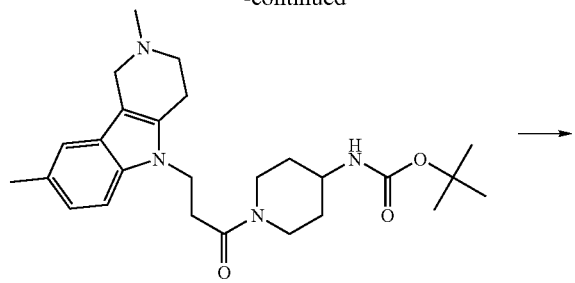

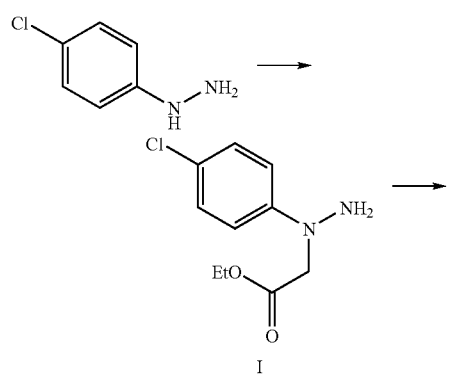

Example 15

Preparation of 3-(1,2,3,4-tetrahydro-2,8-dimethylpyrido[4,3-b]indol-5-yl)propanoic acid (CD47)

A mixture of ethyl 3-(1,2,3,4-tetrahydro-2,8-dimethylpyrido[4,3-b]indol-5-yl)propanoate (100 mg, 0.33 mmol) (1.5 g) and NaOH (3N, 30 ml) in ethanol (30 ml) was stirred at 50° C. for 3 h after which it was cooled to RT and neutralized with conc. HCl. The solvent was removed under reduced pressure to obtain crude 3-(1,2,3,4-tetrahydro-2,8-dimethylpyrido[4,3-b]indol-5-yl)propanoic acid.

Example 16

Preparation of CD63

-continued

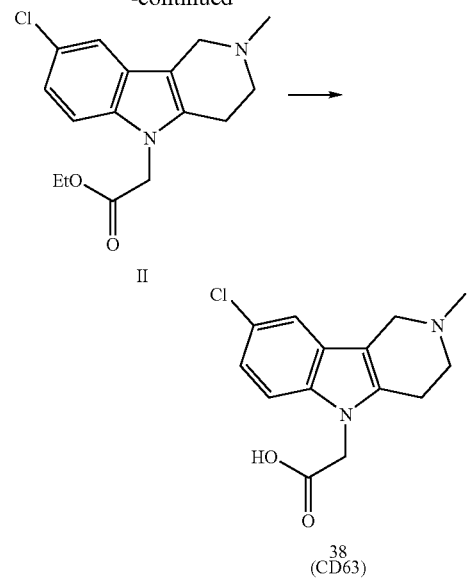

The reaction described above for 4-chlorophenylhydrazine, which can be extended to any appropriately substituted phenylhydrazine, with ethyl bromo (or chloro)acetate under appropriate alkylating conditions results in the formation of the internally substituted hydrazine (I). The reaction of (I) with N-methyl-4-piperidone results in the formation of the carboline (II). The hydrolysis of (II) gives the acid 38.

Example 17

Preparation of CD23-CD27 and CD54

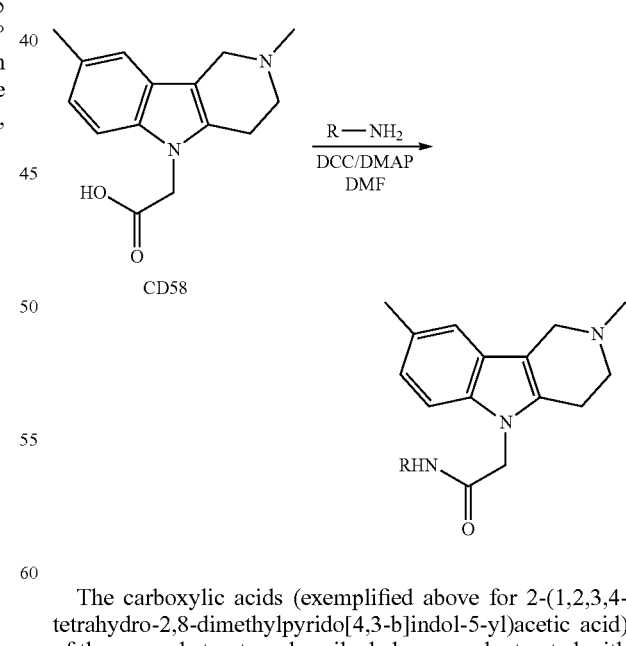

The carboxylic acids (exemplified above for 2-(1,2,3,4-tetrahydro-2,8-dimethylpyrido[4,3-b]indol-5-yl)acetic acid) of the general structure described above can be treated with DCC/DMAP in an appropriate solvent, such as dimethylformamide or methylene chloride followed by treatment with a desired amine ($R_a$—$NH_2$) to provide the corresponding amides. Isolation and purification of these amides can be carried out using standard work up and normal phase or reverse phase chromatographic methods.

Example 18

Preparation of CD2-CD5 and CD29-CD31

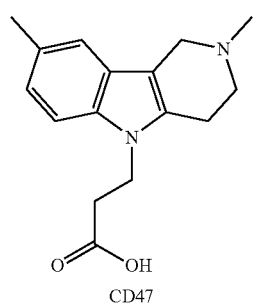
CD47

$\xrightarrow{\text{R—NH}_2}{\text{DCC/DMAP}\atop\text{DMF}}$

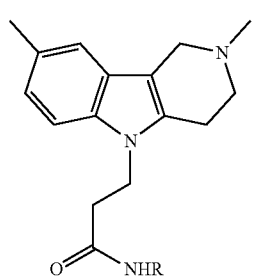

The carboxylic acids (exemplified above for 3-(1,2,3,4-tetrahydro-2,8-dimethylpyrido[4,3-b]indol-5-yl)propanoic acid of the general structure described above can be treated with DCC/DMAP in an appropriate solvent, such as dimethylformamide or methylene chloride followed by treatment with a desired amine ($R_a$—$NH_2$) to provide the corresponding amides. Isolation and purification of these amides can be carried out using standard work up and normal phase or reverse phase chromatographic methods.

Example 19

Preparation of CD33, CD34 and CD35

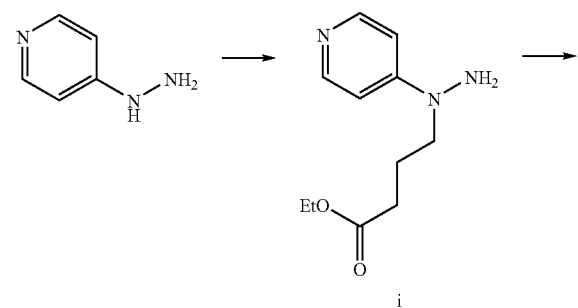
i

-continued

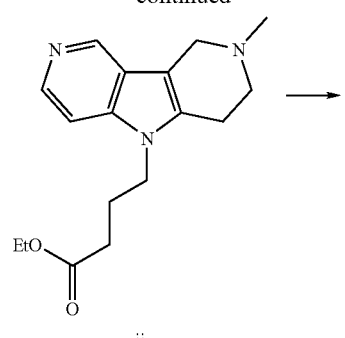

ii

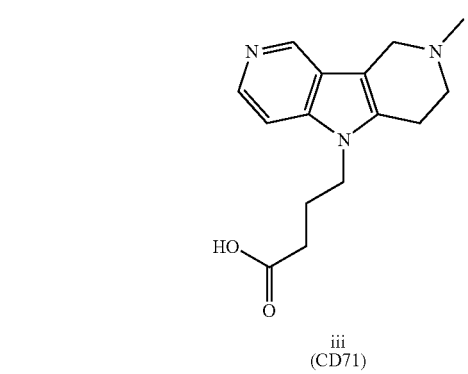

iii
(CD71)

$\xrightarrow{\text{R—OH}}{\text{DCC/DMAP}\atop\text{DMF}}$

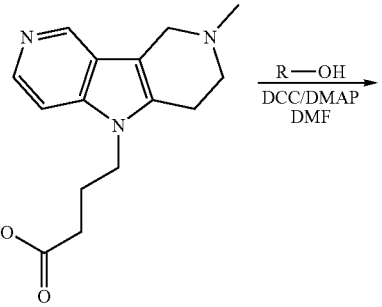

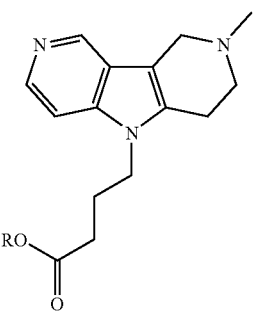

The reaction of a 4-pyridylhydrazine with ethyl 4-bromo (or chloro)butanoate under appropriate alkylating conditions results in the formation of the internally substituted hydrazine (i) The reaction of (i) with N-methyl-4-piperidone results in the formation of the carboline (ii). The hydrolysis of (ii) gives the acid (iii). The carboxylic acids, including (iii) can be treated with DCC/DMAP in an appropriate solvent, such as dimethylformamide or methylene chloride followed by treatment with a desired alcohol (R—OH) to provide the corresponding esters. Isolation and purification of these esters can be carried out using standard work up and normal phase or reverse phase chromatographic methods.

Example 20

Preparation of CD36, CD37 and CD38

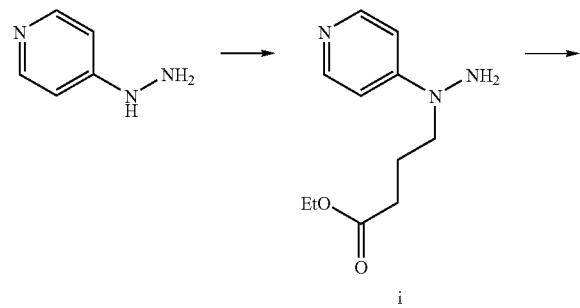

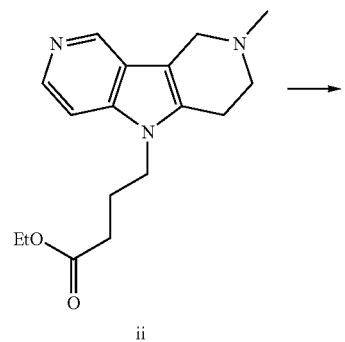

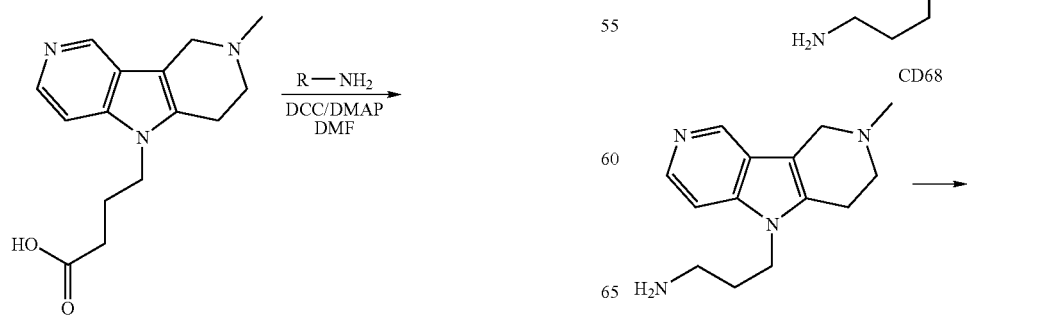

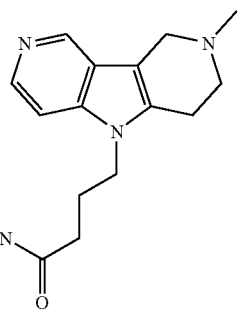

The reaction of a 4-pyridylhydrazine with ethyl 4-bromo (or chloro)butanoate under appropriate alkylating conditions results in the formation of the internally substituted hydrazine (i). The reaction of (i) with N-methyl-4-piperidone results in the formation of the carboline (ii). The hydrolysis of (ii) gives the acid (iii). The carboxylic acids, including (iii) can be treated with DCC/DMAP in an appropriate solvent, such as dimethylformamide or methylene chloride followed by treatment with a desired amine ($R_a$—$NH_2$) to provide the corresponding amides. Isolation and purification of these amides can be carried out using standard work up and normal phase or reverse phase chromatographic methods.

Example 21

Preparation of CD39, CD40 and CD41

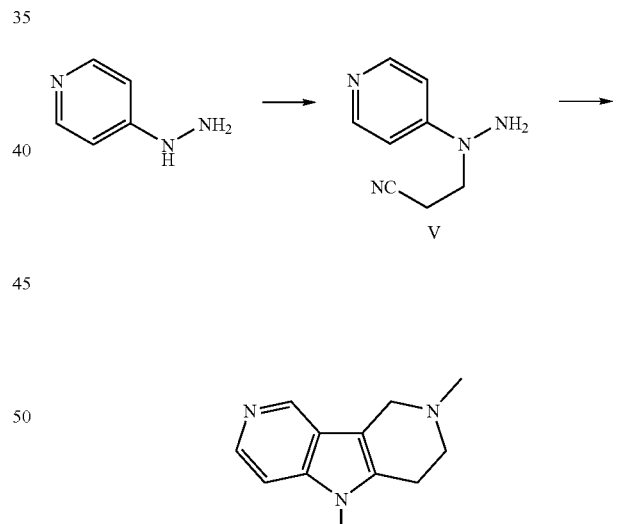

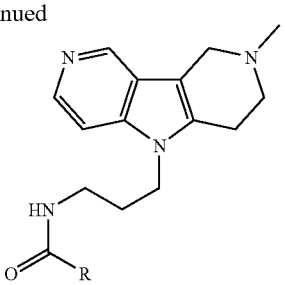

The reaction of a 4-pyridylhydrazine with 3-bromo (or chloro)propionitrile under appropriate alkylating conditions results in the formation of the internally substituted hydrazine (V) which upon treatment with N-methyl-4-piperidone and reduction of the corresponding carboline results in the formation of the amine (CD68). The conversion of the amine (CD68) to the amides described above can be carried out using standard peptide coupling conditions in an appropriate solvent, such as dimethylformamide or methylene chloride followed by treatment with desired acids, to provide the corresponding amides. Isolation and purification of these amides can be carried out using standard work up and normal phase or reverse phase chromatographic methods.

Example 22

Preparation of CD42, CD43, CD44 and CD45

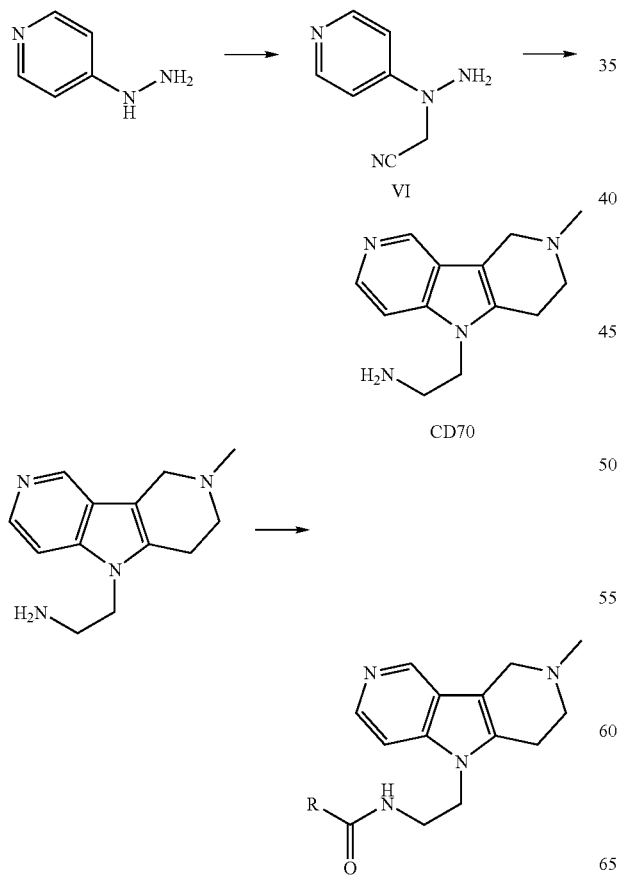

The reaction of a 4-pyridylhydrazine with bromo (or chloro) acetonitrile under appropriate alkylating conditions results in the formation of the internally substituted hydrazine (VI) which upon treatment with N-methyl-4-piperidone and reduction of the corresponding carboline results in the formation of the amine (CD70). The conversion of the amine (CD70) to the amides described above can be carried out using standard peptide coupling conditions in an appropriate solvent, such as dimethylformamide or methylene chloride followed by treatment with desired acids, to provide the corresponding amides. Isolation and purification of these amides can be carried out using standard work up and normal phase or reverse phase chromatographic methods.

Example 23

Preparation of CD46

A mixture of ethyl 2-(8-chloro-1,2,3,4-tetrahydro-2-methylpyrido[4,3-b]indol-5-yl)acetate and NaOH in ethanol was stirred at 50° C. for 3 h after which it was cooled to RT and neutralized with conc. HCl. The solvent was removed under reduced pressure to obtain crude 2-(8-chloro-1,2,3,4-tetrahydro-2-methylpyrido[4,3-b]indol-5-yl)acetic acid.

Example 24

Preparation of CD51

A mixture of ethyl 2-(8-chloro-1,2,3,4-tetrahydro-2-methylpyrido[4,3-b]indol-5-yl)acetate (100 mg) and dimethylamine (1 ml) was heated at 120° C. for 15 h to obtain 2-(8-chloro-1,2,3,4-tetrahydro-2-methylpyrido[4,3-b]indol-5-yl)-N,N-dimethylacetamide after purification on neutral alumina chromatography eluting with methanol-dichloromethane gradient. The free base was converted into its oxalate salt by treatment of oxalic acid (1 equiv) in anhydrous THF.

Example 25

Preparation of CD17

4-Chlorophenylhydrazine hydrochloride, ethyl 3-bromopropionate and triethylamine in ethanol were stirred at 25° C. for 1 h after which the contents were heated at 90° C. for 3 h. The contents were cooled to 25° C. and evaporated to dryness. The residue was acidified with ethanolic HCl and the volatiles were removed under reduced pressure. Ethanol was added followed by N-methyl-4-piperidone hydrochloride. Heating was continued at 90° C. for 16 h. The contents were concentrated in vacuo, basified by adding saturated aqueous NaHCO3, and extracted with ethyl acetate. The organic layer was dried over anhydrous sodium sulfate and concentrated. The crude product was purified by chromatography on neutral alumina using methanol-dichloromethane gradient to obtain ethyl 3-(8-chloro-1,2,3,4-tetrahydro-2-methylpyrido[4,3-b]indol-5-yl)propanoate.

Example 26

Preparation of CD52 and CD60

A mixture of ethyl 3-(8-chloro-1,2,3,4-tetrahydro-2-methylpyrido[4,3-b]indol-5-yl)propanoate (CD17) (100 mg) and dimethylamine (1 ml) was heated at 120° C. for 15 h to obtain 3-(8-chloro-1,2,3,4-tetrahydro-2-methylpyrido[4,3-b]indol- 5-yl)-N,N-dimethylpropanamide (CD52) after purification on neutral alumina chromatography eluting with methanol-dichloromethane gradient. The free base was converted into its HCl salt by treatment of ethanol-HCl.

Compound CD60 is prepared according to the process described herein using appropriately substituted reagents.

Example 27

Preparation of CD57

Preparation of the title compound was carried out according by using p-tolylhydrazine hydrochloride, ethyl bromoacetate, triethylamine and N-methyl-4-piperidone hydrochloride in ethanol to obtain ethyl 2-(1,2,3,4-tetrahydro-2,8-dimethylpyrido[4,3-b]indol-5-yl)acetate after purification on neutral alumina chromatography eluting with dichloromethane-hexane gradient.

Example 28

Preparation of CD58

A mixture of ethyl 2-(1,2,3,4-tetrahydro-2,8-dimethylpyrido[4,3-b]indol-5-yl)acetate and NaOH in ethanol was stirred at 50° C. for 3 h after which it was cooled to RT and neutralized with conc. HCl. The solvent was removed under reduced pressure to obtain crude 2-(1,2,3,4-tetrahydro-2,8-dimethylpyrido[4,3-b]indol-5-yl)acetic acid.

Example 29

Preparation of CD23

A mixture of ethyl 2-(1,2,3,4-tetrahydro-2,8-dimethylpyrido[4,3-b]indol-5-yl)acetate (100 mg) and ethylamine (1 ml) was heated at 120° C. for 15 h to obtain N-ethyl-2-(1,2,3,4-tetrahydro-2,8-dimethylpyrido[4,3-b]indol-5-yl)acetamide (CD23) after purification on neutral alumina chromatography eluting with methanol-dichloromethane gradient. The free base was converted into its oxalate salt by treatment of oxalic acid (1 equiv) in anhydrous THF.

Example 30

Preparation of CD26

2-(1,2,3,4-tetrahydro-2,8-dimethylpyrido[4,3-b]indol-5-yl)acetic acid (CD58) was mixed with EDCI and benzylamine and the reaction mixture was stirred for 16 h to obtain N-benzyl-2-(1,2,3,4-tetrahydro-2,8-dimethylpyrido[4,3-b]indol-5-yl)acetamide after purification on neutral alumina chromatography eluting with methanol-dichloromethane gradient. The free base was converted into its oxalate salt by treatment of oxalic acid (1 equiv) in anhydrous THF.

Example 31

Preparation of CD28

A mixture of ethyl 2-(8-chloro-1,2,3,4-tetrahydro-2-methylpyrido[4,3-b]indol-5-yl)acetate (100 mg) and cyclopentylamine (1 ml) was heated at 120° C. for 15 h to obtain 2-(8-chloro-1,2,3,4-tetrahydro-2-methylpyrido[4,3-b]indol-5-yl)-N-cyclopentylacetamide after purification on neutral alumina chromatography eluting with methanol-dichloromethane gradient. The free base was converted into its oxalate salt by treatment of oxalic acid (1 equiv) in anhydrous THF.

Example 32

Preparation of CD53

2-(1,2,3,4-tetrahydro-2,8-dimethylpyrido[4,3-b]indol-5-yl)ethanamine was mixed with EDCI and pyridine-4-carboxylic acid in dichloromethane and the reaction mixture was stirred for 16 h to obtain N-(2-(1,2,3,4-tetrahydro-2,8-dimethylpyrido[4,3-b]indol-5-yl)ethyl)isonicotinamide as TFA salt after purification by reverse-phase chromatography (C-18, 500 mm×50 mm, Mobile Phase A=0.05% TFA in water, B=0.05

Example 33

Preparation of CD54

2-(1,2,3,4-tetrahydro-2,8-dimethylpyrido[4,3-b]indol-5-yl)acetic acid (CD58) was mixed with EDCI and 4-fluoroaniline and the reaction mixture was stirred for 16 h to obtain N-(4-fluorophenyl)-2-(1,2,3,4-tetrahydro-2,8-dimethylpyrido[4,3-b]indol-5-yl)acetamide after purification on neutral alumina chromatography eluting with methanol-dichloromethane gradient. The free base was converted into its oxalate salt by treatment of oxalic acid (1 equiv) in anhydrous THF.

Example 34

Preparation of CD12

2-(8-chloro-1,2,3,4-tetrahydro-2-methylpyrido[4,3-b]indol-5-yl)acetic acid was mixed with EDCI and isopropanol and the reaction mixture was stirred for 16 h to obtain isopropyl 2-(8-chloro-1,2,3,4-tetrahydro-2-methylpyrido[4,3-b]indol-5-yl)acetate after purification on neutral alumina chromatography eluting with methanol-dichloromethane gradient. The free base was converted into its oxalate salt by treatment of oxalic acid (1 equiv) in anhydrous THF.

Example 35

Preparation of CD30

3-(1,2,3,4-tetrahydro-2,8-dimethylpyrido[4,3-b]indol-5-yl)propanoic acid was mixed with EDCI and aniline in dichloromethane and the reaction mixture was stirred for 16 h to obtain CD30 after purification on neutral alumina chromatography eluting with methanol-dichloromethane gradient. The free base was converted into its oxalate salt by treatment of oxalic acid (1 equiv) in anhydrous THF.

Example 36

Preparation of CD32

A mixture of ethyl 3-(8-chloro-1,2,3,4-tetrahydro-2-methylpyrido[4,3-b]indol-5-yl)propanoate (CD17) (100 mg) and cyclopentylamine (1 ml) was heated at 120° C. for 15 h to obtain 3-(8-chloro-1,2,3,4-tetrahydro-2-methylpyrido[4,3-b]indol-5-yl)-N-cyclopentylpropanamide (CD32) after purification on neutral alumina chromatography eluting with methanol-dichloromethane gradient. The free base was converted into its oxalate salt by treatment of oxalic acid (1 equiv) in anhydrous THF.

Example 37

Preparation of CD55

A mixture of ethyl 3-(8-chloro-1,2,3,4-tetrahydro-2-methylpyrido[4,3-b]indol-5-yl)propanoate (CD17) and NaOH in ethanol was stirred at 50° C. for 3 h after which it was cooled to RT and neutralized with conc. HCl. The solvent was removed under reduced pressure to obtain crude 3-(8-chloro-1,2,3,4-tetrahydro-2-methylpyrido[4,3-b]indol-5-yl)propanoic acid.

Example 38

Preparation of CD56

2-(8-chloro-1,2,3,4-tetrahydro-2-methylpyrido[4,3-b]indol-5-yl)acetic acid was mixed with EDCI and 1-butanol and the reaction mixture was stirred for 16 h to obtain butyl 2-(8-chloro-1,2,3,4-tetrahydro-2-methylpyrido[4,3-b]indol-5-yl)acetate after purification on neutral alumina chromatography eluting with methanol-dichloromethane gradient. The free base was converted into its oxalate salt by treatment of oxalic acid (1 equiv) in anhydrous THF.

Example 39

Preparation of CD4

3-(1,2,3,4-tetrahydro-2,8-dimethylpyrido[4,3-b]indol-5-yl)propanoic acid was mixed with EDCI (78 mg, 0.4 mmol) and cyclohexylamine in dichloromethane and the reaction mixture was stirred for 16 h to obtain N-cyclohexyl-3-(1,2,3,4-tetrahydro-2,8-dimethylpyrido[4,3-b]indol-5-yl)propanamide after purification on neutral alumina chromatography eluting with methanol-dichloromethane gradient.

Example 40

Preparation of CD48

Ethyl 2-(8-chloro-1,2,3,4-tetrahydro-2-methylpyrido[4,3-b]indol-5-yl)acetate (0.1 g, 0.35 mmol) was taken in 4 ml aqueous ammonia and heated at 120 deg C. for 5 min in microwave. The solid product precipitated out after the reaction was filtered through a Buchner funnel and washed with 10% sodium bicarbonate (10 ml×2) followed by demineralised water (10 ml×2) wash. Product was vacuum dried and was taken in 5 ml ethanolic HCl, stirred for 15 min, concentrated in vacuo to afford 38 mg of 2-(8-chloro-1,2,3,4-tetrahydro-2-methylpyrido[4,3-b]indol-5-yl)acetamide as hydrochloride salt. $^1$H NMR (DMSO)HCl Salt 10.38 (bs, 1H), 7.67 (s, 1H), 7.58 (s, 1H), 7.43 (d, 1H), 7.38 (s, 1H), 7.18 (d, 1H), 4.79 (d, 2H), 4.62 (d, 1H), 4.21-4.31 (m, 1H), 3.68-3.81 (m, 1H), 3.42-3.53 (m, 1H), 3.04-3.14 (m, 2H), 2.96 (s, 3H).

Example 40A

A mixture of ethyl 2-(8-chloro-1,2,3,4-tetrahydro-2-methylpyrido[4,3-b]indol-5-yl)acetate (100 mg) and piperidine (1 ml) was heated at 120° C. for 15 h to obtain 2-(8-chloro-1,2,3,4-tetrahydro-2-methylpyrido[4,3-b]indol-5-yl)-1-(piperidin-1-yl)ethanone as TFA salt after purification by reverse-phase chromatography (C-18, 500 mm×50 mm, Mobile Phase A=0.05% TFA in water, B=0.05

Example 41

Preparation of CD14

2-(8-chloro-1,2,3,4-tetrahydro-2-methylpyrido[4,3-b]indol-5-yl)acetic acid was mixed with EDCI and benzyl alcohol and the reaction mixture was stirred for 16 h to obtain benzyl 2-(8-chloro-1,2,3,4-tetrahydro-2-methylpyrido[4,3-b]indol-5-yl)acetate after purification on neutral alumina chromatography eluting with methanol-dichloromethane gradient. The free base was converted into its oxalate salt by treatment of oxalic acid (1 equiv) in anhydrous THF.

Example 42

Preparation of CD24

A mixture of ethyl 2-(1,2,3,4-tetrahydro-2,8-dimethylpyrido[4,3-b]indol-5-yl)acetate (100 mg) and isopropylamine (1 ml) was heated at 120° C. for 15 h to obtain 2-(1,2,3,4-tetrahydro-2,8-dimethylpyrido[4,3-b]indol-5-yl)-N-isopropylacetamide after purification on neutral alumina chromatography eluting with methanol-dichloromethane gradient. The free base was converted into its oxalate salt by treatment of oxalic acid (1 equiv) in anhydrous THF.

Example 43

Preparation of CD31

3-(1,2,3,4-tetrahydro-2,8-dimethylpyrido[4,3-b]indol-5-yl)propanoic acid was mixed with EDCI and cyclohexylmethanamine in dichloromethane and the reaction mixture was stirred for 16 h to obtain N-(cyclohexylmethyl)-3-(1,2,3,4-tetrahydro-2,8-dimethylpyrido[4,3-b]indol-5-yl)propanamide after purification on neutral alumina chromatography eluting with methanol-dichloromethane gradient. The free base was converted into its oxalate salt by treatment of oxalic acid (1 equiv) in anhydrous THF.

The compounds prepared according to the Examples are further detailed in Table 4.

TABLE 4

| | | | | | | | | HPLC |
|---|---|---|---|---|---|---|---|---|
| | | | | | Synthetic Data | | | |
| Example No. | Compound No. | Salt | MW | NMR Solvent | NMR Data | MS Observed | HPLC Method[1] | HPLC RT (min) |
| 1 | CD1 | Free Base | 300.40 | CDCl3 | 7.2 (s, 1H), 7.18 (d, 1H), 7.0 (d, 1H), 4.3 (t, 2H), 4.1 (q, 2H), 3.7 (s, 2H), | 301 | 2 | 5.06 |

TABLE 4-continued

| | | | | | | | | |
|---|---|---|---|---|---|---|---|---|
| 2 | CD6 | Oxalate Salt | 404.46 | DMSO | 2.9 (s, 4H), 2.7 (t, 2H), 2.6 (s, 3H), 2.4 (s, 3H), 1.25 (t, 3H) 7.4 (d, 1H), 7.2 (s, 1H), 7.0 (d, 1H), 4.1 (t, 2H), 4.0 (q, 2H), 3.4 (m, 2H), 3.05 (m, 2H), 2.9 (s, 3H), 2.5 (m, 2H), 2.4 (s, 3H), 2.3 (t, 2H), 1.9 (m, 2H), 1.15 (t, 3H). | 315 | 1 | 5.81 |
| 3 | CD11 | Free Base | 306.79 | CDCl3 | 7.4 (s, 1H), 7.05 (s, 2H), 4.7 (s, 2H), 4.2 (q, 2H), 3.65 (s, 2H), 3.0-2.8 (m, 4H), 2.6 (s, 3H), 1.25 (t, 3H). | — | — | — |
| 4 | CD59 | Free Base | 320.82 | CDCl3 | 7.65 (d, 1H), 7.3 (d, 1H), 7.1 (d, 1H), 4.3 (t, 2H), 4.1 (q, 2H), 3.65 (s, 2H), 2.9 (s, 4H), 2.7 (t, 2H), 2.6 (s, 3H), 1.2 (t, 3H). | — | — | — |
| 5 | CD61 | TFA Salt | 353.34 | CDCl3 | 7.35-7.15 (m, 3H), 4.9 (m, 2H), 4.7 (m, 1H), 4.1 (m, 1H), 3.9 (m, 1H), 3.4 (m, 2H), 3.1 (m, 1H), 3.05 (s, 3H), 2.4 (s, 3H). | 240 | 1 | 4.88 |
| 6 | CD9 | TFA Salt | 532.7782 | CDCl3 | 7.25 (d, 1H), 7.2 (s, 1H), 7.05 (d, 1H), 5.65 (t, 1H), 4.65 (s, 2H), 4.6 (m, 1H), 4.4.3 (m, 1H), 4.2-4.0 (m, 2H), 3.8 (bs, 1H), 3.5 (m, 2H), 3.45-3.2 (m, 2H), 3.0 (s, 3H), 2.95 (m, 1H), 2.4 (s, 3H). | 318 | 1 | 6.22 |
| 7 | CD50 | TFA Salt | 479.47 | CDCl3 | 13.1 (bs, 1H), 8.2 (s, 1H), 7.3 (m, 1H), 7.1-6.95 (m, 3H), 6.8 (t, 2H), 4.8-4.6 (m, 1H), 4.6-4.5 (m, 1H), 4.2 (m, 1H), 4.1 (m, 1H), 3.8 (m, 1H), 3.65 (m, 1H), 3.3 (m, 1H), 3.1 (m, 1H), 3.05 (s, 3H), 2.8-2.6 (m, 2H), 2.3 (s, 3H) | 366 | 1 | 5.77 |
| 8 | CD2 | Free Base | 285.39 | CDCl3 | 7.2 (d, 1H), 7.15 (s, 1H), 7.0 (d, 1H), 5.40 (bs, 1H), 4.4 (t, 2H), 3.8 (s, 2H), 3.0 (s, 4H), 2.65 (s, 3H), 2.55 (d, 3H), 2.5 (t, 2H), 2.4 (s, 3H). | 286 | 1 | 4.42 |
| 9 | CD3 | Free Base | 299.41 | CDCl3 | 7.2 (m, 2H), 6.95 (d, 1H), 5.1 (bs, 1H), 4.35 (t, 2H), 3.65 (s, 2H), 3.1 (m, 2H), 2.85 (m, 4H), 2.55 (s, 3H), 2.5 (t, 2H), 2.4 (s, 3H), 0.9 (t, 3H). | 300 | 1 | 4.67 |
| 10 | CD5 | Free base | 339.47 | CDCl3 | 7.2 (m, 2H), 6.95 (d, 1H), 5.05 (d, 1H), 4.35 (t, 2H), 4.0 (sext, 1H), 3.65 (s, 2H), 2.9-2.8 (m, 4H), 2.55 (s, 3H), 2.5 (t, 2H), 2.4 (s, 3H), 1.9-0.8 (t, 8H). | 340 | 1 | 5.39 |

TABLE 4-continued

| | | | | | | | | |
|---|---|---|---|---|---|---|---|---|
| 11 | CD7 | Free base | 313.44 | CDCl3 | 7.2 (m, 2H), 7.0 (d, 1H), 5.3 (bs, 1H), 4.1 (t, 2H), 3.65 (s, 2H), 3.2 (m, 2H), 2.8 (m, 4H), 2.55 (s, 3H), 2.4 (s, 3H), 2.15-2.0 (m, 4H), 1.05 (t, 3H). | 314 | 1 | 4.94 |
| 12 | CD62 | TFA Salt | 357.37 | DMSO | 7.35 (d, 1H), 7.2 (s, 1H), 7.0 (d, 1H), 4.25 (t, 2H), 4.0 (bs, 2H), 3.4 (bs, 2H), 3.0 (m, 4H), 2.8 (s, 3H), 2.3 (s, 3H). | — | — | — |
| 13 | CD8 | TFA Salt | 568.642 | CDCl3 | mixture of rotamers 7.4-7.0 (m, 3H), 4.8-2.8 (m, 15H), 3.05 and 3.0 (s, 3H), 2.4 (s, 3H), 2.2 (s, 1H), 1.8-1.5 (m, 4H), 1.4 (s, 9H) | 455 | 1 | 6.06 |
| 14 | CD10 | bis-TFA salt | 582.548 | CDCl3 | 11.45 (bs, 1H), 10.05 (bs, 1H), 9.4 (bs, 1H), 7.4-7.0 (m, 3H), 6.6 (bs, 1H), 4.8-4.6 (m, 2H), 4.4-3.8 (m, 6H), 3.65-2.8 (m, 6H), 3.1 and 3.05 (s, 3H), 2.8-2.5 (m, 1H), 2.45 and 2.4 (s, 3H), 2.0-1.6 (m, 4H). | 355 | 1 | 3.93 |
| 26 | CD60 | TFA Salt | 386.37 | — | — | — | — | — |

[1]
Method-1  Column: YMC ODS-A 150 mm × 4.6 mm × 5μ, ID: E-AC-1/06/COL/013
  Mobile Phase: A: 0.05% TFA in Water/B: 0.05% TFA in Acetonitrile
  Inj. Vol: 10 μL, Col. Temp.: 30° C., Flow rate: 1.4 mL/min
  Gradient: 5% B to 95% B in 8 min, Hold for 1.5 min, 9.51-12 min 5% B
Method-2  Column: YMC ODS-A 150 mm × 4.6 mm × 5μ, ID: E-AC-1/06/COL/013
  Mobile Phase: A: 0.05% TFA in Water/B: 0.05% TFA in Acetonitrile
  Inj. Vol: 10 μL, Col. Temp.: 30° C., Flow rate: 1.2 mL/min
  Gradient: 10% B to 80% B in 5 min, Hold for 2 min, 7.01-10 min 10% B The compounds prepared according to the General Methods described herein and the synthetic procedures are further detailed below.

Example 44

Preparation of 3-(1,2,3,4-tetrahydro-2,8-dimethylpyrido[4,3-b]indol-5-yl)-1-methylpyrrolidin-2-one (Compound 71)

A suspension of NaH (36 mg, 1.5 mmol) and 2,3,4,5-tetrahydro-2,8-dimethyl-1H-pyrido[4,3-b]indole (100 mg, 0.5 mmol) in DMF (5 mL) was stirred at 0° C. 3-bromo-1-methylpyrrolidin-2-one (176 mg, 1.0 mmol) in DMF (3 mL) was added dropwise to the reaction mixture which was stirred at RT for 12 hours. After completion of the reaction, the reaction mixture was quenched with ice cold water and the product extracted with Ethyl Acetate. The organic layer isolated was washed with water and dried over sodium sulfate. The solvent was removed under reduced pressure and the crude obtained was purified by column chromatography to obtain 20 mg of 3-(1,2,3,4-tetrahydro-2,8-dimethylpyrido[4,3-b]indol-5-yl)-1-methylpyrrolidin-2-one. $^1$H NMR (CDCl$_3$) FREEBASE 7.10 (s, 1H), 7.05 (d, 1H), 6.92 (d, 1H), 5.05 (m, 1H), 4.80 (m, 1H), 3.80 (m, 1H), 3.50 (m, 2H), 3.40 (m, 1H), 3.20 (m, 3H), 3.0 (s, 3H), 2.80 (s, 3H), 2.40 (s, 3H), 2.20 (m, 2H).

Compound 70 (CD72) and Compound 72 are prepared according to the procedure for Compound 71 using the appropriate starting materials.

Example 45

Preparation of 2-(1,2,3,4-tetrahydro-2,8-dimethylpyrido[4,3-b]indol-5-yl)cyclohexanol (Compound 73)

2,8-dimethyl-2,3,4,5-tetrahydro-1H-pyrido[4,3-b]indole (1 gm, 5 mmol) was taken in DMF (10 ml). NaH (300 mg, 12.5 mmol) was added to it and the reaction mixture stirred at RT for 15 min. 7-oxabicyclo[4.1.0]heptane (0.9 ml, 9.0 mmol) was taken in DMF (3 ml) and added drop wise to the reaction mixture. After complete addition, reaction mixture was heated at 60-65° C. overnight. The reaction was monitored by LCMS. After completion of the reaction, reaction mixture was cooled to RT and quenched with water, extracted with ethyl acetate (3×25 ml), dried over sodium sulfate and concentrated under vacuum to obtain the crude product. This crude was purified by silica gel column chromatography (Eluent: 20% Methanol in DCM) to get 900 mg of 2-(1,2,3,4-tetrahydro-2,8-dimethylpyrido[4,3-b]indol-5-yl)cyclohexanol as yellow semi solid. $^1$H NMR (CDCl$_3$) FREE BASE 7.37-7.30 (m, 2H), 7.20 (s, 1H), 4.37-4.22 (bs, 1H), 3.67-3.64 (s, 1H), 3.61-3.57 (m, 2H), 3.0-2.80 (m, 3H), 2.60-2.40 (m, 7H), 1.98-1.82 (m, 4H), 1.50-1.38 (m, 4H).

Example 46

Preparation of 2,8-dimethyl-5-(prop-2-ynyl)-2,3,4,5-tetrahydro-1H-pyrido[4,3-b]indole (CD73)

p-Tolylhydrazine hydrochloride (600 mg, 3.7 mmol), propargyl bromide (80 wt % solution in toluene, 0.34 ml, 3.7 mmol), triethylamine (1.5 ml, 11.3 mmol) and N-methyl-4-piperidone hydrochloride (316 mg, 2.1 mmol) were taken in ethanol (15 ml) to obtain 80 mg of 2, 3,4,5-tetrahydro-2,8-dimethyl-5-(prop-2-ynyl)-1H-pyrido[4,3-b]indole after purification on silica gel (230-400 mesh) chromatography, eluting with methanol-dichloromethane gradient. $^1$H NMR (CDCl$_3$) 7.30-7.25 (d, 1H), 7.20 (s, 1H), 7.00-6.90 (d, 1H), 4.80 (s, 2H), 3.70 (s, 2H), 2.95 (m, 4H), 2.60 (s, 3H), 2.40 (s, 3H), 2.10-2.00 (t, 1H).

Example 47

Preparation of N-benzyl-3-(1,2,3,4-tetrahydro-2,8-dimethylpyrido[4,3-b]indol-5-yl)propanamide (CD74)

Ethyl 3-(1,2,3,4-tetrahydro-2,8-dimethylpyrido[4,3-b]indol-5-yl)propanoate (200 mg, 0.66 mmol) was added to benzylamine (2.0 ml, excess) and the reaction mixture was heated at 100° C. for 14 h. After completion of the reaction (monitored by LCMS) it was concentrated and basified with aqueous saturated sodium bicarbonate and extracted with ethyl acetate. The organic layer was concentrated to dryness and the crude obtained was purified by silica gel chromatography (Eluent: 10% MeOH in dichloromethane) to get 70 mg (yield: 29.16%) of N-benzyl-3-(1,2,3,4-tetrahydro-2,8-dimethylpyrido[4,3-b]indol-5-yl)propanamide as a free base. To the free base (40 mg, 0.11 mmol) dissolved in THF (5.0 ml), oxalic acid (13 mg, 0.10 mmol) in THF (5.0 ml) was added slowly, the mixture was stirred at RT for 20 minutes and the solid obtained was filtered, washed with ether and dried to get 35 mg (yield: 71.4%) of N-benzyl-3-(1,2,3,4-tetrahydro-2,8-dimethylpyrid[4,3-b]indol-5-yl)propanamide as oxalate salt. $^1$H NMR (DMSO) 7.50-7.30 (t, 3H), 7.20-7.10 (m, 3H), 7.0-6.90 (m, 2H), 4.40-4.30 (m, 4H), 4.30-4.20 (t, 2H), 4.0 (s, 2H), 3.10 (m, 2H), 2.90 (s, 3H), 2.60-2.50 (t, 3H), 2.40 (s, 3H).

Example 48

Preparation of 2-(8-chloro-1,2,3,4-tetrahydro-2-methylpyrido[4,3-b]indol-5-yl)-N-cyclohexylacetamide (CD75)

A solution of ethyl 2-(8-chloro-1,2,3,4-tetrahydro-2-methylpyrido[4,3-b]indol-5-yl)acetate (500 mg, 1.63 mmol) in oxalyl chloride (2.0 g, 16.33 mmol) was stirred at 25° C. for 3 h. After completion of the reaction (monitored by LCMS), cyclohexyl amine (1.0 ml, excess) was added to it and the reaction mixture heated at 80° C. for 3 h. The reaction mixture was concentrated and basified with aqueous saturated sodium bicarbonate and extracted with ethyl acetate. The organic layer was concentrated to dryness and the resulting crude was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml) to obtain 10 mg (yield: 2.0%) of 2-(8-chloro-1,2,3,4-tetrahydro-2-methylpyrido[4,3-b]indol-5-yl)-N-cyclohexylacetamide as TFA salt. $^1$H NMR (DMSO) 10.0 (bs, 1H), 8.30 (d, 1H), 7.60 (s, 1H), 7.5 (d, 1H), 7.21 (d, 1H), 4.80 (m, 2H), 4.6 (m, 1H), 4.30 (m, 1H), 3.80 (m, 1H), 3.41 (m, 2H), 3.10 (bs, 2H), 3.0 (s, 3H), 1.80-1.20 (m, 10H).

Example 49

Preparation of N-(2-(1,2,3,4-tetrahydro-2,8-dimethylpyrido[4,3-b]indol-5-yl)ethyl)isobutyramide (CD76)

A mixture of 2-(1,2,3,4-tetrahydro-2,8-dimethylpyrido[4,3-b]indol-5-yl)ethanamine (100 mg, 0.411 mmol), isobutyric acid (36 mg, 0.411 mmol), N,N'-dicyclohexylcarbodiimide (93 mg, 0.452 mmol) and 4-dimethylaminopyridine (55 mg, 0.452 mmol) in dry dichloromethane (5.0 ml) were stirred at room temperature for 4 h. The reaction mixture was filtered through Celite and concentrated using rotary evaporator to afford 16 mg of N-(2-(1,2,3,4-tetrahydro-2,8-dimethylpyrido[4,3-b]indol-5-yl)ethyl)isobutyramide as TFA Salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml). $^1$H NMR (DMSO) 9.95 (bs, 1H), 7.9 (t, 1H), 7.4 (d 1H), 7.2 (s, 1H), 7.0 (d, 1H), 4.5-4.61 (m, 1H), 4.1-4.28 (m, 3H), 3.7-3.9 (m, 2H), 3.1-3.2 (m, 2H), 2.95 (s, 3H), 2.4 (s, 3H), 2.19-2.3 (m, 1H), 1.2-1.38 (m, 2H), 0.9 (d, 6H).

Example 50

Preparation of N-(2-(1,2,3,4-tetrahydro-2,8-dimethylpyrido[4,3-b]indol-5-yl)ethyl)cyclohexanecarboxamide (CD77)

A mixture of 2-(1,2,3,4-tetrahydro-2,8-dimethylpyrido[4,3-b]indol-5-yl)ethanamine (100 mg, 0.41 mmol), cyclohexane carboxylic acid (52 mg, 0.41 mmol), N,N'-dicyclohexylcarbodiimide (93 mg, 0.45 mmol) and 4-dimethylaminopyridine (55 mg, 0.45 mmol) in dry dichloromethane (2.5 ml) were stirred at room temperature for 3 h. The reaction mixture was filtered through Celite and concentrated using rotary evaporator to afford 10 mg of N-(2-(1,2,3,4-tetrahydro-2,8-dimethylpyrido[4,3-b]indol-5-yl)ethyl)cyclohexanecarboxamide as TFA salt after purification by reversed-phase chromatography (C-18, 500 mm×50 mm, Mobile Phase A=0.05% TFA in water, B=0.05% TFA in acetonitrile, Gradient: 10% B to 80% B in 30 min, injection vol. 5 ml). $^1$H NMR (DMSO) 9.94 (bs, 1H), 7.86 (t, 1H), 7.38 (d, 1H), 7.11 (s, 1H), 7.0 (d, 1H), 4.56-4.63 (m, 1H), 4.22-4.29 (m, 1H), 4.08-4.13 (m, 3H), 3.72-3.81 (m, 3H), 3.08-3.14 (m, 3H), 2.97 (s, 3H), 2.38 (s, 3H), 1.95-2.0 (m, 1H), 1.50-1.84 (m, 5H), 1.02-1.2 (m, 4H).

Example 51

Preparation of 2-chloro-4-fluoro-N-(2-(1,2,3,4-tetrahydro-2,8-dimethylpyrido[4,3-b]indol-5-yl)ethyl)benzamide (CD78)

A mixture of 2-(1,2,3,4-tetrahydro-2,8-dimethylpyrido[4,3-b]indol-5-yl)ethanamine (100 mg, 0.41 mmol), 2-chloro 4-fluoro benzoic acid (71.8 mg, 0.41 mmol), N,N'-dicyclohexylcarbodiimide (93 mg, 0.45 mmol) and 4-dimethylaminopyridine (55.22 mg, 0.45 mmol) in dry dichloromethane (2.5 ml) were stirred at room temperature for 3 h. The reaction mixture was filtered through Celite and concentrated by rotary evaporation to obtain 2.93 mg of 2-chloro-4-fluoro-N-(2-(1,2,3,4-tetrahydro-2,8-dimethylpyrido[4,3-b]indol-5-yl)

ethyl)benzamide as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 0.5 ml). $^1$H NMR (DMSO) 10.0 (bs, 1H), 8.6 (t, 1H), 7.5 (d, 1H), 7.4 (d, 1H), 7.1-7.25 (m, 3H), 7.0 (d, 1H), 4.55-4.60 (m, 1H), 4.15-4.35 (m, 4H), 3.70-3.8 (m, 2H), 3.09-3.2 (m, 3H), 2.95 (s, 3H), 2.4 (s, 3H).

Example 52

Preparation of 2-(1,2,3,4-tetrahydro-2,8-dimethylpyrido[4,3-b]indol-5-yl)acetamide (CD79)

Ethyl 2-(1,2,3,4-tetrahydro-2,8-dimethylpyrido[4,3-b]indol-5-yl)acetate (0.5 g, 1.75 mmol) was taken in 4 ml aqueous ammonia and microwaved at 120° C. for 5 min using Initiator (Biotage Microwave). The solid product precipitated out after the reaction was filtered through Buchner funnel and washed with 10% sodium bicarbonate (10 ml×2) followed by demineralised water (10 ml×2) wash. Product was vacuum dried and was taken in 5 ml ethanolic HCl, stirred for 15 minutes, concentrated in vacuo to afford 13 mg of 2-(1,2,3,4-tetrahydro-2,8-dimethylpyrido[4,3-b]indol-5-yl)acetamide as HCl salt. $^1$H NMR (DMSO) 10.2 (bs, 1H), 7.62 (s, 1H), 7.21-7.3 (m, 3H), 6.9 (d, 1H), 4.75 (s, 2H), 4.45-4.51 (m, 1H), 4.21-4.25 (m, 1H), 3.12-3.17 (m, 4H), 2.97 (s, 3H), 2.19 (s, 3H).

Example 53

Preparation of tert-butyl 4-(2-(1,2,3,4-tetrahydro-2,8-dimethylpyrido[4,3-b]indol-5-yl)ethylcarbamoyl) piperidine-1-carboxylate and N-(2-(1,2,3,4-tetrahydro-2,8-dimethylpyrido[4,3-b]indol-5-yl)ethyl) piperidine-4-carboxamide (CD 80)

A mixture of 2-(1,2,3,4-tetrahydro-2,8-dimethylpyrido[4,3-b]indol-5-yl)ethanamine (100 mg, 0.41 mmol), 1-(tert-butoxycarbonyl)piperidine-4-carboxylic acid (94 mg, 0.41 mmol), N,N'-dicyclohexylcarbodiimide (93 mg, 0.45 mmol) and 4-dimethylaminopyridine (55 mg, 0.45 mmol) in dry dichloromethane (2.5 ml) were stirred at room temperature for 3 h. The reaction mixture was filtered through Celite and concentrated using rotary evaporator to obtain 14 mg of tert-butyl 4-(2-(1,2,3,4-tetrahydro-2,8-dimethylpyrido[4,3-b]indol-5-yl)ethylcarbamoyl)piperidine-1-carboxylate after purification by reverse-phase chromatography (C-18, 500 mm×50 mm, Mobile Phase A=0. 05% TFA in water, B=0.05% TFA in acetonitrile, Gradient: 10% B to 80% B in 30 min, injection vol. 5 ml). The compound obtained was taken in 3 ml of HCl in dioxane and stirred for 1 h to obtain 5 mg of N-(2-(1,2,3,4-tetrahydro-2,8-dimethylpyrido[4,3-b]indol-5-yl)ethyl)piperidine-4-carboxamide as HCl Salt. $^1$H NMR (DMSO) 10.78 (bs, 1H), 8.1 (bs, 1H), 7.40 (d, 1H), 7.2 (s, 1H), 7.05 (d, 1H), 4.6-4.2 (m, 1H), 4.3-4.2 (m, 1H), 4.2 (m, 2H), 4.0-3.8 (m, 3H), 3.35-3.05 (m, 4H), 3.0 (s, 3H), 2.95-2.8 (m, 2H), 2.4 (s, 3H), 2.3-2.2 (m, 1H), 2.1-2.00 (m, 1H), 1.8-1.6 (m, 4H).

Example 54

Preparation of 4-fluoro-N-(2-(1,2,3,4-tetrahydro-2,8-dimethylpyrido[4,3-b]indol-5-yl)ethyl)benzamide (CD81)

A mixture of 2-(1,2,3,4-tetrahydro-2,8-dimethylpyrido[4,3-b]indol-5-yl)ethanamine (0.1 g, 0.41 mmol), 4-fluoro benzoic acid (57 mg, 0.41 mmol), N,N'-dicyclohexylcarbodiimide (93 mg, 0.45 mmol) and 4-dimethylaminopyridine (55 mg, 0.45 mmol) in dry dichloromethane (2.5 ml) were stirred at room temperature for 3 h. The reaction mixture was filtered through Celite and concentrated by rotary evaporation to obtain 19.22 mg of 4-fluoro-N-(2-(1,2,3,4-tetrahydro-2,8-dimethylpyrido[4,3-b]indol-5-yl)ethyl)benzamide as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml). $^1$H NMR (DMSO) 9.98 (bs, 1H), 8.72 (t, 1H), 7.80-7.84 (m, 2H), 7.45 (d, 1H), 7.25-7.30 (m, 2H), 7.20 (s, 1H), 7.0 (d, 1H), 4.50-4.59 (m, 1H), 4.17-4.30 (m, 2H), 3.73-3.80 (m, 2H), (3.50-3.59 (m, 3H), 3.05-3.15 (m, 2H), 2.92 (s, 3H), 2.37 (s, 3H).

Example 55

Preparation of 3-(8-chloro-1,2,3,4-tetrahydro-2-methylpyrido[4,3-b]indol-5-yl)propanamide (CD82)

Ethyl 3-(8-chloro-1,2,3,4-tetrahydro-2-methylpyrido[4,3-b]indol-5-yl)propanoate (0.1 g, 0.315 mmol) was taken in 4 ml aqueous ammonia and microwaved at 120° C. for 5 minutes. The solid product precipitated out after the reaction was filtered through Buchner funnel and washed with 10% sodium bicarbonate (10 ml×2) followed by demineralised water (10 ml×2) wash to obtain 1.25 mg of 3-(8-chloro-1,2,3,4-tetrahydro-2-methylpyrido[4,3-b]indol-5-yl)propanamide as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml). $^1$H NMR (DMSO) 9.85 (bs, 1H), 7.5-7.6 (m, 2H), 7.4 (s, 1H), 7.2 (d, 1H), 6.85 (s, 1H), 4.6-4.7 (m, 2H), 4.4 (t, 2H), 3.7-3.8 (m, 2H), 3.1-3.2 (m, 4H), 3.0 (s, 3H).

Example 56

Preparation of N-(2-(1,2,3,4-tetrahydro-2,8-dimethylpyrido[4,3-b]indol-5-yl)ethyl)cyclopentanecarboxamide (CD83)

A mixture of 2-(1,2,3,4-tetrahydro-2,8-dimethylpyrido[4,3-b]indol-5-yl)ethanamine (100 mg, 0.41 mmol), cyclopentane carboxylic acid (46 mg, 0.41 mmol), N,N'-dicyclohexylcarbodiimide (93 mg, 0.45 mmol) and 4-dimethylaminopyridine (55 m g, 0.45 mmol) in dry dichloromethane (2.5 ml) were stirred at room temperature for 3 h. The reaction mixture was filtered through Celite and concentrated to obtain 40 mg of N-(2-(1,2,3,4-tetrahydro-2,8-dimethylpyrido[4,3-b]indol-5-yl)ethyl)cyclopentanecarboxamide as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 0.5 ml). $^1$H NMR (DMSO) 9.98-10.09 (bs, 1H), 7.93 (t, 1H), 7.37 (d, 1H), 7.20 (s, 1H), 7.0 (d, 1H), 4.59-4.63 (m, 1H), 4.2-4.3 (m, 1H), 4.07-4.15 (m, 2H), 3.73-3.84 (m, 2H), 3.07-3.15 (m, 2H), 2.99 (s, 3H), 2.59-2.68 (m, 2H), 2.4-2.48 (m, 1H), 2.38 (s, 3H), 1.4-1.84 (m, 8H).

Example 57

Preparation of N-(2-(1,2,3,4-tetrahydro-2,8-dimethylpyrido[4,3-b]indol-5-yl)ethyl)-3-methylpyridine-4-carboxamide (CD84)

A mixture of 2-(1,2,3,4-tetrahydro-2,8-dimethylpyrido[4,3-b]indol-5-yl)ethanamine (0.1 g, 0.411 mmol), 3-methylpyridine-4-carboxylic acid (0.056 g, 0.411 mmol), N,N'-dicyclohexylcarbodiimide (0.093 g, 0.452 mmol) and 4-dimethylaminopyridine (0.055 g, 0.452 mmol) in dry dichloromethane (2.0 ml) were stirred at room temperature for 4 h. To the reaction mixture was added 10 ml of water and the product extracted with dichloromethane (10 ml×3). Combined dichloromethane layers were dried over sodium sulfate and concentrated under reduced pressure to obtain 7 mg of N-(2-(1,2,3,4-tetrahydro-2,8-dimethylpyrido[4,3-b]indol-5-yl)ethyl)-3-methylpyridine-4-carboxamide as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml). $^1$H NMR (DMSO) 10.05 (bs, 1H), 8.7 (t, 1H), 8.45-8.55 (m, 2H), 7.4 (d, 1H), 7.22 (s, 1H), 7.15 (d, 1H), 7.0 (d, 1H), 4.6 (d, 1H), 3.72-3.85 (m, 3H), 3.4-3.6 (m, 3H), 3.1-3.2 (m, 3H), 3.0 (s, 3H), 2.4 (s, 3H), 2.2 (s, 3H).

Example 58

Preparation of 3-(8-chloro-2-methyl-3,4-dihydro-1H-pyrido[4,3-b]indol-5(2H)-yl)propan-1-ol (CD87)

To a solution of 5-allyl-8-chloro-2-methyl-2,3,4,5-tetrahydro-1H-pyrido[4,3-b]indole (300 mg, 1.15 mmol, 1 equiv) in 6 ml of dry THF was added 0.5M 9-borabicyclo[3.3.1]nonane (2.54 ml, 1.26 mmol, 1.1 equiv) dropwise at RT. After 90 min, a second portion of 9-borabicyclo[3.3.1]nonane (2.3 ml, 1.15 mmol) was added and stirred for 16 h. It was quenched with 8 ml of 20% NaOH and 4 ml of 30% H2O2 solution at 5-10° C. under stirring for 30 minutes. The reaction mixture was diluted with ethyl acetate (20 ml) followed by washing with brine, dried over sodium sulfate and concentrated under reduced pressure to obtain the crude product which was purified by preparative HPLC to give 3-(8-chloro-2-methyl-3,4-dihydro-1H-pyrido[4,3-b]indol-5(2H)-yl)propan-1-ol as a TFA salt. $^1$H NMR (DMSO) 10.0 (bs, 1H), 7.55-7.51 (m, 2H), 7.18-7.15 (m, 1H), 4.62-4.50 (m, 1H), 4.27-4.25 (m, 1H), 4.19-4.16 (t, 2H), 3.78 (bs, 1H), 3.36-3.34 (m, 3H), 3.16 (bs, 2H), 2.99 (s, 3H), 1.8-1.78 (t, 2H).

Example 59

Preparation of 5-(2-bromoethyl)-8-chloro-2-methyl-2,3,4,5-tetrahydro-1H-pyrido[4,3-b]indole (CD88)

A solution of 2-(8-chloro-2-methyl-3,4-dihydro-1H-pyrido[4,3-b]indol-5(2H)-yl)ethanol (0.2 g, 0.75 mmol) in aqueous HBr (2 mL) was heated at 120° C. for 15 h. The reaction was monitored by TLC and LCMS. The reaction mixture was basified with solid sodium bicarbonate, extracted with ethyl acetate. Organic layer was dried over sodium sulfate and concentrated under reduced pressure to obtain crude product which was purified by silica gel (100-200 mesh) chromatography followed by preparative TLC to obtain 5 mg of 5-(2-bromoethyl)-8-chloro-2-methyl-2,3,4,5-tetrahydro-1H-pyrido[4,3-b]indole as a free base. The free base (0.005 g 0.0152 mmol) was further dissolved in 2 mL of THF, oxalic acid (0.001 g, 0.015 mmol) in THF (1 mL) was added to it and the resulting mixture was stirred for 30 min at room temperature. The precipitate obtained was filtered and dried under vacuum to afford 1.5 mg of 5-(2-bromoethyl)-8-chloro-2,3,4,5-tetrahydro-2-methyl-1H-pyrido[4,3-b]indole as oxalate salt. $^1$H NMR (CD$_3$OD) 7.55 (s, 1H), 7.5 (d, 1H), 7.2 (d, 1H), 4.6 (t, 2H), 4.5 (s, 2H), 3.8 (t, 2H), 3.7-3.6 (m, 2H), 3.3 (bs, 2H), 3.1 (s, 3H).

Example 60

Preparation of 2-(8-chloro-2-methyl-3,4-dihydro-1H-pyrido[4,3-b]indol-5(2H)-yl)ethanol (CD89)

To a solution of lithium aluminum hydride (0.059 g, 1.5 mmol) in THF (30 mL) was added ethyl 2-(8-chloro-2-methyl-3,4-dihydro-1H-pyrido[4,3-b]indol-5(2H)-yl)acetate (0.4 g, 1.3 mmol) in THF (10 mL) drop wise at 0° C. The reaction mixture was further heated at 100° C. for 6 h. Reaction was monitored by TLC and LCMS. On completion of the reaction, reaction mixture was quenched with H2O:NaOH:H2O (1:1:3) and the contents were filtered. The filtrate obtained was extracted with Ethyl acetate. Combined organic layers were dried over sodium sulfate and concentrated under reduced pressure to obtain crude product (300 mg). 100 mg of the crude was purified by preparative TLC to obtain 5 mg of 2-(8-chloro-2-methyl-3,4-dihydro-1H-pyrido[4,3-b]indol-5(2H)-yl)ethanol as free base. The free base (0.015 g 0.056 mmol) was further dissolved in THF (2 mL), oxalic acid (0.007 g, 0.056 mmol) in THF (1 mL) was added to it and the resulting mixture was further stirred for 30 min at room temperature. The precipitate obtained was filtered and dried under vacuum to afford 20 mg of 2-(8-chloro-2-methyl-3,4-dihydro-1H-pyrido[4,3-b]indol-5(2H)-yl)ethanol as an oxalate salt. $^1$H NMR (CD3OD) 7.45 (s, 1H), 7.4 (d, 1H), 7.1 (d, 1H), 4.3 (s, 2H), 4.2 (t, 2H), 3.9 (t, 2H), 3.5 (t, 2H), 3.2 (t, 2H), 2.9 (s, 3H).

Example 61

Preparation of 2-(2,8-dimethyl-3,4-dihydro-1H-pyrido[4,3-b]indol-5(2H)-yl)ethanol (CD90)

Lithium Aluminum Hydride (0.088 g, 2.3 mmol) was charged in dry THF (5 mL) and the contents cooled to 0° C. 2-(2,8-dimethyl-3,4-dihydro-1H-pyrido[4,3-b]indol-5(2H)-yl)acetic acid (0.2 g, 0.77 mmol) was then added to it portion wise. The reaction mixture was refluxed overnight. The reaction mixture was cooled to 0° C. and quenched with aqueous sodium sulfate. The solid formed was filtered through Celite, washed with THF, dried over anhydrous sodium sulfate and concentrated under reduced pressure to obtain the crude product, which was then purified by column chromatography to give 2-(2,8-dimethyl-3,4-dihydro-1H-pyrido[4,3-b]indol-5(2H)-yl)ethanol. 10 mg of it was taken in dry THF (2 mL), oxalic acid (5 mg) was added to it. The solvent was evaporated under reduced pressure to afford 0.1 g of 2-(2,8-dimethyl-3,4-dihydro-1H-pyrido[4,3-b]indol-5(2H)-yl)ethanol as oxalate salt. $^1$H NMR (DMSO) 7.4 (d, 1H), 7.2 (s, 1H), 7.0 (d, 1H), 4.4 (bs, 1H), 4.2 (s, 2H), 3.7 (bs, 2H), 3.2 (bs, 2H), 2.9 (s, 3H), 2.6-2.4 (m, 4H), 2.3 (s, 3H).

Example 62

Preparation of (2-bromoethyl)-2,8-dimethyl-2,3,4,5-tetrahydro-1H-pyrido[4,3-b]indole (CD91)

Aqueous HBr (0.9 ml, 10 times) was added to 2-(2,8-dimethyl-3,4-dihydro-1H-pyrido[4,3-b]indol-5(2H)-yl)ethanol (0.09 g, 0.368 mole) and the contents heated to 120° C. for 10 hrs. The reaction mixture was cooled to 0° C. and basified with saturated NaOH Solution. The product was extracted with ethyl acetate, the combined organic layers were dried over anhydrous sodium sulfate and concentrated to obtain the crude product which was purified by preparative HPLC to get 5-(2-bromoethyl)-2,8-dimethyl-2,3,4,5-tetrahydro-1H-pyrido[4,3-b]indole as TFA salt. $^1$H NMR (CD3OD) 2.4, 3H(s); 3.15, 3H(s); 3.5-3.65, 2H (m); 3.7-3.8, 2H (t); 3.85-3.95, 2H (m); 4.3-4.4, 2H (m); 4.5-4.6, 2H (t); 7.05-7.1, 1H (d); 7.25-7.3, 1H(s); 7.35-7.4, 1H (d).

Example 63

Preparation of 3-(2,8-dimethyl-3,4-dihydro-1H-pyrido[4,3-b]indol-5(2H)-yl)propanenitrile (CD92)

2,8-dimethyl-2,3,4,5-tetrahydro-1H-pyrido[4,3-b]indole (1.5 g, 7.5 mmol) was taken in 20 ml of benzene: toluene mixture (1:1) along with acrylonitrile (1 ml, 15 mmol), cooled to 0° C., followed by addition of triton base (0.3 ml). The contents were stirred for 15 min. Acrylonitrile and triton base (same amount) were added and stirred at RT for 1 h. The reaction was monitored by TLC and LCMS. On completion of the reaction, reaction mixture was quenched with water, extracted with ethyl acetate, dried over anhydrous sodium sulfate and evaporated under reduced pressure to obtain solid material, which was crystallized using diethyl ether to yield 3-(2,8-dimethyl-3,4-dihydro-1H-pyrido[4,3-b]indol-5(2H)-yl)propanenitrile (yield: 1 g). $^1$H NMR (CDCl$_3$) 7.25 (s, 1H), 7.18-7.15 (d, 1H), 7.08-7.03 (d, 1H), 4.38-4.32 (t, 2H), 3.70-3.65 (m, 2H), 2.95-2.90 (m, 4H), 2.78-2.70 (t, 2H), 2.58 (s, 3H), 2.45 (s, 3H).

Example 64

Preparation of 3-(8-chloro-2-methyl-3,4-dihydro-1H-pyrido[4,3-b]indol-5(2H)-yl)propanenitrile (CD94)

8-chloro-2-methyl-2,3,4,5-tetrahydro-1H-pyrido[4,3-b]indole (1.00 g, 4.5 mmol) was stirred in benzene (15 mL) and toluene (20 mL). To this solution acrylonitrile (0.5 mL, 7.5 mmol) was added. The resulting reaction mixture was stirred at 0° C. for 10 minutes. Ice cold solution of 1 ml of Triton-B® was added to it. The reaction mixture was again stirred at room temperature for 4 h. The reaction was monitored by TLC in 10% Methanol-dichloromethane. Water was added to the reaction mixture and extracted organic layer was given water wash (3 times). The organic layer was then concentrated and purified by silica gel (100-200 mesh) chromatography using 0-10% methanol:dichloromethane as eluent. The obtained 3-(8-chloro-2-methyl-3,4-dihydro-1H-pyrido[4,3-b]indol-5(2H)-yl)propanenitrile was converted into its oxalate salt. $^1$H NMR (DMSO) 7.65 (d, 1H), 7.55 (s, 1H), 7.20 (d, 1H), 4.50 (t, 2H), 4.30 (m, 2H), 3.40 (m, 2H), 3.20 (m, 2H), 3.0 (t, 2H), 2.90 (s, 3H).

Example 65

Preparation of CD12

Ethyl 2-(8-chloro-1,2,3,4-tetrahydro-2-methylpyrido[4,3-b]indol-5-yl)acetate (100 mg, 0.32 mmol) was added to propan-2-ol (1.0 ml, excess) and the reaction mixture was heated at 100 deg C for 14 h. After completion of the reaction (monitored by LCMS) reaction mixture was concentrated and basified with aqueous saturated sodium bicarbonate, extracted with ethyl acetate. The organic layer was concentrated to dryness and the crude obtained was purified by silica gel chromatography (Eluent: 10% MeOH in dichloromethane) to get 10 mg (yield: 10%) of isopropyl 2-(8-chloro-1,2,3,4-tetrahydro-2-methylpyrido[4,3-b]indol-5-yl) acetate. The free base product (10 mg, 0.03 mmol) was dissolved in THF (1.0 ml), oxalic acid (4 mg, 0.03 mmol) in THF (1.0 ml) was added slowly, the mixture was stirred at RT for 20 minutes and the solid obtained was filtered, washed with ether and dried to get 10 mg (yield: 83%) of isopropyl 2-(8-chloro-1,2,3,4-tetrahydro-2-methylpyrido[4,3-b]indol-5-yl)acetate as oxalate salt. $^1$H NMR (DMSO) OXALATE SALT 7.60 (s, 1H), 7.50 (d, 1H), 7.20 (d, 1H), 5.1 (s, 2H), 4.90 (m, 1H), 4.50 (m, 1H), 4.20 (m, 1H), 3.5 (m, 2H), 3.10 (bs, 2H), 3.0 (s, 3H), 1.10 (d, 6H).

Example 66

Preparation of CD13

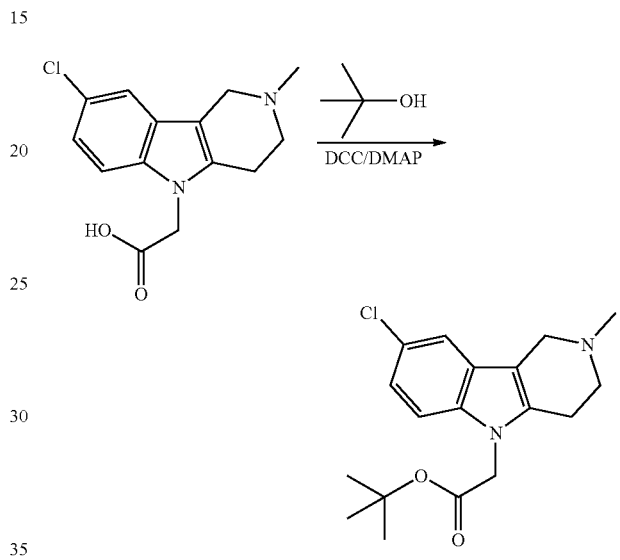

A mixture of 8-chloro-1,2,3,4-tetrahydro-2-methylpyrido[4,3-b]indole-5-carboxylic acid (150 mg, 0.540 mmol), N,N'-dicyclohexylcarbodiimide (133 mg, 0.647 mmol) and 4-dimethylaminopyridine (99 mg, 0.810 mmol) in dry dichloromethane (4.0 ml) were stirred at room temperature for 15 minutes. To this reaction mixture was added t-butanol (48 mg, 0.647 mmol). The reaction mixture was stirred at room temperature for 18 h. The product was extracted with dichloromethane and washed with water. The combined organic layer was dried over sodium sulfate and concentrated to afford 85 mg of tert-butyl 2-(8-chloro-1,2,3,4-tetrahydro-2-methylpyrido[4,3-b]indol-5-yl)acetate as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 0.5 ml). $^1$H NMR (DMSO) TFA SALT 10.1 (bs, 1H), 7.58 (d, 1H), 7.5 (d, 1H), 7.18 (d, 1H), 5.1 (dd, 2H), 4.65 (m, 1H), 4.3 (m, 1H), 3.8 (m, 1H), 3.5 (m, 1H), 3.02-3.14 (m, 2H), 2.9 (s, 3H), 1.2 (s, 9H).

Example 67

Preparation of CD15

To a solution of 2-(8-chloro-1,2,3,4-tetrahydro-2-methylpyrido[4,3-b]indol-5-yl)acetic acid (200 mg, 0.7 mmol) and cyclohexyl methanol (80 mg, 0.7 mmol) in dichloromethane (10 ml) were added N,N'-dicyclohexylcarbodiimide (177 mg, 0.86 mmol) and 4-dimethylaminopyridine (105 mg, 0.86 mmol) and the contents were stirred at 25 deg C. for 16 h. The reaction mixture was concentrated to dryness to obtain the crude compound which was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml) to give 30 mg (11.3%) of cyclohexylmethyl 2-(8-chloro-1,2,3,4-tetrahydro-2-methylpyrido[4,3-b]indol-5-yl)acetate as TFA salt. $^1$H NMR (DMSO) TFA SALT 10.39 (bs, 1H), 7.60 (s, 1H), 7.50 (d, 1H), 7.2 (d, 1H), 5.3-5.1 (dd, 2H), 4.70 (d, 1H), 4.30 (bs, 1H), 4.0 (d, 2H), 3.85 (bs, 1H), 3.50 (bs, 1H), 3.10 (s, 2H), 2.85 (s, 3H), 1.60-0.90 (m, 11H).

Example 68

Preparation of CD16

A mixture of 2-(8-chloro-1,2,3,4-tetrahydro-2-methylpyrido[4,3-b]indol-5-yl)acetic acid (150 mg, 0.53 mmol), thionyl chloride (0.6 ml) and cyclopentanol (1.5 ml, 16.48 mmol) were heated at 90 deg C. for 3 h. After completion of the reaction (monitored by LCMS), solvent was removed in vacuo and purified by silica gel (230-400 mesh) chromatography, eluting with methanol-dichloromethane gradient to obtain 30 mg of title compound as free base. To a solution of title compound (30 mg, 0.08) in dry THF (5 ml) was added a solution of oxalic acid (11 mg, 0.08 mmol) in THF (2 ml) dropwise. The resulting mixture was stirred for 10 min and the solid obtained was filtered and dried to obtain 15 mg of title compound as oxalate salt. $^1$H NMR (DMSO) OXALATE SALT 7.80 (s, 1H), 7.50-7.40 (d, 1H), 7.20-7.10 (d, 1H), 5.15 (bs, 1H), 5.1 (s, 2H), 4.3 (bs, 2H), 3.5 (bs, 2H), 3.05 (bs, 2H), 2.90 (s, 3H), 1.90-0.80 (m, 8H).

Example 69

Preparation of CD18

3-(8-Chloro-1,2,3,4-tetrahydro-2-methylpyrido[4,3-b]indol-5-yl)propanoic acid (0.1 g, 0.34 mmol) in dichloromethane (3 ml) was cooled to 0° C. Oxalyl chloride (0.04 ml, 0.41 mmol) was added drop-wise to the reaction mixture. A catalytic amount (1 drop) of dimethyl formamide was added to the reaction mixture. Reaction mixture was stirred for 1 h at room temperature. Excess oxalyl chloride was distilled off under reduced pressure. To this residue, solution of isopropyl alcohol (0.028 ml, 0.374 mmol) in dichloromethane (2 ml) and 4-dimethylaminopyridine (0.055 g, 0.45 mmol) was added under nitrogen at room temperature and reaction mass was stirred for 30 min at room temperature. Reaction mixture was quenched with water and neutralized with 10% sodium bicarbonate, extracted with Ethyl acetate (10 ml×2). Combined organic layers dried over sodium sulfate and concentrated under reduced pressure to obtain crude product which was further purified by flash column chromatography using Methanol:dichloromethane (5:95) as eluent to afford 27 mg of product. This product was stirred in THF (2 ml) and oxalic Acid (10 mg, 0.080 mmol) for 15 min and the mixture was concentrated under vacuo to afford 31 mg. of isopropyl 3-(8-chloro-1,2,3,4-tetrahydro-2-methylpyrido[4,3-b]indol-5-yl)propanoate as oxalate salt. $^1$H NMR (DMSO) OXALATE SALT 7.60-7.50 (m, 2H), 7.20 (d, 1H), 4.80 (m, 1H), 4.40 (m, 4H), 3.4 (m, 1H), 3.8 (m, 1H), 3.4 (m, 2H), 2.90 (s, 3H), 2.70 (t, 2H), 1.10 (d, 6H).

Example 70

Preparation of CD20

3-(8-Chloro-1,2,3,4-tetrahydro-2-methylpyrido[4,3-b]indol-5-yl)propanoic acid (0.1 g, 0.34 mmol) in dichloromethane (3 ml) was cooled to 0° C. Oxalyl chloride (0.04 ml, 0.41 mmol) was added drop-wise to the reaction mixture. A catalytic amount (1 drop) of dimethyl formamide was added to the reaction mixture. Reaction mixture was stirred for 1 h at room temperature. Excess oxalyl chloride was distilled off under reduced pressure. To this residue the solution of benzyl alcohol (0.038 ml, 0.374 mmol) in 2 ml dichloromethane and 4-dimethylaminopyridine (0.055 g, 0.45 mmol) were added under nitrogen at room temperature and reaction mixture was stirred for 30 minutes at room temperature. Reaction mixture was quenched with water and neutralized with 10% sodium bicarbonate, extracted with ethyl acetate (10 ml×2). Combined organic layers dried over sodium sulfate and concentrated under reduced pressure to obtain crude product which was further purified by flash column chromatography using Methanol:dichloromethane (5:95) as eluent to afford 23 mg of product. This product was stirred in THF (2 ml) and oxalic acid (7 mg, 0.06 mmol) for 15 min and mixture was concentrated under vacuo to afford 35 mg of benzyl 3-(8-chloro-1,2,3,4-tetrahydro-2-methylpyrido[4,3-b]indol-5-yl)propanoate as oxalate salt. $^1$H NMR (DMSO) OXALATE SALT 7.26 (d, 2H), 7.35-7.40 (m, 3H), 7.20-7.25 (m, 2H), 7.15 (d, 1H), 5.1 (s, 2H), 4.4 (m, 4H), 3.4 (m, 2H), 3.19-3.0 (m, 2H), 2.95 (s, 3H), 2.8 (m, 2H).

Example 71

Preparation of CD21

3-(8-Chloro-1,2,3,4-tetrahydro-2-methylpyrido[4,3-b]indol-5-yl)propanoic acid (0.1 g, 0.34 mmol) was dissolved in dichloromethane (3 ml) and cooled to 0 deg C. Oxalyl chloride (0.04 ml, 0.41 mmol) was added drop-wise to the reaction mixture. A catalytic amount (1 drop) of dimethyl formamide was added to the reaction mixture. Reaction mixture was stirred for 1 h at room temperature. Excess oxalyl chloride was distilled off under reduced pressure. To this residue, solution of cyclohexyl methanol (0.046 ml, 0.374 mmol) in dichloromethane (2 ml) and 4-dimethylaminopyridine (0.055 g, 0.45 mmol) were added under nitrogen at room temperature and reaction mixture was stirred for 30 min at room temperature. Reaction mixture was quenched with water and neutralized with 10% sodium bicarbonate, extracted with Ethyl acetate (10 ml×2). Combined organic layers were dried over sodium sulfate and concentrated under reduced pressure to obtain crude product which was further purified by flash column chromatography using Methanol:dichloromethane (5:95) as eluent to afford −20 mg of product. This product was stirred in THF (2 ml) and oxalic acid (6 mg, 0.0515 mol) for 15 min and the mixture was concentrated under vacuo to afford 26 mg of cyclohexylmethyl 3-(8-chloro-1,2,3,4-tetrahydro-2-methylpyrido[4,3-b]indol-5-yl)propanoate as oxalate salt. $^1$H NMR (DMSO) OXALATE SALT 7.52-7.56 (m, 2H), 7.15 (d, 1H), 4.4 (t, 2H), 4.26 (bs, 2H), 3.80 (d, 2H), 3.50 (bs, 2H), 3.1 (bs, 2H), 2.90 (s, 3H), 2.80 (t, 2H), 1.70-0.807 (m, 11H).

Example 72

Preparation of CD22

3-(8-Chloro-1,2,3,4-tetrahydro-2-methylpyrido[4,3-b]indol-5-yl)propanoic acid (0.1 g, 0.34 mmol) was dissolved in dichloromethane (3 ml) and cooled to 0 deg C. Oxalyl chloride (0.04 ml, 0.41 mmol) was added drop-wise to the reaction mixture. A catalytic amount (1 drop) of dimethyl formamide was added to the reaction mixture. Reaction mixture was stirred for 1 h at room temperature. Excess oxalyl chloride was distilled off under reduced pressure. To this residue, solution of cyclopentanol (0.034 g, 0.374 mmol) in 2 ml dichloromethane and 4-dimethylaminopyridine (0.055 g, 0.45 mmol) were added under nitrogen at room temperature and reaction mixture was stirred for 30 min at room temperature. Reaction mixture was quenched with water and neutralized with 10% sodium bicarbonate, extracted with Ethyl acetate (10 ml×2). Combined organic layers were dried over sodium sulfate and concentrated under reduced pressure to obtain crude product which was further purified by flash column chromatography using Methanol:dichloromethane (5:95) as eluent to afford 20 mg of product. This product was stirred in THF (2 ml) and oxalic acid (7 mg, 0.0555 mol) for 15 min and the mixture was concentrated under vacuo to afford 27 mg of cyclopentyl 3-(8-chloro-1,2,3,4-tetrahydro-2-methylpyrido[4,3-b]indol-5-yl)propanoate as oxalate salt. $^1$H NMR (DMSO) OXALATE SALT 7.4-7.6 (m, 2H), 7.2 (d, 1H), 5.0-5.10 (m, 2H), 4.35 (t, 2H), 3.8-3.2 (m, 5H), 2.9 (s, 3H), 2.8 (m, 2H), 1.8-1.9 (m, 3H), 1.4-1.6 (m, 5H).

Example 73

Preparation of CD49

Ethyl 3-(1,2,3,4-tetrahydro-2,8-dimethylpyrido[4,3-b]indol-5-yl)propanoate (0.1 g, 0.33 mmol) was taken in 4 ml aqueous ammonia and heated at 120 deg C. for 5 min using in microwave. The solid product precipitated out after the reaction was filtered through a Buchner funnel and washed with 10% sodium bicarbonate (10 ml×2) followed by demineralised water (10 ml×2) wash to obtain 1.25 mg of 3-(1,2,3,4-tetrahydro-2,8-dimethylpyrido[4,3-b]indol-5-yl)propanamide as TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml). $^1$H NMR (DMSO) TFA SALT 9.85 (bs, 1H), 7.4-7.45 (m, 2H), 7.2 (s, 1H), 7.0 (d, 1H), 6.85 (s, 1H), 4.3-4.2 (m, 3H), 3.6-3.4 (m, 2H), 3.2-3.1 (m, 2H), 3.0 (s, 3H), 2.7 (m, 2H), 2.3 (s, 3H).

Example 74

Preparation of CD25

To a solution of 2-(1,2,3,4-tetrahydro-2,8-dimethylpyrido[4,3-b]indol-5-yl)acetic acid (200 mg, 0.77 mmol) in dichloromethane (20 ml) was added N,N'-dicyclohexylcarbodiimide (191 mg, 0.92 mmol) followed by the addition of 4-dimethylaminopyridine (113 mg, 0.93 mmol) and tert butylamine (67 mg, 0.93 mmol). The resulting mixture was stirred at 25 deg C. for 14 h. The solvent was removed in vacuo and purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml) to obtain 35 mg of N-tert-butyl-2-(1,2,3,4-tetrahydro-2,8-dimethylpyrido[4,3-b]indol-5-yl)acetamide as trifluoroacetic acid salt. $^1$H NMR (DMSO-D2O) TFA SALT 7.21-7.20 (d, 2H), 7.0-6.95 (d, 1H), 4.60-4.50 (d, 2H), 3.75-3.65 (m, 2H), 3.50-3.38 (m, 2H), 3.10-3.0 (m, 2H), 2.90 (s, 3H), 2.30 (s, 3H), 1.20 (s, 9H).

Example 75

Preparation of CD27 p-Tolylhydrazine hydrochloride (500 mg, 3.16 mmol), 2-chloro-N-(cyclohexylmethyl)acetamide (600 mg, 3.16 mmol), triethylamine (1.31 ml, 9.4 mmol) and ethanol (20 ml) were stirred together to obtain 870 mg of 2-(1-p-tolylhydrazinyl)-N-(cyclohexylmethyl)acetamide. The intermediate (870 mg, 3.15 mmol) and N-methyl-4-piperidone hydrochloride (471 mg, 3.16 mmol) were taken in ethanolic HCl (20 ml) and stirred at RT for 15 min, after which the solvent was removed in vacuo. The reaction mixture obtained was taken in ethanol and heated at 90 deg C. for 14 h. After completion of the reaction (monitored by LCMS), the reaction mixture was concentrated to dryness and basified with aqueous saturated sodium bicarbonate, extracted with ethyl acetate. The organic layer was separated, dried over sodium sulfate and concentrated to obtain the crude product which was purified by silica gel chromatography (Eluent: 10% MeOH in dichloromethane) to yield 70 mg (yield: 6.27%) of N-(cyclohexylmethyl)-2-(1,2,3,4-tetrahydro-2,8-dimethylpyrido[4,3-b]indol-5-yl)acetamide. The freebase obtained (70 mg, 0.19 mmol) was dissolve d in THF (10.0 ml), oxalic acid (24 mg, 0.19 mmol) in THF (10.0 ml) was added slowly, the mixture was stirred at RT for 20 min and the solid obtained was filtered, washed with ether and dried to get 70 mg (yield: 80.4%) of N-(cyclohexylmethyl)-2-(1,2,3,4-tetrahydro-2,8-dimethylpyrido[4,3-b]indol-5-yl)acetamide as oxalate salt. $^1$H NMR (DMSO-D2O) OXALATE SALT 8.3-8.2 (t, 1H), 7.30 (d, 1H), 7.2 (s, 1H), 7.0-6.9 (d, 1H), 4.70 (s, 2H), 4.3 (bs, 2H), 3.80-3.2 (m, 4H), 3.1 (bs, 2H), 2.90 (s, 3H), 2.30 (s, 3H), 1.70-1.50 (m, 5H), 1.40-1.30 (m, 1H), 1.20-1.0 (m, 4H), 0.90-0.70 (m, 1H).

Example 76

Preparation of CD29

To a solution of tert-butyl amine (1.0 gm, 13.6 mmol) in dichloromethane (50 ml) was added 3-chloropropionyl chloride (2.06 g, 16.3 mmol) and NaOH (650 mg, 16.25 in 2.0 ml H2O) solution simultaneously at −20 deg C. for 1 h. The reaction mixture was allowed to stir for 1 h at RT. The organic layer was washed with 5% HCl followed by 5% aqueous sodium bicarbonate. The organic layer was dried and concentrated to get 2.23 g (yield: 99%) N-tert-butyl-3-chloropropanamide as white solid. To a solution of p-Tolylhydrazine hydrochloride (500 mg, 3.16 mmol) in ethanol (15 ml) was added triethylamine (1.31 ml, 9.4 mmol) and N-tert-butyl-3-chloropropanamide (510 mg, 3.12 mmol). The resulting reaction mixture was heated at 90 deg C. for 14 hrs. The reaction mixture was concentrated to dryness and basified with aqueous saturated sodium bicarbonate, extracted with ethyl acetate. The organic layer was dried over sodium sulfate and concentrated to obtain the crude, which was purified by silica gel chromatography (Eluent: 10% MeOH in dichloromethane) to obtain 500 mg (yield: 63.3%) of 3-(1-p-tolylhydrazinyl)-N-tert-butylpropanamide. The amide obtained (500 mg, 2.0 mmol) and N-methyl-4-piperidone hydrochloride (298 mg, 2.0 mmol) were dissolved in ethanolic HCl (20 ml) and stirred at RT for 15 minutes. The solvent was removed in vacuo. The reaction mixture obtained was dissolved in ethanol and heated at 90 deg C. for 14 h. After completion of the reaction (monitored by LCMS), the reaction mixture was concentrated to dryness and basified with aqueous saturated sodium bicarbonate, extracted with ethyl acetate, the organic layer was dried over sodium sulfate and concentrated. The crude obtained was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 ml) to obtain 10 mg (yield: 1.12%) of the desired product as TFA salt. $^1$H NMR (DMSO- D2O) TFA SALT 7.30-7.25 (d, 1H), 7.20 (s, 1H), 7.0-6.95 (d, 1H), 4.5 (m, 1H), 4.30-4.15 (m, 3H), 3.70-3.65 (m, 1H), 3.50-3.30 (m, 1H), 3.20-3.10 (m, 2H), 2.90 (s, 3H), 2.50-2.40 (d, 2H), 2.30 (s, 3H), 1.10 (s, 9H).

Example 77

Determination of the Ability of Compounds of the Invention to Bind a Histamine Receptor Histamine $H_1$ To evaluate in radioligand binding assays the activity of compounds of the invention, human recombinant histamine $H_1$ receptor expressed in Chinese hamster ovary (CHO) cells (De Backer, M. D. et al., Biochem. Biophys. Res. Comm. 197(3):1601, 1993) in a modified Tris-HCl buffer (50 mM Tris-HCl, pH 7.4, 2 mM $MgCl_2$, 100 mM NaCl, 250 mM Sucrose) was used. Compounds of the invention were incubated with 1.2 nM [$^3$H]Pyrilamine for 180 minutes at 25° C. Non-specific binding was estimated in the presence of 1 µM pyrilamine. Receptor proteins were filtered and washed, the filters were then counted to determine [$^3$H]Pyrilamine specifically bound. Compounds were screened at 1 µM, using 1% DMSO as vehicle. Biochemical assay results are presented as the percent inhibition of specific binding in Table 5.

Histamine $H_2$

To evaluate in radioligand binding assays the activity of compounds of the invention, human recombinant histamine $H_2$ receptor expressed in Chinese hamster ovary (CHO) K1 cells (Ruat, M., Proc. Natl. Acad. Sci. USA. 87(5):1658, 1990) in a 50 mM Phosphate buffer, pH 7.4 was used. Compounds of the invention were incubated with 0.1 nM [$^{125}$I] aminopotentidine for 120 minutes at 25° C. Non-specific binding was estimated in the presence of 3 µM Tiotidine. Receptor proteins were filtered and washed, the filters were then counted to determine [$^{125}$I]Aminopotentidine specifically bound. Compounds were screened at 1 µM, using 1% DMSO as vehicle. Biochemical assay results are presented as the percent inhibition of specific binding in Table 5.

Histamine $H_3$

To evaluate in radioligand binding assays the activity of compounds of the invention, human recombinant histamine $H_3$ receptor expressed in Chinese hamster ovary (CHO-K1) cells (Yanai K et al. Jpn J. Pharmacol. 65(2): 107, 1994; Zhu Y et al. Mol. Pharmacol. 59(3): 434, 2001) in a modified Tris-HCl buffer (50 mM Tris-HCl, pH 7.4, 5 mM $MgCl_2$, 0.04% BSA) is used. Compounds of invention are incubated with 3 nM [$^3$H]R(−)-α-Methylhistamine for 90 minutes at 25° C. Non-specific binding is estimated in the presence of 1 µM R(−)-α-Methylhistamine. Receptor proteins are filtered and washed, the filters are then counted to determine [$^3$H]R(−)-α-Methylhistamine specifically bound. Compounds are screened at 1 µM or lower, using 1% DMSO as vehicle. Compounds of the invention are tested in this biochemical assay and percent inhibition of specific binding is determined. Biochemical assay results are presented as the percent inhibition of specific binding.

Example 78

Determination of the Ability of Compounds of the Invention to Bind a Imidazoline $I_2$ Receptor Central Imidazoline $I_2$ To evaluate in radioligand binding assays the activity of compounds of the invention, rat central imidazoline $I_2$ receptor obtained from Wistar Rat cerebral cortex (Brown, C. M. et al., Br. J. Pharmacol. 99:803, 1990) in a modified Tris-HCl buffer (50 mM Tris-HCl buffer, pH 7.4, 0.5 mM EDTA) was used. Compounds of the invention were incubated with 2 nM [$^3$H]Idazoxan for 30 minutes at 25° C. Non-specific binding was estimated in the presence of 1 µM Idazoxan. Receptor proteins were filtered and washed, the filters were then counted to determine [$^3$H]Idazoxan specifically bound. Compounds were screened at 1 µM or lower, using 1% DMSO as vehicle. Compounds of the invention were tested in this biochemical assay and percent inhibition of specific binding was determined. Biochemical assay results are presented as the percent inhibition of specific binding in Table 5.

TABLE 5

| | Binding data | | |
|---|---|---|---|
| | Imidazoline $I_2$ | Histamine Binding (1 µM) | |
| Compound No. | Central (1 µM) | $H_1$ | $H_2$ |
| 1 | 18 | 34 | 8 |
| 2 | 8 | 52 | 5 |
| 3 | 27 | 2 | 23 |
| 4 | 54 | 60 | 20 |
| 5 | 53 | 96 | 48 |
| 6 | 52 | 46 | 0 |
| 7 | 47 | −10 | 33 |
| 8 | 57 | 101 | 74 |
| 9 | 9 | −228 | −44 |
| 10 | 25 | 99 | 28 |
| 11 | 5 | 101 | 7 |
| 12 | | 101 | 40 |
| 13 | 16 | 96 | 51 |
| 14 | | 98 | 89 |
| 15 | 23 | 99 | 47 |
| 17 | | 96 | 64 |
| 19 | | 101 | 81 |
| 20 | | 95 | 93 |
| 21 | | 98 | 82 |
| 22 | 51 | 85 | 11 |
| 23 | 1 | 65 | 1 |
| 24 | | 44 | 5 |
| 25 | 18 | 72 | 9 |
| 26 | | 66 | 22 |
| 27 | 8 | 63 | 5 |
| 28 | | 21 | 18 |
| 29 | | 84 | 34 |
| 30 | 61 | 18 | 41 |
| 31 | 33 | 45 | 20 |
| 45 | 24 | 82 | 3 |
| 46 | | 52 | −5 |
| 47 | 47 | 90 | 53 |
| 48 | 18 | 73 | 4 |
| 49 | 58 | 82 | 5 |
| 50 | 24 | 47 | 9 |
| 51 | 12 | 85 | 8 |
| 52 | 14 | 98 | 23 |
| 53 | | 51 | 12 |
| 59 | 64 | 60 | 5 |
| 60 | 6 | 50 | 3 |
| 61 | 40 | 32 | 13 |
| 62 | 42 | 63 | 39 |
| 63 | 41 | 86 | 35 |
| 64 | 16 | 62 | −3 |
| 65 | 23 | 34 | −7 |
| 66 | | 66 | 49 |
| 67 | | 70 | −6 |
| 68 | | 58 | 31 |
| 69 | | 88 | 14 |
| 73 | | 2 | 8 |
| CD1 | 55 | 101 | 35 |
| CD17 | 62 | 100 | 46 |
| CD46 | 28 | 69 | −3 |
| CD47 | 3 | 25 | 16 |
| CD55 | 3 | 22 | −2 |
| CD57 | | 100 | 28 |
| CD58 | 3 | 5 | 5 |

TABLE 5-continued

Binding data

| Compound No. | Imidazoline I$_2$ Central (1 μM) | Histamine Binding (1 μM) H$_1$ | H$_2$ |
|---|---|---|---|
| CD61 | 60 | 98 | 15 |
| CD62 | 13 | 44 | 65 |
| CD73 | 73 | 96 | 19 |
| CD87 |  | 97 | 18 |
| CD88 |  | 98 | 64 |
| CD89 |  | 92 | 14 |
| CD90 |  | 60 | 11 |
| CD91 |  | 98 | 65 |
| CD92 |  | 99 | 8 |
| CD94 |  | 97 | 2 |

Example 79

Determination of the ability of compounds of the invention to bind an adrenergic receptor Adrenergic α$_{1A}$ To evaluate in radioligand binding assays the activity of compounds of the invention, rat adrenergic α$_{1A}$ receptor obtained from Wistar Rat submaxillary glands (Michel, A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 minutes at 25° C. Non-specific binding was estimated in the presence of 10 μM phentolamine. Receptor proteins were filtered and washed, the filters were then counted to determine [$^3$H]Prozosin specifically bound. Compounds of the invention were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 6.

Adrenergic α$_{1B}$

To evaluate in radioligand binding assays the activity of compounds of the invention, rat adrenergic α$_{1B}$ receptor obtained from Wistar Rat liver (Garcia-S'ainz, J. A. et al., Biochem. Biophys. Res. Commun. 186:760, 1992; Michel A. D. et al. Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 minutes at 25° C. Non-specific binding was estimated in the presence of 10 μM phentolamine. Receptor proteins were filtered and washed, the filters were then counted to determine [$^3$H]Prozosin specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 6.

Adrenergic α$_{1D}$

To evaluate in radioligand binding assays the activity of compounds of the invention, human recombinant adrenergic α$_{1D}$ receptor expressed in human embryonic kidney (HEK-293) cells (Kenny, B. A. et al. Br. J. Pharmacol. 115(6):981, 1995) in a 50 mM Tris-HCl buffer, pH 7.4, was used. Compounds of invention were incubated with 0.6 nM [$^3$H]Prozosin for 60 minutes at 25° C. Non-specific binding was estimated in the presence of 10 μM phentolamine. Receptor proteins were filtered and washed, the filters were then counted to determine [$^3$H]Prozosin specifically bound. Compounds were screened at 1 μM or lower, using 1% DMSO as vehicle. Biochemical assay results are presented as the percent inhibition of specific binding in Table 6.

Adrenergic α$_{2A}$

To evaluate in radioligand binding assays the activity of compounds of the invention, human recombinant adrenergic α$_{2A}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 minutes at 25° C. MK912 is (2S-trans)-1,3,4,5',6,6',7,12b-octahydro-1',3'-dimethyl-spiro[2H-benzofuro[2,3-a]quinolizine-2,4'(1'H)-pyrimidin]-2'(3'H)-one hydrochloride Non-specific binding was estimated in the presence of 10 μM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 μM or lower, using 1% DMSO as vehicle. Biochemical assay results are presented as the percent inhibition of specific binding in Table 6.

Adrenergic α$_{2B}$

To evaluate in radioligand binding assays the activity of compounds of the invention, human recombinant adrenergic α$_{2B}$ receptor expressed in Chinese hamster ovary (CHO-K1) cells (Uhlen S et al. Eur. J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [3H]Rauwolscine for 60 minutes at 25° C. Non-specific binding was estimated in the presence of 10 μM Prozosin. Receptor proteins were filtered and washed, the filters were then counted to determine [$^3$H]Rauwolscine specifically bound. Compounds were screened at 1 μM or lower, using 1% DMSO as vehicle. Biochemical assay results are presented as the percent inhibition of specific binding in Table 6.

Adrenergic α$_{2C}$

To evaluate in radioligand binding assays the activity of compounds of the invention, human recombinant adrenergic α$_{2C}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of the invention were incubated with 1 nM [$^3$H]MK-912 for 60 minutes at 25° C. Non-specific binding was estimated in the presence of 10 μM WB-4101. Receptor proteins were filtered and washed, the filters were then counted to determine [$^3$H]MK-912 specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 6.

Example 80

Determination of the Ability of Compounds of the Invention to Bind a Dopamine Receptor Dopamine D$_{2L}$ To evaluate in radioligand binding assays the activity of compounds of the invention, human recombinant dopamine D$_{2L}$ receptor expressed in Chinese hamster ovary (CHO) cells (Grandy, D. K. et al. Proc. Natl. Acad. Sci. USA. 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H] Spiperone for 120 minutes at 25° C. Non-specific binding was estimated in the presence of 10 µM Haloperidol. Receptor proteins were filtered and washed, the filters were then counted to determine [$^3$H]Spiperone specifically bound. Compounds were screened at 1 µM or lower, using 1% DMSO as vehicle. Biochemical assay results are presented as the percent inhibition of specific binding in Table 6.

TABLE 6

Inhibition of ligand binding to aminergic G protein-coupled receptors by compounds of the invention

| Compound No. | Adrenergic (1 µM) | | | | | | Dopamine (1 µM) |
| --- | --- | --- | --- | --- | --- | --- | --- |
| | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 1 | 5 | 13 | 20 | 18 | 51 | 4 | |
| 2 | 10 | 22 | 17 | 35 | 55 | 2 | |
| 3 | 8 | 14 | 45 | 14 | 80 | 1 | |
| 4 | 35 | 41 | 64 | 45 | 93 | 4 | |
| 5 | 69 | 77 | 70 | 74 | 98 | 50 | |
| 6 | 18 | 31 | 0 | 59 | 36 | 48 | |
| 7 | 54 | 62 | 67 | 73 | 86 | 36 | |
| 8 | 82 | 80 | 72 | 90 | 102 | 22 | |
| 9 | 5 | 21 | 11 | 20 | 25 | −8 | 2 |
| 10 | | | 50 | 40 | 71 | | 12 |
| 11 | | | 38 | 25 | 69 | | 10 |
| 12 | | | 13 | 12 | 45 | | 23 |
| 13 | | | 55 | 73 | 97 | | 38 |
| 14 | | | 72 | 79 | 103 | | 31 |
| 15 | | | 58 | 67 | 95 | | 26 |
| 17 | | | 73 | 90 | 106 | | 13 |
| 19 | | | 83 | 86 | 106 | | 31 |
| 20 | | | 90 | 95 | 103 | | 19 |
| 21 | | | 88 | 95 | 103 | | 35 |
| 22 | | | 23 | 40 | 58 | | −2 |
| 23 | | | 15 | 12 | 18 | | 5 |
| 24 | | | −4 | 10 | 13 | | 3 |
| 25 | | | 22 | 2 | 38 | | −3 |
| 26 | | | 32 | 22 | 45 | | −4 |
| 27 | | | 18 | 12 | 35 | | −2 |
| 28 | | | 58 | 44 | 85 | | −1 |
| 29 | | | 74 | 78 | 79 | | 2 |
| 30 | | | 73 | 74 | 104 | | 7 |
| 31 | | | 61 | 37 | 91 | | 9 |
| 45 | | | 12 | 16 | 18 | | 7 |
| 46 | | | 7 | 44 | 46 | | 4 |
| 47 | | | 80 | 73 | 96 | | −3 |
| 48 | | | 10 | 20 | 13 | | −6 |
| 49 | | | 18 | 83 | 76 | | 9 |
| 50 | | | 37 | 38 | 70 | | 7 |
| 51 | | | 29 | 22 | 82 | | 19 |
| 52 | | | 58 | 38 | 89 | | 22 |
| 53 | | | 62 | 54 | 86 | | −2 |
| 59 | | | 56 | 45 | 96 | | 4 |
| 60 | | | 22 | 23 | 52 | | 18 |
| 61 | | | 28 | 46 | 70 | | −3 |
| 62 | | | 64 | 40 | 92 | | 5 |
| 63 | | | 56 | 65 | 98 | | 7 |
| 64 | | | 20 | 9 | 40 | | 2 |
| 65 | | | 11 | 17 | 12 | | 7 |
| 66 | | | 76 | 70 | 107 | | −2 |
| 67 | | | 32 | 79 | 72 | | −1 |
| 68 | | | 66 | 62 | 84 | | 1 |
| 69 | | | 30 | 25 | 39 | | 4 |
| 73 | | | 6 | 11 | −2 | | −3 |
| CD1 | 79 | 42 | 54 | 62 | 95 | 42 | |
| CD17 | | | 70 | 87 | 99 | | 22 |
| CD46 | | | 10 | 13 | 35 | | 3 |
| CD47 | | | 6 | 17 | 24 | | 4 |
| CD55 | | | 14 | −2 | 10 | | 3 |
| CD57 | | | 39 | 45 | 65 | | 12 |
| CD58 | | | 0 | −7 | −6 | | 2 |
| CD61 | 82 | 94 | 74 | 73 | 89 | 39 | |
| CD62 | | | 34 | 42 | 32 | | 26 |
| CD73 | 65 | 84 | 57 | 70 | 101 | 43 | |
| CD87 | | | 75 | 79 | 103 | | 10 |
| CD88 | | | 94 | 80 | 104 | | 27 |
| CD89 | | | 69 | 70 | 100 | | 0 |
| CD90 | | | 23 | 22 | 61 | | −8 |
| CD91 | | | 88 | 86 | 102 | | 15 |
| CD92 | | | 78 | 76 | 94 | | 3 |
| CD94 | | | 74 | 73 | 86 | | 1 |

Example 81

Determination of the Ability of Compounds of the Invention to Bind a Serotonin Receptor Serotonin (5-Hydroxytryptamine) 5-HT$_{1A}$ To evaluate in radioligand binding assays the activity of compounds of the invention, human recombinant serotonin (5-Hydroxytryptamine) 5-HT1A receptor expressed in Chinese hamster ovary (CHO-K1) cells (Martin G R and Humphrey P P A. Neuropharmacol. 33:261, 1994; May J A, et al. J Pharmacol Exp Ther. 306(1): 301, 2003) in a modified Tris-HCl buffer (50 mM Tris-HCl, pH 7.4, 0.1% Ascorbic Acid, 0.5 mM EDTA, 10 mM MgSO$_4$) is used. Compounds of invention are incubated with 1.5 nM [$^3$H]8-OH-DPAT for 60 minutes at 25° C. Non-specific binding is estimated in the presence of 10 µM Metergoline. Receptor proteins are filtered and washed, the filters are counted to determine [$^3$H] 8-OH-DPAT specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{1B}$

To evaluate in radioligand binding assays the activity of compounds of the invention, serotonin (5-Hydroxytryptamine) 5-HT1B receptor from Wistar Rat cerebral cortex (Hoyer et al. Eur. J. Pharmacol. 118: 1, 1985; Pazos et al. Eur J. Pharmacol. 106: 531, 1985) in a modified Tris-HCl buffer (50 mM Tris-HCl, pH 7.4, 154 mM NaCl, 10 µM Pargyline, 30 µM Isoprenaline) is used. Compounds of invention are incubated with 10 µM [$^{125}$I]Cyanopindolol for 90 minutes at 37° C. Non-specific binding as estimated in the presence of 10 µM Serotonin (5-HT). Receptor proteins are filtered and washed, the filters are counted to determine [$^{125}$I] Cyanopindolol specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{2A}$

To evaluate in radioligand binding assays the activity of compounds of the invention, human recombinant serotonin (5-Hydroxytryptamine) 5-HT$_{2A}$ receptor expressed in Chinese hamster ovary (CHO-K1) cells (Bonhaus, D. W. et al. Br. J. Pharmacol. 115:622, 1995; Saucier, C. and Albert, P. R., J. Neurochem. 68:1998, 1997) in a 50 mM Tris-HCl buffer, pH 7.4, was used. Compounds of the invention were incubated with 0.5 nM [$^3$H]Ketanserin for 60 minutes at 25° C. Non-specific binding was estimated in the presence of 1 µM Mianserin. Receptor proteins were filtered and washed, the filters were then counted to determine [$^3$H] Ketanserin specifically bound. Compounds were screened at 1 μM or lower, using 1% DMSO as vehicle. Biochemical assay results are presented as the percent inhibition of specific binding in Table 7.

Serotonin (5-Hydroxytryptamine) 5-HT$_{2B}$

To evaluate in radioligand binding assays the activity of compounds of the invention, human recombinant serotonin (5-Hydroxytryptamine) 5-HT$_{2B}$ receptor expressed in Chinese hamster ovary (CHO-K1) cells (Bonhaus, D. W. et al., Br. J. Pharmacol. 115:622, 1995) in a modified Tris-HCl buffer (50 mM Tris-HCl, pH 7.4, 4 mM CaCl$_2$, 0.1% Ascorbic Acid) was used. Compounds of invention were incubated with 1.2 nM [$^3$H]Lysergic acid diethylamide (LSD) for 60 minutes at 37° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 7.

Serotonin (5-Hydroxytryptamine) 5-HT$_{2C}$

To evaluate in radioligand binding assays the activity of compounds of the invention, human recombinant serotonin (5-Hydroxytryptamine) 5-HT$_{2C}$ receptor expressed in Chinese hamster ovary (CHO-K1) cells (Wolf, W. A. and Schutz, J. S., J. Neurochem. 69:1449, 1997) in a modified Tris-HCl buffer (50 mM Tris-HCl, pH 7.4, 0.1% Ascorbic Acid, 10 μM Pargyline) was used. Compounds of the invention were incubated with 1 nM [$^3$H]Mesulergine for 60 minutes at 25° C. Non-specific binding was estimated in the presence of 1 μM Mianserin. Receptor proteins were filtered and washed, the filters were then counted to determine [$^3$H]Mesulergine specifically bound. Compounds were screened at 1 μM or lower, using 1% DMSO as vehicle. Biochemical assay results are presented as the percent inhibition of specific binding in Table 7.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller K et al. Synapse. 11:58, 1992; Boess F G et al. Neuropharmacol. 36:637, 1997) in a modified Tris-HCl buffer (50 mM Tris-HCl, pH 7.4, 1 mM EDTA, 5 mM MgCl$_2$) is used. Compounds of invention are incubated with 0.69 nM [$^3$H]GR-65630 for 60 minutes at 25° C. Non-specific binding is estimated in the presence of 10 μM MDL-72222. Receptor proteins are filtered and washed, the filters are counted to determine [$^3$H]GR-65630 specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman C J et al. Br J. Pharmacol. 109:618, 1993) in a 50 mM Tris-HCl, pH 7.4, is used. Compounds of invention are incubated with 0.7 nM [$^3$H]GR-113808 for 30 minutes at 25° C. Non-specific binding is estimated in the presence of 30 μM Serotonin (5-HT). Receptor proteins are filtered and washed, the filters are counted to determine [$^3$H] GR-113808 specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT5A receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM MgCl$_2$, 0.5 mM EDTA) was used. Compounds of the invention were incubated with 1.7 nM [$^3$H]Lysergic acid diethylamide (LSD) for 60 minutes at 37° C. Non-specific binding was estimated in the presence of 100 μM Serotonin (5-HT). Receptor proteins were filtered and washed, the filters were then counted to determine [$^3$H]LSD specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 7.

Serotonin (5-Hydroxytryptamine) 5-HT$_6$

To evaluate in radioligand binding assays the activity of compounds of the invention, human recombinant serotonin (5-Hydroxytryptamine) 5-HT$_6$ receptor expressed in human HeLa cells (Monsma, F. J. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 minutes at 37° C. Non-specific binding was estimated in the presence of 5 μM Serotonin (5-HT). Receptor proteins were filtered and washed, the filters were then counted to determine [3H]LSD specifically bound. Compounds were screened at 1 μM or lower, using 1% DMSO as vehicle. Biochemical assay results are presented as the percent inhibition of specific binding in Table 7.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. L. et al., J. Pharmacol. Exp. Ther. 268:1403, 1994; Shen, Y. et al., J. Biol. Chem. 268:18200, 1993) in a modified Tris-HCl buffer (50 mM Tris-HCl, pH 7.4, 10 mM MgCl$_2$, 0.5 mM EDTA) was used. Compounds of invention were incubated with 5.5 nM [$^3$H] Lysergic acid diethylamide (LSD) for 2 hours at 25° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Biochemical assay results are presented as the percent inhibition of specific binding in Table 7.

TABLE 7

Inhibition of ligand binding to aminergic G protein-coupled receptors by compounds of the invention

| | Serotonin (1 μM) | | | | | |
|---|---|---|---|---|---|---|
| Compound No. | 5-HT$_{2A}$ | 5-HT$_{2B}$ | 5-HT$_{2C}$ | 5-HT$_{5A}$ | 5-HT$_6$ | 5-HT$_7$ |
| 1 | 30 | 23 | 20 | 4 | 8 | 33 |
| 2 | 22 | 20 | −5 | 14 | 19 | 47 |
| 3 | 63 | 21 | 29 | 35 | 19 | 36 |
| 4 | 53 | 40 | 36 | 47 | 28 | 59 |
| 5 | 91 | 77 | 96 | 62 | 88 | 95 |

TABLE 7-continued

Inhibition of ligand binding to aminergic G protein-coupled receptors by compounds of the invention Serotonin (1 μM)

| Compound No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|
| 6 | 30 | 21 | 45 | 25 | 23 | 43 |
| 7 | 42 | 31 | 23 | 44 | 3 | 4 |
| 8 | 99 | 64 | 99 | 60 | 83 | 75 |
| 9 | 15 | −5 | 29 | −6 | −5 | −8 |
| 10 | | | 92 | | 69 | |
| 11 | | | 71 | | 66 | |
| 12 | 81 | | 83 | | 67 | |
| 13 | | | 91 | | 101 | |
| 14 | 103 | | 94 | | 106 | |
| 15 | | | 94 | | 96 | |
| 17 | 84 | | 91 | | 99 | |
| 19 | 95 | | 96 | | 100 | |
| 20 | 102 | | 88 | | 93 | |
| 21 | 98 | | 100 | | 100 | |
| 22 | | | 81 | | 27 | |
| 23 | | | 37 | | 3 | |
| 24 | 9 | | 21 | | 6 | |
| 25 | | | 61 | | 58 | |
| 26 | 89 | | 54 | | 34 | |
| 27 | | | 28 | | 13 | |
| 28 | 17 | | 35 | | 47 | |
| 29 | 96 | | 73 | | 43 | |
| 30 | | | 93 | | 18 | |
| 31 | | | 76 | | 34 | |
| 45 | | | 52 | | 5 | |
| 46 | 33 | | 65 | | 11 | |
| 47 | | | 90 | | 63 | |
| 48 | | | 37 | | 12 | |
| 49 | | | 47 | | 24 | |
| 50 | | | 35 | | −1 | |
| 51 | | | 70 | | 30 | |
| 52 | | | 85 | | 83 | |
| 53 | 39 | | 51 | | 22 | |
| 59 | | | 72 | | 22 | |
| 60 | | | 35 | | 22 | |
| 61 | | | 27 | | 10 | |
| 62 | | | 54 | | 19 | |
| 63 | | | 72 | | 31 | |
| 64 | | | 45 | | 5 | |
| 65 | | | 24 | | 3 | |
| 66 | 98 | | 93 | | 35 | |
| 67 | 55 | | 65 | | 24 | |
| 68 | 77 | | 40 | | 15 | |
| 69 | 30 | | 24 | | −4 | |
| 73 | 50 | | 52 | | 7 | 5 |
| CD1 | 89 | 54 | 93 | 39 | 78 | 85 |
| CD17 | | | 96 | | 101 | |
| CD46 | | | 30 | | 39 | |
| CD47 | | | 25 | | 11 | |
| CD55 | | | 11 | | −3 | |
| CD57 | 92 | | 96 | | 67 | |
| CD58 | | | −19 | | −5 | |
| CD61 | 77 | 43 | 73 | 52 | 68 | 94 |
| CD62 | | | 28 | | 12 | |
| CD73 | 87 | 94 | 92 | 63 | 83 | 91 |
| CD87 | 66 | | 79 | | 35 | |
| CD88 | 98 | | 84 | | 87 | |
| CD89 | 70 | | 84 | | 36 | |
| CD90 | 58 | | 91 | | 7 | |
| CD91 | 96 | | 98 | | 88 | |
| CD92 | 67 | | 61 | | 47 | |
| CD94 | 60 | | 71 | | 40 | |

Example 82

Determination of Serotonin (5-Hydroxytryptamine) 5-HT$_{2a}$ Agonist/Antagonist Activity of Compounds of the Invention To determine for agonist or antagonist activity of a test compound e.g. a compound of the invention, in functional assays, human recombinant serotonin 5-HT$_2$A receptor expressed in human embryonic kidney (HEK-293) cells (Jerman J C, Brough S J, Gager T, Wood M, Coldwell M C, Smart D and Middlemiss D N. Eur J Pharmacol, 414: 23-30, 2001) is used. Cells are suspended in DMEM buffer, and distributed in microplates. A cytoplasmic calcium fluorescent indicator which varies proportionally to the free cytosolic Ca$^{2+}$ ion concentration is mixed with probenicid in HBSS buffer complemented with 20 mM Hepes (pH 7.4), added into each well and equilibrated with the cells for 30 min at 37° C. followed by 30 min at 22° C.

To measure agonist effects, a test compound, reference agonist or HBSS buffer (basal control) is added to the cells and changes in fluorescence intensity are measured using a microplate reader. For stimulated control measurements, 5-HT at 100 nM is added in separate assay wells.

The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the test compound, reference antagonist or HBSS buffer is followed by the addition of 3 nM 5-HT or HBSS buffer (basal control) prior the fluorescence measurements. The results are expressed as a percent inhibition of the control response to 3 nM 5-HT. The standard reference antagonist is ketanserin, which is tested in each experiment at several concentrations to generate a concentration-response curve from which its IC$_{50}$ value is calculated. Compounds are screened at 3 μM or lower, using DMSO as vehicle.

Example 83

Determination of Serotonin (5-Hydroxytryptamine) 5-HT$_6$ Agonist/Antagonist Activity of Compounds of the Invention To determine for agonist or antagonist activity of a test compound, e.g., a compound of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M. W. Cloning, characterisation and chromosomal localization of a human 5-HT6 serotonin receptor, J. Neurochem., 66: 47, 1996) and the activity of the test compound is determined by measuring their effects on cAMP production using the Homogeneous Time Resolved Fluorescence (HTRF) detection method. Cells are suspended in HBSS buffer complemented with HEPES 20 mM (pH 7.4) and 500 μM IBMX, and then distributed in microplates and incubated for 45 min at 37° C. in the absence (control) or presence of a test compound or the reference agonist or antagonist.

For agonist determinations, stimulated control measurement, separate assay wells contain 10 μM 5-HT. Following incubation, the cells are lysed and the fluorescence acceptor (D2-labeled cAMP) and fluorescence donor (anti-cAMP antibody labeled with europium cryptate) are added. After 60 min at room temperature, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 μM 5-HT. The standard reference agonist is 5-HT, which is tested in each experiment at several concentrations to generate a concentration-response curve from which its $EC_{50}$ value is calculated.

For antagonist determinations, the reference agonist 5-HT is added at a final concentration of 100 nM. For basal control measurements, separate assay wells do not contain 5-HT. Following 45 min incubation at 37° C., the cells are lysed and the fluorescence acceptor (D2-labeled cAMP) and fluorescence donor (anti-cAMP antibody labeled with europium cryptate) are added.

After 60 min at room temperature, the fluorescence transfer is measured as mentioned above. The results are expressed as a percent inhibition of the control response to 100 nM 5-HT. The standard reference antagonist is methiothepin Example 84

Determination of Dopamine $D_{2L}$ Antagonist Activity of Compounds

To determine for agonist or antagonist activity of a test compound, e.g. a compound of the invention, in functional assays, human recombinant dopamine $D_{2L}$ receptor stably expressed in Chinese hamster ovary (CHO) cells (Senogles S E et al. J. Biol. Chem. 265(8): 4507, 1990) is used. The test compound is pre-incubated with the membranes (0.1 mg/ml) and 10 mM GDP in modified HEPES buffer (20 mM HEPES, pH 7.4, 100 mM NaCl, 10 mM $MgCl_2$, 1 mM DTT, 1 mM EDTA) for 20 minutes and Scintillation Proximity Assay (SPA) beads are added for another 60 minutes at 30° C. The reaction is initiated by 0.3 nM $[^{35}S]GTP\gamma S$ for an additional 15 minute incubation period. Increase of $[^{35}S]GTP\gamma S$ binding by 50 percent or more (≧50%) relative to the 1 mM dopamine response by the test compound indicates possible dopamine $D_{2L}$ receptor agonists activity. Inhibition of a 10 µM dopamine-induced increase of $[^{35}S]GTP\gamma S$ binding response by 50 percent or more (≧50%) by the test compound indicated receptor antagonist activity. Compounds are screened at 3 µM or lower, using 0.4% DMSO as vehicle. Assay results are presented as the percent response of specific binding.

Example 85

Determination of Dopamine $D_{2S}$ Antagonist Activity of Compounds

To determine for agonist or antagonist activity of a test compound, e.g. a compound of the invention, in functional assays, human recombinant dopamine $D_{2S}$ receptor stably expressed in Chinese hamster ovary (CHO) cells (Gilliland S L and Alper R H. Naunyn-Schmiedeberg's Archives of Pharmacology. 361: 498, 2000) is used. The test compound is pre-incubated with the membranes (0.05 mg/ml) and 3 µM GDP in modified HEPES buffer (20 mM HEPES, pH 7.4, 100 mM NaCl, 10 mM $MgCl_2$, 1 mM DTT, 1 mM EDTA) for 20 minutes and Scintillation Proximity Assay (SPA) beads are then added for another 60 minutes at 30° C. The reaction is initiated by 0.3 nM $[^{35}S]GTP\gamma S$ for an additional 30 minute incubation period. Increase of $[^{35}S]GTP\gamma S$ binding by 50 percent or more (≧50%) relative to the 100 µM dopamine response by the test compound indicates possible dopamine $D_{2S}$ receptor agonists activity. Inhibition of a 3 µM dopamine-induced increase of $[^{35}S]GTP\gamma S$ binding response by 50 percent or more (≧50%) by the test compound indicated receptor antagonist activity. Compounds are screened at 3 µM or lower, using 0.4% DMSO as vehicle. Assay results are presented as the percent response of specific binding.

Example 86

Determination for Agonist or Antagonist Activity of Compounds in a Histamine $H_1$ Functional Assay To determine for agonist or antagonist activity of a test compound, e.g. a compound of the invention, in functional assays, human recombinant Histamine $H_1$ receptor expressed in human embryonic kidney (HEK-293) cells (Miller, T. R., Witte, D. G., Ireland, L. M., Kang, C. H., Roch, J. M., Masters, J. N., Esbenshade, T. A And Hancock, A. A. J. Biomol. Screen., 4: 249-258, 1999) is used. Cells are suspended in DMEM buffer, and then distributed in microplates. A cytoplasmic calcium fluorescent indicator, which varies proportionally to the free cytosolic $Ca^{2+}$ ion concentration, is mixed with probenicid in HBSS buffer complemented with 20 mM Hepes (pH 7.4) and is then added into each well and equilibrated with the cells for 30 min at 37° C. and then for another 30 min at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the test compound, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example 87

Increase of Neurite Outgrowth of Neurons that are Cultured with a Test Compound

Neurite Outgrowth in Cortical Neurons

Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation is prepared in Leibovitz's medium (L15; Gibco). The cortex is dissected out, and the meninges are removed. Trypsin (Gibco) is used to dissociate cortical C with DNAse I. The cells are triturated for 30 minutes with a pipette in Dulbecco's Modified Eagle Media ("DMEM"; Gibco) with 10% Fetal Bovine Serum ("FBS") (Gibco) and centrifuged at 350×g for 10 minutes at room temperature. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or a test compound, e.g. a compound of the invention, are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth.

Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue is cut to small pieces. The cells are separated by 15-min incubation with DNase and papain. The cells are collected by centrifugation (1500 rpm, 5 min). The tissue is triturated with a pipette and the cells are plated using the micro-islet protocol (20 000 cells in 25 µl medium) on poly-L-lysine coated 48 wells, in MEM supplemented with 2 mM glutamine, 0.1 µg/ml gentamicin, 10% heat-inactivated fetal bovine serum (FBS-HI) and 10% heat-inactivated horse serum (HS-HI). After the cells had attached to the well, 250 µl medium is added to the wells. Four hours after plating the medium is changed to fresh medium (MEM with supplements and 5% HS-HI) containing test compound at 0.5, 5 and 50 nM concentrations. As positive controls BDNF (50, 100 and/or 150 ng/ml), and/or NGF (50 ng/ml and/or 100 ng/ml) are used. After 2 days in vitro, the cell's conditioned media are collected from plates before fixing the cells. The media samples are centrifuged 13 000 rpm 3 min to get rid of cell debris. The samples are stored at −20 C for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min and washed once with PBS. The fixed cells are first permeabilized and non-specific binding is blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software.

The number of wells per compound concentration used is 6 (n=6). All data are presented as mean±standard deviation (SD) or standard error of mean (SEM), and differences are considered to be statistically significant at the $p<0.05$ level. Statistical analysis is performed using StatsDirect statistical software. Differences between group means are analyzed by using 1-way-ANOVA followed by Dunnet's test (comparison to the vehicle treated group).

Example 88

Use of an In Vivo Model to Evaluate the Ability of Compounds to Enhance Cognition, Learning and Memory in Scopolamine Treated Rats The two-trial object recognition paradigm developed by Ennaceur and Delacour in the rat is used as a model of episodic memory. Ennaceur, A., and Delacour, J. (1988), *Behav. Brain Res.* 31:47-59. The paradigm is based on spontaneous exploratory activity of rodents and does not involve rule learning or reinforcement. The object recognition paradigm is sensitive to the effects of ageing and cholinergic dysfunction. See, e.g., Scali, C., et al. (1994), *Neurosci. Lett.* 170:117-120; and Bartolini, L., et al. (1996), *Biochem. Behav.* 53:277-283.

Male Sprague-Dawley rats between six and seven weeks old, weighing between 220-300 grams are obtained from Centre d'Elevage (Rue Janvier, B. P. 55, Le Genest-Saint-Isle 53940, France). The animals are housed in groups of 2 to 4 in polypropylene cages (with a floor area of 1032 cm$^2$) under standard conditions: at room temperature (22±2° C.), under a 12 hour light/12 hour dark cycle, with food and water provided ad libitum. Animals are permitted to acclimate to environmental conditions for at least 5 days before therapy began, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for three minutes in the presence of two objects (habituation). Animals to be tested are placed in the experimental room at least 30 minutes before testing.

On the day of the experiment, animals are submitted to two trials separated by an interval of 120 minutes. During the first, or acquisition, trial ($T_1$), rats are placed in the arena, which is prepared with two identical objects. The time required for each animal to complete 15 seconds of object exploration is determined, with a cut-off time of four minutes. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for three minutes, and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured: (1) time required to achieve 15 seconds of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel} - T_{Familiar}$) is evaluated. The % of animals in each group with $T_{Novel} - T_{Familiar}$ greater than or equal to 5 seconds is also derived; described as % of good learners.

Animals not meeting a minimal level of object exploration are excluded from the study as having naturally low levels of spontaneous exploration. Thus, only rats exploring the objects for at least five seconds ($T_{Novel} + T_{Familiar} > 5$ seconds) are included in the study.

Animals are randomly assigned to groups of 14. A test compound, e.g. a compound of the invention, and controls are administered to animals the groups as follows: Solutions of compounds are prepared freshly each day at a concentration of 0.25 mg/ml using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil or its vehicle and scopolamine are administered intraperitoneally forty minutes before the acquisition trial ($T_1$). Compounds or their vehicle are administered by gavage twenty-five minutes before the acquisition trial ($T_1$), i.e., five minutes after administration of scopolamine. The volume of administration is 5 ml/kg body weight for compounds administered intraperitoneally, and 10 ml/kg for compounds administered orally. Recognition scores and % of good learners is determined.

Example 89

Use of an In Vivo Model to Determine the Ability of Compounds to Treat, Prevent and/or Delay the Onset and/or the Development of Schizophrenia in Pcp Treated Animals In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidene, which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci. 43(4):375-385). Standard experimental protocols may be employed in this or in other animal models. One protocol involves PCP-induced hyperactivity.

Male C57Bl/6J mice from Jackson Laboratories (Bar Harbor, Me.) are used. Mice are received at 6-weeks of age. Upon receipt, mice are assigned unique identification numbers (tail marked) and are group-housed with 4 mice/cage in OPTI mouse ventilated cages. All animals remained housed in groups of four during the remainder of the study. All mice are acclimated to the colony room for at least two weeks prior to testing and are subsequently tested at an average age of 8 weeks of age. During the period of acclimation, mice are examined on a regular basis, handled, and weighed to assure adequate health and suitability. Animals are maintained on a 12/12 light/dark cycle. The room temperature is maintained between 20 and 23° C. with a relative humidity maintained between 30% and 70%. Food and water are provided ad libitum for the duration of the study. In each test, animals are randomly assigned across treatment groups.

The open filed (OF) test assesses locomotor behavior. The open field chambers are Plexiglas square chambers (27.3× 27.3×20.3 cm; Med Associates Inc., St Albans, Vt.) surrounded by infrared photo beams (16×16×16) to measure horizontal and vertical activity. The analysis is configured to divide the open field into a center and periphery zone. Distance traveled is measured from horizontal beam breaks as the mouse moved whereas rearing activity is measured from vertical beam breaks.

Mice (10 to 12 animals per treatment group) are brought to the activity experimental room for at least 1 hr acclimation to the experimental room conditions prior to testing. Eight animals are tested in each run. The vehicle (10% DMSO or 5% PEG200 and 1% Tween 80), or the test compound dissolved in 5% PEG200, 1% Tween80 is administered orally 30 min prior to PCP injection. Clozapine (1 mg/kg) is dissolved in 10% DMSO and administered i.p. 30 min prior to PCP injection. The mice are placed in the OF chambers for 30 min following which either water or PCP (5 mg/kg) dissolved in sterile injectable water and administered i.p. and placed back in the OF chambers for a 60-minute session. At the end of each OF test session the OF chambers are thoroughly cleaned.

Data are analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fell above or below 2 standard deviations from the mean are removed from the final analyses. An effect is considered significant if $p<0.05$. Total distances traveled and total rearing for the test compound is determined.

In an alternative method, the protocol is as described above with the exception of the treatment groups which are as follows: all injections are at a dose volume of 10 ml/kg. The test compound is dissolved in Phosphate Buffered Saline (PBS) and administered orally 30 min prior to PCP injection. Clozapine (0.5 and 1.0 mg/kg) is dissolved in 10% DMSO and administered i.p. 30 min prior to Phencyclidine (PCP) injection. PCP (5.0 mg/kg) is dissolved in sterile injectable water and administered i.p. Total distances traveled for the test compound is determined.

Example 90

Use of an In Vivo Model to Determine the Ability of Compounds to Treat, Prevent and/or Delay the Onset and/or the Development of Schizophrenia in Amphetamine Treated Animals Male C57Bl/6J mice from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12/12 light/dark cycle. The room temperature is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglass square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 hr acclimation prior to start of treatment. Animals are administered with vehicle, clozapine or test compound and placed in the OF. The time of administration of client compound to each animal is recorded. Baseline activity is recorded for 30 min following which mice receive amphetamine (4 mg/kg) or water placed back in the OF chambers for a 60-minute session. At the end of each open field test session the OF chambers are thoroughly cleaned. Typically ten to twelve mice are tested in each group. Test compound doses typically range from 0.01 mg/kg to 50 mg/kg.

Data are analyzed by analysis of variance (ANOVA) followed by post-hoc comparisons where appropriate. An effect is considered significant if p<0.05. Data are represented as the mean and standard error to the mean (s.e.m.)

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of the Formula (E):

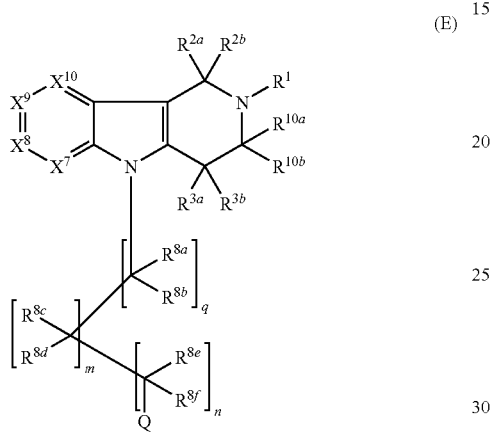

or a salt thereof, wherein:
  $R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
  each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a cycloalkyl moiety or a carbonyl moiety;
  each $R^{3a}$ and $R^{3b}$ is independently H, substituted or unsubstituted $C_1$-$C_8$ alkyl, halo, cyano hydroxyl, alkoxy, nitro or $R^{3a}$ and $R^{3b}$ are taken together with the carbon to which they are attached to form a cycloalkyl moiety or a carbonyl moiety;
  each $X^7$, $X^8$, $X^9$ and $X^{10}$ is independently $CR^4$;
  m and q are independently 0 or 1;
  n is 1;
  each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
  each $R^{8a}$, $R^{8b}$, $R^{8c}$, $R^{8d}$, $R^{8e}$ and $R^{8f}$ is independently H, hydroxyl, substituted or unsubstituted alkyl or is taken together with the carbon to which it is attached and a geminal $R^{8(a\text{-}f)}$ to form a cycloalkyl moiety;
  each $R^{10a}$ and $R^{10b}$ is independently H, substituted or unsubstituted $C_1$-$C_8$ alkyl, halo, hydroxyl, alkoxyl or $R^{10a}$ and $R^{10b}$ are taken together with the carbon to which they are attached to form a cycloalkyl moiety or a carbonyl moiety; and
  Q is acyclic or cyclic acylamino, acyloxy, aminoacyl, or aminocarbonylalkoxy;
  provided that: Q is cyclic acylamino only when each of m, n and q is 1, and (ii) the compound is other than a compound selected from the group consisting of compounds: 2H-Pyrido[4,3-b]indole-2-carboxylic acid, 5-[2-(dimethylamino)-2-oxoethyl]-1,3,4,5-tetrahydro-8-[(4-methyl-1-piperidinyl)carbonyl]-, 1,1-dimethylethyl ester (Compound No. 1x); 5H-Pyrido[4,3-b]indole-5-acetamide, 1,2,3,4-tetrahydro-N,N-dimethyl-8-[(4-methyl-1-piperidinyl)carbonyl]- (Compound No. 2x); 5H-Pyrido[4,3-b]indole-5-acetamide, 2-cyclobutyl-1,2,3,4-tetrahydro-N,N-dimethyl-8-[(4-methyl-1-piperidinyl)carbonyl]- (Compound No. 3x); 5H-Pyrido[4,3-b]indole-5-acetamide, 2-cyclohexyl-1,2,3,4-tetrahydro-N,N-dimethyl-8-[(4-methyl-1-piperidinyl)carbonyl] (Compound No. 4x); 5H-Pyrido[4,3-b]indole-5-acetamide, 2-cyclopentyl-1,2,3,4-tetrahydro-N,N-dimethyl-8-[(4-methyl-1-piperidinyl)carbonyl]- (Compound No. 5x); 5H-Pyrido[4,3-b]indole-5-acetamide, 8-formyl-1,2,3,4-tetrahydro-2-(1-methylethyl)- (Compound No. 6x); 5H-Pyrido[4,3-b]indole-5-acetamide, 1,2,3,4-tetrahydro-2-(1-methylethyl)- (Compound No. 11x); 5H-Pyrido[4,3-b]indole-5-acetamide, 1,2,3,4-tetrahydro-2,8-bis(1-methylethyl)- (Compound No. 12x); 5H-Pyrido[4,3-b]indole-5-acetamide, 1,2,3,4-tetrahydro-8-methyl-2-(1-methylethyl)- (Compound No. 13x); 5H-Pyrido[4,3-b]indole-5-acetamide, N-cyclohexyl-1,2,3,4-tetrahydro-2-(1-methylethyl)- (Compound No. 14x); 5H-Pyrido[4,3-b]indole-5-acetamide, N-cyclopentyl-1,2,3,4-tetrahydro-2-(1-methylethyl)- (Compound No. 15x); and 5H-Pyrido[4,3-b]indole-5-propanamide, 1,2,3,4-tetrahydro-2-methyl- (Compound No. 63x); and salts thereof.

2. The compound of claim 1 wherein the compound is selected from the group consisting of compounds:

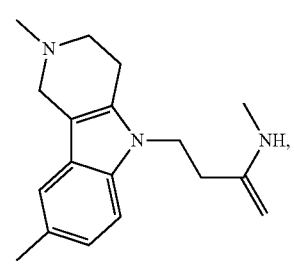

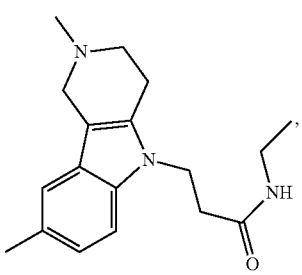
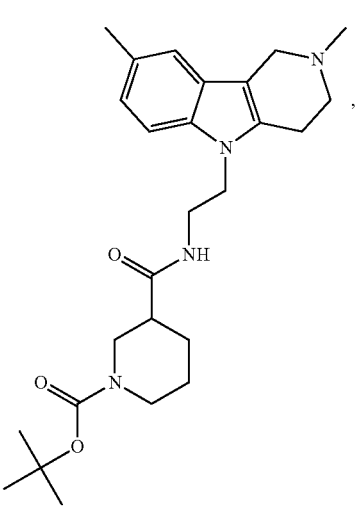
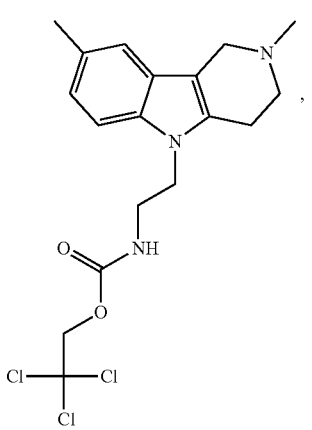
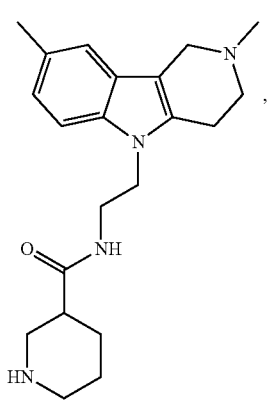
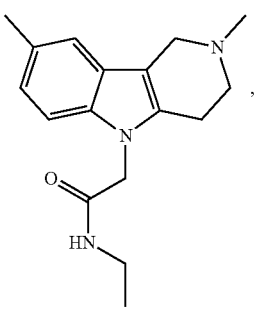

23
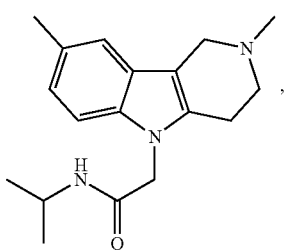
24
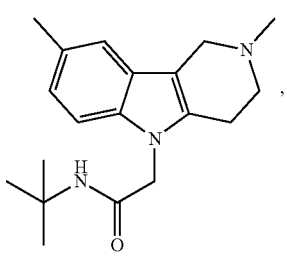
25
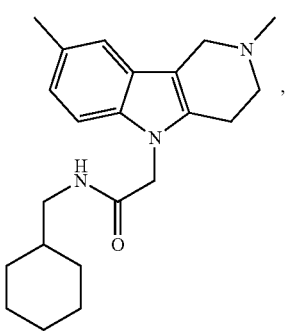
26
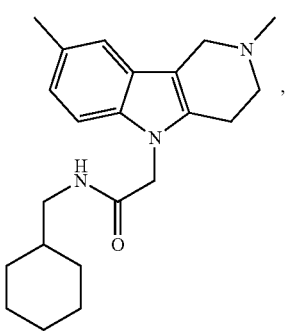
27
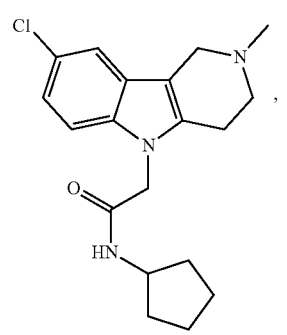
28
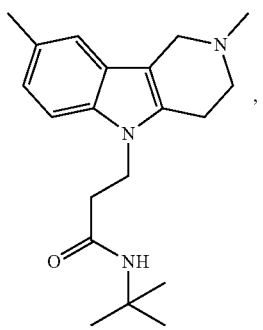
29
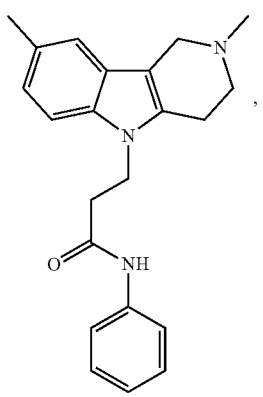
30
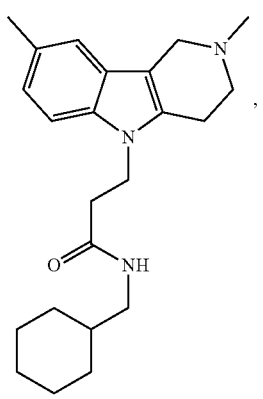
31
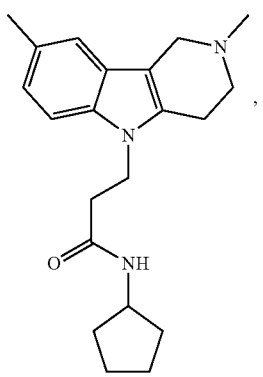

197
-continued
45
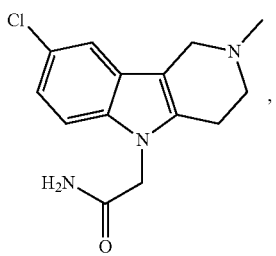
46
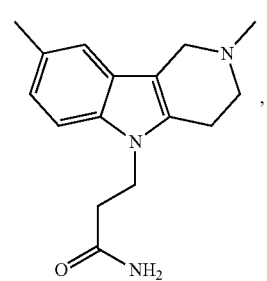
47
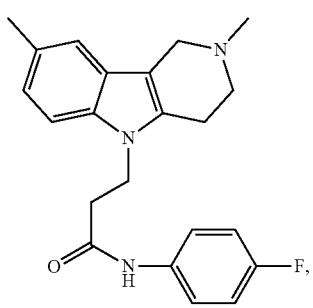
48
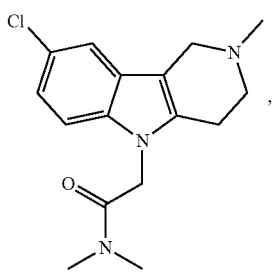
49
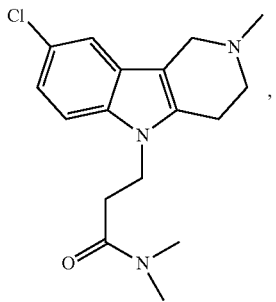
198
-continued
50
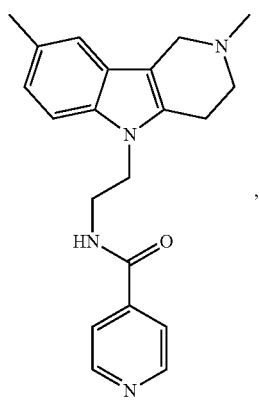
51
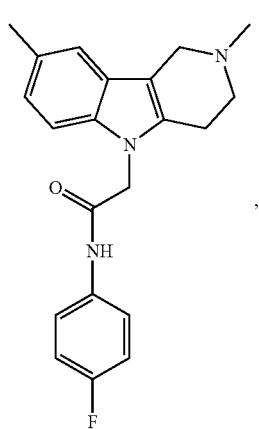
53
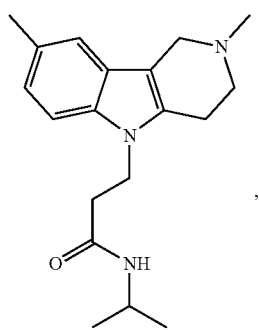
54
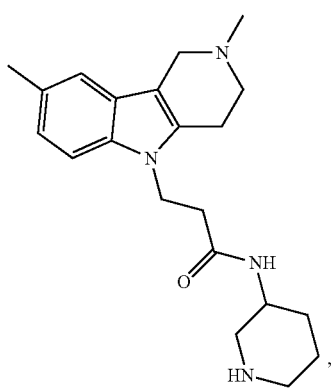

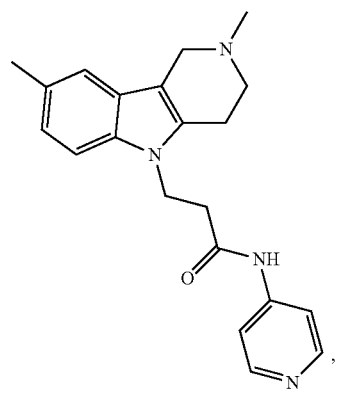
55
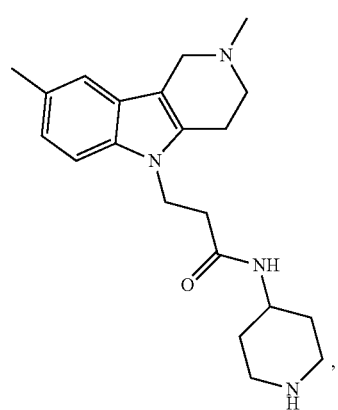
56
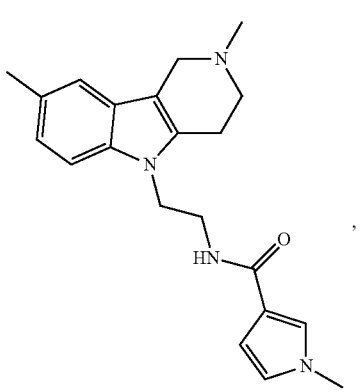
57
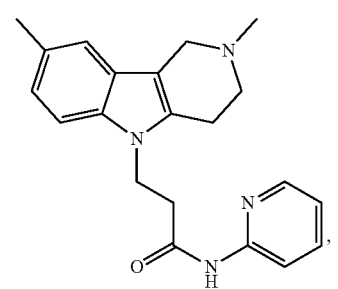
58
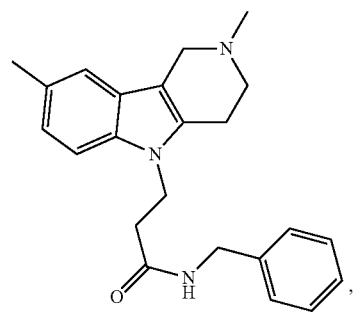
59
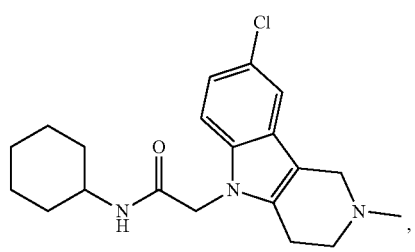
60
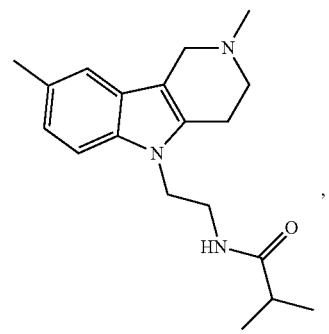
61
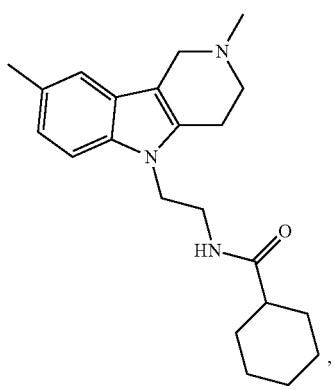
62

63 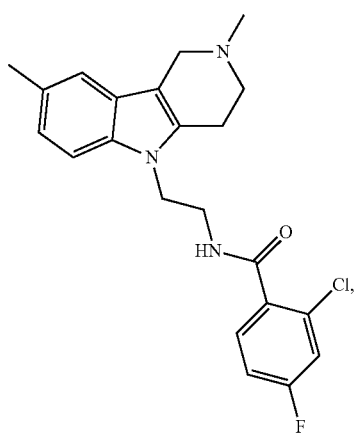

64 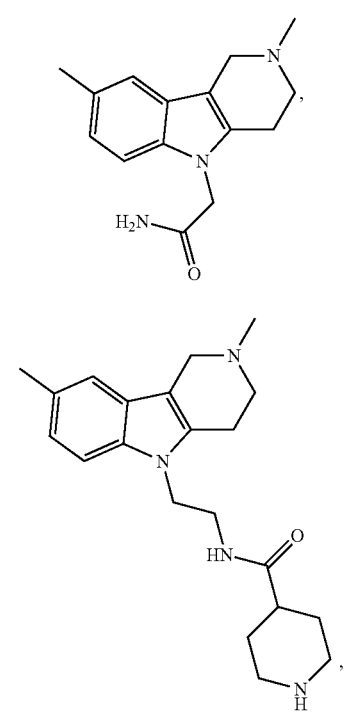

65

66 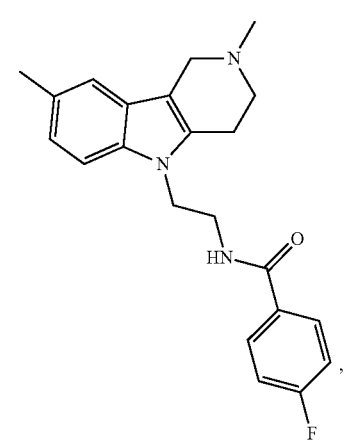

67 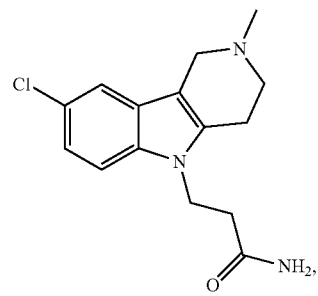

68 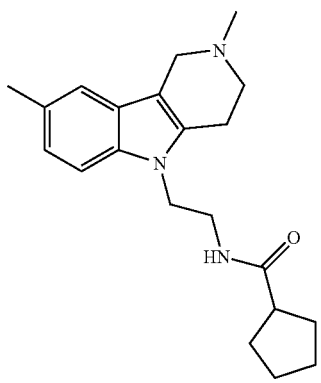 and

69 or a salt thereof.

3. The compound of claim 1, or a salt thereof, wherein each $X^7$, $X^8$ and $X^{10}$ is $CR^4$ where $R^4$ is H, $X^9$ is $CR^4$ where $R^4$ is chloro, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino or aminoacyl.

4. The compound of claim 1, or a salt thereof, wherein each $X^7$, $X^8$ and $X^{10}$ is $CR^4$ where $R^4$ is H, $X^9$ is $CR^4$ where $R^4$ is methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acyclic acylamino or aminoacyl.

5. The compound of claim 1, or a salt thereof, wherein each $X^7$, $X^8$ and $X^{10}$ is $CR^4$ where $R^4$ is H, $X^9$ is $CR^4$ where $R^4$ is chloro or methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is acylamino of the formula —C(O)NHR' where R' is unsubstituted or substituted alkyl, unsubstituted or substituted cycloalkyl, unsubstituted or substituted aryl, unsubstituted or substituted heteroaryl or unsubstituted or substituted heterocyclyl.

6. The compound of claim 1, or a salt thereof, wherein each $X^7$, $X^8$ and $X^{10}$ is $CR^4$ where $R^4$ is H, $X^9$ is $CR^4$ where $R^4$ is methyl, $R^1$ is methyl, each $R^{2a}$, $R^{2b}$, $R^{3a}$, $R^{3b}$, $R^{10a}$ and $R^{10b}$ is H, each $R^{8a}$, $R^{8b}$, $R^{8c}$, $R^{8d}$, $R^{8e}$ and $R^{8f}$ is H when present and Q is of the formula —NHC(O)R' where R' is alkyl, substituted alkyl, aryl, substituted aryl, heteroaryl, substituted heteroaryl, heterocyclyl, substituted heterocyclyl, alkoxy or substituted alkoxy.

7. A compound of the formula (Vf):

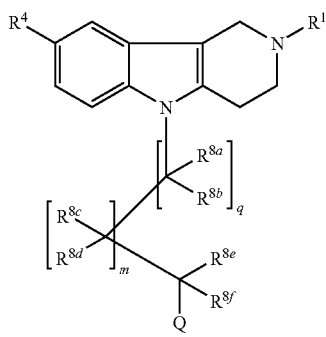

(Vf)

wherein:
R$^1$ is methyl;
R$^4$ is chloro or methyl;
m and q are independently 0 or 1;
each $R^{8a}$, $R^{8b}$, $R^{8c}$, $R^{8d}$, $R^{8e}$ and $R^{8f}$ is independently H, hydroxyl, substituted or unsubstituted alkyl or is taken together with the carbon to which it is attached and a geminal $R^{8(a-f)}$ to form a cycloalkyl moiety; and
Q is acyclic or cyclic acylamino, acyloxy, aminoacyl or aminocarbonylalkoxy; or a salt thereof.

8. The compound of claim 7, or a salt thereof, wherein R$^1$ is methyl and R$^4$ is chloro.

9. The compound of claim 7, or a salt thereof, wherein R$^1$ and R$^4$ are methyl and Q is acyclic acylamino, acyloxy, aminoacyl or aminocarbonylalkoxy.

10. The compound of claim 1, or a salt thereof, wherein the compound modulates at least one of the following receptors: adrenergic receptor, serotonin receptor, dopamine receptor and histamine receptor.

11. A pharmaceutical composition comprising a compound according to any one of claims 1, 2 and 7, or a salt thereof, and a pharmaceutically acceptable carrier.

12. The compound of claim 1, or a salt thereof, wherein X$^9$ is CR$^4$ where R$^4$ is halo or alkyl.

13. The compound of claim 1, or a salt thereof, wherein X$^9$ is CR$^4$ where R$^4$ is chloro or methyl.

14. The compound of claim 1, or a salt thereof, wherein each X$^7$, X$^8$ and X$^{10}$ is CR$^4$ where R$^4$ is H.

15. The compound of claim 1, or a salt thereof, wherein each of $R^{2a}$, $R^{2b}$, $R^{3a}$, $R^{3b}$, $R^{10a}$ and $R^{10b}$ is H.

16. The compound of claim 1, or a salt thereof, wherein R$^1$ is methyl.

17. The compound of claim 1, or a salt thereof, wherein at least one of m and q is 1.

18. The compound of claim 1, or a salt thereof, wherein q is 0 and m is 1.

19. The compound of claim 1, or a salt thereof, wherein each $R^{8a}$, $R^{8b}$, $R^{8c}$, $R^{8d}$, $R^{8e}$ and $R^8$, when present, is H.

20. The compound of claim 1, or a salt thereof, wherein Q is an acylamino of the formula —C(O)NHR' where R' is unsubstituted or substituted alkyl, substituted cycloalkyl, unsubstituted or substituted aryl, unsubstituted or substituted heteroaryl or unsubstituted or substituted heterocyclyl.

21. The compound of claim 1, or a salt thereof, wherein Q is of the formula —NHC(O)R' where R' is alkyl, substituted alkyl, aryl, substituted aryl, heteroaryl, substituted heteroaryl, heterocyclyl, substituted heterocyclyl, alkoxy or substituted alkoxy.

22. A method of treating a cognitive disorder, psychotic disorder, neurotransmitter-mediated disorder or a neuronal disorder in an individual comprising administering to an individual in need thereof an effective amount of a compound of claim 1, or a salt thereof.

23. A kit comprising a compound according to claim 1 and instructions for use in the treatment of a cognitive disorder, psychotic disorder, neurotransmitter-mediated disorder or a neuronal disorder.

* * * * *